United States Patent
Carrell et al.

(10) Patent No.: US 11,401,552 B2
(45) Date of Patent: Aug. 2, 2022

(54) METHODS OF IDENTIFYING MALE FERTILITY STATUS AND EMBRYO QUALITY

(71) Applicants: University of Utah Research Foundation, Salt Lake City, UT (US); The University Of Southern California, Los Angeles, CA (US)

(72) Inventors: Douglas T. Carrell, Salt Lake City, UT (US); Bradley Cairns, Salt Lake City, UT (US); Kenneth I. Aston, Salt Lake City, UT (US); Timothy Jenkins, Salt Lake City, UT (US); Andrew David Smith, Los Angeles, CA (US); Philip James Uren, Pasadena, CA (US); Alan Horsager, Pasadena, CA (US)

(73) Assignees: University of Utah Research Foundation, Salt Lake City, UT (US); The University of Southern California, Los Angeles, CA (US)

( * ) Notice: Subject to any disclaimer, the term of this patent is extended or adjusted under 35 U.S.C. 154(b) by 672 days.

(21) Appl. No.: 15/750,715

(22) PCT Filed: Aug. 8, 2016

(86) PCT No.: PCT/US2016/046060
§ 371 (c)(1),
(2) Date: Feb. 6, 2018

(87) PCT Pub. No.: WO2017/024311
PCT Pub. Date: Feb. 9, 2017

(65) Prior Publication Data
US 2019/0112659 A1 Apr. 18, 2019

Related U.S. Application Data

(60) Provisional application No. 62/201,907, filed on Aug. 6, 2015.

(51) Int. Cl.
| | | |
|---|---|---|
| *C12Q 1/6883* | (2018.01) | |
| *C12Q 1/68* | (2018.01) | |
| *G16B 20/00* | (2019.01) | |
| *A61B 17/43* | (2006.01) | |

(52) U.S. Cl.
CPC ............ *C12Q 1/6883* (2013.01); *A61B 17/43* (2013.01); *C12Q 1/68* (2013.01); *G16B 20/00* (2019.02); *C12Q 2600/112* (2013.01); *C12Q 2600/118* (2013.01); *C12Q 2600/154* (2013.01); *G01N 2800/367* (2013.01)

(58) Field of Classification Search
CPC .................................................. G16B 20/00
See application file for complete search history.

(56) References Cited

U.S. PATENT DOCUMENTS

| | | |
|---|---|---|
| 6,998,235 B2 | 2/2006 | Kennedy et al. |
| 2009/0093430 A1 | 4/2009 | Lockstone et al. |
| 2009/0246771 A1 | 10/2009 | Laird et al. |
| 2009/0299645 A1 | 12/2009 | Colby et al. |
| 2010/0234242 A1 | 9/2010 | Petronis et al. |
| 2012/0220475 A1 | 8/2012 | Petronis et al. |
| 2013/0338032 A1 | 12/2013 | Godler |
| 2014/0166486 A1 | 6/2014 | Carrell et al. |
| 2016/0208327 A1 | 2/2016 | Carrell et al. |

FOREIGN PATENT DOCUMENTS

| | | |
|---|---|---|
| CN | 101360835 A | 2/2009 |
| CN | 101449161 A | 6/2009 |
| CN | 102137938 A | 7/2011 |
| CN | 103103256 A | 5/2013 |
| WO | 2003025215 A1 | 3/2003 |
| WO | 2007/039234 A2 | 4/2007 |
| WO | 2019048927 A2 | 3/2019 |

OTHER PUBLICATIONS

Rajender et al., Epigenetics, spermatogenesis, and male infertility, 2011, Mutation Research, 727, p. 62-71 (Year: 2011).*
Ombelet et al., Semen quality and prediction of IUI success in male subfertility: a systematic review, 2014, Reproductive BioMedicine Online, 28, p. 300-309 (Year: 2014).*
Beck et al., The methylome: approaches for global DNA methylation profiling, 2008, Trends in Genetics, 24(5), p. 231-237 (Year: 2008).*
Louie et al., A Genome-wide DNA Methylation Study in Azoospermic testes, 2014, ASRM Abstracts, 102(3), Supplement, p. e354 (Year: 2014).*
Duran et al., Intrauterine insemination: a systemic review on determinants of success, 2002, Human Reproduction Update, 8(4), p. 373-384 (Year: 2002).*
Morris et al, Analysis Pipelines and packages for Infinium HumanMethylome450 BeadChip (450k) data, 2015, Methods, 72, p. 3-8 (Year: 2015).*
Urdinguio et al., Aberrant DNA methylation patterns of spermatozoa in men with unexplained infertility, 2015, Human Reproduction, 30(5), p. 1014-1028 and supplementary (Year: 2015).*
Smith et al., illuminaio: An open source IDAT parsing tool for Illumina microarrays, 2013, F1000Research, 2:264, p. 1-7 (Year: 2013).*
Adorján et al., "Tumour class prediction and discovery by microarray-based DNA methylation analysis," Nucleic Acids Research, Information Retrieval Ltd., Mar. 2002, vol. 30, No. 5, p. e21.

(Continued)

*Primary Examiner* — Olivia M. Wise
*Assistant Examiner* — Kaitlyn L Minchella
(74) *Attorney, Agent, or Firm* — Michael Best & Friedrich LLP

(57) ABSTRACT

Methods are provided of identifying a male fertility condition in a subject. Methods of performing a fertility treatment and an in vitro fertilization procedure are also provided. The methods may comprise determining the DNA methylation pattern of DNA extracted from a semen sample of a subject.

19 Claims, 14 Drawing Sheets

(56) References Cited

OTHER PUBLICATIONS

European Patent Office Action for Application No. 16834003.2 dated Jun. 4, 2020 (7 pages).
Aston et al., Genome-wide sperm deoxyribonucleic acid methylation is altered in some men with abnormal chromatin packaging or poor in vitro fertilization embryogenesis. Fertility and Sterility (Feb. 2012), pp. 285-292 vol. 97, No. 2.
Bibikova et al., High density DNA methylation array with single CpG site resolution. Genomics (Oct. 2011), pp. 288-295, vol. 98.
Aryee et al., "Minfi: a flexible and comprehensive Bioconductor package for the analysis of Infinium DNA methylation microarrays," Bioinformatics, 2014, 30(10):1363-9.
Barratt et al., "Diagnostic tools in male infertility—the question of sperm dysfunction," Asian Journal of Andrology, 2011, 13(1):53-58.
Benjamini et al., "Controlling The False Discovery Rate—A Practical And Powerful Approach To Multiple Testing," Journal of the Royal Statistical Society, Series B, 1995, 57(1):289-300.
Bonde et al., "Relation between semen quality and fertility: a population-based study of 430 first-pregnancy planners," Lancet, 1998, 352(9135):1172-7.
Brazil et al., "Quality control of laboratory methods for semen evaluation in a multicenter research study," Journal of Andrology, 2004, 25(4):645-56.
Burkman et al., "The hemizona assay (HZA): development of a diagnostic test for the binding of human spermatozoa to the human hemizona pellucida to predict fertilization potential," Fertility and Sterility, 1988, 49(4):688-97.
Cooper et al., "World Health Organization reference values for human semen characteristics," Human Reproduction Update, 2010, 16(3):231-45.
Dam et al., "Homozygous mutation in SPATA16 is associated with male infertility in human globozoospermia," American Journal of Human Genetics, 2007, 81(4):813-20.
Ellnati et al., "Globozoospermia is mainly due to DPY19L2 deletion via non-allelic homologous recombination involving two recombination hotspots," Human Molecular Genetics, 2012, 21(16):3695-702.
Esteves et al., "Critical appraisal of World Health Organization's new reference values for human semen characteristics and effect on diagnosis and treatment of subfertile men," Urology, 2012, 79(1):16-22.
European Patent Office Extended Search Report for Application No. 16834003.2 dated May 21, 2019 (8 pages).
Gandini et al., "News from the European Academy of Andrology. Italian pilot study for an external quality control scheme in semen analysis and antisperm antibiotics detection," International Journal of Andrology, 2000, 23(1):1-3.
Guzick et al., "Sperm morphology, motility, and concentration in fertile and infertile men," The New England Journal of Medicine, 2001, 345(19):1388-93.
Haas Jr. et al., "Immunologic infertility: identification of patients with antisperm antibody," New England Journal of Medicine, 1980, 303(13):722-7.
Hall et al., The WEKA Data Mining Software: An Update. SIGKDD Explorations, 2009, 11(1):10-18.
Hammoud et al., "Alterations in sperm DNA methylation patterns at imprinted loci in two classes of infertility," Fertility and Sterility, 2010, 94(5): 1728-1733.
Harbuz et al., "A recurrent deletion of DPY19L2 causes infertility in man by blocking sperm head elongation and acrosome formation," American Journal of Human Genetics, 2011, 88(3):351-61.
International Search Report and Written Opinion for Application No. PCT/US2016/046060 dated Oct. 31, 2016 (14 pages).
Kläver et al., "DNA methylation in spermatozoa as a prospective marker in andrology," Andrology, 2013, 1(5):731-740.
Koscinski et al., "DPY19L2 deletion as a major cause of globozoospermia," American Journal of Human Genetics, 2011, 88(3):344-50.

Lanfranco et al., "Klinefelter's syndrome," Lancet, 2004, 364(9430):273-83.
Lee et al., "Capacitation and acrosome reactions in human spermatozoa monitored by a chlortetracycline fluorescence assay," Fertility and Sterility, 1987, 48(4):649-58.
Leushuis et al., "Reproducibility and reliability of repeated semen analyses in male partners of subfertile couples," Fertility and Sterility, 2010, 94(7):2631-5.
Maksimovic et al., "SWAN: Subset-quantile Within Array Normalization for Illumina Infinium HumanMethylation450 BeadChips," Genome Biology, 2012, 13(6):R44.
Neuwinger et al., "External quality control in the andrology laboratory: an experimental multicenter trial," Fertility and Sterility, 1990, 54(2):308-14.
Platt, "Sequential Minimal Optimization: A Fast Algorithm for Training Support Vector Machines," Advances in kernel methods—support vector learning, 1998, 21 pages.
Sanchez et al., "A new method for evaluation of the acrosome reaction in viable human spermatozoa," Andrologia, 1991, 23(3):197-203.
Tiepolo et al., "Localization of factors controlling spermatogenesis in the nonfluorescent portion of the human Y chromosome long arm," Human Genetics, 1976, 34(2):119-24.
Yanagimachi et al., "The use of zona free animal ova as a test system for the assessment of the fertilizing capazity of human spermatozoa," Biology of Reproduction, 1976, 15(4):471-6.
Zini et al., "Sperm DNA damage is associated with an increased risk of pregnancy loss after IVF and ICSI: systematic review and meta-analysis," Human Reproduction, 2008, 23(12):2663-8.
China National Intellectual Property Administration First Office Action and Search Report for Application No. 201680057796.1 dated Apr. 29, 2021 (21 pages including English translation).
Bohacek et al., "Epigenetic Inheritance of Disease and Disease Risk", Neuropsychopharmacology, 2013, vol. 38, pp. 220-236.
Jenkins et al., "Age-associated sperm DNA methylation alterations: possible implications in offspring disease susceptibility", PLoS Genetics, 2014, 10(7):e1004458, 13 pages.
Houshdaran et al., "Widespread Epigenetic Abnormalities Suggest a Broad DNA Methylation Erasure Defect in Abnormal Human Sperm," PLoS ONE, 2007, 2(12):e1289.
Schagdarsurengin et al., "Analysing the sperm epigenome: roles in early embryogenesis and assisted reproduction," Nature Reviews Urology, 2012, 9:609-619.
Seisenberger et al., "The dynamics of genome-wide DNA methylation reprogramming in mouse primordial germ cells," Molecular Cell, 2012, 48:849-862.
Martin-Trujillo et al., "Genotype of an individual single nucleotide polymorphism regulates DNA methylation at the TRPC3 alternative promoter," Epigenetics, 2011, 6(10):1236-1241.
Krausz et al., "Novel insights into DNA methylation features in spermatozoa: stability and peculiarities," PLoS ONE, 2012, 7(10):e44479.
Benchaib et al., "Influence of global sperm DNA methylation on IVF results," Human Reproduction, 2005, 20(3):768-773.
Pacheco et al., "Integrative DNA Methylation and Gene Expression Analyses Identify DNA Packaging and Epigenetic Regulatory Genes Associated with Low Motility Sperm", PLoS One, 2011, vol. 6, No. 6, e20280 and Supplemental Tables.
Benner, "Evolution, language and analogy in fuctional genomics", TRENDS in Genetics, vol. 17, No. 7, 2001, pp. 414-418.
Brinkman et al., "Whole-genome DNA methylation profiling using MethylCap-seq", Methods, 2010, 6 pages.
Brooks et al., "Promoter Methylation and the Detection of Breast Cancer", Cancer Causes Control, vol. 20, No. 9, 2009, pp. 1539-1550.
Butcher et al., "AutoMeDIP-seq: A high-throughput, whole genome, DNA methylation assay", Methods, vol. 52, 2010, pp. 223-231.
Caley et al., "The Priniciples of cancer treatment by chemotherapy", Surgery, vol. 30, Issue 4, 2012, pp. 186-190.
Cottrell, "Molecular diagnostic applications of DNA methylation technology", Clinical Biochemistry, vol. 37, Issue 7, 2004, pp. 595-604.

(56) References Cited

OTHER PUBLICATIONS

Dohle et al., "EAU Guidelines on Male Infertility", European Urology, vol. 48, pp. 703-711.

Down et al., "A Bayesian deconvolution strategy for immunoprecipitation-based DNA methylome analysis", Nat Biotechnol., vol. 26, No. 7, 2008, pp. 779-785.

Ehrlich, "DNA methylation in cancer: too much, but also too little", Oncogene, vol. 21, 2002, pp. 5400-5413.

Guerrero-Bosagna et al., "Epigenetic Transgenerational Actions of Vinclozolin on Promoter Regions of the Sperm Epigenome", PLoSOne, vol. 5, No. 9, 2010, e13100 (17 pages).

Iizarry et al., "Genome-wide methylation analysis of human colon cancer reveals similar hypo-and hypermethylation at conserved tissue-specific CpG shores", Nat Genet., 2009, vol. 41, No. 2, pp. 178-186.

Madi et al., "The determination of tissue-specific DNA methylation patterns in forensic biofluids using bisulfite modification and pyrosequencing", Electrophoresis, 2012, vol. 33, pp. 1736-1745.

Younglai et al., "Reproductive Toxicology of Environmental Toxicants: Emerging Issues and Concerns", Current Pharmaceutical Design, vol. 13, 2007, pp. 3005-3019.

Mohn et al., "Genetics and epigenetics: stability and plasticity during cellular differentiation", Cell Press, 2009, pp. 129-136.

Rauch et al., "DNA Methylation profiling using the methylated-CpG island recovery assay (MIRA)", Methods, 2010, vol. 52, No. 3, pp. 213-217.

Sabbioni et al., "Multigene Methylation Analysis of Gastrointestinal Tumors", Mol. Diag., vol. 7, No. 3, 2003, pp. 201-207.

Skinner et al., "Epigenetic transgenerational actions of environmental factors in disease etiology", Trends in Endocrinology and Metabolism, vol. 21, No. 4, 2010, pp. 214-222.

Skinner et al., "Role of CpG deserts in the epigenetic transgenerational inheritance of differential DNA methylation regions", BMC Genomics, vol. 15, No. 692, 2014, 6 pages.

Thirlwell et al., "Suffocating cancer: hypoxia-associated epimutations as targets for cancer therapy", Clinical Epigenetics, vol. 3, No. 9, 2011, pp. 1-9.

Ushijima, "Detection and interpretation of altered methylation patterns in cancer cells", Nature Reviews: Cancer, vol. 5, 2005, pp. 223-231.

Walsh et al., "Cytosine methylation and mammalian development", Genes & Development, vol. 13, 1999, pp. 26-34.

Zhang et al., "DNA Methylation Analysis of Chromosome 21 Gene Promoters at Single Base Pair and Single Allele Resolution", PLoSOne Genetics, 2009, vol. 5, No. 3, e1000438 (15 pages).

Thu et al., "Methylation Analysis by DNA Immunoprecipitation", J. Cell Physiol., vol. 222, 2010, pp. 522-531.

Australian Patent Office Examination Report for Application No. 2016301189 dated Aug. 25, 2021 (5 pages).

\* cited by examiner

METHODS OF IDENTIFYING MALE FERTILITY STATUS AND EMBRYO QUALITY

CROSS-REFERENCE TO RELATED APPLICATIONS

This application is the U.S. National Stage filing under 35 U.S.C. § 371 of International Patent Application No. PCT/US2016/046060, filed Aug. 8, 2016, which claims the benefit of U.S. Provisional Application No. 62/201,907, filed Aug. 6, 2015, each of which is hereby incorporated by reference in its entirety.

TECHNICAL FIELD

The present disclosure relates to methods of identifying a male fertility condition in a subject. The disclosure also relates to methods of identifying embryo quality. More particularly, the disclosure relates to methods of performing a fertility treatment.

BACKGROUND

Male infertility diagnosis can be determined by the standard semen analysis. With the exception of modifications to criteria for morphological grading, the semen analysis has generally changed little over the past several decades. Studies have evaluated the prognostic value of the various semen parameters evaluated by the standard semen analysis (see Esteves S C et al. Urology. 2012; 79(1):16-22; Barratt C L et al. Asian Journal of Andrology. 2011; 13(1):53-8; and Bonde J P et al. Lancet. 1998; 352(9135):1172-7, each of which is incorporated by reference herein in its entirety). While the parameters assessed may be a benchmark in evaluating a man's fertility potential, with the exception of severely diminished sperm count or motility, however, the predictive value of the semen analysis for fertility is generally modest. A study of the predictive value of the semen analysis indicated that while the semen analysis can be useful for classifying men as sub-fertile, of indeterminate fertility, or fertile, it is generally ineffective for diagnosing infertility because many infertile men display semen parameters that fall within normal ranges (see Guzick D S et al. The New England Journal of Medicine. 2001; 345(19): 1388-93, which is incorporated by reference herein in its entirety).

The main parameters evaluated in the semen analysis, namely sperm count, motility, viability, and morphology, can be somewhat subjective, and consequently they can be subject to technical error. While continual training and assessment, quality control measures, and proficiency testing may all serve to minimize technical error, studies have demonstrated that coefficients of variation (CVs) between labs and technicians can fall in the 20-30% range, with higher CVs reported in some studies (see Gandini L et al. International Journal of Andrology. 2000; 23(1):1-3; Neuwinger J et al. Fertility and Sterility. 1990; 54(2):308-14; and Brazil C et al. Journal of Andrology. 2004; 25(4): 645-56, each of which is incorporated by reference herein in its entirety).

In addition to technical variability, semen parameters within the same individual can vary between collections, with CVs of around 30% between two collections from the same man, based on a recent study that evaluated more than 5,000 men (see Leushuis E et al. Fertility and Sterility. 2010; 94(7):2631-5, which is incorporated by reference herein in its entirety). Given this variability, the World Health Organization (WHO) recommends that at least two semen analyses be performed prior to clinical decision-making (see World Health Organization. WHO laboratory manual for the examination and processing of human semen. 5th ed. Geneva: World Health Organization; 2010, which is incorporated by reference herein in its entirety).

Lastly, the predictive value of the various semen parameters can be limited. Studies have been performed to characterize semen parameters in healthy, fertile men, and fertile and sub-fertile ranges have been defined for each of the parameters assessed (see Cooper T G et al. Human Reproduction Update. 2010; 16(3):231-45 and Guzick D S et al. The New England Journal of Medicine. 2001; 345(19): 1388-93, each of which is incorporated by reference herein in its entirety). Nevertheless, the parameters assessed by the standard semen analysis can fall short of predicting fertility potential.

Adjunct tests have been developed, such as sperm DNA damage assessment, capacitation and acrosome reaction tests, egg and zona penetration assays, anti-sperm antibody testing, and aneuploidy screening (see Zini A et al. Human Reproduction. 2008; 23(12):2663-8; Sanchez R et al. Andrologia. 1991; 23(3):197-203; Lee M A et al. Fertility and Sterility. 1987; 48(4):649-58; Haas G G, Jr. et al. The New England Journal of Medicine. 1980; 303(13):722-7; Burkman L J et al. Fertility and Sterility. 1988; 49(4):688-97; and Yanagimachi R et al. Biology of Reproduction. 1976; 15(4): 471-6, each of which is incorporated by reference herein in its entirety), and while these tests can be helpful in characterizing fertility potential in select patients, the predictive values of the assays can be suboptimal (see Yanagimachi R et al. Biology of Reproduction. 1976; 15(4):471-6, which is incorporated by reference herein in its entirety).

A few genetic markers for male infertility have been identified, such as Y chromosome microdeletions (see Tiepolo L et al. Human Genetics. 1976; 34(2):119-24, which is incorporated by reference herein in its entirety), Klinefelter syndrome (see Lanfranco F et al. Lancet. 2004; 364(9430): 273-83, which is incorporated by reference herein in its entirety), and DPY19L and SPATA16 mutations (see Dam A H et al. American Journal of Human Genetics. 2007; 81(4): 813-20; Elinati E et al. Human Molecular Genetics. 2012; 21(16):3695-702; Harbuz R et al. American Journal of Human Genetics. 2011; 88(3):351-61; and Koscinski I et al. American Journal of Human Genetics. 2011; 88(3):344-50, each of which is incorporated by reference herein in its entirety), among others. These genetic features, however, are generally associated with extreme male infertility phenotypes including severe oligozoospermia, nonobstructive azoospermia, and complete globozoospermia, thus accounting for a small percentage of infertile men.

Epigenetics can refer to modifiable but generally stable, heritable modifications to the DNA or chromatin packaging. Direct DNA modifications can consist of methylation alteration to the 5-carbon position of cytosine bases, generally in the context of cytosine-guanine dinucleotides (CpGs).

BRIEF DESCRIPTION OF THE DRAWINGS

The embodiments disclosed herein will become more fully apparent from the following description and appended claims, taken in conjunction with the accompanying drawings.

DETAILED DESCRIPTION

Figure 1A:
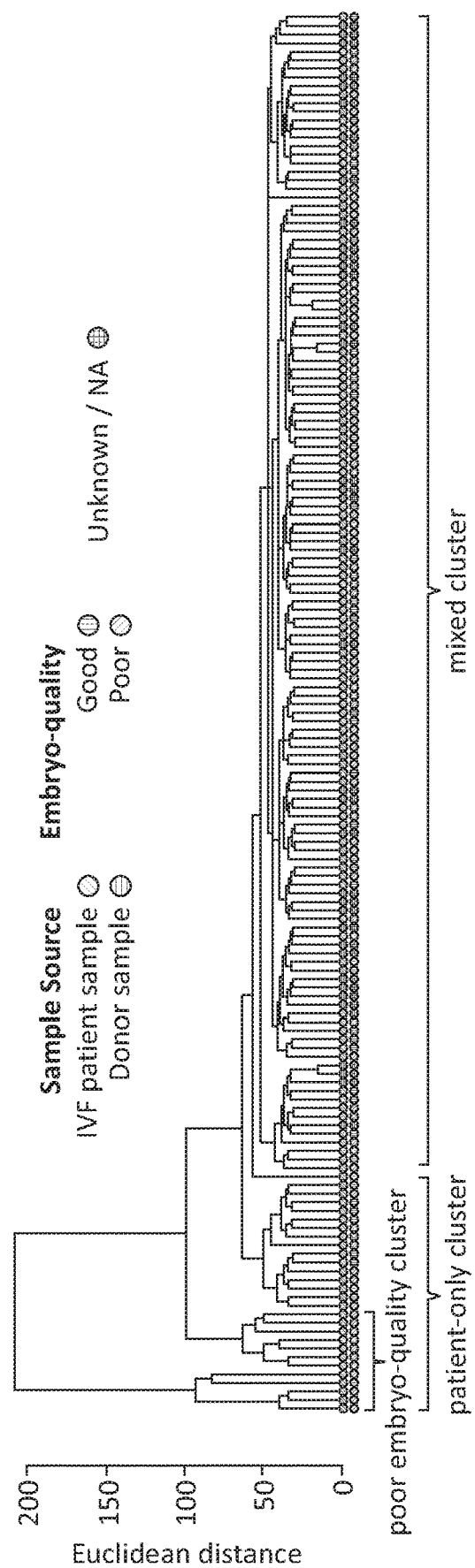
FIG. 1A depicts hierarchical clustering of 163 neat samples based on global methylation profile. An out-group of exclusively patient samples with a sub-group strongly enriched for poor embryo samples is apparent.

The present disclosure provides methods of identifying a male fertility condition in a subject and/or predicting a level of male fertility in a subject. This disclosure also provides methods of identifying and/or predicting embryo quality. Furthermore, the disclosure provides methods of performing fertility treatments.

It will be readily understood that the embodiments, as generally described herein, are exemplary. The following more detailed description of various embodiments is not intended to limit the scope of the present disclosure, but is merely representative of various embodiments. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified.

A "subject" is defined herein as a mammal that may experience a male fertility condition, a male fertility abnormality, decreased fertility, and/or a level of infertility. Examples of subjects include, but are not limited to, humans, horses, pigs, cattle, dogs, cats, rabbits, and aquatic mammals.

A "methylation pattern" is defined herein as the methylation of a region of genetic material (e.g., a region of a DNA molecule); methylation of a region may include methylation of a plurality of regions. Such methylation can include the absence and/or presence of methylation in a region, the extent of methylation of a region, and/or the actual methylated sequence of the region.

A "genome-wide methylation pattern" or a "genome-wide DNA methylation pattern" is defined herein as the methylation of a representative portion, a significant portion, and/or a substantial portion of a genome. For example, a genome-wide methylation pattern may comprise a majority of CpGs from CpG islands, a portion of CpG sites outside of CpG islands, and/or a portion of non-CpG sites in the genome of a subject. In another example, a genome-wide methylation pattern may comprise a pattern of methylation at loci across the genome rather than at specific genes and/or genomic features.

A "control pattern of methylation" or a "control pattern of DNA methylation" is defined herein as a pattern of methylation from a population of males, or a representative sample thereof, that is indicative of a fertile male. A control pattern of methylation can be generated using techniques known in the art. For example, the control pattern of methylation can be an average pattern of methylation generated from a population of males, or a representative sample thereof, that are determined to be fertile (e.g., normozoospermic males with proven fertility).

An "aberrant pattern of methylation" or an "aberrant pattern of DNA methylation" is defined herein as a methylation pattern that deviates from a control pattern of methylation to an extent that is indicative of a male fertility condition. For example, an aberrant pattern of methylation may be significantly different from a control pattern of methylation, or aberrant patterns of methylation may be significantly different from control patterns of methylation. In another example, a control pattern of methylation may be significantly different from an aberrant pattern of methylation, or control patterns of methylation may be significantly different from aberrant patterns of methylation. Methylation pattern differences may be observed at a plurality of consistently, or substantially consistently, altered loci, or methylation pattern differences may be manifest as increased variability in subjects having aberrant methylation patterns compared with control methylation patterns.

In some embodiments, differences between aberrant patterns of methylation and control patterns of methylation may be determined at a single CpG level. For example, one or more CpGs may exhibit statistically significant differences in mean methylation between control groups and aberrant groups. In certain embodiments, differences between aberrant patterns of methylation and control patterns of methylation may be determined at an aggregate region level. For example, one or more CpGs within a given region may exhibit statistically significant differences in mean methylation between control groups and aberrant groups, and/or the region as a whole may exhibit a statistically significant difference in mean methylation level.

In various embodiments, differences between aberrant patterns of methylation and control patterns of methylation may be determined from genome-wide comparisons. For example, the differences between aberrant patterns of methylation and control patterns of methylation may be determined by simultaneously, or substantially simultaneously, comparing methylation patterns based on all profilable CpGs, substantially all profilable CpGs, or a large subset of CpGs. In certain embodiments, an analysis of the differences between aberrant patterns of methylation and control patterns of methylation may be determined in terms of "distance." For example, each sample may represent a point in n-dimensional space, wherein "n" is the number of profilable or profiled CpGs. In terms of "distance," the "n" dimensions can be reduced to a single dimension, and it can be determined if the "distance" of an aberrant profile from a reference point shows a statistically significant difference from those one or more "distances" observed for control profiles.

In some embodiments, a maximally discriminative model may be utilized. For example, some machine learning methods may aim to learn the maximally discriminative model, regardless of whether any difference between groups or features reaches statistical significance.

A "male fertility condition" is defined herein as a condition that renders in a male subject some level of infertility, a fertility abnormality, and/or decreased fertility. Those of ordinary skill in the art are capable of distinguishing various levels of infertility, all of which would be considered to be within the present scope.

The present disclosure provides devices, methods, and systems for detecting fertility in a subject. In one aspect, for example, a method for identifying an aberrant pattern of methylation associated with a male fertility condition may include assaying a pattern of methylation (e.g., a test pattern of methylation) of a representative portion, a significant portion, and/or a substantial portion of a genome of a subject, and comparing the assayed pattern of methylation from the subject with a control pattern of DNA methylation to identify an aberrant pattern of methylation associated with a male fertility condition.

In another aspect, a method for identifying a male fertility condition may include assaying the degree of methylation or a methylation pattern of a representative portion, a significant portion, and/or a substantial portion of a genome of sperm from a subject (e.g., test sperm), and comparing the degree of methylation or the methylation pattern of the sperm from the subject with a control degree of methylation or a methylation pattern from control sperm to determine a male fertility condition.

In one aspect of the present invention, a useful method for assaying DNA methylation can include bisulfite treatment. Treating DNA with a bisulfite such as sodium bisulfite can convert unmethylated cytosines to uracils; methylated cytosines can resist deamination and thus generally remain unchanged. The cytosine to uracil transition following bisulfite treatment can provide a useful assay of the methylation pattern or profile of a region of genetic material. Following such treatment, the genetic material can be sequenced to determine the specific methylation pattern.

Bisulfite treatment can be utilized in analyzing a few candidate loci, or it can be used to perform a broader genome-wide analysis. If a genome-wide or partially genome-wide analysis is desired, genetic material can be captured on an array of genome loci.

In addition, methods according to the instant disclosure may be useful in predicting success with various treatments of reproductive disorders such as IVF or other artificial reproductive techniques.

Another aspect of the disclosure relates to methods of identifying a male infertility condition in a subject. In some embodiments, a male infertility condition may be a condition in a male subject that is associated with some level of infertility, a fertility abnormality, and/or decreased fertility. In certain embodiments, a method of identifying a male infertility condition may comprise extracting genetic material such as DNA from a semen sample from a subject. In some embodiments, the semen sample may be a whole ejaculate sample. In some other embodiments, the semen sample may be purified, for example, by somatic cell lysis. Somatic cell lysis may reduce or eliminate white blood cell contamination in the semen sample. In some other embodiments, the semen sample may be purified by a density gradient purification. In certain embodiments, the semen sample, or the purified semen sample, may be pelleted (i.e., via centrifugation) and/or visually inspected to determine whether substantially all contaminating cells are absent from or have been removed from the semen sample.

The method may also comprise identifying a methylation pattern of the extracted DNA. In some embodiments, the methylation pattern may be a genome-wide methylation pattern. For example, the methylation pattern may include an assessment of the methylation status of cytosines and/or CpG dinucleotides from positions across the genome. Further, the method may comprise comparing the methylation pattern of the extracted DNA to a control pattern of DNA methylation. In various embodiments, the method may comprise determining if the methylation pattern of the extracted DNA is significantly different from the control pattern of DNA methylation, wherein a significantly different methylation pattern of the extracted DNA may indicate that the subject has a male fertility condition.

In some embodiments, the methylation pattern may be based on a methylation status of at least 50,000 cytosines from the extracted DNA. For example, the methylation pattern may comprise the methylation status of at least 50,000 cytosines (i.e., whether or not cytosines disposed in at least 50,000 positions in the genome are methylated). In some embodiments, the methylation pattern may be based on a methylation status of at least 100,000 cytosines from the extracted DNA, of at least 200,000 cytosines from the extracted DNA, of at least 300,000 cytosines from the extracted DNA, of at least 485,000 cytosines from the extracted DNA, or of another suitable number of cytosines from the extracted DNA.

In some other embodiments, the methylation pattern may be based on a methylation status of at least 50,000 CpG dinucleotides from the extracted DNA. For example, the methylation pattern may comprise the methylation status of at least 50,000 CpG dinucleotides (i.e., whether or not cytosines disposed in at least 50,000 CpG dinucleotide positions in the genome are methylated). In some embodiments, the methylation pattern may be based on a methylation status of at least 100,000 CpG dinucleotides from the extracted DNA, of at least 200,000 CpG dinucleotides from the extracted DNA, of at least 300,000 CpG dinucleotides from the extracted DNA, of at least 485,000 CpG dinucleotides from the extracted DNA, or of another suitable number of CpG dinucleotides from the extracted DNA.

In certain embodiments, the methylation pattern of the extracted DNA may be identified by a method selected from, but not limited to, analyzing the methylation pattern via a DNA methylation array, pyrosequencing, reduced representation bisulfite sequencing, targeted bisulfite sequencing, genome-wide bisulfite sequencing, bisulfite patch PCR, or a combination thereof. In various embodiments, the methylation pattern of the extracted DNA may be identified by a method comprising treating at least a portion of the extracted DNA with bisulfite, amplifying the bisulfite-treated DNA, hybridizing the amplified DNA to a DNA methylation array, and/or processing the hybridized DNA methylation array to determine the methylation pattern of the extracted DNA.

Another aspect of the disclosure relates to a method of performing a fertility treatment. In some embodiments, the method may comprise identifying a subject with a male fertility condition. In various embodiments, the method may comprise identifying a DNA methylation pattern from a semen sample of the subject. The method may also comprise comparing the identified DNA methylation pattern to a control pattern of DNA methylation. The control pattern of DNA methylation may be a methylation pattern from DNA extracted from semen samples from a control population of fertile males. The method may further comprise classifying whether the identified DNA methylation pattern is significantly different from the control pattern of DNA methylation or whether the identified methylation pattern is not significantly different from the control pattern of DNA methylation. In certain embodiments, if the identified methylation pattern is significantly different from the control pattern of DNA methylation, the method may comprise collecting a sample from the subject for use in an IVF procedure. In various embodiments, if the identified methylation pattern is not significantly different from the control pattern of DNA methylation, the method may comprise collecting a semen sample from the subject for use in an artificial insemination procedure.

As discussed above, in some embodiments, the methylation pattern may be based on a methylation status of at least 50,000 cytosines from the extracted DNA. For example, the methylation pattern may comprise the methylation status of at least 50,000 cytosines (i.e., whether or not cytosines disposed in at least 50,000 positions in the genome are methylated). In some embodiments, the methylation pattern may be based on a methylation status of at least 100,000 cytosines from the extracted DNA, of at least 200,000 cytosines from the extracted DNA, of at least 300,000 cytosines from the extracted DNA, of at least 485,000 cytosines from the extracted DNA, or of another suitable number of cytosines from the extracted DNA.

As discussed above, in some other embodiments, the methylation pattern may be based on a methylation status of at least 50,000 CpG dinucleotides from the extracted DNA. For example, the methylation pattern may comprise the methylation status of at least 50,000 CpG dinucleotides (i.e., whether or not cytosines disposed in at least 50,000 CpG dinucleotide positions in the genome are methylated). In some embodiments, the methylation pattern may be based on a methylation status of at least 100,000 CpG dinucleotides from the extracted DNA, of at least 200,000 CpG dinucleotides from the extracted DNA, of at least 300,000 CpG dinucleotides from the extracted DNA, of at least 485,000 CpG dinucleotides from the extracted DNA, or of another suitable number of CpG dinucleotides from the extracted DNA. In certain embodiments, as discussed above, the method of fertility treatment may comprise purifying the semen sample.

Another aspect of the disclosure relates to a method of performing an IVF procedure. In some embodiments, the method may comprise identifying a subject with a male fertility condition. In various embodiments, the method may comprise identifying a DNA methylation pattern from a semen sample of the subject. The method may also comprise comparing the identified DNA methylation pattern to a control pattern of DNA methylation. The control pattern of DNA methylation may be a methylation pattern from DNA extracted from semen samples from a control population of fertile subjects. The method may further comprise classifying whether the identified DNA methylation pattern is significantly different from the control pattern of DNA methylation or whether the identified methylation pattern is not significantly different from the control pattern of DNA methylation. In certain embodiments, if the identified methylation pattern is significantly different from the control pattern of DNA methylation, the method may comprise collecting a sample from the subject for use in an intracytoplasmic sperm injection (ICSI) procedure. In various embodiments, if the identified methylation pattern is not significantly different from the control pattern of DNA methylation, the method may comprise collecting a semen sample from the subject for use in a microdrop IVF procedure.

Yet another aspect of the disclosure relates to a method of identifying or predicting IVF embryo quality. In certain embodiments, sperm DNA methylation patterns may be a predictor of embryo quality following IVF.

In various embodiments, a method of predicting embryo quality may comprise collecting a semen sample from a subject, extracting DNA from a portion of the semen sample, identifying a methylation pattern of the extracted DNA, comparing the methylation pattern of the extracted DNA to a control pattern of DNA methylation, and/or determining if the methylation pattern of the extracted DNA is significantly different from the control pattern of DNA methylation, wherein a significantly different methylation pattern of the extracted DNA may indicate that an embryo generated via fertilization with the semen sample is at risk of being a poor-quality IVF embryo.

In some embodiments, the accuracy, the sensitivity, and/or the positive predictive value of the method for detecting a male infertility condition may be greater than 60%. In some other embodiments, the accuracy, the sensitivity, and/or the positive predictive value of the method for detecting a male infertility condition may be greater than 65%, greater than 70%, greater than 75%, greater than 80%, greater than 85%, greater than 90%, or greater than 99%. In certain embodiments, the accuracy, the sensitivity, and/or the positive predictive value of the method for detecting IVF embryo quality may be greater than 60%. In certain other embodiments, the accuracy, the sensitivity, and/or the positive predictive value of the method for detecting IVF embryo quality may be greater than 65%, greater than 70%, greater than 75%, greater than 80%, greater than 85%, greater than 90%, or greater than 99%.

The present disclosure additionally provides kits for testing for a male fertility condition in a subject. Such a kit can include a kit housing containing assay components operable to detect a test pattern of methylation of genetic material from a semen sample from the subject, instructions describing how to perform an assay using the assay components, and a control pattern of DNA methylation to compare with the test pattern of methylation or to test for a male fertility condition or embryo quality.

A variety of kit housings are contemplated, and are sufficient to contain the assay components, the instructions, and the control pattern of DNA methylation. Such a kit can comprise an assembly of the required elements and any helpful instructions to perform such methods and tests, for assaying genome-wide methylation to determine a likelihood of a fertility condition or to determine embryo quality. In some aspects, the kit housing can contain a receptacle for containing and/or transporting sperm.

Additionally, in some aspects the kit can contain a genome array, PCR materials, or the like. Furthermore, the assay components included in the kit can be used to perform any assay capable of determining methylation patterns of genetic material. Non-limiting examples can include a DNA methylation array assay; capture or PCR reagents for pyrosequencing, reduced representation bisulfite sequencing, targeted bisulfite sequencing, genome-wide bisulfite sequencing, bisulfite patch PCR, or a combination thereof; and tools (e.g., computational tools) for data analysis and/or data interpretation.

It should be noted that an assay component can be any component or material used to perform an assay. The control pattern of DNA methylation can be provided in a number of formats. For example, the control pattern of DNA methylation can be provided as printed media, electronic media, biological material, and the like. Additionally, the control pattern of DNA methylation can be derived from a variety of regions of genetic material.

In one aspect, an assay can use a custom-designed DNA methylation array that covers a representative portion, a significant portion, and/or a substantial portion of a genome. Such an assay can specifically use semen samples processed by a density gradient preparation or other sperm preparation techniques used for assisted reproductive technology (ART). The selected sperm population used for testing can be a representative pool of sperm population used for ART (e.g., IVF, ICSI, etc.).

DNA methylation is the attachment or coupling of a methyl group to DNA at a given locus. The human genome comprises about 27 million loci that can be methylated (i.e., CpG dinucleotides). At each of these loci, in an individual cell, the DNA is either methylated or it is not methylated (i.e., there are only two possible values). As a given sperm sample may contain millions of cells, each having its own copy of the genome, the measurement of DNA methylation in a sperm sample may be the fraction of sperm cells in the sperm sample that have methylation at a given locus. For example, a value of 0 (zero) for a given locus may indicate that all sperm cells in the sperm sample are unmethylated. A value of 1 (one) for a given locus may indicate that all sperm cells in the sperm sample are methylated. A value of 0.5 for a given locus may indicate that half of the sperm cells in the sperm sample are methylated. Accordingly, a full human methylome can be about 27 million numbers, each ranging from 0 to 1.

To determine if a particular locus is aberrantly methylated, in certain embodiments, an expected range of normal methylation at the particular locus may first be defined. Accordingly, a subsequent methylation level seen outside of the expected range of normal methylation at the particular locus (e.g., either higher than the maximum or lower than the minimum) may then be considered an aberrant or abnormal methylation level.

An expected range of normal methylation at a particular locus can be determined in multiple ways. In some embodiments, given a set of n methylomes from known-fertile sperm donors, for a given locus there are n numbers ranging from 0 to 1, one for each known-fertile donor. First, the highest a % values and the lowest a % values can be discarded (in various embodiments, a=2.5%, however, other values are also within the scope of this disclosure). The maximum normal methylation level at this locus can be defined as b higher than the highest remaining value (or 1, whichever is smaller). Similarly, the minimum normal methylation level at this locus can be defined as b lower than the smallest remaining value (or 0, whichever is larger). In some embodiments, b=0.2, however, other values are also within the scope of this disclosure. The value of 0.2 is specific to Illumina's 450K Human Methylation array (the "450K HM chip"), and is derived from Bibikova et al. (2011, Genomics. 2011; 98:288-295, which is incorporated by reference herein in its entirety) where the claim is made that the 450K HM chips "can detect a delta beta of 0.2 with 99% confidence" ('beta' refers to the chips' estimate of the methylation level at a given locus, 'delta' can be read as 'change in').

In some other embodiments, given a set of n methylomes from known-fertile sperm donors, the parameters of a beta distribution ($\alpha$, $\beta$) can be estimated from the n methylation levels at a given locus (standard methods can be used to estimate these, e.g., maximum likelihood estimate, method of moments, etc.). Two critical values (x and x') in the distribution can be located such that $Pr(X<x|\alpha, \beta)<p$ and $Pr(X>x'|\alpha, \beta)<p$, where X is the random variable which the n measures of methylation are assumed to have been sampled from. Any subsequent methylation level at this locus which is less than x or greater than x' can then be considered aberrant. Furthermore, p can be corrected for multiple hypothesis testing using, for example, the Bonferoni method.

In certain embodiments, an additional constraint can be added where a subsequent methylation measure at a given locus is only considered aberrant if it exceeds the critical values and the absolute value of the difference between the new methylation measure and either the mean of the beta distribution exceeds some threshold (e.g., a value of 0.2 for the 450K HM chip). In some embodiments, a variation on this approach can involve not immediately computing the critical value, but using the beta distribution's cumulative distribution function to compute p-values for all loci, then correcting these for multiple hypothesis testing using, for example, the method of Benjamini and Hochberg (see Benjamini Y and Hochberg Y. Journal of the Royal Statistical Society, Series B. 1995; 57(1):289-300, which is incorporated by reference herein in its entirety).

Loci that exhibit a relationship between aberrant methylation and fertility outcome or embryo quality can be identified. In various embodiments, there can be n samples from known-fertile donors and m samples from infertile men. First, a reference fertile methylome can be determined using one of the methods described above. Then, for each sample (i.e., fertile or infertile) those loci that have methylation levels outside of the normal range can be identified. For each locus, a contingency table can be computed (see Table 1).

TABLE 1

Contingency Table

|  | Fertile | Infertile |
| --- | --- | --- |
| Aberrantly methylated | A | B |
| Not aberrantly methylated | C | D |

With reference to Table 1, A is the count of the number of samples from known-fertile donors where aberrant methylation was observed at this locus, B is the count of the number of samples from infertile men where aberrant methylation was observed at this locus, C is the count of samples from known-fertile men where aberrant methylation was not observed at this locus, and D is the count of samples from infertile men where aberrant methylation was not observed at this locus. A standard statistical test called Fisher's exact test can be applied to the contingency table (e.g., Table 1) to determine whether there is a statistically significant association between fertility status and aberrant methylation at this locus.

In various embodiments, the method or process for determining embryo quality can be similar to the process described above for determining fertility status, but with the labels "Fertile" and "Infertile" in Table 1 replaced with "Good embryo quality" and "Poor embryo quality," respectively.

In certain embodiments, a subject may be shown a histogram depicting a distribution of the number of differentially methylated loci that are usually detected in fertile donors and infertile patients (or good/poor embryo patients), and where the subject falls on the distribution. Generally, fertile-donors/good-embryo-quality patients may have few aberrations, while infertile patients or poor-embryo-quality patients may have more aberrations.

Genes exhibiting a relationship between aberrant methylation and fertility outcome and/or embryo quality can be determined. In various embodiments, for every human gene, the number of loci with significant association between aberrant methylation and fertility outcome (or embryo quality) either overlapping the gene body, or 5 kilobases upstream of one of the gene's transcription start sites can be counted (referred to herein as "Method 1"). If the number of loci exceeds a predetermined threshold, for example, 2 loci, then it can be considered that the gene is differentially methylated. This method does not require p-values to be computed for individual loci and can be easily computationally tractable.

In some embodiments, a sliding window of fixed length can be moved across at least a portion of the whole genome. Determination of aberrant methylation within the window can be conducted as discussed above (referred to herein as "Method 2").

In certain embodiments, Methods 1 and 2, as described above, can be conducted where p-values are available for individual loci. Stouffer's method or Fisher's method can be used for p-value combination to derive a region-wide p-value. In various embodiments, a hidden Markov model can be trained to segment the genome into regions of aberrant methylation and no aberrant methylation.

Genes can be ranked by prevalence of aberrant methylation. To determine which genes are likely to be most explanatory for fertility outcome or embryo-quality, genes can be ranked based on the number of infertile (or poor embryo-quality) samples present in a database where aberrant methylation is observed at these genes.

Two ranked lists of genes have also been compiled. Genes at the top of each list show statistically significant associations between aberrant methylation and infertility (or poor embryo-quality), and are observed aberrantly methylated in the largest number of patients. Table 2 is a ranked list of genes that are aberrantly methylated in infertile patients. The number to the left of the gene name is the number of patients. Table 3 is a ranked list of genes that are aberrantly methylated in poor embryo-quality patients. As in Table 2, the number to the left of the gene name in Table 3 is the number of patients. Only genes which exhibit an association with fertility and/or embryo quality are included in each of the lists.

TABLE 2

Infertility Genes, Ranked

| | | | | | |
|---|---|---|---|---|---|
| 64 SORCS2 | 26 ZNF137P | 21 B4GALNT2 | 19 ABHD8 | 19 STON1- | 18 MAGEA10- |
| 60 STARD13 | 25 C7orf50 | 21 BCYRN1 | 19 ANO1 | GTF2A1L | MAGEA5 |
| 52 STARD13-AS2 | 25 CSMD1 | 21 C1orf186 | 19 ASTN2 | 19 TBC1D16 | 18 MAGEC2 |
| 50 PTPRN2 | 25 EDNRB | 21 C3orf24 | 19 ATF6B | 19 TBCB | 18 MDC1 |
| 48 INPP5A | 25 FAM107B | 21 CARD14 | 19 ATRAID | 19 TMEM88 | 18 MEG3 |
| 46 HLA-DPB2 | 25 GABARAPL3 | 21 CEND1 | 19 C5orf63 | 19 TRIM39 | 18 MEST |
| 45 MDGA2 | 25 GABRA2 | 21 CSGALNACT1 | 19 C6orf89 | 19 TRIM39- | 18 MESTIT1 |
| 42 CNTNAP5 | 25 HDAC4 | 21 DFNA5 | 19 CALD1 | RPP21 | 18 MIR4456 |
| 42 ZBTB46 | 25 HEATR2 | 21 EPPIN | 19 CNTROB | 19 TRIM71 | 18 MORC1 |
| 40 CHST8 | 25 ITPKB | 21 EPPIN-WFDC6 | 19 COL9A2 | 19 USP49 | 18 MTRNR2L8 |
| 40 TBCD | 25 LINC00461 | 21 FMN2 | 19 CSAG1 | 19 VIPR2 | 18 MTSS1L |
| 38 LINC00535 | 25 NHSL1 | 21 GNG12-AS1 | 19 CSNK1A1P1 | 19 VWA1 | 18 MTX2 |
| 38 XXYLT1 | 25 PRKAG2 | 21 HAS1 | 19 CTCFL | 19 WDR90 | 18 NEURL1B |
| 35 ABT1 | 25 PSORS1C1 | 21 HLA-DPA1 | 19 CTU1 | 19 WLS | 18 NFYA |
| 35 LOC100507034 | 25 TESPA1 | 21 LAMA2 | 19 CYB5D1 | 19 ZNF843 | 18 NNAT |
| | 25 ZFP57 | 21 MFF | 19 DDAH2 | 18 ACTG1 | 18 NOSIP |
| 35 PFKP | 25 ZNF774 | 21 PCDHA5 | 19 DNAH14 | 18 ADAMTS10 | 18 NT5C1B |
| 35 SCARB1 | 24 C19orf47 | 21 PCDHA6 | 19 FAM227B | 18 ADCY10P1 | 18 NT5C1B-RDH14 |
| 33 FCGBP | 24 CALHM1 | 21 PSD3 | 19 FLJ12334 | 18 ALDH4A1 | |
| 33 RASGRF2 | 24 COX8C | 21 PWWP2B | 19 FTMT | 18 ALDH9A1 | 18 OCA2 |
| 32 ATXN10 | 24 ID3 | 21 RAB40C | 19 GLTSCR1 | 18 ANO9 | 18 OPCML |
| 32 MAGI2 | 24 LINGO3 | 21 USP53 | 19 GPR128 | 18 ARHGAP22 | 18 OR2AE1 |
| 32 RNF222 | 24 MYEOV | 21 WDR27 | 19 HCG18 | 18 ARHGAP27 | 18 PBX1 |
| 31 B3GNTL1 | 24 PCDHA1 | 21 ZNF167 | 19 HNRNPA1L2 | 18 ARHGEF18 | 18 PDE9A |
| 31 EPHA1-AS1 | 24 PCDHA2 | 20 ADAMTS2 | 19 HOXA3 | 18 BLCAP | 18 PDXDC1 |
| 31 NRXN2 | 24 PCDHA3 | 20 ARHGEF10 | 19 HYMAI | 18 BOLL | 18 PRKAR1B |
| 31 PKHD1L1 | 24 PCDHA4 | 20 B3GALT6 | 19 IL16 | 18 C10orf47 | 18 PRSS50 |
| 31 RHBDF2 | 24 PLD3 | 20 BRDT | 19 IRS2 | 18 C19orf35 | 18 QRSL1 |
| 31 SLC25A22 | 24 PPP2R2D | 20 CCDC169-SOHLH2 | 19 KBTBD13 | 18 C6orf201 | 18 RAD51B |
| 31 SNTG2 | 24 PRTN3 | | 19 KCNAB3 | 18 CDK2AP1 | 18 RBFOX1 |
| 31 SPRR2D | 24 SLC25A24 | 20 CCDC88B | 19 KIF26B | 18 EFNA2 | 18 RLTPR |
| 31 TSNAX-DISC1 | 24 TM4SF19-TCTEX1D2 | 20 CENPW | 19 KRT36 | 18 EIF2AK4 | 18 RNU6-81 |
| 31 TTC7B | | 20 COL5A1 | 19 LHCGR | 18 EXOC2 | 18 RTN4IP1 |
| 30 APOL6 | 24 TRIM10 | 20 CUX1 | 19 LOC100128714 | 18 FAM170B | 18 SAMD4A |
| 30 MOB2 | 24 TRIM15 | 20 DIP2C | | 18 FAM217A | 18 SCGB1C1 |
| 30 NFIC | 24 UNC79 | 20 DYNC1LI1 | 19 LOC100133612 | 18 FAM50B | 18 SH3BP5L |
| 30 PRDM15 | 23 ADAD2 | 20 GRASP | | 18 FARP1 | 18 SPDYC |
| 29 INTS1 | 23 ATP10A | 20 HCG17 | 19 LOC100287834 | 18 FIZ1 | 18 SPERT |
| 29 LRP5 | 23 BEX1 | 20 KDM6B | | 18 FKBPL | 18 SPRED3 |
| 29 PXDNL | 23 C15orf59 | 20 MAGEB1 | 19 LOC100292680 | 18 FOXP1 | 18 SRGAP3 |
| 29 SLC6A19 | 23 ESRRG | 20 MIMT1 | 19 LOC653160 | 18 FTHL17 | 18 STK10 |
| 29 SPECC1 | 23 ITIH1 | 20 NSUN7 | 19 LOC729121 | 18 GATA6 | 18 STK32C |
| 29 TLR6 | 23 KCND2 | 20 PACRG | 19 MAGEA12 | 18 GGN | 18 TAF7 |
| 28 AGAP1 | 23 OSBPL5 | 20 PACRG-AS1 | 19 MAGEB2 | 18 GIMAP1 | 18 TAPBP |
| 28 BMP3 | 23 PABPC1P2 | 20 PCDHA7 | 19 MRPL34 | 18 GPRC5A | 18 TBC1D1 |
| 28 CAMTA1 | 23 PLXND1 | 20 PCDHA8 | 19 MSH5-SAPCD1 | 18 GPX6 | 18 TCEAL3 |
| 28 FEZ2 | 23 POMT2 | 20 PDZD2 | | 18 GZF1 | 18 TMEM160 |
| 28 MIR548O2 | 23 SLC9A3 | 20 PEG3 | 19 NME8 | 18 HDGFL1 | 18 TRIO |
| 28 PRDM16 | 23 TAF1C | 20 PFKFB3 | 19 NUBP2 | 18 HIST1H1T | 18 TTC22 |
| 28 PUM2 | 22 DNAJB6 | 20 PLEKHF1 | 19 OPRD1 | 18 HLA-DQB2 | 18 TUBA3C |
| 28 RPS6KA2 | 22 F10 | 20 PTPRD | 19 PCDHA10 | 18 INPP5F | 18 TUBB |
| 28 TMEM72-AS1 | 22 GALNTL5 | 20 RBFOX3 | 19 PCDHA9 | 18 JAKMIP3 | 18 VPS51 |
| 28 ZC3H12D | 22 GIMAP1-GIMAP5 | 20 RECQL5 | 19 PLAGL1 | 18 JARID2 | 18 WDR25 |
| 27 AP5Z1 | | 20 SDF4 | 19 PTRF | 18 KRAS | 18 WDR60 |
| 27 BLOC1S5-TXNDC5 | 22 MIR662 | 20 SENP3 | 19 PXDN | 18 LGALS9C | 18 WFDC1 |
| | 22 MSLN | 20 SENP3-EIF4A1 | 19 RAB32 | 18 LINC00482 | 18 WIPF1 |
| 27 HLA-A | 22 NLRP14 | 20 SLC25A51P1 | 19 RELB | 18 LOC100506733 | 18 WRAP73 |
| 27 ZC3H11A | 22 QRICH2 | 20 SLC9C1 | 19 RERE | 18 LOC219731 | 18 ZBTB22 |
| 26 ANO7 | 22 RAMP3 | 20 SOHLH2 | 19 RGPD4 | 18 LOC440700 | 18 ZNF100 |
| 26 BST2 | 22 RNU5D-1 | 20 TNKS2 | 19 SHANK2 | 18 LOC641367 | 18 ZNF354A |
| 26 CSF1R | 22 RNU5E-1 | 20 TNNT3 | 19 SIGIRR | 18 LOC653486 | 18 ZNF74 |
| 26 GPR123 | 22 SMAP1 | 20 TXNDC15 | 19 SLC5A6 | 18 LRFN1 | 18 ZNF747 |
| 26 NDRG1 | 22 UTS2D | 20 ZIM2 | 19 SMAD6 | 18 MACROD2 | 18 ZNF775 |
| 26 S100A9 | 21 AHRR | 20 ZNF579 | 19 SPSB3 | 18 MAGEA10 | 17 ACAP3 |
| 26 TRABD | 21 ASIC4 | 20 ZNF660 | 16 APBA1 | 16 GAGE2E | 17 ACOT4 |
| 17 ADAD1 | 17 LOC401010 | 17 SCARA5 | 16 AR | 16 GAGE8 | 16 MYT1L |
| 17 ADARB2 | 17 LOC401242 | 17 SDK1 | 16 ARHGEF17 | 16 GLB1L2 | 16 NAALADL2 |
| 17 ADGB | 17 LOC442028 | 17 SELT | 16 BCL2L2- | 16 GLI2 | 16 NAP1L5 |
| 17 AGAP3 | 17 LOC493754 | 17 SEMA3B | | | 16 NEDD4L |

TABLE 2-continued

Infertility Genes, Ranked

| | | | | | |
|---|---|---|---|---|---|
| 17 AGFG1 | 17 LOC729176 | 17 SGK223 | PABPN1 | 16 GML | 16 NFIX |
| 17 AGRN | 17 LY9 | 17 SLC27A1 | 16 BCOR | 16 GNAS | 16 NOS1AP |
| 17 ANKRD11 | 17 MAP7D1 | 17 SLMO1 | 16 BTBD19 | 16 GPR75 | 16 NOS3 |
| 17 ANKRD30A | 17 MAPK8IP3 | 17 SMG6 | 16 C16orf7 | 16 GPR75-ASB3 | 16 NPHP3 |
| 17 ANO3 | 17 MGAT4C | 17 SOAT2 | 16 C16orf90 | 16 GREM2 | 16 NPHP3- |
| 17 ATP11A | 17 MIR335 | 17 SOHLH1 | 16 C19orf25 | 16 GRWD1 | ACAD11 |
| 17 BAIAP2L2 | 17 MIR4485 | 17 SPN | 16 C1orf87 | 16 GTPBP3 | 16 NPHP3-AS1 |
| 17 BEND2 | 17 MXI1 | 17 ST20 | 16 C3orf45 | 16 HCG4B | 16 NRSN1 |
| 17 BRCA1 | 17 MYOM2 | 17 ST20-MTHFS | 16 C3orf77 | 16 HERC3 | 16 NTNG2 |
| 17 C11orf95 | 17 NGFRAP1 | 17 STAU2 | 16 C4orf22 | 16 HGC6.3 | 16 NYAP2 |
| 17 C1orf228 | 17 NOBOX | 17 STK31 | 16 C5orf47 | 16 HHLA2 | 16 OXR1 |
| 17 C1orf61 | 17 NPFFR2 | 17 SVIL | 16 C6orf147 | 16 HIVEP2 | 16 P2RX4 |
| 17 C2 | 17 NR5A2 | 17 SYTL1 | 16 C7orf72 | 16 HMHA1 | 16 P2RY1 |
| 17 CAMK1D | 17 OBSCN | 17 TENM4 | 16 CCDC130 | 16 HOOK2 | 16 PABPC3 |
| 17 CARD11 | 17 PCDHB16 | 17 TEX12 | 16 CCDC71L | 16 IGDCC3 | 16 PABPN1 |
| 17 CCDC129 | 17 PCDHB7 | 17 TFAP2E | 16 CCDC80 | 16 ITSN2 | 16 PAG1 |
| 17 CCDC79 | 17 PCDHB8 | 17 TM7SF2 | 16 CDC14C | 16 JAKMIP1 | 16 PAGE3 |
| 17 CCER1 | 17 PCDHB9 | 17 TMEM151A | 16 CECR1 | 16 KCNB2 | 16 PCDHB17 |
| 17 CCNB3 | 17 PCDHGA1 | 17 TMUB1 | 16 CELSR3 | 16 KCNG2 | 16 PCSK4 |
| 17 CDKN3 | 17 PCDHGA10 | 17 TNFRSF18 | 16 CHORDC1 | 16 KCNQ1 | 16 PDE11A |
| 17 CERS1 | 17 PCDHGA11 | 17 TNRC18 | 16 CLASP2 | 16 KCNQ1OT1 | 16 PDHA2 |
| 17 CHD7 | 17 PCDHGA12 | 17 TNXB | 16 CLEC4C | 16 KIF13B | 16 PGK2 |
| 17 CHST6 | 17 PCDHGA2 | 17 TRIM50 | 16 CLK2P | 16 KLHDC7B | 16 PHLPP1 |
| 17 CRYL1 | 17 PCDHGA3 | 17 TTYH3 | 16 CLUAP1 | 16 KRBA1 | 16 PKIA |
| 17 DCAF4 | 17 PCDHGA4 | 17 TUBA3E | 16 CNNM1 | 16 LDHD | 16 PLA2G4E |
| 17 DDX3Y | 17 PCDHGA5 | 17 U2AF1L4 | 16 CNP | 16 LFNG | 16 PLVAP |
| 17 DISC1 | 17 PCDHGA6 | 17 UBE3B | 16 CNTNAP1 | 16 LIG1 | 16 POM121L12 |
| 17 DMKN | 17 PCDHGA7 | 17 UGT1A10 | 16 COL11A2 | 16 LINC00221 | 16 POM121L9P |
| 17 DNAH12 | 17 PCDHGA8 | 17 UGT1A3 | 16 COL22A1 | 16 LINC00473 | 16 PON2 |
| 17 EEPD1 | 17 PCDHGA9 | 17 UGT1A4 | 16 COL9A1 | 16 LINC00668 | 16 PPP1R18 |
| 17 EHMT2 | 17 PCDHGB1 | 17 UGT1A5 | 16 CPE | 16 LMTK3 | 16 PROKR1 |
| 17 ELMSAN1 | 17 PCDHGB2 | 17 UGT1A6 | 16 CT45A1 | 16 | 16 PRSS35 |
| 17 FAM58BP | 17 PCDHGB3 | 17 UGT1A7 | 16 CTAG2 | LOC100128881 | 16 PRSS55 |
| 17 FAM9A | 17 PCDHGB4 | 17 UGT1A8 | 16 CTNNA3 | 16 | 16 PSORS1C2 |
| 17 FASTK | 17 PCDHGB5 | 17 UGT1A9 | 16 CUX2 | LOC100129794 | 16 RAB13 |
| 17 FKBP6 | 17 PCDHGB6 | 17 VPS37B | 16 CXorf36 | 16 | 16 RASGEF1C |
| 17 FRMD1 | 17 PCDHGB7 | 17 WDR88 | 16 DLG2 | LOC100130581 | 16 RBM15B |
| 17 GALNT14 | 17 PLEC | 17 ZBTB7A | 16 DMRTB1 | 16 | 16 RBPJ |
| 17 GDF1 | 17 PLEKHG5 | 17 ZFPM1 | 16 DNAJA4 | LOC100132831 | 16 REPIN1 |
| 17 GINS4 | 17 PNLDC1 | 17 ZNF282 | 16 DNAJB3 | 16 LOC255025 | 16 RFX1 |
| 17 GPR133 | 17 PNMA1 | 17 ZNF469 | 16 DOK2 | 16 LOC340094 | 16 RNF220 |
| 17 GPR158 | 17 PPM1H | 17 ZNF668 | 16 DPEP3 | 16 LOC389641 | 16 RNU6-71 |
| 17 GPR39 | 17 PPP1R13L | 17 ZNF696 | 16 DPP6 | 16 LOC407835 | 16 RP1 |
| 17 GRIN2D | 17 PPP1R2P9 | 17 ZNF764 | 16 DVL3 | 16 LOC619207 | 16 RPH3AL |
| 17 H1FNT | 17 PPT2 | 17 ZNF784 | 16 ELF5 | 16 LOC643441 | 16 RPL13 |
| 17 HLA-DQB1 | 17 PPT2-EGFL8 | 17 ZNF865 | 16 ERLIN2 | 16 LOC731789 | 16 RPS27 |
| 17 HSPA7 | 17 PRDM9 | 17 ZSWIM4 | 16 ERO1L | 16 LPCAT1 | 16 RPS6KA4 |
| 17 IFITM2 | 17 PRNP | 17 ZYX | 16 FAM100A | 16 LRFN3 | 16 RTN1 |
| 17 IGFLR1 | 17 PRPS1L1 | 16 AATK | 16 FAM197Y2 | 16 LRRC38 | 16 RYR2 |
| 17 IL18 | 17 PRRT1 | 16 ACE2 | 16 FAM197Y5 | 16 LRRIQ3 | 16 SALL3 |
| 17 KCNJ14 | 17 PSENEN | 16 ACRC | 16 FAM47A | 16 LRRTM3 | 16 SBK2 |
| 17 KCNQ2 | 17 RABIF | 16 ADARB1 | 16 FAM83A | 16 MAD1L1 | 16 SDCCAG8 |
| 17 KCNT1 | 17 RAI1 | 16 AGAP2 | 16 FAM9B | 16 MAGEB6 | 16 SEL1L2 |
| 17 KHDC1 | 17 RARG | 16 AGBL4 | 16 FBXL18 | 16 MBD3 | 16 SELK |
| 17 KIAA0513 | 17 RASA3 | 16 AHDC1 | 16 FHAD1 | 16 MCCC1 | 16 SEPT9 |
| 17 KIAA2013 | 17 RBM11 | 16 AKAP12 | 16 FIGLA | 16 MEX3A | 16 SH2B2 |
| 17 KIFC1 | 17 RFESD | 16 AKT3 | 16 FLJ42875 | 16 MIR1237 | 16 SH2B3 |
| 17 KRTAP5-4 | 17 RGS14 | 16 ANK1 | 16 FPGT | 16 MIR4648 | 16 SIM1 |
| 17 LINC00359 | 17 RGS7 | 16 ANKFY1 | 16 FPGT-TNNI3K | 16 MIR548F5 | 16 SIVA1 |
| 17 LOC100506122 | 17 RIN3 | 16 ANKRD20A9P | 16 FRAS1 | 16 MOB3C | 16 SKI |
| 17 LOC100506229 | 17 RLBP1 | 16 ANKRD24 | 16 GAB1 | 16 MT1IP | 16 SLC12A6 |
| 17 LOC116437 | 17 RNF113B | 16 ANKRD33B | 16 GAGE2A | 16 MTMR1 | 16 SLC25A16 |
| 16 SLC25A3P1 | 17 RPS7 | 16 ANO8 | 16 GAGE2C | 16 MUC4 | 16 SLC25A21 |
| 16 SLC2A5 | 17 SBNO2 | 16 AP2M1 | 16 GAGE2D | 16 MYO7B | 16 SLC25A31 |
| 16 SLC30A8 | 15 ABHD16B | 15 DIS3L2 | 15 | 15 PDE1A | 15 TFAP4 |
| 16 SLC44A2 | 15 ABR | 15 DLGAP2 | LOC100507584 | 15 PDXK | 15 TGFB1 |
| 16 SLC8A3 | 15 ADNP2 | 15 DMRTC2 | 15 | 15 PKD1 | 15 THBS4 |
| 16 SMYD3 | 15 ADORA1 | 15 DOCK4 | LOC100873065 | 15 PLEKHB1 | 15 TKTL1 |
| 16 SNAR-I | 15 AIPL1 | 15 DPPA2 | 15 LOC153684 | 15 PODXL2 | 15 TMEM132A |
| 16 SNX20 | 15 ALDH3B1 | 15 DUSP8 | 15 LOC255512 | 15 POLG | 15 TMEM161A |
| 16 SORBS2 | 15 AMDHD2 | 15 DZIP1 | 15 LOC285577 | 15 POLR3A | 15 TMEM237 |
| 16 SPTB | 15 AMPD3 | 15 EEF1E1- | 15 LOC646762 | 15 POU5F2 | 15 TMPRSS9 |
| 16 SRD5A2 | 15 ANKRD2 | MUTED | 15 LOC728743 | 15 PP2D1 | 15 TOLLIP |
| 16 SSR4P1 | 15 ANKRD9 | 15 EGFR | 15 LOC729080 | 15 PRELP | 15 TOMM20L |
| 16 SSX7 | 15 AP1M2 | 15 EHD2 | 15 LPIN1 | 15 PRR5 | 15 TPD52L2 |
| 16 ST14 | 15 APC | 15 EHD4 | 15 LRBA | 15 PRSS22 | 15 TRIM29 |
| | 15 APCDD1L | 15 ENOPH1 | 15 LRG1 | 15 R3HDM4 | 15 TRIM7 |
| | 15 APOE | 15 EVL | 15 LRP1B | 15 RAB40B | 15 TRPM4 |

TABLE 2-continued

Infertility Genes, Ranked

| | | | | | |
|---|---|---|---|---|---|
| 16 STK11 | 15 ARAP1 | 15 FAM13C | 15 LRRC72 | 15 RALBP1 | 15 TSPY2 |
| 16 STK3 | 15 ARHGEF2 | 15 FAM172A | 15 LTC4S | 15 RASAL3 | 15 TTC21B |
| 16 SYCE1 | 15 ARHGEF4 | 15 FAM184B | 15 LUZP4 | 15 RASIP1 | 15 TTC40 |
| 16 SYDE1 | 15 ART3 | 15 FAM221A | 15 LY6G6C | 15 RBM24 | 15 TUG1 |
| 16 SYTL3 | 15 ASB4 | 15 FHOD1 | 15 LYPD4 | 15 RBM44 | 15 UCKL1 |
| 16 TBC1D17 | 15 ATP6V0C | 15 FLRT2 | 15 MAB21L2 | 15 RBM45 | 15 UFSP2 |
| 16 TCTEX1D2 | 15 ATP8A2 | 15 FMN1 | 15 MAEL | 15 RBMS1 | 15 ULK3 |
| 16 TCTEX1D4 | 15 B4GALT7 | 15 FMNL1 | 15 MAG | 15 REXO1L2P | 15 UNC13A |
| 16 TCTN1 | 15 BASP1 | 15 FTLP10 | 15 MAGEB16 | 15 RFPL3-AS1 | 15 UNC80 |
| 16 TDRD12 | 15 BCL2L12 | 15 FZD5 | 15 MAGIX | 15 RGL3 | 15 USP42 |
| 16 TEX14 | 15 BLOC1S5 | 15 GAB2 | 15 MANBAL | 15 RGS12 | 15 USP6NL |
| 16 TMEM140 | 15 BOD1L2 | 15 GAB4 | 15 MAST4 | 15 RNF19B | 15 WHSC2 |
| 16 TMEM175 | 15 BRSK1 | 15 GABRB1 | 15 MCMDC2 | 15 RNF39 | 15 XAGE3 |
| 16 TMEM247 | 15 C10orf71 | 15 GAGE12F | 15 ME3 | 15 RNU5F-1 | 15 YDJC |
| 16 TNFAIP8 | 15 C14orf79 | 15 GAGE12I | 15 MGC2752 | 15 ROBO1 | 15 ZBTB47 |
| 16 TNFRSF10A | 15 C2orf27A | 15 GAGE4 | 15 MGC72080 | 15 RPS24 | 15 ZFHX4 |
| 16 TNFRSF25 | 15 C3orf30 | 15 GAGE5 | 15 MIR3065 | 15 RYR1 | 15 ZFYVE28 |
| 16 TNFSF12-TNFSF13 | 15 C4orf47 | 15 GAGE7 | 15 MIR4695 | 15 S100A13 | 15 ZNF19 |
| 16 TNFSF13 | 15 C6orf25 | 15 GFM1 | 15 MIR4785 | 15 S1PR4 | 15 ZNF26 |
| 16 TRAPPC12 | 15 C9orf170 | 15 GGTLC1 | 15 MIR548AP | 15 SALL4 | 15 ZNF423 |
| 16 TRPV2 | 15 CACNA2D1 | 15 GNAS-AS1 | 15 MIR5703 | 15 SBF1P1 | 15 ZNF628 |
| 16 TSNAX | 15 CACNA2D4 | 15 GNG7 | 15 MMP13 | 15 SCAMP2 | 15 ZNF701 |
| 16 TSPY1 | 15 CADM4 | 15 GPR146 | 15 MOB3A | 15 SEMA6A | 15 ZNF735 |
| 16 TSPY4 | 15 CALML3 | 15 GPR25 | 15 MORC2 | 15 SETBP1 | 15 ZNF768 |
| 16 TTTY23 | 15 CALML5 | 15 GRAMD2 | 15 MPHOSPH6 | 15 SLAIN2 | 15 ZNF787 |
| 16 TTTY23B | 15 CAPS2 | 15 GSDMD | 15 MRI1 | 15 SLC22A3 | 15 ZNF837 |
| 16 TUBA3D | 15 CBFA2T3 | 15 GSE1 | 15 MYEOV2 | 15 SLC25A29 | 14 ACER3 |
| 16 TYK2 | 15 CBX4 | 15 HAPLN4 | 15 MYO1F | 15 SLC34A2 | 14 ACOT11 |
| 16 UBAP1L | 15 CCDC116 | 15 HEBP1 | 15 N4BP1 | 15 SLC35D1 | 14 ACSF3 |
| 16 UCHL3 | 15 CCDC141 | 15 HHIPL1 | 15 N6AMT2 | 15 SLC38A5 | 14 ACSL5 |
| 16 UNC5B | 15 CCDC88C | 15 HLA-L | 15 NAF1 | 15 SLC6A16 | 14 ACTR8 |
| 16 UNC5D | 15 CCDC96 | 15 HLTF | 15 NAT14 | 15 SLC7A7 | 14 ACYP2 |
| 16 USB1 | 15 CCRL2 | 15 HLTF-AS1 | 15 NBR2 | 15 SLCO3A1 | 14 ADAM18 |
| 16 VENTXP7 | 15 CDKL1 | 15 HNRPDL | 15 NELF | 15 SNORD116-11 | 14 ADAP1 |
| 16 WFIKKN1 | 15 CENPJ | 15 HTR7P1 | 15 NFATC2 | 15 SNORD116-12 | 14 ADCY9 |
| 16 WNT5A | 15 CGNL1 | 15 IFITM5 | 15 NIPA2 | 15 SNORD116-13 | 14 ADORA3 |
| 16 XIST | 15 CHD6 | 15 IGSF11 | 15 NMUR2 | 15 SNTG1 | 14 AEBP1 |
| 16 XKR4 | 15 CHDH | 15 IGSF21 | 15 NOTCH3 | 15 SPATA13 | 14 AGMO |
| 16 YBX1 | 15 CHST11 | 15 IL22 | 15 NOTCH4 | 15 SPO11 | 14 AHNAK |
| 16 ZBTB7C | 15 CHST12 | 15 IRAK2 | 15 NOVA2 | 15 SREBF1 | 14 AKAP10 |
| 16 ZC3H8 | 15 CHST2 | 15 IRF3 | 15 NSUN4 | 15 SV2B | 14 ALG1 |
| 16 ZFP64 | 15 CILP2 | 15 ITGAX | 15 NTM | 15 SYCP3 | 14 ALOX12 |
| 16 ZGLP1 | 15 CPEB1 | 15 KATNAL2 | 15 NUBPL | 15 TADA2B | 14 ALPK1 |
| 16 ZNF219 | 15 CR1L | 15 KCNH5 | 15 NUDT9P1 | 15 TAF4 | 14 ALPK3 |
| 16 ZNF319 | 15 CXorf21 | 15 KCNH8 | 15 NXN | 15 TAS2R60 | 14 AMT |
| 16 ZNF354B | 15 CXorf61 | 15 KCNIP1 | 15 OASL | 15 TBX6 | 14 ANKRD13B |
| 16 ZNF365 | 15 CYB561 | 15 KIAA1875 | 15 OOEP | 15 TCEAL6 | 14 ANKRD20A11P |
| 16 ZNF384 | 15 CYP4F2 | 15 KPRP | 15 OSBP2 | 15 TCEB3B | 14 ANO2 |
| 16 ZNF444 | 15 CYP4X1 | 15 KRT18P55 | 15 OSMR | 15 TCEB3C | 14 APBA2 |
| 16 ZNF611 | 15 CYTH1 | 15 KRT28 | 15 PAOX | 15 TCP11 | 14 APOBR |
| 16 ZNF678 | 15 DAB1 | 15 LCK | 15 PARK2 | 15 TDRD6 | 14 APTX |
| 16 ZNF777 | 15 DAZL | 15 LINC00340 | 15 PC | 15 TENM2 | 14 ARHGEF19 |
| 16 ZSCAN10 | 15 DIRAS3 | 15 LOC100129931 | 15 PCDHB14 | 15 TES | 14 ARL4C |
| 14 ASPHD1 | 14 DLC1 | 14 HNRNPUL2-BSCL2 | 15 PCDHB6 | 15 TEX28 | 14 TPTE2P5 |
| 14 ATF6 | 14 DLEU7 | 14 MGC34034 | 14 MGARP | 14 RAP1A | 14 TRERF1 |
| 14 ATF7IP | 14 DLEU7-AS1 | 14 HOXA4 | 14 MGC3771 | 14 RAP1GAP2 | 14 TREX1 |
| 14 ATOH7 | 14 DLK1 | 14 HRAS | 14 MIR1225 | 14 RAP2A | 14 TRIM2 |
| 14 AUTS2 | 14 DNAJC17 | 14 HS6ST1 | 14 MIR148A | 14 RASSF8 | 14 TRIM41 |
| 14 B3GNT6 | 14 DNM1L | 14 IGF2BP1 | 14 MIR1973 | 14 RBM46 | 14 TRPV4 |
| 14 BCL11A | 14 DOK6 | 14 IGSF9 | 14 MIR548W | 14 RBM47 | 14 TSPAN17 |
| 14 BCLAF1 | 14 DPP9 | 14 IGSF9B | 14 MIR618 | 14 RBMXL2 | 14 TSPAN31 |
| 14 BMP8A | 14 DPPA5 | 14 IL17RA | 14 MMP28 | 14 REM2 | 14 TSPAN32 |
| 14 BRAF | 14 DSCR4 | 14 IL21R | 14 MMP9 | 14 RHBDF1 | 14 TSPYL5 |
| 14 BRCA2 | 14 DSCR8 | 14 INSL6 | 14 MON1B | 14 RIPK4 | 14 TSPYL6 |
| 14 BRI3 | 14 DTX1 | 14 INSR | 14 MRC2 | 14 RNF103-CHMP3 | 14 TXNDC12 |
| 14 BSCL2 | 14 DUSP21 | 14 IQCG | 14 MRPL55 | 14 RPL13AP3 | 14 UGT1A1 |
| 14 BTBD2 | 14 EBF1 | 14 ITGB2 | 14 MSH4 | 14 RPL6 | 14 UHRF1BP1L |
| 14 C10orf32-AS3MT | 14 ECE1 | 14 ITGB5 | 14 MSI2 | 14 RREB1 | 14 VIPR1 |
| 14 C10orf76 | 14 EEF1DP3 | 14 ITPRIPL2 | 14 MSRA | 14 RRP1B | 14 VPREB1 |
| 14 C11orf21 | 14 EFCAB9 | 14 KCND3 | 14 MTMR14 | 14 RWDD3 | 14 VSIG2 |
| 14 C12orf5 | 14 EHMT1 | 14 KCNK3 | 14 MYADML | 14 RXRA | 14 VWA7 |
| 14 C13orf45 | 14 ELAVL4 | 14 KCNV2 | 14 MYO16 | 14 SCRN2 | 14 WDR69 |
| 14 C15orf38 | 14 EMD | 14 KDM2B | 14 NBEAL2 | 14 SDPR | 14 WTAPP1 |
| 14 C15orf38-AP3S2 | 14 ERCC2 | 14 KDM4B | 14 NCOR2 | 14 SELM | 14 YPEL4 |
| 14 C15orf62 | 14 ESCO2 | 14 KIF2B | 14 NDUFA11 | 14 SEMA6B | 14 ZAR1L |
| | 14 ESPNP | 14 KLK15 | 14 NEIL1 | 14 SERF2-C15ORF63 | 14 ZC3H12C |
| | 14 EVPL | 14 KRTAP17-1 | 14 NFATC1 | | 14 ZFP42 |

TABLE 2-continued

Infertility Genes, Ranked

| | | | | | |
|---|---|---|---|---|---|
| 14 C15orf63 | 14 FAM122C | 14 KRTAP19-5 | 14 NFATC4 | 14 SERINC4 | 14 ZFP92 |
| 14 C17orf98 | 14 FAM155A | 14 KTI12 | 14 NHP2 | 14 SERPINE1 | 14 ZFPM2 |
| 14 C1QTNF7 | 14 FAM3A | 14 L3MBTL1 | 14 NHSL2 | 14 SEZ6L2 | 14 ZFY |
| 14 C2orf74 | 14 FAM46D | 14 LAMA4 | 14 NICN1 | 14 SH3TC1 | 14 ZNF18 |
| 14 CAPN3 | 14 FAM47C | 14 LCOR | 14 NID1 | 14 SHMT1 | 14 ZNF205 |
| 14 CARHSP1 | 14 FAM53A | 14 LIN7A | 14 NOD2 | 14 SLC17A9 | 14 ZNF217 |
| 14 CASP2 | 14 FAM57B | 14 LINC00226 | 14 NRXN1 | 14 SLC22A18 | 14 ZNF311 |
| 14 CATSPER2 | 14 FAM83B | 14 LINC00351 | 14 NYX | 14 SLC22A31 | 14 ZNF467 |
| 14 CCDC117 | 14 FAM83H | 14 LINC00588 | 14 ORAI3 | 14 SLC25A2 | 14 ZNF524 |
| 14 CCDC162P | 14 FANCF | 14 LINC00674 | 14 OSCAR | 14 SLC6A8 | 14 ZNF589 |
| 14 CCDC17 | 14 FBXL19 | 14 LOC100131094 | 14 PAPOLB | 14 SMOC2 | 14 ZNF648 |
| 14 CCDC25 | 14 FCHO2 | | 14 PARP4 | 14 SNX8 | 14 ZNF665 |
| 14 CD7 | 14 FHIT | 14 LOC100286922 | 14 PAX8 | 14 SOCS5 | 14 ZNF688 |
| 14 CDH11 | 14 FHOD3 | | 14 PBX2 | 14 SPACA1 | 14 ZNF689 |
| 14 CDH23 | 14 FLJ46906 | 14 LOC100287704 | 14 PCDHB4 | 14 SPG21 | 14 ZNF718 |
| 14 CDX1 | 14 FLNA | | 14 PEBP4 | 14 SPI1 | 14 ZNF77 |
| 14 CETN1 | 14 FOXK1 | 14 LOC100506451 | 14 PER3 | 14 SPON1 | 14 ZNRD1-AS1 |
| 14 CHCHD6 | 14 GABRQ | | 14 PHYHIP | 14 SPSB4 | 14 ZPBP |
| 14 CHURC1-FNTB | 14 GAK | 14 LOC100506713 | 14 PIGH | 14 SPTBN5 | 14 ZSCAN5A |
| 14 CKLF-CMTM1 | 14 GAL3ST1 | 14 LOC283692 | 14 PITPNM1 | 14 SRRM2 | 13 AAED1 |
| 14 CLDN10 | 14 GALE | 14 LOC284100 | 14 PIWIL2 | 14 SRRM2-AS1 | 13 ACBD3 |
| 14 CLDN18 | 14 GAS7 | 14 LOC285441 | 14 PLCB2 | 14 SRRM4 | 13 ACTL9 |
| 14 CLN3 | 14 GGT7 | 14 LOC285501 | 14 PLCH1 | 14 SSX2IP | 13 ADAM19 |
| 14 CMIP | 14 GLUL | 14 LOC286094 | 14 PLEKHA5 | 14 STX11 | 13 ADAM8 |
| 14 CMTM1 | 14 GNG13 | 14 LOC339803 | 14 POU2AF1 | 14 STYX | 13 ADAMTS17 |
| 14 CORO1B | 14 GNG3 | 14 LOC339894 | 14 PPAP2C | 14 SUGT1P3 | 13 ADRBK1 |
| 14 CPN1 | 14 GPR143 | 14 LOC643406 | 14 PPCDC | 14 SYCE1L | 13 ADSSL1 |
| 14 CRH | 14 GPR160 | 14 LOC644649 | 14 PRICKLE2 | 14 SYN1 | 13 AFAP1 |
| 14 CSMD2 | 14 GPR20 | 14 LOC654433 | 14 PRKCH | 14 SYNE2 | 13 AGER |
| 14 CST9 | 14 GPR4 | 14 LOXHD1 | 14 PRR12 | 14 TAF5 | 13 AGPAT4 |
| 14 CTAGE1 | 14 GPRC5C | 14 LRFN2 | 14 PRR23A | 14 TAGLN2 | 13 AGTR1 |
| 14 CTNNB1 | 14 GPRIN1 | 14 LRRC56 | 14 PRR5-ARHGAP8 | 14 TCEAL4 | 13 AJAP1 |
| 14 CTPS1 | 14 GPSM2 | 14 LRRC7 | 14 PRSS41 | 14 TDGF1 | 13 ALOX5AP |
| 14 CUL4B | 14 GRIN3B | 14 LRRC73 | 14 PTDSS2 | 14 TECTA | 13 ANKAR |
| 14 CXCL9 | 14 GRK7 | 14 LST1 | 14 PTGDR2 | 14 TEF | 13 ANTXR2 |
| 14 DAPK1 | 14 GTDC1 | 14 LTB | 14 PTK6 | 14 TEX264 | 13 AP3B2 |
| 14 DCLK2 | 14 GUCY2D | 14 LTBP4 | 14 PTPRE | 14 TKTL2 | 13 APBB2 |
| 14 DDX1 | 14 HCN1 | 14 MAFK | 14 PVRL4 | 14 TMEM132B | 13 APC2 |
| 14 DGKD | 14 HEXB | 14 MAGEL2 | 14 PVT1 | 14 TMEM132C | 13 ARID3A |
| 14 DKFZp566F0947 | 14 HIPK2 | 14 MATN4 | 14 RAB27A | 14 TMEM139 | 13 ARL2 |
| 14 DKFZp686O1327 | 14 HIST1H3A | 14 MBD1 | 14 RAB37 | 14 TMEM151B | 13 ARL2-SNX15 |
| | 14 HLA-J | 14 MCM5 | 14 RAC1 | 14 TMEM56-RWDD3 | 13 ARPC2 |
| | 14 HLCS | 14 MEX3D | 14 RADIL | 14 TOP2B | 13 ASAP3 |
| | 14 HMG20B | 13 FFAR1 | 13 KBTBD5 | 13 MC1R | 13 ASB16 |
| 13 ASCL2 | 13 CLCA4 | 13 FKRP | 13 KCNA1 | 13 MCF2L | 13 PEG10 |
| 13 ASIC1 | 13 CLCN6 | 13 FLJ39653 | 13 KCNH2 | 13 MCF2L2 | 13 PELI1 |
| 13 ASPDH | 13 CLEC16A | 13 FNTB | 13 KCNK4 | 13 MESDC1 | 13 PES1 |
| 13 ASPG | 13 CLIP2 | 13 FOXN4 | 13 KCNMB2 | 13 MEX3B | 13 PFN3 |
| 13 ASPH | 13 CNDP2 | 13 FOXO3B | 13 KEAP1 | 13 MFSD6L | 13 PIK3CG |
| 13 ATG5 | 13 CNR2 | 13 FOXR1 | 13 KIAA0528 | 13 MGC16121 | 13 PIK3R6 |
| 13 ATP1A1 | 13 COL6A4P2 | 13 FRMD4A | 13 KIAA1522 | 13 MIB2 | 13 PKD2L2 |
| 13 ATP6V1C1 | 13 COL9A3 | 13 FRMD8 | 13 KIF16B | 13 MINK1 | 13 PKDREJ |
| 13 AURKC | 13 COX4I2 | 13 FRMPD4 | 13 KIF23 | 13 MIR1204 | 13 PLA2G16 |
| 13 BAI2 | 13 COX7B2 | 13 FZD1 | 13 KIF3B | 13 MIR1224 | 13 PLCL2 |
| 13 BCAR1 | 13 CPLX1 | 13 GABBR1 | 13 KIF3C | 13 MIR1256 | 13 PLIN5 |
| 13 BCKDK | 13 CPLX2 | 13 GAGE10 | 13 KIF5B | 13 MIR196A1 | 13 POLR3G |
| 13 BCMO1 | 13 CPPED1 | 13 GALNT5 | 13 KLF15 | 13 MIR223 | 13 POMC |
| 13 BGN | 13 CRTAC1 | 13 GALNT9 | 13 KLF8 | 13 MIR23A | 13 PON3 |
| 13 BHMT2 | 13 CSDE1 | 13 GCFC2 | 13 KLHDC5 | 13 MIR24-2 | 13 POTEA |
| 13 BLOC1S1-RDH5 | 13 CTAGE7P | 13 GCSAML-AS1 | 13 KLHDC7A | 13 MIR27A | 13 POTEF |
| 13 BMP2 | 13 CTBP2 | 13 GDF9 | 13 KLHL36 | 13 MIR371B | 13 PPARD |
| 13 BNIPL | 13 CUEDC1 | 13 GHDC | 13 KRT83 | 13 MIR372 | 13 PPP1R13B |
| 13 BOLA3 | 13 CXXC1 | 13 GK2 | 13 L3MBTL4 | 13 MIR373 | 13 PPP1R2P3 |
| 13 BOLA3-AS1 | 13 CYB5R3 | 13 GNPDA1 | 13 LANCL2 | 13 MIR4750 | 13 PROX1 |
| 13 BRE | 13 CYP26C1 | 13 GPC2 | 13 LGALS9 | 13 MIR542 | 13 PRR25 |
| 13 BRE-AS1 | 13 CYR61 | 13 GPR45 | 13 LGR6 | 13 MMP23A | 13 PRSS42 |
| 13 BTBD11 | 13 DCAF4L1 | 13 GPR68 | 13 LIMCH1 | 13 MMP23B | 13 PSMA8 |
| 13 C10orf118 | 13 DCAF4L2 | 13 GPR97 | 13 LIMK1 | 13 MRGPRE | 13 PTPRQ |
| 13 C10orf32 | 13 DCAF8L1 | 13 GRIN2B | 13 LINC00301 | 13 MRPS6 | 13 R3HCC1L |
| 13 C11orf20 | 13 DCP1B | 13 GRTP1 | 13 LINC00332 | 13 MSTO2P | 13 RAB11FIP1 |
| 13 C11orf67 | 13 DCTN4 | 13 GTF2B | 13 LINC00346 | 13 MTHFD2 | 13 RAB40AL |
| 13 C12orf40 | 13 DDAH1 | 13 GYS1 | 13 LINC00379 | 13 MTSS1 | 13 RABGAP1L |
| 13 C15orf43 | 13 DDC | 13 H2BFWT | 13 LINC00629 | 13 MXRA8 | 13 RAD52 |
| 13 C17orf65 | 13 DDX11 | 13 HAUS7 | 13 LINC00637 | 13 MYBPC2 | 13 RARB |
| 13 C1QTNF4 | 13 DDX43 | 13 HBS1L | 13 LOC100289673 | 13 MYH14 | 13 RB1 |
| 13 C1orf145 | 13 DDX53 | 13 HDLBP | | 13 MYO1H | 13 RBKS |
| 13 C1orf146 | 13 DLEU2 | 13 HEATR7A | | 13 MYO7A | 13 RBM8A |
| | 13 DMGDH | | | | |

TABLE 2-continued

Infertility Genes, Ranked

| | | | | | |
|---|---|---|---|---|---|
| 13 C1orf56 | 13 DNAJC15 | 13 HIST1H1A | LOC100506994 | 13 N4BP2L1 | 13 RBP4 |
| 13 C22orf45 | 13 DND1 | 13 HIST1H2BH | 13 | 13 NAT8L | 13 RBPJL |
| 13 C2orf65 | 13 DNHD1 | 13 HIST1H4A | LOC100507266 | 13 NCAM1 | 13 RCC1 |
| 13 C3orf14 | 13 DNLZ | 13 HIST1H4G | 13 | 13 NCK2 | 13 RCCD1 |
| 13 C8orf40 | 13 DOK7 | 13 HIST3H3 | LOC100507377 | 13 NDNF | 13 RDH5 |
| 13 C9orf47 | 13 DRD5 | 13 HLA-DPB1 | 13 | 13 NECAB1 | 13 RELL1 |
| 13 C9orf69 | 13 E2F7 | 13 HLA-F | LOC100507463 | 13 NEIL2 | 13 RHOXF1 |
| 13 CACNA1A | 13 EFCAB10 | 13 HMGCL | 13 | 13 NEU1 | 13 RHOXF2 |
| 13 CACNG6 | 13 ELAVL3 | 13 HMGCLL1 | LOC100996291 | 13 NEURL3 | 13 RHOXF2B |
| 13 CADM2 | 13 ELF2 | 13 HNF4A | 13 LOC148696 | 13 NGDN | 13 RIBC2 |
| 13 CAMSAP3 | 13 ELK2AP | 13 HNRNPC | 13 LOC282980 | 13 NGFR | 13 RNF103 |
| 13 CAMTA2 | 13 ELTD1 | 13 HOXA-AS3 | 13 LOC284454 | 13 NKAIN3 | 13 ROBO2 |
| 13 CAPG | 13 EMC10 | 13 HOXC4 | 13 LOC284998 | 13 NLRP11 | 13 RORA |
| 13 CARD9 | 13 EMILIN1 | 13 HPCAL1 | 13 LOC285768 | 13 NLRP4 | 13 RPL17- |
| 13 CASZ1 | 13 EMP1 | 13 HSH2D | 13 LOC387723 | 13 NR3C1 | C18ORF32 |
| 13 CBX6 | 13 EP400NL | 13 HSPBP1 | 13 LOC643339 | 13 NR4A3 | 13 RPRM |
| 13 CCDC74B-AS1 | 13 EPHA8 | 13 ICA1 | 13 LOC644669 | 13 NRBF2 | 13 RSF1 |
| 13 CCNB1 | 13 EPHX4 | 13 ICA1L | 13 LOC84856 | 13 NTSR2 | 13 RUNX1 |
| 13 CCR10 | 13 ERRFI1 | 13 ICAM3 | 13 LPAR3 | 13 NUCB1 | 13 RUNX3 |
| 13 CCZ1 | 13 EXOC6B | 13 IKZF4 | 13 LPCAT2 | 13 ONECUT3 | 13 S100A1 |
| 13 CCZ1B | 13 F2RL3 | 13 IL18BP | 13 LRP8 | 13 OPLAH | 13 S100B |
| 13 CD151 | 13 FAM125B | 13 IL1RAPL2 | 13 LRRC37BP1 | 13 OPRK1 | 13 S1PR1 |
| 13 CD300LF | 13 FAM136A | 13 IL4I1 | 13 LRRC4B | 13 OR2C3 | 13 S1PR3 |
| 13 CD47 | 13 FAM171A2 | 13 IL5RA | 13 LY6K | 13 OXCT1 | 13 SBK1 |
| 13 CDC14B | 13 FAM47B | 13 INCENP | 13 LY86 | 13 PAGE2B | 13 SCAF1 |
| 13 CDCA3 | 13 FAM48B1 | 13 INF2 | 13 MAATS1 | 13 PARD3 | 13 SCNN1A |
| 13 CDH12 | 13 FAM49B | 13 INPP4A | 13 MAGEA1 | 13 PCDHA11 | 13 SECTM1 |
| 13 CDR2L | 13 FAM71E1 | 13 IQCE | 13 MAGED2 | 13 PCDHB15 | 13 SEL1L3 |
| 13 CELF6 | 13 FANCC | 13 ITGA4 | 13 MALL | 13 PCDHB3 | 13 SEMA5A |
| 13 CEP85L | 13 FBLN7 | 13 ITGA6 | 13 MAN1C1 | 13 PCDHGB8P | 13 SERPINA1 |
| 13 CERS3 | 13 FBRSL1 | 13 ITIH5 | 13 MAP3K11 | 13 PCSK2 | 13 SH2D3A |
| 13 CHRNA10 | 13 FBXL7 | 13 JAK2 | 13 MAP3K6 | 13 PDE4D | 13 SH3BP2 |
| 13 CHST13 | 13 FBXW8 | 13 JPH3 | 13 MBLAC2 | 13 PDE8B | 13 SH3BP5 |
| 13 CIITA | 13 FEZ1 | 13 KAZALD1 | 13 MBTPS1 | 13 PDS5B | 13 SH3D21 |
| 13 SH3PXD2A | 13 TTTY4 | 12 ALDH3A1 | 12 C2CD2 | 12 CNNM2 | 12 EZH1 |
| 13 SH3RF3 | 13 TTTY4B | 12 ALOX5 | 12 C2orf27B | 12 COASY | 12 FA2H |
| 13 SH3RF3-AS1 | 13 TTTY4C | 12 ALOXE3 | 12 C3orf67 | 12 COL16A1 | 12 FAM110B |
| 13 SHANK3 | 13 TUBB3 | 12 ANG | 12 C5orf42 | 12 COL18A1 | 12 FAM170A |
| 13 SHISA2 | 13 TULP2 | 12 ANGEL2 | 12 C5orf58 | 12 COL27A1 | 12 FAM183B |
| 13 SKP2 | 13 TXLNB | 12 ANGPT2 | 12 C6orf15 | 12 COL2A1 | 12 FAM189A1 |
| 13 SLC12A9 | 13 TXNRD2 | 12 ANKMY1 | 12 C7orf45 | 12 COL4A2 | 12 FAM20B |
| 13 SLC15A1 | 13 UBE2U | 12 ANKRD30BL | 12 C8orf22 | 12 COL6A6 | 12 FAM48B2 |
| 13 SLC16A9 | 13 UNC5A | 12 ANKRD31 | 12 C8orf44-SGK3 | 12 CRBN | 12 FAM9C |
| 13 SLC20A2 | 13 UNC93B1 | 12 ANKRD34B | 12 C8orf46 | 12 CREB3L1 | 12 FAT1 |
| 13 SLC22A18AS | 13 UPB1 | 12 AP4S1 | 12 C9orf40 | 12 CROCCP3 | 12 FBLIM1 |
| 13 SLC25A37 | 13 UQCRQ | 12 APCDD1 | 12 CA14 | 12 CRSP8P | 12 FBXL16 |
| 13 SLC25A45 | 13 USP29 | 12 APLNR | 12 CACNA1H | 12 CSNK1A1L | 12 FBXL8 |
| 13 SLC43A2 | 13 USP5 | 12 APOA5 | 12 CACNB1 | 12 CTAGE11P | 12 FBXO17 |
| 13 SLC44A4 | 13 USP7 | 12 APOB | 12 CACNG2 | 12 CTNNA2 | 12 FBXO21 |
| 13 SLC4A3 | 13 VGLL4 | 12 APOBEC3A_B | 12 CALHM3 | 12 CTSO | 12 FCAMR |
| 13 SLC52A3 | 13 VTI1A | 12 ARFRP1 | 12 CALML4 | 12 CUL1 | 12 FERMT3 |
| 13 SLC5A3 | 13 VWA5B2 | 12 ARHGAP4 | 12 CAPNS1 | 12 CX3CR1 | 12 FGFR1 |
| 13 SLC6A2 | 13 WBP2NL | 12 ARHGEF25 | 12 CASP5 | 12 CYB5R2 | 12 FIBCD1 |
| 13 SLCO6A1 | 13 WDR24 | 12 ARHGEF33 | 12 CASP7 | 12 CYP46A1 | 12 FIGNL1 |
| 13 SMAD3 | 13 WDR43 | 12 ARHGEF9 | 12 CAV1 | 12 CYTH4 | 12 FIS1 |
| 13 SMARCD1 | 13 WDR65 | 12 ARID5A | 12 CCDC11 | 12 DACH1 | 12 FKBP5 |
| 13 SMC1B | 13 WIZ | 12 ARMCX5- | 12 CCDC112 | 12 DACT1 | 12 FLII |
| 13 SMYD4 | 13 WNT7A | GPRASP2 | 12 CCDC115 | 12 DCAF6 | 12 FLJ25363 |
| 13 SNAR-H | 13 WRNIP1 | 12 ARNT2 | 12 CCDC144B | 12 DCC | 12 FLJ25758 |
| 13 SNRPD1 | 13 ZBTB12 | 12 AS3MT | 12 CCDC155 | 12 DCTN2 | 12 FLJ30403 |
| 13 SNRPN | 13 ZBTB16 | 12 ASB2 | 12 CCDC172 | 12 DDX11-AS1 | 12 FLJ42289 |
| 13 SNX25 | 13 ZBTB20 | 12 ASPSCR1 | 12 CCDC177 | 12 DDX54 | 12 FLJ42627 |
| 13 SNX29 | 13 ZBTB20-AS1 | 12 ATF7IP2 | 12 CCDC27 | 12 DENND3 | 12 FLJ45974 |
| 13 SOGA3 | 13 ZCCHC13 | 12 ATG7 | 12 CCDC33 | 12 DLGAP1 | 12 FNDC1 |
| 13 SOX30 | 13 ZFHX3 | 12 ATP2A3 | 12 CCDC36 | 12 DMAP1 | 12 FOPNL |
| 13 SPAG7 | 13 ZMIZ1 | 12 ATP6AP1L | 12 CCDC73 | 12 DNAH6 | 12 FSD1L |
| 13 SPRED2 | 13 ZMYND8 | 12 ATRIP | 12 CCDC8 | 12 DNALI1 | 12 FSTL1 |
| 13 SPTBN4 | 13 ZNF213 | 12 ATXN3 | 12 CCKBR | 12 DNM3 | 12 FXYD2 |
| 13 SSBP2 | 13 ZNF275 | 12 ATXN7L1 | 12 CCT3 | 12 DNM3OS | 12 FXYD6-FXYD2 |
| 13 SSBP3 | 13 ZNF286A | 12 B4GALNT3 | 12 CCT6A | 12 DOCK9 | 12 G3BP2 |
| 13 STAG3 | 13 ZNF286B | 12 BAIAP2 | 12 CD300LG | 12 DOHH | 12 GABRA5 |
| 13 STK32A | 13 ZNF324B | 12 BAIAP2-AS1 | 12 CD58 | 12 DOM3Z | 12 GAGE12B |
| 13 SUV420H1 | 13 ZNF366 | 12 BCAS3 | 12 CDC25A | 12 DTWD1 | 12 GAGE12C |
| 13 TAP2 | 13 ZNF385A | 12 BCCIP | 12 CDC42BPB | 12 DUOX1 | 12 GAGE12D |
| 13 TCN2 | 13 ZNF438 | 12 BFAR | 12 CDH18 | 12 DUSP2 | 12 GAGE12E |
| 13 TDRD1 | 13 ZNF517 | 12 BIRC8 | 12 CDH5 | 12 DYM | 12 GAGE12G |
| 13 TENM3 | 13 ZNF521 | 12 BLOC1S1 | 12 CDH6 | 12 DYNC1LI2 | 12 GAGE12H |
| 13 TEX101 | 13 ZNF532 | 12 BNIP2 | 12 CDIPT | 12 DYSF | 12 GALNT2 |

TABLE 2-continued

Infertility Genes, Ranked

| | | | | | |
|---|---|---|---|---|---|
| 13 TEX13A | 13 ZNF653 | 12 BNIP3 | 12 CDK12 | 12 E2F6 | 12 GAN |
| 13 TFDP1 | 13 ZNF672 | 12 BOLA1 | 12 CDK19 | 12 EBNA1BP2 | 12 GAPDH |
| 13 TFF2 | 13 ZNF746 | 12 BPI | 12 CEACAM21 | 12 EBPL | 12 GATA2 |
| 13 TGIF2LX | 13 ZNF786 | 12 BRD1 | 12 CENPF | 12 ECEL1P2 | 12 GATM |
| 13 TGM5 | 13 ZNF853 | 12 BRSK2 | 12 CEP120 | 12 ECHDC1 | 12 GCK |
| 13 THSD7B | 12 ABCA13 | 12 BVES | 12 CEP170 | 12 EGFLAM | 12 GEMIN5 |
| 13 TMC1 | 12 ABCA7 | 12 BVES-AS1 | 12 CFDP1 | 12 EIF4E2 | 12 GGACT |
| 13 TMEM173 | 12 ABHD12 | 12 C11orf49 | 12 CHMP6 | 12 ELANE | 12 GIP |
| 13 TMEM229B | 12 ABLIM2 | 12 C11orf54 | 12 CHODL | 12 ELF4 | 12 GJA5 |
| 13 TNFAIP8L2-SCNM1 | 12 ACER2 | 12 C12orf75 | 12 CHRM4 | 12 ELOVL2 | 12 GJA8 |
| 13 TNFRSF1A | 12 ACIN1 | 12 C14orf162 | 12 CHRNB3 | 12 ELOVL2-AS1 | 12 GJB1 |
| 13 TP73 | 12 ACTL7B | 12 C14orf28 | 12 CHST15 | 12 ELOVL7 | 12 GJD3 |
| 13 TPM4 | 12 ACTN1 | 12 C15orf60 | 12 CIT | 12 ELP6 | 12 GLIS1 |
| 13 TRAPPC10 | 12 ADAT3 | 12 C17orf110 | 12 CKLF | 12 EML4 | 12 GMCL1P1 |
| 13 TRIM27 | 12 ADCY8 | 12 C17orf97 | 12 CLCF1 | 12 ENPEP | 12 GNA14 |
| 13 TRIM43 | 12 AFF3 | 12 C19orf66 | 12 CLDN4 | 12 EPCAM | 12 GNA15 |
| 13 TRIM5 | 12 AGA | 12 C1orf101 | 12 CLDN9 | 12 ERBB2IP | 12 GORASP2 |
| 13 TRIM62 | 12 AGBL5 | 12 C1orf106 | 12 CLHC1 | 12 EREG | 12 GPATCH8 |
| 13 TRIP6 | 12 AICDA | 12 C1orf159 | 12 CLIC1 | 12 ESPNL | 12 GPR108 |
| 13 TRPM2 | 12 AIFM1 | 12 C1orf177 | 12 CLIC3 | 12 ESRRB | 12 GPR112 |
| 13 TSKS | 12 AIP | 12 C1orf204 | 12 CLIC6 | 12 ETV6 | 12 GPR132 |
| 13 TTC38 | 12 AKNA | 12 C1orf65 | 12 CLP1 | 12 EVPLL | 12 GPRASP2 |
| 13 TTLL11 | 12 AKR1E2 | 12 C1orf85 | 12 CLTB | 12 EXOC8 | 12 GPT |
| 12 GRK5 | 12 ALDH1A3 | 12 C22orf43 | 12 CLYBL | 12 EYA2 | 12 GRB10 |
| 12 GRK5 | 12 KIF13A | 12 LOC400794 | 12 MXRA7 | 12 PPFIA3 | 12 SH2D3C |
| 12 GRM4 | 12 KIF5A | 12 LOC440356 | 12 MYH9 | 12 PPIG | 12 SH2D4B |
| 12 GSPT1 | 12 KIF6 | 12 LOC441601 | 12 MYL7 | 12 PPM1N | 12 SH2D7 |
| 12 GUSBP11 | 12 KIF7 | 12 LOC63930 | 12 MYL9 | 12 PPP1CC | 12 SHARPIN |
| 12 HAPLN1 | 12 KIRREL3 | 12 LOC729177 | 12 MYLK-AS1 | 12 PPP1R11 | 12 SHFM1 |
| 12 HECW1 | 12 KLF13 | 12 LOC90834 | 12 MYO3A | 12 PPP1R12B | 12 SIGLEC15 |
| 12 HERC2 | 12 KLF17 | 12 LOX | 12 MYO9B | 12 PPP1R16A | 12 SLA |
| 12 HIBCH | 12 KLF6 | 12 LPPR3 | 12 MYOM3 | 12 PPP1R36 | 12 SLC12A4 |
| 12 HIST1H2AA | 12 KLHL17 | 12 LPPR5 | 12 NAIF1 | 12 PPP2R3C | 12 SLC13A4 |
| 12 HIST1H2BA | 12 KLHL21 | 12 LRP12 | 12 NBEA | 12 PRAM1 | 12 SLC17A7 |
| 12 HIVEP1 | 12 KLHL25 | 12 LRTM2 | 12 NCALD | 12 PRKACA | 12 SLC22A16 |
| 12 HLA-DOA | 12 KLHL33 | 12 LRTOMT | 12 NCDN | 12 PRMT2 | 12 SLC22A4 |
| 12 HLA-DQA2 | 12 KLK4 | 12 LTBP3 | 12 NCKAP5 | 12 PRMT8 | 12 SLC25A25 |
| 12 HLA-G | 12 L3MBTL3 | 12 LTBR | 12 NCOA2 | 12 PRSS3 | 12 SLC25A48 |
| 12 HLA-H | 12 LAG3 | 12 LY86-AS1 | 12 NDRG3 | 12 PSD | 12 SLC2A1 |
| 12 HMCN1 | 12 LAIR1 | 12 LYSMD2 | 12 NEDD1 | 12 PSEN2 | 12 SLC2A14 |
| 12 HMGN3 | 12 LBX2 | 12 MAB21L1 | 12 NEK3 | 12 PSKH1 | 12 SLC35C1 |
| 12 HOMER3 | 12 LBX2-AS1 | 12 MAGEA4 | 12 NFIA | 12 PSME1 | 12 SLC35F3 |
| 12 HOXB-AS3 | 12 LIMS2 | 12 MAMSTR | 12 NGLY1 | 12 PSTK | 12 SLC37A1 |
| 12 HOXC5 | 12 LINC00029 | 12 MAOB | 12 NIPA1 | 12 PSTPIP1 | 12 SLC38A10 |
| 12 HOXC6 | 12 LINC00032 | 12 MAP3K5 | 12 NKX6-3 | 12 PTCHD3 | 12 SLC3A1 |
| 12 HRASLS | 12 LINC00460 | 12 MAP7D2 | 12 NOC2L | 12 PTPLB | 12 SLC45A2 |
| 12 HRH1 | 12 LINC00474 | 12 MAPKAPK2 | 12 NONO | 12 PTPN4 | 12 SLC47A2 |
| 12 HS3ST1 | 12 LINC00477 | 12 MARK2 | 12 NPAS1 | 12 PTPRA | 12 SLC6A11 |
| 12 HSF2BP | 12 LINC00577 | 12 MARK4 | 12 NPAS1 | 12 PTPRH | 12 SLC9A3R1 |
| 12 ICAM2 | 12 LINC00606 | 12 MBP | 12 NRGN | 12 PUS7L | 12 SLC9A9 |
| 12 IDO2 | 12 LMNB2 | 12 MC3R | 12 OBFC1 | 12 QPCT | 12 SLFN5 |
| 12 IL17RE | 12 LMO2 | 12 MCHR1 | 12 OPHN1 | 12 RAB15 | 12 SLPI |
| 12 IL17REL | 12 LOC100128993 | 12 MCM3AP | 12 OR10Q1 | 12 RAB33A | 12 SMARCA2 |
| 12 IL21R-AS1 | 12 LOC100128993 | 12 MCPH1 | 12 OR8U8 | 12 RAB3C | 12 SMEK3P |
| 12 IMP4 | 12 LOC100129520 | 12 MDGA1 | 12 OR9Q2 | 12 RAB7A | 12 SMPDL3B |
| 12 INPP5D | 12 LOC100129520 | 12 MEI1 | 12 ORAI1 | 12 RAPGEFL1 | 12 SNED1 |
| 12 IQSEC1 | 12 LOC100129620 | 12 MESP2 | 12 OSBPL3 | 12 RASGEF1A | 12 SNIP1 |
| 12 IQSEC3 | 12 LOC100129620 | 12 MFAP4 | 12 OTUD3 | 12 RASGEF1B | 12 SNORA14B |
| 12 IRAK4 | 12 LOC100129917 | 12 MGC2889 | 12 OXSM | 12 RASSF2 | 12 SNORD123 |
| 12 IRF2 | 12 LOC100129917 | 12 MGMT | 12 OXT | 12 RAVER1 | 12 SNORD58A |
| 12 IRF5 | 12 LOC100130776 | 12 MGRN1 | 12 PACSIN1 | 12 RBCK1 | 12 SNORD58B |
| 12 IRGQ | 12 LOC100130776 | 12 MIA3 | 12 PAGE2 | 12 RBM25 | 12 SNORD58C |
| 12 IRS1 | 12 LOC100130872 | 12 MIR143HG | 12 PAGE5 | 12 RBM6 | 12 SNORD73A |
| 12 ISCU | 12 LOC100130872 | 12 MIR145 | 12 PALD1 | 12 RBPMS | 12 SNORD93 |
| 12 ISM1 | 12 LOC100130987 | 12 MIR199A2 | 12 PANX2 | 12 RCBTB2 | 12 SNX16 |
| 12 ISPD | 12 LOC100130987 | 12 MIR2110 | 12 PARN | 12 REREP3 | 12 SOGA1 |
| 12 ITFG3 | 12 LOC100131089 | 12 MIR4426 | 12 PART1 | 12 RFPL4B | 12 SPATA16 |
| 12 ITGA7 | 12 LOC100131089 | 12 MIR4499 | 12 PBK | 12 RIN1 | 12 SPATA2 |
| 12 ITGB2-AS1 | 12 LOC100131496 | 12 MIR4656 | 12 PCGF3 | 12 RIN2 | 12 SPON2 |
| 12 ITGBL1 | 12 LOC100131496 | 12 MIR5001 | 12 PCNXL2 | 12 RNASE4 | 12 SPRTN |
| 12 IZUMO1 | 12 LOC100131551 | 12 MIR5093 | 12 PDE3A | 12 RNF17 | 12 SRPK3 |
| 12 JAK3 | 12 LOC100131551 | 12 MIR516B2 | 12 PDE7B | 12 RNF213 | 12 SRSF5 |
| 12 JAZF1 | 12 LOC100131726 | 12 MIR520G | 12 PDLIM4 | 12 RPL17 | 12 SSX3 |
| 12 JMJD8 | 12 LOC100131726 | 12 MIR548AA2 | 12 PDLIM7 | 12 RPP25 | 12 STARD3NL |
| 12 KBTBD8 | 12 LOC100144597 | 12 MIR548D2 | 12 PEMT | 12 RPS27A | 12 STK19 |
| 12 KCNG1 | 12 LOC100144597 | 12 MIR596 | 12 PGRMC1 | 12 RPS3A | 12 SUMF2 |
| 12 KCNIP2 | 12 LOC100288198 | 12 MIR602 | 12 PHF14 | 12 RPS6KL1 | 12 SUZ12P1 |
| 12 KCNIP3 | 12 LOC100288198 | 12 MKNK1 | 12 PHF16 | 12 RRAD | 12 SYN2 |

TABLE 2-continued

Infertility Genes, Ranked

| | | | | | |
|---|---|---|---|---|---|
| 12 KCNQ1DN | 12 | 12 MKRN2 | 12 PIM1 | 12 RSPH1 | 12 SYNGR2 |
| 12 KCTD10 | LOC100289187 | 12 MKX | 12 PINX1 | 12 RTN2 | 12 SYNJ2 |
| 12 KCTD5 | 12 | 12 MLC1 | 12 PION | 12 SAE1 | 12 SYNPR |
| 12 KDM6A | LOC100294145 | 12 MLK7-AS1 | 12 PIP5K1P1 | 12 SART3 | 12 SYNPR-AS1 |
| 12 KHDC3L | 12 | 12 MLX | 12 PITPNM2 | 12 SCAMP4 | 12 SYS1 |
| 12 KIAA0226 | LOC100505806 | 12 MMADHC | 12 PIWIL1 | 12 SCML4 | 12 SYS1-DBNDD2 |
| 12 KIAA0319L | 12 | 12 MOK | 12 PLA2G4D | 12 SCTR | 12 TAF1D |
| 12 KIAA0391 | LOC100507433 | 12 MOV10L1 | 12 PLCD3 | 12 SCYL1 | 12 TBC1D4 |
| 12 KIAA0753 | 12 LOC145663 | 12 MPHOSPH8 | 12 PLEKHA6 | 12 SEC14L1 | 12 TBC1D9B |
| 12 KIAA0922 | 12 LOC220906 | 12 MPST | 12 PLEKHH3 | 12 SENP5 | 12 TBKBP1 |
| 12 KIAA1383 | 12 LOC283683 | 12 MR1 | 12 PLXNB3 | 12 SERHL2 | 12 TECR |
| 12 KIAA1429 | 12 LOC284661 | 12 MRPL22 | 12 PNMA5 | 12 SESN2 | 12 TET1 |
| 12 KIAA1549 | 12 LOC375196 | 12 MSH5 | 12 PNPLA6 | 12 SETDB1 | 12 TFEB |
| 12 KIDINS220 | 12 LOC400043 | 12 MTHFR | 12 PNPT1 | 12 SGCE | 12 TG |
| 12 THEGL | 12 YJEFN3 | 11 AQP2 | 11 CBR4 | 11 DOCK8 | 11 GGNBP1 |
| 12 THTPA | 12 ZADH2 | 11 ARHGAP26 | 11 CBX5 | 11 DPM1 | 11 GJA9 |
| 12 TIGD1 | 12 ZBTB7B | 11 ARHGEF10L | 11 CBX7 | 11 DPP4 | 11 GJA9-MYCBP |
| 12 TIMM13 | 12 ZC3H12A | 11 ARPC1B | 11 CCBP2 | 11 DUS4L | 11 GLRA1 |
| 12 TIMP4 | 12 ZC3H3 | 11 ASB8 | 11 CCDC107 | 11 DYNC2H1 | 11 GLUD1P3 |
| 12 TIPIN | 12 ZCCHC7 | 11 ASCC2 | 11 CCDC146 | 11 EDAR | 11 GNPNAT1 |
| 12 TLL2 | 12 ZDHHC14 | 11 ASIC3 | 11 CCDC50 | 11 EHHADH | 11 GP6 |
| 12 TM2D3 | 12 ZEB2 | 11 ASNA1 | 11 CCNJL | 11 EIF3J | 11 GPR12 |
| 12 TMEM190 | 12 ZFHX2 | 11 ATAT1 | 11 CD44 | 11 EIF4A3 | 11 GPR157 |
| 12 TMEM200B | 12 ZFYVE26 | 11 ATMIN | 11 CD52 | 11 ELL | 11 GPR77 |
| 12 TMEM209 | 12 ZG16B | 11 ATOH8 | 11 CD6 | 11 ELOVL4 | 11 GPSM1 |
| 12 TMEM51 | 12 ZGPAT | 11 ATP2C2 | 11 CDC42EP4 | 11 EML6 | 11 GPX3 |
| 12 TMEM9 | 12 ZHX1 | 11 ATP5D | 11 CDCP2 | 11 ENG | 11 GRAMD3 |
| 12 TNFRSF11A | 12 ZHX1- | 11 ATP5J2 | 11 CDH2 | 11 EPDR1 | 11 GRAP2 |
| 12 TNFRSF8 | C8ORF76 | 11 ATP5J2- | 11 CDK20 | 11 EPHA4 | 11 GRHL2 |
| 12 TNFSF11 | 12 ZNF101 | PTCD1 | 11 CES1P1 | 11 EPM2AIP1 | 11 GRIK4 |
| 12 TNK1 | 12 ZNF195 | 11 ATP6V0D1 | 11 CHD5 | 11 EPRS | 11 GRIN3A |
| 12 TNPO3 | 12 ZNF200 | 11 ATP6V1B1 | 11 CHD9 | 11 ERGIC1 | 11 GRK4 |
| 12 TOMM20 | 12 ZNF251 | 11 ATP8B2 | 11 CHGA | 11 ERI3 | 11 GSPT2 |
| 12 TOR3A | 12 ZNF259 | 11 ATXN8OS | 11 CHRNB2 | 11 ERO1LB | 11 GTF3C3 |
| 12 TPO | 12 ZNF277 | 11 AVPR1B | 11 CHST3 | 11 EXOC3 | 11 GTF3C4 |
| 12 TRADD | 12 ZNF280A | 11 B9D1 | 11 CHTOP | 11 EXOSC1 | 11 GTPBP1 |
| 12 TRIM14 | 12 ZNF32 | 11 BAK1 | 11 CKAP2 | 11 EXOSC2 | 11 GUCY1B2 |
| 12 TRIM43B | 12 ZNF32-AS3 | 11 BCAT1 | 11 CLDN6 | 11 EXOSC3 | 11 GULP1 |
| 12 TRIM65 | 12 ZNF341 | 11 BCDIN3D | 11 CLK2 | 11 EXOSC6 | 11 GXYLT1 |
| 12 TSACC | 12 ZNF354C | 11 BDKRB1 | 11 CLPB | 11 EZR | 11 GYG2 |
| 12 TSC22D4 | 12 ZNF385C | 11 BEND4 | 11 CMYA5 | 11 F7 | 11 HCG11 |
| 12 TSHZ1 | 12 ZNF396 | 11 BID | 11 CNFN | 11 FABP7 | 11 HCG22 |
| 12 TST | 12 ZNF428 | 11 BIN2 | 11 CNNM4 | 11 FAIM3 | 11 HCN3 |
| 12 TTC39A | 12 ZNF461 | 11 BLK | 11 COG5 | 11 FAM188A | 11 HDAC7 |
| 12 TTLL7 | 12 ZNF527 | 11 BMP6 | 11 COL20A1 | 11 FAM18A | 11 HDGF |
| 12 TUBA8 | 12 ZNF540 | 11 BMP8B | 11 COMMD7 | 11 FAM195A | 11 HEATR8-TTC4 |
| 12 TUBB8 | 12 ZNF542 | 11 BMS1P4 | 11 CORO1C | 11 FAM19A2 | 11 HELLS |
| 12 TUBGCP2 | 12 ZNF555 | 11 BOC | 11 COX6C | 11 FAM208A | 11 HELZ2 |
| 12 TXLNA | 12 ZNF576 | 11 BRAT1 | 11 COX7C | 11 FAM222A | 11 HIGD1A |
| 12 UBA7 | 12 ZNF599 | 11 BRD4 | 11 CPEB3 | 11 FAM222A-AS1 | 11 HILPDA |
| 12 UBAC2 | 12 ZNF622 | 11 BRF1 | 11 CPNE7 | 11 FAM5C | 11 HIST1H1D |
| 12 UBE2DNL | 12 ZNF782 | 11 BTBD3 | 11 CREB3L3 | 11 FBXO15 | 11 HIST1H4F |
| 12 UBE2MP1 | 12 ZNF785 | 11 BTK | 11 CRTC3 | 11 FBXO46 | 11 HLA-DMB |
| 12 UBQLN1 | 12 ZNF831 | 11 BUB1B | 11 CSDC2 | 11 FBXO47 | 11 HLX |
| 12 UBXN2B | 12 ZNRD1 | 11 BZRAP1 | 11 CSNK1G3 | 11 FCHO1 | 11 HMG20A |
| 12 UCHL1 | 12 ZSCAN18 | 11 BZRAP1-AS1 | 11 CST6 | 11 FERMT1 | 11 HMHB1 |
| 12 UCK2 | 11 AARD | 11 C10orf11 | 11 CTBS | 11 FLJ13197 | 11 HNMT |
| 12 ULK2 | 11 AARS | 11 C10orf90 | 11 CTDSPL | 11 FLJ20518 | 11 HNRNPA1 |
| 12 UROS | 11 ABCB8 | 11 C16orf45 | 11 CUL4A | 11 FLJ27354 | 11 HNRNPA1P10 |
| 12 USP1 | 11 ABCC1 | 11 C16orf74 | 11 CXCL12 | 11 FLJ35946 | 11 HOMER1 |
| 12 USP18 | 11 ABCC3 | 11 C16orf91 | 11 CXXC5 | 11 FMR1NB | 11 HORMAD1 |
| 12 USP45 | 11 ACAA2 | 11 C17orf64 | 11 CYB5B | 11 FNBP1 | 11 HOXA2 |
| 12 UXS1 | 11 ACTR1A | 11 C18orf1 | 11 CYP2E1 | 11 FOXA2 | 11 HOXB2 |
| 12 VAMP3 | 11 ADAM2 | 11 C19orf38 | 11 DAXX | 11 FOXK1 | 11 HOXB3 |
| 12 VCX | 11 ADAMTS4 | 11 C19orf43 | 11 DAZAP2 | 11 FOXL2 | 11 HOXB6 |
| 12 VPS13D | 11 ADAMTSL3 | 11 C1QTNF3- | 11 DCAF12L2 | 11 FOXRED2 | 11 HSPA6 |
| 12 VSIG8 | 11 AGXT2L2 | AMACR | 11 DCAF16 | 11 FRG2C | 11 HSPB9 |
| 12 VWC2L | 11 AHNAK2 | 11 C1QTNF8 | 11 DDI1 | 11 FSD2 | 11 HTR3A |
| 12 VWDE | 11 AK7 | 11 C20orf197 | 11 DDX25 | 11 FUZ | 11 HTR3E |
| 12 VWF | 11 AKAP7 | 11 C2CD4C | 11 DDX31 | 11 FZR1 | 11 HUS1B |
| 12 WAC | 11 ALDH1L1 | 11 C2orf18 | 11 DDX4 | 11 GABRB3 | 11 IER5 |
| 12 WARS | 11 ALOX12P2 | 11 C3orf72 | 11 DEDD | 11 GABRD | 11 IFT140 |
| 12 WARS2 | 11 AMACR | 11 C3orf74 | 11 DEDD2 | 11 GABRP | 11 IL17RC |
| 12 WBP1L | 11 AMIGO2 | 11 C5orf49 | 11 DEF8 | 11 GAGE12J | 11 IL28B |
| 12 WNK2 | 11 AMIGO3 | 11 C5orf55 | 11 DEFB1 | 11 GAS5 | 11 ING2 |
| 12 WNT6 | 11 AMMECR1L | 11 C6orf136 | 11 DENND1A | 11 GBA | 11 INTS6 |
| 12 WRB | 11 ANK2 | 11 C8orf42 | 11 DENND1C | 11 GBE1 | 11 ISLR2 |
| 12 WTIP | 11 ANKRD45 | 11 C8orf76 | 11 DERL1 | 11 GBF1 | 11 ISOC1 |

TABLE 2-continued

Infertility Genes, Ranked

| | | | | | |
|---|---|---|---|---|---|
| 12 XPO4 | 11 ANKRD7 | 11 C9orf66 | 11 DHX58 | 11 GCOM1 | 11 ITGAL |
| 12 XRCC5 | 11 ANP32C | 11 CACNG8 | 11 DLL3 | 11 GDF5 | 11 ITPK1 |
| 12 YBEY | 11 AP2A1 | 11 CAMKMT | 11 DNAJC27 | 11 GEMIN8P4 | 11 JAK1 |
| 12 YIF1B | 11 AQP10 | 11 CAV2 | 11 DNAJC27-AS1 | 11 GFOD1 | 11 KALRN |
| 11 KANK4 | 11 MAGEA2B | 11 OR6B2 | 11 RBMXL3 | 11 SNORD78 | 11 TPGS1 |
| 11 KAT2A | 11 MAMDC2 | 11 OSBPL7 | 11 RBMY1F | 11 SNORD79 | 11 TPTE |
| 11 KCNC1 | 11 MAP1LC3B2 | 11 PABPN1L | 11 RCVRN | 11 SNORD80 | 11 TRIB1 |
| 11 KCNN3 | 11 MAP3K12 | 11 PACS1 | 11 RFC1 | 11 SNORD81 | 11 TRIM42 |
| 11 KHDRBS1 | 11 MAP3K14 | 11 PALM | 11 RGMB | 11 SNX18 | 11 TRMT10C |
| 11 KIAA1211 | 11 MAP7 | 11 PAQR4 | 11 RGN | 11 SP140L | 11 TRPC5 |
| 11 KIAA1211L | 11 MARCH1 | 11 PARP11 | 11 RGS20 | 11 SPA17 | 11 TSHZ3 |
| 11 KIAA1598 | 11 MARCH10 | 11 PATL1 | 11 RHOB | 11 SPAG16 | 11 TTC39B |
| 11 KIF19 | 11 MDFI | 11 PCDH19 | 11 RHOH | 11 SPATA3 | 11 UBE2G1 |
| 11 KLF11 | 11 MED25 | 11 PCDHA12 | 11 RHOU | 11 SPESP1 | 11 UBE2H |
| 11 KLF3 | 11 MEGF6 | 11 PCDHA13 | 11 RNF123 | 11 SPG7 | 11 UBN2 |
| 11 KLHDC2 | 11 METTL20 | 11 PCDHB13 | 11 ROR2 | 11 SPOCD1 | 11 UBXN11 |
| 11 KLHL1 | 11 MIDN | 11 PDGFD | 11 RORC | 11 SPOCK3 | 11 UCN3 |
| 11 KRBOX1 | 11 MINPP1 | 11 PDGFRB | 11 RP1-177G6.2 | 11 SPTSSB | 11 USP35 |
| 11 KREMEN2 | 11 MIPEPP3 | 11 PEAK1 | 11 RPL22 | 11 SRC | 11 VGLL3 |
| 11 KRT16P3 | 11 MIR1297 | 11 PER2 | 11 RPL31P11 | 11 SRPRB | 11 VPS36 |
| 11 KRT81 | 11 MIR1468 | 11 PET112 | 11 RPS6KA1 | 11 SRRT | 11 VTRNA2-1 |
| 11 KRTAP2-1 | 11 MIR150 | 11 PGBD5 | 11 RRN3P2 | 11 SRY | 11 VWA3B |
| 11 LAMTOR1 | 11 MIR1976 | 11 PHAX | 11 RTN4 | 11 ST7 | 11 VWCE |
| 11 LILRB1 | 11 MIR3607 | 11 PID1 | 11 S100A8 | 11 ST7-AS2 | 11 WDFY3 |
| 11 LIN9 | 11 MIR4633 | 11 PITX2 | 11 SAP30BP | 11 STAB1 | 11 WDFY3-AS2 |
| 11 LINC00511 | 11 MIR4710 | 11 PITX3 | 11 SASH3 | 11 STAP2 | 11 WHAMM |
| 11 LINC00523 | 11 MIR548H4 | 11 PKN1 | 11 SCARF2 | 11 STK24 | 11 WNT10B |
| 11 LIPK | 11 MIR5680 | 11 PLA2G3 | 11 SCN4B | 11 STRA8 | 11 XK |
| 11 LMAN1L | 11 MIR615 | 11 PLEKHA7 | 11 SCNM1 | 11 STRN3 | 11 XRCC3 |
| 11 LMLN | 11 MIXL1 | 11 PLEKHF2 | 11 SCNN1D | 11 STX1B | 11 ZBTB11 |
| 11 LMO4 | 11 MKS1 | 11 PLOD1 | 11 SDCBP | 11 SULT1C4 | 11 ZBTB37 |
| 11 LOC100009676 | 11 MLH1 | 11 PLXNC1 | 11 SDR16C5 | 11 SUSD5 | 11 ZC3H14 |
| 11 LOC100128164 | 11 MOB3B | 11 PML | 11 SEC62 | 11 SYCN | 11 ZCCHC16 |
| 11 LOC100132111 | 11 MOCS3 | 11 PNMA2 | 11 SEMA3G | 11 SYNC | 11 ZDHHC16 |
| 11 LOC100271702 | 11 MORN1 | 11 PODNL1 | 11 SEPSECS | 11 SYNGR3 | 11 ZFX |
| 11 LOC100506207 | 11 MPND | 11 POLR2M | 11 SERPINB5 | 11 SYNPO2 | 11 ZFX-AS1 |
| 11 LOC100507384 | 11 MRPL4 | 11 POU2F2 | 11 SERPINE2 | 11 TACR1 | 11 ZMIZ2 |
| 11 LOC100507424 | 11 MRPS17 | 11 PPDPF | 11 SERPING1 | 11 TAF3 | 11 ZNF131 |
| 11 LOC150185 | 11 MRPS22 | 11 PPFIBP2 | 11 SFRP4 | 11 TBC1D14 | 11 ZNF232 |
| 11 LOC283688 | 11 MST1R | 11 PPM1G | 11 SGCB | 11 TBX22 | 11 ZNF239 |
| 11 LOC283731 | 11 MTF1 | 11 PPP1R9A | 11 SGK3 | 11 TCF7L1 | 11 ZNF326 |
| 11 LOC284688 | 11 MTL5 | 11 PPP3R2 | 11 SGOL1 | 11 TCTN3 | 11 ZNF470 |
| 11 LOC284837 | 11 MTMR7 | 11 PRAME | 11 SH3BP4 | 11 TDRD10 | 11 ZNF496 |
| 11 LOC285540 | 11 MUC21 | 11 PRAP1 | 11 SH3TC2 | 11 TDRKH | 11 ZNF549 |
| 11 LOC286177 | 11 MYCBP | 11 PRDM11 | 11 SHE | 11 TEAD3 | 11 ZNF610 |
| 11 LOC286467 | 11 MYH13 | 11 PREPL | 11 SIAE | 11 TEX10 | 11 ZNF716 |
| 11 LOC339166 | 11 MYLK2 | 11 PRKCDBP | 11 SIM2 | 11 TFB1M | 11 ZNF772 |
| 11 LOC339524 | 11 N4BP3 | 11 PRKCE | 11 SIRPB2 | 11 TFDP3 | 11 ZNF850 |
| 11 LOC348120 | 11 NAA11 | 11 PRL | 11 SIX2 | 11 TGFA | 11 ZNF862 |
| 11 LOC348761 | 11 NACA2 | 11 PRMT7 | 11 SKIL | 11 TIMP2 | 11 ZNHIT6 |
| 11 LOC285540 | 11 NAT2 | 11 PROP1 | 11 SLC19A1 | 11 TIPARP | 11 ZSCAN21 |
| 11 LOC286177 | 11 NCAPG | 11 PRRT4 | 11 SLC1A5 | 11 TIPARP-AS1 | 10 ABI1 |
| 11 LOC286467 | 11 NDUFS2 | 11 PSMB2 | 11 SLC22A8 | 11 TLE2 | 10 ACTB |
| 11 LOC339166 | 11 NECAB3 | 11 PTCH1 | 11 SLC25A18 | 11 TMC6 | 10 ADI1 |
| 11 LOC339524 | 11 NEK10 | 11 PTGIS | 11 SLC26A6 | 11 TMC8 | 10 AFF1 |
| 11 LOC348120 | 11 NFAM1 | 11 PTPLAD1 | 11 SLC35B3 | 11 TMEFF2 | 10 AGBL3 |
| 11 LOC348761 | 11 NFE2L2 | 11 PTPRO | 11 SLC38A9 | 11 TMEM108 | 10 AGRP |
| 11 LOC389247 | 11 NIM1 | 11 PTPRR | 11 SLC39A11 | 11 TMEM119 | 10 ANK3 |
| 11 LOC645212 | 11 NIPSNAP1 | 11 PTPRU | 11 SLC39A12 | 11 TMEM179 | 10 ANKRD17 |
| 11 LOC648691 | 11 NKD1 | 11 PUS3 | 11 SLC46A1 | 11 TMEM204 | 10 ANKRD26P1 |
| 11 LOC727982 | 11 NOL4 | 11 PXDC1 | 11 SLC52A2 | 11 TMEM249 | 10 ANKRD33 |
| 11 LPAR5 | 11 NOP14 | 11 PYGO1 | 11 SLC5A10 | 11 TMEM44-AS1 | 10 AP1B1 |
| 11 LPIN2 | 11 NOX5 | 11 PYROXD2 | 11 SLC5A11 | 11 TMEM63A | 10 APOBEC3B |
| 11 LRCH2 | 11 NPAS3 | 11 R3HDML | 11 SLC6A12 | 11 TMEM71 | 10 APOBEC3H |
| 11 LRIG1 | 11 NPNT | 11 RAB17 | 11 SLCO5A1 | 11 TMOD2 | 10 APOL2 |
| 11 LRPPRC | 11 NRIP2 | 11 RAB25 | 11 SLIT1 | 11 TNFAIP2 | 10 ARHGEF26 |
| 11 LRRC8C | 11 NSMCE1 | 11 RAB41 | 11 SLIT3 | 11 TNFRSF12A | 10 ARHGEF26-AS1 |
| 11 LYPLA1 | 11 NTF3 | 11 RAD51C | 11 SLITRK5 | 11 TNS3 | |
| 11 LYSMD1 | 11 NUDT4 | 11 RAD54L2 | 11 SMIM1 | 11 TOMM7 | 10 ARHGEF28 |
| 11 LZTFL1 | 11 NUDT4P1 | 11 RARA | 11 SMTN | 11 TOP1MT | 10 ARID5B |
| 11 MAF | 11 NUMA1 | 11 RASL10A | 11 SNORD44 | 11 TP73-AS1 | 10 ARX |
| 11 MAGEA2 | 11 OMA1 | 11 RBM33 | 11 SNORD47 | 11 TPD52L3 | 10 ATP5F1 |
| 10 ATP5G2 | 10 DNAJA2 | 10 KCNMB3 | 10 NUAK2 | 10 SCO2 | 10 TTC34 |
| 10 B3GALT5 | 10 DNAJC5G | 10 KHK | 10 OAT | 10 SDC1 | 10 TYMP |
| 10 B3GALTL | 10 DOCK11 | 10 KIAA0586 | 10 OBSL1 | 10 SDHC | 10 UBE2E1 |
| 10 B3GAT2 | 10 DOK3 | 10 KIAA0895L | 10 ODF2L | 10 SDK2 | 10 UBE2I |
| 10 B4GALT1 | 10 DOT1L | 10 KRT17 | 10 OR8H2 | 10 SENP7 | 10 UQCC |
| 10 BCL10 | 10 DPYSL4 | 10 LAMB3 | 10 ORC2 | 10 SERP2 | 10 USH1G |

TABLE 2-continued

Infertility Genes, Ranked

| | | | | | |
|---|---|---|---|---|---|
| 10 BFSP2 | 10 EFCAB5 | 10 LAMC3 | 10 OSTCP1 | 10 SHROOM2 | 10 USP22 |
| 10 BNIP3L | 10 EIF2B3 | 10 LAX1 | 10 OTOP2 | 10 SIRT1 | 10 USP6 |
| 10 BST1 | 10 EIF2C1 | 10 LINC00240 | 10 OTUD6A | 10 SLC16A3 | 10 USP9X |
| 10 BTBD1 | 10 EIF5 | 10 LINC00607 | 10 PACS2 | 10 SLC25A3 | 10 VCX3A |
| 10 C11orf87 | 10 EME2 | 10 LINC00652 | 10 PARVG | 10 SLC25A4 | 10 VENTXP1 |
| 10 C11orf92 | 10 ENOSF1 | 10 LMNB1 | 10 PAWR | 10 SLC25A5 | 10 VKORC1 |
| 10 C11orf93 | 10 EPHB3 | 10 LMO1 | 10 PCTP | 10 SLC34A1 | 10 WBSCR27 |
| 10 C17orf109 | 10 EPS15L1 | 10 LOC100131626 | 10 PDE1B | 10 SLC35A3 | 10 WDR18 |
| 10 C1orf114 | 10 ERBB4 | 10 LOC100216546 | 10 PDE6B | 10 SLC35G1 | 10 WDR76 |
| 10 C1orf170 | 10 ESRP2 | 10 LOC100270804 | 10 PDGFB | 10 SLC38A2 | 10 WDR77 |
| 10 C1orf173 | 10 EXO1 | 10 LOC100287944 | 10 PDYN | 10 SLC38A7 | 10 XPC |
| 10 C1orf53 | 10 EXOC3L1 | 10 LOC100505549 | 10 PDZD7 | 10 SLC44A3 | 10 YIPF4 |
| 10 C3orf37 | 10 F12 | 10 LOC100505622 | 10 PENK | 10 SLC4A2 | 10 ZFAND4 |
| 10 C3orf38 | 10 FAM171B | 10 LOC100506710 | 10 PGPEP1 | 10 SLC7A4 | 10 ZFAT |
| 10 C4BPA | 10 FAM176A | 10 LOC100653515 | 10 PGPEP1L | 10 SLC8A2 | 10 ZIM3 |
| 10 CA6 | 10 FAM182B | 10 LOC255167 | 10 PHC2 | 10 SLMAP | 10 ZNF169 |
| 10 CADPS | 10 FAM59B | 10 LOC375295 | 10 PHLDA2 | 10 SMOC1 | 10 ZNF238 |
| 10 CALML6 | 10 FAM83G | 10 LOC389705 | 10 PIP5K1A | 10 SNORA38 | 10 ZNF300P1 |
| 10 CAND2 | 10 FANCG | 10 LOC646329 | 10 PLEKHG3 | 10 SNRK | 10 ZNF37A |
| 10 CAPN12 | 10 FBN2 | 10 LOC646999 | 10 POM121C | 10 SNRPE | 10 ZNF451 |
| 10 CARD6 | 10 FCER2 | 10 LOC731223 | 10 POSTN | 10 SOS1 | 10 ZNF586 |
| 10 CASR | 10 FIGN | 10 LPP | 10 PPAP2B | 10 SOX10 | 10 ZNF609 |
| 10 CAV3 | 10 FITM1 | 10 LRGUK | 10 PPARA | 10 SP110 | 9 ADCY3 |
| 10 CCDC48 | 10 FLJ34503 | 10 LSM3 | 10 PPP2R5B | 10 SP140 | 9 ADHFE1 |
| 10 CCDC53 | 10 FOLH1 | 10 LTBP2 | 10 PRMT6 | 10 SPAG4 | 9 ANKRD10 |
| 10 CCDC86 | 10 FOXR2 | 10 MAPKAPK3 | 10 PROS1 | 10 SPAM1 | 9 ARHGAP31 |
| 10 CCHCR1 | 10 FUNDC2P2 | 10 MAPRE2 | 10 PRRC2A | 10 SSX6 | 9 ARL4A |
| 10 CCR6 | 10 GAS2L3 | 10 MARCH9 | 10 PSD4 | 10 STARD10 | 9 ATL2 |
| 10 CD247 | 10 GATA4 | 10 MCM10 | 10 PTH2R | 10 STARD5 | 9 ATP9A |
| 10 CDC37 | 10 GATSL3 | 10 MDM1 | 10 PTPN18 | 10 SULT1E1 | 9 ATXN1 |
| 10 CDH4 | 10 GBX1 | 10 MFAP1 | 10 PTPN6 | 10 SUSD3 | 9 BCL11B |
| 10 CDH7 | 10 GDAP1 | 10 MFSD12 | 10 PTPRJ | 10 SUZ12 | 9 BEX2 |
| 10 CDK4 | 10 GDPD2 | 10 MFSD6 | 10 PTPRN | 10 SV2C | 9 BHMT |
| 10 CDK5 | 10 GEMIN8 | 10 MIR3150B | 10 PYCR2 | 10 SYNM | 9 C17orf101 |
| 10 CECR7 | 10 GIPC1 | 10 MIR3615 | 10 RAB11B | 10 SYT3 | 9 C2orf61 |
| 10 CELF2 | 10 GJA3 | 10 MIR548AN | 10 RAB5A | 10 TAF2 | 9 C6orf58 |
| 10 CGGBP1 | 10 GLOD5 | 10 MIR561 | 10 RAD21 | 10 TAGAP | 9 C6orf7 |
| 10 CHRM1 | 10 GLYATL3 | 10 MIR661 | 10 RAD21-AS1 | 10 TARS | 9 C7orf23 |
| 10 CILP | 10 GNA11 | 10 MIR675 | 10 RALGPS2 | 10 TARSL2 | 9 C9orf43 |
| 10 CNGA4 | 10 GPHN | 10 MMRN2 | 10 RAMP2 | 10 TBC1D12 | 9 CACNA1E |
| 10 CNR1 | 10 GPIHBP1 | 10 MPRIP | 10 RAMP2-AS1 | 10 TCF12 | 9 CACNA2D2 |
| 10 COL4A1 | 10 GPR114 | 10 MPZ | 10 RASAL2 | 10 TCF19 | 9 CAD |
| 10 COPS2 | 10 GPR124 | 10 MRPS28 | 10 RASAL2-AS1 | 10 TCFL5 | 9 CANT1 |
| 10 CPNE5 | 10 GPR137B | 10 MRPS34 | 10 RBMY1J | 10 TEAD1 | 9 CD22 |
| 10 CRCP | 10 GPR50 | 10 MSGN1 | 10 REC8 | 10 TFAP2D | 9 CD28 |
| 10 CRX | 10 GRIK5 | 10 MTFMT | 10 REXO2 | 10 TFE3 | 9 CD79B |
| 10 CRYM | 10 GRIN2A | 10 MYO15A | 10 RFWD3 | 10 TGM2 | 9 CDHR5 |
| 10 CRYM-AS1 | 10 GUCY2GP | 10 MYZAP | 10 RFX4 | 10 THRAP3 | 9 CDSN |
| 10 CS | 10 H19 | 10 NDUFB4 | 10 RNF111 | 10 TIMM21 | 9 CHSY1 |
| 10 CT45A6 | 10 HEATR8 | 10 NEK9 | 10 RP9P | 10 TIMM9 | 9 CR2 |
| 10 CTNNBIP1 | 10 HECW2 | 10 NINJ2 | 10 RPA4 | 10 TMEM178B | 9 CRB1 |
| 10 CTR9 | 10 HOXA5 | 10 NIT2 | 10 RPL36A | 10 TMEM74 | 9 CRIM1 |
| 10 CTSW | 10 HS3ST3B1 | 10 NME3 | 10 RPL36A-HNRNPH2 | 10 TNK2 | 9 CYGB |
| 10 CYB561D1 | 10 HSD17B7 | 10 NR1 | | 10 TOR1B | 9 DLG4 |
| 10 CYP26B1 | 10 HTR2C | | 10 RSPH3 | 10 TPCN2 | 9 DMD |
| 10 DAPK3 | 10 IL19 | | 10 RYK | 10 TRAPPC9 | 9 DMRT2 |
| 10 DCSTAMP | 10 IL4R | | 10 S100A10 | 10 TREH | 9 DNMBP |
| 10 DDR1 | 10 INHA | | 10 S100P | 10 TREML2 | 9 DNMT3A |
| 10 DDX27 | 10 IPO11 | | 10 SAGE1 | 10 TRIT1 | 9 EFHA1 |
| 10 DIAPH2 | 10 KAT6A | | 10 SAMD14 | 10 TSPY3 | 9 EHBP1 |
| 10 DLX6-AS1 | 10 KCNA3 | | 10 SCMH1 | 10 TTC24 | 9 EXD3 |
| 10 DNAH17 | 10 KCNAB1 | | 10 SCN9A | 10 TTC33 | 9 FAM134B |
| 9 FGF14 | 9 PPIEL | 8 ARID3B | 8 EML5 | 8 LOC284023 | 8 RPS4X |
| 9 FGF14-AS2 | 9 PPP2CA | 8 ARVCF | 8 ENO4 | 8 LOC338799 | 8 RTDR1 |
| 9 FGF14-IT1 | 9 PRCD | 8 ATG16L2 | 8 EP400 | 8 LOC339822 | 8 SAP25 |
| 9 FGF17 | 9 PRDX2 | 8 ATP10B | 8 EPB41L5 | 8 LOC643401 | 8 SAPCD1 |
| 9 FKBP4 | 9 PRKD2 | 8 ATP5G1 | 8 EPHA7 | 8 LPP-AS2 | 8 SCAI |
| 9 FLYWCH2 | 9 PRPF31 | 8 AXL | 8 ERG | 8 LRCH4 | 8 SCD |
| 9 FSCN1 | 9 PRR23C | 8 BAG2 | 8 EXOC3L2 | 8 LRRC1 | 8 SEPT1 |
| 9 FXYD1 | 9 PSMC1 | 8 BCL2L10 | 8 FAM111A | 8 LYPD6B | 8 SERINC5 |
| 9 FXYD7 | 9 RANBP17 | 8 BCL3 | 8 FAM129A | 8 MACF1 | 8 SET |
| 9 GDNF | 9 RHBDL2 | 8 BHLHB9 | 8 FAM219A | 8 MAGI2-AS3 | 8 SFSWAP |
| 9 GET4 | 9 RNASEH2A | 8 C10orf105 | 8 FAM81A | 8 MAML3 | 8 SLAIN1 |
| 9 GRK6 | 9 RNF157 | 8 C11orf80 | 8 FAM96A | 8 MAP2K3 | 8 SLC12A8 |
| 9 GTSF1 | 9 RNF2 | 8 C12orf23 | 8 FAT3 | 8 MAPK10 | 8 SLC22A20 |
| 9 HEXIM2 | 9 RPTOR | 8 C17orf61 | 8 FBLN1 | 8 METTL14 | 8 SLC6A6 |
| 9 HIBADH | 9 RRP1 | 8 C17orf61-PLSCR3 | 8 FEM1A | 8 MFI2 | 8 SLC7A2 |
| 9 HIST1H3E | 9 RUFY1 | | 8 FLJ43860 | 8 MIR130B | 8 SMAD7 |

TABLE 2-continued

Infertility Genes, Ranked

| | | | | | |
|---|---|---|---|---|---|
| 9 IDS | 9 SARS | 8 C1orf158 | 8 FRMD4B | 8 MIR26A2 | 8 SNCG |
| 9 KIAA1804 | 9 SBF2 | 8 C1orf233 | 8 FTL | 8 MIR301B | 8 SNX1 |
| 9 KIAA2022 | 9 SCT | 8 C1orf52 | 8 FUT4 | 8 MIR4534 | 8 SORL1 |
| 9 KIF1C | 9 SEC23B | 8 C20orf26 | 8 GAL3ST3 | 8 MIR589 | 8 SPATA21 |
| 9 KLHL6 | 9 SEMA5B | 8 C3orf52 | 8 GC | 8 MPC1L | 8 STARD8 |
| 9 KLK1 | 9 SERGEF | 8 C6orf123 | 8 GFPT1 | 8 MRPL9 | 8 TACR3 |
| 9 KLK8 | 9 SHROOM3 | 8 CACNA1C | 8 GLI3 | 8 MRPS9 | 8 TADA3 |
| 9 KLK9 | 9 SLC18A2 | 8 CACNA1F | 8 GLOD4 | 8 MSANTD1 | 8 TCEA2 |
| 9 KRT73 | 9 SLC4A11 | 8 CAMK2B | 8 GMCL1 | 8 NAGLU | 8 TCEB3CL |
| 9 LAMC2 | 9 SLC6A7 | 8 CCDC164 | 8 GNG12 | 8 NAV2 | 8 TEX26-AS1 |
| 9 LAT | 9 SLITRK2 | 8 CCDC22 | 8 GPR85 | 8 NCAPG2 | 8 THOC2 |
| 9 LDHAL6B | 9 SLMO2 | 8 CCDC81 | 8 GPRIN3 | 8 NECAP2 | 8 THRA |
| 9 LEMD2 | 9 SLMO2-ATP5E | 8 CCDC82 | 8 HIST1H2AC | 8 NLGN2 | 8 THSD7A |
| 9 LGI4 | 9 SMARCA5 | 8 CCDC85A | 8 HIST1H2BC | 8 NLRP3 | 8 TLR5 |
| 9 LIMD1 | 9 SNURF | 8 CCM2 | 8 HMOX2 | 8 NOSTRIN | 8 TM4SF19 |
| 9 LOC100132215 | 9 SPATC1 | 8 CCNI2 | 8 HNRNPM | 8 NOX4 | 8 TMCO4 |
| 9 LOC339975 | 9 ST18 | 8 CCSAP | 8 HOTTIP | 8 NPY1R | 8 TMEM105 |
| 9 LOC494141 | 9 SUMO3 | 8 CCT4 | 8 HOXA13 | 8 NTPCR | 8 TMEM135 |
| 9 LOC646278 | 9 TBR1 | 8 CD164 | 8 HOXA6 | 8 NUS1 | 8 TMEM14C |
| 9 LONRF2 | 9 TCIRG1 | 8 CDH10 | 8 IBA57 | 8 OAZ3 | 8 TNFAIP8L3 |
| 9 LTB4R | 9 TCL1B | 8 CDK10 | 8 IL28RA | 8 OPA3 | 8 TNFRSF1B |
| 9 MAGT1 | 9 TFPT | 8 CDON | 8 IL6R | 8 PARD3B | 8 TNFRSF21 |
| 9 MAML2 | 9 TKT | 8 CENPBD1 | 8 INCA1 | 8 PCDHB19P | 8 TOX |
| 9 MAP3K10 | 9 TMC7 | 8 CHAF1B | 8 ING1 | 8 PDLIM3 | 8 TP53I13 |
| 9 MAST1 | 9 TONSL | 8 CHEK1 | 8 INPP5B | 8 PF4V1 | 8 TPCN1 |
| 9 MBTPS2 | 9 TRAF3IP3 | 8 CHKB-CPT1B | 8 IPCEF1 | 8 PFKFB2 | 8 TRAF3IP2 |
| 9 MCOLN1 | 9 TRMT10A | 8 CHSY3 | 8 IRF2BPL | 8 PGAM1 | 8 TRAF3IP2-AS1 |
| 9 MELK | 9 TRPS1 | 8 CIDEB | 8 IRF7 | 8 PGLYRP2 | 8 TRAM1L1 |
| 9 METTL16 | 9 VCL | 8 CLEC2L | 8 JRKL | 8 PHACTR1 | 8 TRIM36 |
| 9 METTL22 | 9 VPS28 | 8 CMAHP | 8 KANK2 | 8 PIP4K2A | 8 TRIM51GP |
| 9 METTL9 | 9 VRK2 | 8 CMTM2 | 8 KAT6B | 8 PLD1 | 8 TRIM61 |
| 9 MGST1 | 9 WNT5B | 8 COL23A1 | 8 KCNE1L | 8 PLEKHH1 | 8 TRIML1 |
| 9 MIR219-2 | 9 WWTR1 | 8 COPE | 8 KCNMA1 | 8 PLIN4 | 8 TRPC3 |
| 9 MIR2964A | 9 ZBTB17 | 8 CPT1B | 8 KIAA0146 | 8 PMF1-BGLAP | 8 TSPAN10 |
| 9 MIR320E | 9 ZC3HC1 | 8 CRELD2 | 8 KIF1A | 8 POLR2I | 8 TSPAN11 |
| 9 MIR371A | 9 ZNF268 | 8 CRISPLD2 | 8 KRT85 | 8 PPP2R2C | 8 UBE2D2 |
| 9 MIR550A1 | 9 ZNF358 | 8 CRNKL1 | 8 KTN1 | 8 PPP3CC | 8 UCN |
| 9 MN1 | 9 ZNF575 | 8 CSF2 | 8 KTN1-AS1 | 8 PRKCZ | 8 UMODL1 |
| 9 MTTP | 9 ZNRF2 | 8 CTDSP2 | 8 LATS2 | 8 PRKDC | 8 UNC13B |
| 9 MUC2 | 8 ABHD14A | 8 DAB2 | 8 LEF1-AS1 | 8 PROSAPIP1 | 8 VAMP8 |
| 9 MYO1E | 8 ABHD14A-ACY1 | 8 DCHS1 | 8 LEFTY1 | 8 PSKH2 | 8 VASH1 |
| 9 MYO1G | | 8 DDX11L2 | 8 LINC00441 | 8 QRFP | 8 VHL |
| 9 NDST4 | 8 ABHD14B | 8 DDX19B | 8 LINC00620 | 8 RAB36 | 8 VPS13B |
| 9 NDUFA12 | 8 ACVR1B | 8 DDX49 | 8 LINC00640 | 8 RASD1 | 8 VSIG4 |
| 9 NDUFS8 | 8 ADAM30 | 8 DGUOK | 8 LINC00643 | 8 RCOR2 | 8 VSTM5 |
| 9 NPSR1 | 8 ADAMTS19 | 8 DISP2 | 8 LIPH | 8 RHOBTB1 | 8 WDR13 |
| 9 OSM | 8 ADCY2 | 8 DLG5 | 8 LOC100144603 | 8 RHOF | 8 WWP2 |
| 9 OTX1 | 8 ADRA2A | 8 DNAI1 | 8 LOC100631378 | 8 RIT2 | 8 YOD1 |
| 9 PASK | 8 AFG3L1P | 8 DNMBP-AS1 | 8 LOC100861402 | 8 RNMTL1 | 8 ZNF267 |
| 9 PGGT1B | 8 AGBL1 | 8 EBAG9 | 8 LOC100996307 | 8 RNPEP | 8 ZNF48 |
| 9 PKM | 8 ALS2CR11 | 8 EBF2 | 8 LOC254312 | 8 RPL10L | 8 ZNF503 |
| 9 POLE3 | 8 AMN | 8 EHBP1L1 | 8 LOC257358 | 8 RPL31 | 8 ZNF503-AS2 |
| 8 ZNF516 | 7 CD164L2 | 7 FECH | 7 KIAA1984-AS1 | 7 MTMR3 | 7 RUSC1-AS1 |
| 8 ZNF556 | 7 CD36 | 7 FEV | 7 KLHL15 | 7 MX2 | 7 S100A2 |
| 8 ZNF564 | 7 CD4 | 7 FGD2 | 7 LAMP3 | 7 MXRA5 | 7 S100Z |
| 8 ZNF679 | 7 CDC42EP1 | 7 FLI1 | 7 LCN10 | 7 MYO5C | 7 SCRT2 |
| 8 ZNF697 | 7 CDH9 | 7 FLJ33534 | 7 LDHC | 7 NACAP1 | 7 SDF2 |
| 8 ZSCAN20 | 7 CDHR1 | 7 FLJ36000 | 7 LEF1 | 7 NAGK | 7 SEC61A2 |
| 7 ABCB6 | 7 CDK18 | 7 FLJ46257 | 7 LIG4 | 7 NAPEPLD | 7 SEMA4G |
| 7 ABHD13 | 7 CEP104 | 7 FLRT3 | 7 LIN54 | 7 NCOA4 | 7 SFXN3 |
| 7 ACP1 | 7 CERK | 7 FN3K | 7 LINC00092 | 7 NDUFB10 | 7 SGK2 |
| 7 ADAMTS1 | 7 CHL1 | 7 FOXF1 | 7 LINC00200 | 7 NLRC4 | 7 SGSM3 |
| 7 ADCK5 | 7 CHST9 | 7 FOXF1-AS1 | 7 LINC00642 | 7 NLRP1 | 7 SH3YL1 |
| 7 AIF1 | 7 CHURC1 | 7 FOXI1 | 7 LMX1B | 7 NPAP1 | 7 SHISA9 |
| 7 ALDH5A1 | 7 CIAO1 | 7 FTCD | 7 LOC100128593 | 7 NPM2 | 7 SIAH3 |
| 7 ALOX15P1 | 7 CLDN15 | 7 FUCA2 | 7 LOC100129138 | 7 NPR2 | 7 SIGLEC17P |
| 7 ALS2CL | 7 CLPSL2 | 7 FZD8 | 7 LOC100130950 | 7 NRG1 | 7 SIX5 |
| 7 AMZ1 | 7 COL4A5 | 7 G6PD | 7 LOC100130992 | 7 NRP1 | 7 SLC10A4 |
| 7 ANKLE1 | 7 COL4A6 | 7 GALNTL2 | 7 LOC100505738 | 7 NRTN | 7 SLC16A14 |
| 7 ANKLE2 | 7 CPA1 | 7 GDE1 | 7 LOC100506178 | 7 NRXN3 | 7 SLC26A9 |
| 7 ANKRD44 | 7 CPT1A | 7 GDPD5 | 7 LOC150568 | 7 NSA2 | 7 SLC28A2 |
| 7 AP2A2 | 7 CRIP2 | 7 GFI1 | 7 LOC339529 | 7 NSMCE2 | 7 SLC35C2 |
| 7 APOA2 | 7 CROCC | 7 GFM2 | 7 LOC340357 | 7 NTNG1 | 7 SLC37A4 |
| 7 AQP1 | 7 CRYBA4 | 7 GINS2 | 7 LOC374443 | 7 NUP210 | 7 SLC39A10 |
| 7 ARPP21 | 7 CRYBB1 | 7 GLRX2 | 7 LOC400685 | 7 NUP210L | 7 SLC9B2 |
| 7 ASNS | 7 CRYBG3 | 7 GLT25D1 | 7 LOC729506 | 7 NXT2 | 7 SMCR7 |
| 7 ASZ1 | 7 CSF3 | 7 GMFG | 7 LRRC4 | 7 OGT | 7 SMPD3 |
| 7 ATG9A | 7 CXCL10 | 7 GNB4 | 7 LSM6 | 7 OSR1 | 7 SMURF1 |

TABLE 2-continued

Infertility Genes, Ranked

| | | | | | |
|---|---|---|---|---|---|
| 7 ATL3 | 7 CXCR2 | 7 GPC5 | 7 LSP1 | 7 OVOL1 | 7 SND1 |
| 7 ATP1B4 | 7 CXCR5 | 7 GPLD1 | 7 LTB4R2 | 7 PAX7 | 7 SNHG12 |
| 7 AZU1 | 7 CYSTM1 | 7 GPR56 | 7 LTBP1 | 7 PCDHB5 | 7 SNORA16A |
| 7 BICD1 | 7 DACT2 | 7 GPR78 | 7 LYN | 7 PHF20 | 7 SOCS7 |
| 7 BIRC5 | 7 DBT | 7 GRID2IP | 7 LYNX1 | 7 PHLDB3 | 7 SPHK1 |
| 7 BRD2 | 7 DCAF12L1 | 7 GSC | 7 MADCAM1 | 7 PIK3R2 | 7 SPIB |
| 7 BTNL2 | 7 DCTPP1 | 7 GSTCD | 7 MAEA | 7 PIPSL | 7 SPIN2A |
| 7 C10orf107 | 7 DCUN1D4 | 7 GUCA2A | 7 MAGEB18 | 7 PITPNC1 | 7 SPNS3 |
| 7 C10orf114 | 7 DDX50 | 7 GUCY1B3 | 7 MAGI1 | 7 PNKD | 7 SPTBN2 |
| 7 C11orf58 | 7 DENND2D | 7 GUCY2C | 7 MANEAL | 7 PNPLA1 | 7 SSPO |
| 7 C11orf63 | 7 DFFB | 7 H6PD | 7 MARS | 7 PPAN-P2RY11 | 7 SSTR4 |
| 7 C16orf11 | 7 DGKZ | 7 HAUS4 | 7 MED31 | 7 PPP1R16B | 7 ST8SIA6 |
| 7 C17orf28 | 7 DHX15 | 7 HAVCR2 | 7 MEF2B | 7 PPP1R1B | 7 STARD3 |
| 7 C19orf55 | 7 DNASE1L1 | 7 HDGFRP2 | 7 MEF2BNB-MEF2B | 7 PPP1R7 | 7 STEAP3 |
| 7 C19orf59 | 7 DUPD1 | 7 HEY2 | 7 METTL5 | 7 PRDM8 | 7 SUN1 |
| 7 C19orf6 | 7 DUSP6 | 7 HIC2 | 7 MFHAS1 | 7 PRSS57 | 7 SUPT6H |
| 7 C1QTNF2 | 7 ECE2 | 7 HMSD | 7 MFI2-AS1 | 7 PSMB7 | 7 SYBU |
| 7 C1QTNF9 | 7 EFHC2 | 7 HOXA10 | 7 MGST2 | 7 PSMD4 | 7 TAF8 |
| 7 C22orf32 | 7 EIF3D | 7 HOXA10-HOXA9 | 7 MICAL3 | 7 PSORS1C3 | 7 TAOK3 |
| 7 C3orf55 | 7 EIF4G1 | | 7 MICALL2 | 7 PTDSS1 | 7 TAZ |
| 7 C4orf36 | 7 ELK4 | 7 HOXB5 | 7 MIR1276 | 7 PTK2B | 7 TBC1D2B |
| 7 C6orf195 | 7 ELMO1 | 7 HSBP1 | 7 MIR143 | 7 PTPN21 | 7 TBC1D9 |
| 7 C8orf48 | 7 ELMO3 | 7 HSPA12B | 7 MIR1915 | 7 PTPN23 | 7 TBL1X |
| 7 CA12 | 7 EMB | 7 HSPA2 | 7 MIR3136 | 7 PUS10 | 7 TCL1A |
| 7 CALB1 | 7 EML1 | 7 IFFO2 | 7 MIR3545 | 7 PUS7 | 7 TEX26 |
| 7 CALCB | 7 EPHA1 | 7 IKBKG | 7 MIR4458 | 7 PYY | 7 TEX30 |
| 7 CALR | 7 EPHA10 | 7 IL12RB1 | 7 MIR4520B | 7 QSER1 | 7 TFDP2 |
| 7 CAMK2G | 7 EPN1 | 7 IL1RN | 7 MIR4707 | 7 RABL6 | 7 THBS1 |
| 7 CAPN8 | 7 ERI1 | 7 IL20RA | 7 MIR4801 | 7 RAVER2 | 7 TMBIM4 |
| 7 CARD10 | 7 ESYT2 | 7 IL2RB | 7 MIR5187 | 7 RCSD1 | 7 TMEM101 |
| 7 CASKIN1 | 7 EXOC3L4 | 7 INS-IGF2 | 7 MIR608 | 7 RGR | 7 TMEM127 |
| 7 CASP10 | 7 EXOSC7 | 7 INTS12 | 7 MIR609 | 7 RLF | 7 TMEM242 |
| 7 CCDC136 | 7 EXOSC9 | 7 IRF2BP1 | 7 MKI67IP | 7 RLIM | 7 TMEM26 |
| 7 CCDC142 | 7 EYA3 | 7 ITGA3 | 7 MLLT1 | 7 RLN1 | 7 TMEM30B |
| 7 CCDC144NL | 7 FAM109B | 7 KCNC2 | 7 MLXIP | 7 RNF212 | 7 TMF1 |
| 7 CCDC85C | 7 FAM173B | 7 KCTD12 | 7 MORF4L1 | 7 RNF6 | 7 TNF |
| 7 CCNC | 7 FAM18B2 | 7 KCTD2 | 7 MPDU1 | 7 ROBO4 | 7 TNFRSF4 |
| 7 CCND3 | 7 FAM18B2-CDRT4 | 7 KDM5C | 7 MRPL53 | 7 RPL3L | 7 TNS1 |
| 7 CCNL1 | | 7 KIAA0664 | 7 MRPS14 | 7 RRAGA | 7 TOMM40L |
| 7 CCP110 | 7 FAM217B | 7 KIAA1239 | 7 MS4A13 | 7 RRP15 | 7 TOR4A |
| 7 CCR1 | 7 FAM8A1 | 7 KIAA1715 | 7 MTMR2 | 7 RSAD2 | 7 TP53I11 |
| 7 CCT5 | 7 FAP | 7 KIAA1984 | | 7 RUSC1 | 7 TPBGL |
| 7 TPM1 | 6 AXDND1 | 6 EBF3 | 6 KCNK9 | 6 MTHFSD | 6 SLC15A4 |
| 7 TPT1-AS1 | 6 B3GNT9 | 6 EEFSEC | 6 KCNS3 | 6 MYLK | 6 SLC22A23 |
| 7 TRAF4 | 6 BBX | 6 EFEMP2 | 6 KIAA1161 | 6 NALCN | 6 SLC25A44 |
| 7 TRAPPC5 | 6 BCL6B | 6 EFS | 6 KIAA1614 | 6 NAV1 | 6 SLC25A5 |
| 7 TRIM68 | 6 BHLHE41 | 6 ELOVL3 | 6 KIAA1671 | 6 NCAPH | 6 SLC25A5-AS1 |
| 7 TSPAN16 | 6 BMPER | 6 ENTPD3 | 6 KIAA1755 | 6 NDE1 | 6 SLC27A5 |
| 7 TSPYL2 | 6 BRF2 | 6 EPAS1 | 6 KIF2A | 6 NEK8 | 6 SLC2A6 |
| 7 TTC5 | 6 BTBD18 | 6 EPHB1 | 6 KLF16 | 6 NKG7 | 6 SLC30A1 |
| 7 TUB | 6 BTBD8 | 6 EPN3 | 6 KLHL2 | 6 NME1-NME2 | 6 SLC30A10 |
| 7 TYROBP | 6 C10orf131 | 6 ERCC1 | 6 KPNA6 | 6 NME2 | 6 SLC30A5 |
| 7 U2AF2 | 6 C11orf40 | 6 ERCC4 | 6 KRCC1 | 6 NME6 | 6 SLC45A4 |
| 7 UBR3 | 6 C17orf107 | 6 EXOC4 | 6 KRI1 | 6 NMS | 6 SLC7A10 |
| 7 UMOD | 6 C1orf105 | 6 EXOSC4 | 6 KRT15 | 6 NPHS2 | 6 SMURF2 |
| 7 UNC119B | 6 C1orf210 | 6 FAM111B | 6 LETM1 | 6 NPY5R | 6 SNORD105 |
| 7 UPK1B | 6 C20orf166 | 6 FAM129B | 6 LGALS2 | 6 NUCKS1 | 6 SNORD105B |
| 7 UVSSA | 6 C22orf26 | 6 FAM134A | 6 LGALS3BP | 6 O3FAR1 | 6 SOWAHD |
| 7 VAT1 | 6 C5orf24 | 6 FAM151B | 6 LGMN | 6 OCLN | 6 SOX15 |
| 7 VAT1L | 6 C5orf27 | 6 FAM155B | 6 LIG3 | 6 OLFML2B | 6 SOX18 |
| 7 VOPP1 | 6 C8orf82 | 6 FAM169A | 6 LILRA6 | 6 OR10C1 | 6 SPATS2L |
| 7 VWA5A | 6 CABIN1 | 6 FAM175B | 6 LILRB3 | 6 PAQR9 | 6 SRRM3 |
| 7 WBSCR17 | 6 CACNA1B | 6 FAM193B | 6 LIPE | 6 PARP6 | 6 SSTR5-AS1 |
| 7 WDR96 | 6 CAPZB | 6 FAM19A5 | 6 LMTK2 | 6 PCDHB2 | 6 STXBP5-AS1 |
| 7 WFDC5 | 6 CASS4 | 6 FAM219B | 6 LNPEP | 6 PCNXL3 | 6 TARBP1 |
| 7 WISP3 | 6 CBLC | 6 FAM41C | 6 LOC100505933 | 6 PCYOX1 | 6 TBX1 |
| 7 ZBTB9 | 6 CCDC144C | 6 FAM82A1 | 6 LOC100652739 | 6 PDF | 6 TDRD5 |
| 7 ZDHHC17 | 6 CCDC151 | 6 FAM89A | 6 LOC150381 | 6 PDLIM5 | 6 THBS2 |
| 7 ZDHHC3 | 6 CCDC71 | 6 FAM98B | 6 LOC256880 | 6 PDZD4 | 6 THSD1 |
| 7 ZFP36L1 | 6 CCND1 | 6 FARSA | 6 LOC344887 | 6 PEA15 | 6 THUMPD1 |
| 7 ZNF284 | 6 CCR2 | 6 FGR | 6 LOC387647 | 6 PEX11G | 6 TIAM2 |
| 7 ZNF343 | 6 CD180 | 6 FLJ30679 | 6 LOC400927 | 6 PFKFB4 | 6 TINAGL1 |
| 7 ZNF350 | 6 CD300A | 6 FLJ37453 | 6 LOC728558 | 6 PIGC | 6 TM4SF1 |
| 7 ZNF37BP | 6 CD320 | 6 FOXE3 | 6 LOC728724 | 6 PIGG | 6 TM4SF5 |
| 7 ZNF398 | 6 CD3EAP | 6 FUK | 6 LRFN4 | 6 PILRB | 6 TMEM120B |
| 7 ZNF490 | 6 CD79A | 6 FUT6 | 6 LRIT3 | 6 PIM2 | 6 TMEM27 |
| 7 ZNF512B | 6 CDC26 | 6 FXC1 | 6 LRP11 | 6 PKDCC | 6 TMEM33 |
| 7 ZNF574 | 6 CDC42SE1 | 6 GAA | 6 LRRC15 | 6 PKNOX2 | 6 TMX2-CTNND1 |

TABLE 2-continued

Infertility Genes, Ranked

| | | | | | |
|---|---|---|---|---|---|
| 7 ZNF619 | 6 CDC5L | 6 GABBR2 | 6 LRRC24 | 6 PMEPA1 | 6 TNFRSF10C |
| 7 ZNF643 | 6 CDKAL1 | 6 GALNTL4 | 6 LRRC25 | 6 PMF1 | 6 TNNI2 |
| 7 ZNF71 | 6 CDKN2D | 6 GCNT2 | 6 LRRC33 | 6 PNLIPRP2 | 6 TOM1 |
| 7 ZNF766 | 6 CEP112 | 6 GDF10 | 6 LTK | 6 POM121 | 6 TPI1P2 |
| 7 ZNF839 | 6 CHRNE | 6 GGT1 | 6 MAB21L3 | 6 PPAN | 6 TRDMT1 |
| 7 ZRANB2 | 6 CIB3 | 6 GIMAP8 | 6 MAGEA8 | 6 PPFIA4 | 6 TRIM22 |
| 7 ZRANB2-AS2 | 6 CKAP2L | 6 GNA12 | 6 MAGEB10 | 6 PPP1R3D | 6 TRIM34 |
| 6 AAMP | 6 CLDND2 | 6 GNA13 | 6 MAL2 | 6 PPP5C | 6 TRIM6-TRIM34 |
| 6 ACP6 | 6 CNIH3 | 6 GPR125 | 6 MAPK1 | 6 PRPF4 | 6 TRPA1 |
| 6 ACTN2 | 6 COG8 | 6 GPT2 | 6 MAPK8IP2 | 6 PRR15 | 6 TTLL4 |
| 6 ADAM12 | 6 COMP | 6 GRAP | 6 MAPT | 6 RAD9B | 6 UPP1 |
| 6 ADAM22 | 6 COX7B | 6 GTDC2 | 6 MAPT-AS1 | 6 RAMP1 | 6 VAX2 |
| 6 ADAM33 | 6 CPNE4 | 6 GUCY1A2 | 6 MARCH11 | 6 RARRES1 | 6 VPS29 |
| 6 ADCYAP1R1 | 6 CPSF6 | 6 HADHA | 6 MBNL2 | 6 RASD2 | 6 WDR12 |
| 6 ADD3 | 6 CR1 | 6 HADHB | 6 MED7 | 6 RASEF | 6 WDR72 |
| 6 AGTPBP1 | 6 CREB5 | 6 HENMT1 | 6 MEDAG | 6 RASGRF1 | 6 WHSC1L1 |
| 6 AGXT | 6 CRELD1 | 6 HERC2P10 | 6 MEG8 | 6 RBBP6 | 6 WWC2 |
| 6 ALDH3B2 | 6 CRLF1 | 6 HIF1A-AS2 | 6 METTL21C | 6 RBM18 | 6 YY1AP1 |
| 6 ALS2CR8 | 6 CRYBA2 | 6 HLA-DRB5 | 6 MFSD1 | 6 RFPL3 | 6 ZAK |
| 6 ANGPTL6 | 6 CTNND2 | 6 HLA-F-AS1 | 6 MINA | 6 RGS10 | 6 ZAP70 |
| 6 ANKRD39 | 6 CXCR1 | 6 HOXA11-AS | 6 MIR1182 | 6 RGS5 | 6 ZBTB40 |
| 6 ANXA1 | 6 CYC1 | 6 HSD17B7P2 | 6 MIR133A2 | 6 RHBDD2 | 6 ZBTB45 |
| 6 APOL1 | 6 CYLD | 6 HSD3B7 | 6 MIR195 | 6 RHOD | 6 ZC3H7A |
| 6 APPL2 | 6 CYP2D6 | 6 HVCN1 | 6 MIR4285 | 6 RNF112 | 6 ZCCHC8 |
| 6 ARF1 | 6 DAAM2 | 6 IL8 | 6 MIR497 | 6 RPL5 | 6 ZDHHC19 |
| 6 ARFIP2 | 6 DAP3 | 6 INIP | 6 MIR497HG | 6 RPS15A | 6 ZIK1 |
| 6 ARHGAP18 | 6 DDX11L10 | 6 INPPL1 | 6 MIR505 | 6 SCGB2A2 | 6 ZNF135 |
| 6 ARHGAP42 | 6 DDX11L9 | 6 IQGAP1 | 6 MIR802 | 6 SDC2 | 6 ZNF281 |
| 6 ARHGAP5 | 6 DLGAP3 | 6 IRF4 | 6 MLLT11 | 6 SEPHS2 | 6 ZNF330 |
| 6 ARL9 | 6 DNAJB14 | 6 KCNJ1 | 6 MOCOS | 6 SHCBP1L | 6 ZNF416 |
| 6 ARSG | 6 DNAJB2 | 6 KCNJ16 | 6 MPP3 | 6 SIPA1L3 | 6 ZNF487P |
| 6 ATP6V1E2 | 6 DYRK4 | 6 KCNK10 | 6 MRRF | 6 SIRPB1 | 6 ZNF594 |
| 6 ZNF605 | 5 EGR1 | 5 MGAT5B | 5 STAT5B | 4 C14orf105 | 4 HS6ST3 |
| 6 ZNF708 | 5 EIF3M | 5 MIER1 | 5 STK16 | 4 C16orf55 | 4 HSD52 |
| 6 ZNF790 | 5 EIF4E3 | 5 MIR137HG | 5 SULF1 | 4 C17orf59 | 4 HSF1 |
| 6 ZSWIM6 | 5 EN2 | 5 MIR3196 | 5 SUN3 | 4 C1QL3 | 4 HSPB2-C11orf52 |
| 6 ZUFSP | 5 EOGT | 5 MIR369 | 5 SWAP70 | 4 C21orf128 | 4 HSPG2 |
| 5 ABCF3 | 5 ESD | 5 MIR409 | 5 TAF7L | 4 C22orf39 | 4 HTRA4 |
| 5 ABCG4 | 5 EYA4 | 5 MIR410 | 5 TAGLN | 4 C2orf40 | 4 HUS1 |
| 5 ACVR1C | 5 FAM118A | 5 MIR412 | 5 TECPR1 | 4 C2orf82 | 4 ICMT |
| 5 ADAM11 | 5 FAM165B | 5 MIR541 | 5 TGFB1I1 | 4 C6orf48 | 4 ISCA1 |
| 5 ADAMTS20 | 5 FAM22D | 5 MIR656 | 5 THAP11 | 4 C7orf55 | 4 ISG15 |
| 5 ALPL | 5 FAM46C | 5 MRGPRF | 5 THNSL2 | 4 C8orf56 | 4 KCNH6 |
| 5 ANGPTL2 | 5 FAM49A | 5 MRPL23-AS1 | 5 TMEM163 | 4 C9orf156 | 4 KCNJ11 |
| 5 AP2B1 | 5 FANCA | 5 MUC5B | 5 TMEM184A | 4 CACNA1I | 4 KCNQ5 |
| 5 ARF4 | 5 FBXL20 | 5 NADK | 5 TMEM184B | 4 CALN1 | 4 KIAA1324 |
| 5 ARSD | 5 FUT3 | 5 NDUFB6 | 5 TMEM45A | 4 CARTPT | 4 KIAA1586 |
| 5 ARSJ | 5 GAS2L1 | 5 NEK7 | 5 TMPRSS4 | 4 CCDC173 | 4 KIAA1751 |
| 5 ASB10 | 5 GLB1L | 5 NEXN | 5 TMX3 | 4 CCDC83 | 4 KIF1B |
| 5 ASGR2 | 5 GLT8D2 | 5 NKAIN4 | 5 TNIK | 4 CD200R1 | 4 KIF21B |
| 5 BATF2 | 5 GPN1 | 5 NPFFR1 | 5 TOP1 | 4 CD3G | 4 KL |
| 5 BGLAP | 5 GPR89B | 5 NPRL3 | 5 TRIM31 | 4 CDH15 | 4 KRT25 |
| 5 BHLHE40 | 5 GTF2A1L | 5 NRK | 5 TRPC2 | 4 CEACAM4 | 4 LINC00202 |
| 5 BIRC7 | 5 HAMP | 5 OLA1 | 5 TRRAP | 4 CELF4 | 4 LINC00469 |
| 5 BMP7 | 5 HCFC1 | 5 OPA1 | 5 TSPAN4 | 4 CHD4 | 4 LMNA |
| 5 BTBD17 | 5 HCG4 | 5 OXLD1 | 5 TSPAN9 | 4 CLEC14A | 4 LOC100131635 |
| 5 C12orf44 | 5 HIF3A | 5 P2RX5 | 5 TYW5 | 4 CMTM6 | 4 LOC202181 |
| 5 C15orf52 | 5 HINFP | 5 P2RX5-TAX1BP3 | 5 UBXN1 | 4 COL8A1 | 4 LOC400558 |
| 5 C19orf26 | 5 HMGA1 | | 5 UNC13D | 4 CORO2A | 4 LOC729732 |
| 5 C19orf77 | 5 HNF1A-AS1 | 5 PAK7 | 5 USP10 | 4 CWC22 | 4 LOH12CR2 |
| 5 C1QL4 | 5 HOMER2 | 5 PARP12 | 5 USP13 | 4 DBC1 | 4 LRP4 |
| 5 C2orf47 | 5 HPS1 | 5 PBOV1 | 5 VDAC3 | 4 DEGS2 | 4 LRRC27 |
| 5 C5orf4 | 5 IGDCC4 | 5 PCDHB10 | 5 WDR52 | 4 DEXI | 4 LRRC40 |
| 5 C5orf45 | 5 IGF2 | 5 PCSK6 | 5 WDR78 | 4 DGAT1 | 4 LRRC6 |
| 5 C7orf55-LUC7L2 | 5 IKBKE | 5 PDCD1 | 5 WTAP | 4 DHX37 | 4 MAD2L2 |
| 5 C7orf57 | 5 IL17C | 5 PHGDH | 5 XKR6 | 4 DMPK | 4 MAPK6 |
| 5 C9orf123 | 5 IMPACT | 5 PIGA | 5 ZCCHC14 | 4 DNAH11 | 4 MAPT-IT1 |
| 5 C9orf3 | 5 IQCA1 | 5 PIN1P1 | 5 ZFC3H1 | 4 DNAJC13 | 4 MDH2 |
| 5 CACNB3 | 5 KCNC4 | 5 PKIG | 5 ZNF554 | 4 DOC2GP | 4 MIR141 |
| 5 CACNB4 | 5 KCNN4 | 5 PLEKHD1 | 5 ZNF645 | 4 DPCR1 | 4 MIR200C |
| 5 CACNG4 | 5 KIAA1210 | 5 POLRMT | 5 ZNF714 | 4 EGR2 | 4 MIR21 |
| 5 CCDC102B | 5 KIAA1244 | 5 PPP1R3G | 4 ABCA1 | 4 ELFN2 | 4 MIR4284 |
| 5 CCDC121 | 5 KIF25 | 5 PRDM2 | 4 ABO | 4 EMID2 | 4 MIR4316 |
| 5 CCDC137 | 5 KLHL26 | 5 PSRC1 | 4 ADCY5 | 4 FAM131C | 4 MIR519D |
| 5 CDH24 | 5 LCP1 | 5 RALGPS1 | 4 ADORA2A | 4 FAM204A | 4 MIR548G |
| 5 CDKN2C | 5 LDB3 | 5 RAN | 4 AMFR | 4 FAM228A | 4 MKLN1 |
| 5 CDX2 | 5 LIMA1 | 5 RAPGEF1 | 4 ANKH | 4 FAM35B | 4 MPP2 |
| | 5 LINC00313 | 5 RHOJ | 4 ANKRD22 | 4 FAM60A | |

TABLE 2-continued

Infertility Genes, Ranked

| | | | | | |
|---|---|---|---|---|---|
| 5 CENPT | 5 LITAF | 5 RNU6-66 | 4 ANO10 | 4 FANK1 | 4 MREG |
| 5 CHRD | 5 LOC100129924 | 5 RPS19BP1 | 4 ANTXR1 | 4 FBXL4 | 4 MTNR1A |
| 5 CHRM5 | 5 LOC100652768 | 5 SCNN1G | 4 AP2S1 | 4 FGF1 | 4 MYO5A |
| 5 CHUK | 5 LOC151171 | 5 SELPLG | 4 ARHGAP29 | 4 FGF9 | 4 NDUFAF5 |
| 5 CLASRP | 5 LOC221122 | 5 SEMA3E | 4 ARHGEF16 | 4 FLOT2 | 4 NEURL4 |
| 5 CMPK1 | 5 LOC554223 | 5 SFMBT2 | 4 ARHGEF3 | 4 FOXC2 | 4 NME7 |
| 5 CNKSR3 | 5 LOC649395 | 5 SFRP2 | 4 ASB13 | 4 FUT2 | 4 NPPA-AS1 |
| 5 COMMD3 | 5 LOC730101 | 5 SGCZ | 4 ASIC2 | 4 GFRA3 | 4 NPTXR |
| 5 COMMD3-BMI1 | 5 LOH12CR1 | 5 SH3GL1 | 4 ATN1 | 4 GIMAP5 | 4 NWD1 |
| 5 CSRP2 | 5 LONRF1 | 5 SIGLEC5 | 4 ATP1A4 | 4 GP1BB | 4 NXF3 |
| 5 CWF19L1 | 5 LPGAT1 | 5 SIRT6 | 4 ATP7A | 4 GPC1 | 4 P2RX1 |
| 5 CYP1B1 | 5 LRRN4 | 5 SKAP2 | 4 AURKB | 4 GPR162 | 4 PALLD |
| 5 DCLK1 | 5 LSP1P3 | 5 SLC10A7 | 4 BAALC | 4 GPS2 | 4 PARP10 |
| 5 DDO | 5 LUC7L | 5 SLC12A7 | 4 BAI1 | 4 GRB14 | 4 PCBP1 |
| 5 DGKG | 5 LUC7L2 | 5 SLC1A4 | 4 BARHL2 | 4 GRINA | 4 PCBP1-AS1 |
| 5 DLGAP1-AS3 | 5 LY75 | 5 SLC26A7 | 4 BCAM | 4 GUSBP2 | 4 PCDH11X |
| 5 DNAH8 | 5 LY75-CD302 | 5 SLCO1C1 | 4 BEGAIN | 4 HERC1 | 4 PCDH15 |
| 5 DRAXIN | 5 MAP1LC3A | 5 SLFN13 | 4 BLZF1 | 4 HES6 | 4 PCGF6 |
| 5 DSCAM | 5 MEF2D | 5 SOX7 | 4 BRD9 | 4 HIP1R | 4 PCSK9 |
| 5 DSCR9 | 5 MEIS3 | 5 SPICE1 | 4 C10orf91 | 4 HNF1B | 4 PEAR1 |
| 5 DUSP28 | 5 MERTK | 5 SRPK2 | 4 C11orf52 | 4 HOXB-AS5 | 4 PGAM2 |
| 5 E2F2 | 5 MGAT3 | 5 SSX1 | 4 C12orf60 | 4 HS1BP3 | 4 PHOSPHO2 |
| 4 PHOSPHO2-KLHL23 | 4 TPD52 | 3 DGKH | 3 MIR3684 | 3 SYNGR1 | 2 ACOXL |
| 4 PLA2G4A | 4 TRIM40 | 3 DIEXF | 3 MIR378D2 | 3 SYNJ2BP | 2 ACPP |
| 4 PLEKHN1 | 4 TRIM59 | 3 DMTF1 | 3 MIR517A | 3 TACC2 | 2 ACPT |
| 4 PLXNA4 | 4 TRIP13 | 3 DOCK1 | 3 MIR518C | 3 TAS1R3 | 2 ACRBP |
| 4 PLXNB2 | 4 TRMT13 | 3 DPY19L2P3 | 3 MIR524 | 3 TBC1D7 | 2 ACSL1 |
| 4 PMVK | 4 TSPAN1 | 3 DSG3 | 3 MIR550A3 | 3 TET2 | 2 ACTL8 |
| 4 PP14571 | 4 TSPAN2 | 3 DZANK1 | 3 MMP21 | 3 TGIF1 | 2 ACTRT3 |
| 4 PPP1R14A | 4 UBE4B | 3 ECSIT | 3 MPPED2 | 3 THADA | 2 ACVR2B |
| 4 PPP4R1L | 4 UPK3B | 3 EGLN2 | 3 MRPL15 | 3 THBS3 | 2 ACVR2B-AS1 |
| 4 PRNT | 4 UTF1 | 3 EIF4A2 | 3 MRPL39 | 3 TIGD3 | 2 ACVRL1 |
| 4 PRSS21 | 4 VANGL2 | 3 EIF4H | 3 MS4A15 | 3 TMEM120A | 2 ACYP1 |
| 4 PRSS33 | 4 VMP1 | 3 FAM101B | 3 MTMR6 | 3 TMEM132D | 2 ADAM10 |
| 4 PTAR1 | 4 WBP11 | 3 FAM124A | 3 MTX1 | 3 TMEM154 | 2 ADAM15 |
| 4 PTGES | 4 ZFR | 3 FAM162B | 3 MUL1 | 3 TMIE | 2 ADAMTS18 |
| 4 RAB22A | 4 ZIC5 | 3 FFAR2 | 3 MYBPC3 | 3 TNFAIP8L2 | 2 ADAMTS5 |
| 4 RAB3A | 4 ZKSCAN4 | 3 FOLR3 | 3 MYCBPAP | 3 TRAK1 | 2 ADAMTSL1 |
| 4 RAB9B | 4 ZNF202 | 3 FRMD6-AS2 | 3 MYF5 | 3 TRPV1 | 2 ADAMTSL5 |
| 4 RABEP1 | 4 ZNF280C | 3 FUOM | 3 MYO10 | 3 TUBA4A | 2 ADCY4 |
| 4 RASGRP2 | 4 ZNF57 | 3 GIPC3 | 3 NAA60 | 3 TUBA4B | 2 ADD2 |
| 4 RNF150 | 4 ZNF687 | 3 GMDS | 3 NAMPT | 3 UBE2D1 | 2 ADNP |
| 4 RNFT2 | 4 ZNRF1 | 3 GRIA3 | 3 NBPF9 | 3 UGT8 | 2 ADORA2B |
| 4 RPN1 | 4 ZYG11A | 3 GRIA4 | 3 NDFIP1 | 3 USP3 | 2 ADRA1B |
| 4 RTKN | 3 ABAT | 3 HAS2 | 3 NHLH2 | 3 UTP14A | 2 ADRA1D |
| 4 RTP2 | 3 ACAD9 | 3 HAS2-AS1 | 3 NKAP | 3 UTY | 2 AEBP2 |
| 4 RUNX1T1 | 3 ADAM5 | 3 HEPHL1 | 3 NOP10 | 3 VENTX | 2 AEN |
| 4 SASS6 | 3 ADAMTS12 | 3 HIST1H2AE | 3 NT5DC1 | 3 VPS39 | 2 AFAP1L1 |
| 4 SATB2 | 3 ADAMTS7 | 3 HLA-DMA | 3 OR10G9 | 3 WIF1 | 2 AFMID |
| 4 SATB2-AS1 | 3 ADAMTS9 | 3 HLA-DRB6 | 3 OR2L13 | 3 WT1 | 2 AGGF1 |
| 4 SCAND3 | 3 ADRA2C | 3 HSF5 | 3 OSBPL9 | 3 WWC3 | 2 AGK |
| 4 SCRN1 | 3 AHCYL2 | 3 HUNK | 3 OXTR | 3 XAF1 | 2 AGL |
| 4 SDS | 3 AHSP | 3 HYLS1 | 3 PADI4 | 3 XCR1 | 2 AGT |
| 4 SDSL | 3 AKAP13 | 3 IGF1 | 3 PDCD1LG2 | 3 ZNF143 | 2 AGTR2 |
| 4 SEPT5 | 3 ALPPL2 | 3 ITGAE | 3 PDP1 | 3 ZNF274 | 2 AGXT2L1 |
| 4 SEPT5-GP1BB | 3 ANXA11 | 3 ITPKA | 3 PDZRN4 | 3 ZNF329 | 2 AHCTF1 |
| 4 SERPINA10 | 3 APOF | 3 JPH1 | 3 PHF19 | 3 ZNF629 | 2 AIFM2 |
| 4 SERPINF2 | 3 ASGR1 | 3 KANK3 | 3 PHLDB2 | 3 ZNF682 | 2 AIFM3 |
| 4 SFT2D3 | 3 ATP1A1OS | 3 KDM3A | 3 PHOSPHO1 | 3 ZNF879 | 2 AIG1 |
| 4 SFTA2 | 3 ATP2C1 | 3 KIAA1551 | 3 PNP | 2 A1BG | 2 AIM1 |
| 4 SLC25A10 | 3 ATP6V0CP3 | 3 KLHDC1 | 3 POLE2 | 2 A1BG-AS1 | 2 AK4 |
| 4 SLC2A9 | 3 ATPBD4 | 3 KLHL20 | 3 POLE4 | 2 A2M-AS1 | 2 AKAP9 |
| 4 SNORD48 | 3 ATPBD4-AS1 | 3 KLHL29 | 3 POU2F1 | 2 AATF | 2 AKIP1 |
| 4 SNORD52 | 3 AVEN | 3 KRT23 | 3 PPAP2A | 2 ABCA17P | 2 AKIRIN2 |
| 4 SOBP | 3 AVL9 | 3 KRT77 | 3 PPIL6 | 2 ABCA3 | 2 AKR1B1 |
| 4 SORCS1 | 3 BCAR3 | 3 LANCL3 | 3 PSMB5 | 2 ABCA4 | 2 AKR7L |
| 4 SP1 | 3 BIN3 | 3 LDLRAD2 | 3 PSMD5 | 2 ABCA8 | 2 AKT2 |
| 4 SRSF11 | 3 BMPR2 | 3 LEKR1 | 3 PSMD6 | 2 ABCB1 | 2 ALDH1L1-AS2 |
| 4 ST5 | 3 BPGM | 3 LOC100499194 | 3 PTGFR | 2 ABCB4 | 2 ALDH1L2 |
| 4 STX1A | 3 BPHL | 3 LOC100499489 | 3 PTPRC | 2 ABCB7 | 2 ALDH2 |
| 4 STYXL1 | 3 C15orf55 | 3 LOC100505687 | 3 PTPRS | 2 ABCB9 | 2 ALG14 |
| 4 SUCLG2 | 3 C20orf112 | 3 LOC100507547 | 3 RAB20 | 2 ABCC4 | 2 ALS2 |
| 4 SULT2B1 | 3 C2orf54 | 3 LOC253039 | 3 RAB39B | 2 ABCD1 | 2 ALX4 |
| 4 SUMF1 | 3 C8orf74 | 3 LOC283050 | 3 RAB4B-EGLN2 | 2 ABHD1 | 2 AMDHD1 |
| 4 SYN3 | 3 CACNA2D3 | 3 LOC283177 | 3 RABL5 | 2 ABHD11 | 2 AMICA1 |
| 4 SYN3 | 3 CCDC57 | 3 LOC344967 | 3 RFX7 | 2 ABHD15 | 2 AMMECR1 |
| 4 SYNCRIP | 3 CCDC90B | 3 LOC440900 | 3 RIMS1 | 2 ABHD3 | 2 AMN1 |
| 4 SYNJ2BP- | 3 CCNY | 3 LOC91948 | 3 RPL22L1 | 2 ABI3 | 2 AMOTL1 |

TABLE 2-continued

Infertility Genes, Ranked

| | | | | | |
|---|---|---|---|---|---|
| COX16 | 3 CD177 | 3 LRP4-AS1 | 3 RTN4RL2 | 2 ABLIM3 | 2 ANGPT4 |
| 4 TBCA | 3 CDR2 | 3 LZTS1 | 3 SAC3D1 | 2 ABP1 | 2 ANKIB1 |
| 4 TCEA3 | 3 CLDN19 | 3 MAP3K1 | 3 SEC31B | 2 ACADS | 2 ANKK1 |
| 4 TCEAL2 | 3 CLDN2 | 3 MARCH2 | 3 SGMS1 | 2 ACADSB | 2 ANKRD13D |
| 4 TEKT4 | 3 CLEC5A | 3 MATR3 | 3 SIGLEC14 | 2 ACAP1 | 2 ANKRD30BP2 |
| 4 TEX11 | 3 CLIC2 | 3 MEIOB | 3 SLC25A42 | 2 ACBD4 | 2 ANKRD34A |
| 4 THEMIS2 | 3 CPT1C | 3 METAP1 | 3 SMPD2 | 2 ACBD5 | 2 ANKRD53 |
| 4 TMEM106C | 3 CSMD3 | 3 MICA | 3 SNORA81 | 2 ACOT7 | 2 ANKRD63 |
| 4 TMEM145 | 3 CYP21A1P | 3 MIR100HG | 3 SOX5 | 2 ACOT8 | 2 ANKS1B |
| 4 TMEM66 | 3 CYP21A2 | 3 MIR1248 | 3 STAMBP | 2 ACOT9 | 2 ANKS3 |
| 4 TNFRSF19 | 3 DAB2IP | 3 MIR125B1 | 3 STAT2 | 2 ACOX2 | 2 ANO4 |
| 4 TNR | 3 DDX46 | 3 MIR200B | 3 SULT6B1 | 2 ACOX3 | 2 ANP32B |
| 2 ANXA2R | 2 ATPIF1 | 2 C12orf29 | 2 C8orf44 | 2 CCIN | 2 CHST5 |
| 2 AOAH | 2 ATXN7 | 2 C12orf56 | 2 C8orf58 | 2 CCL24 | 2 CHTF18 |
| 2 AOX2P | 2 AUH | 2 C12orf73 | 2 C8orf86 | 2 CCL3 | 2 CIRBP |
| 2 AP1S3 | 2 AURKAIP1 | 2 C14orf180 | 2 C9orf116 | 2 CCNB1IP1 | 2 CIRBP-AS1 |
| 2 AP3M2 | 2 AVIL | 2 C14orf182 | 2 C9orf117 | 2 CCND2 | 2 CKB |
| 2 AP4B1-AS1 | 2 AVPI1 | 2 C14orf23 | 2 C9orf169 | 2 CCNG2 | 2 CKS1B |
| 2 AP4E1 | 2 AXIN2 | 2 C14orf64 | 2 C9orf174 | 2 CCNH | 2 CLCC1 |
| 2 APBB1IP | 2 AZIN1 | 2 C15orf27 | 2 C9orf41 | 2 CCR7 | 2 CLCN4 |
| 2 APBB3 | 2 B3GALNT1 | 2 C15orf37 | 2 C9orf50 | 2 CCT2 | 2 CLCN7 |
| 2 APLP2 | 2 B3GNT3 | 2 C15orf41 | 2 CA11 | 2 CCT7 | 2 CLCNKB |
| 2 APOBEC3A | 2 B3GNT5 | 2 C16orf5 | 2 CA5A | 2 CD19 | 2 CLDN23 |
| 2 APOBEC3C | 2 B3GNT8 | 2 C16orf70 | 2 CA7 | 2 CD1D | 2 CLDN5 |
| 2 APOL4 | 2 B4GALNT4 | 2 C17orf103 | 2 CABLES2 | 2 CD244 | 2 CLDN8 |
| 2 APOLD1 | 2 B4GALT3 | 2 C17orf49 | 2 CACNA1D | 2 CD248 | 2 CLDND1 |
| 2 APOOL | 2 BACH2 | 2 C17orf53 | 2 CACNA1S | 2 CD34 | 2 CLEC3B |
| 2 AQP11 | 2 BAHCC1 | 2 C17orf62 | 2 CACTIN-AS1 | 2 CD37 | 2 CLIP1 |
| 2 AQP5 | 2 BAHD1 | 2 C17orf74 | 2 CACUL1 | 2 CD48 | 2 CLMN |
| 2 AQP9 | 2 BAIAP2L1 | 2 C17orf96 | 2 CADM1 | 2 CD59 | 2 CLMP |
| 2 AQPEP | 2 BANP | 2 C18orf32 | 2 CADPS2 | 2 CD68 | 2 CLN5 |
| 2 ARHGAP10 | 2 BATF | 2 C18orf34 | 2 CALHM2 | 2 CD72 | 2 CLNK |
| 2 ARHGAP12 | 2 BCAP31 | 2 C19orf24 | 2 CALM1 | 2 CD82 | 2 CLPTM1 |
| 2 ARHGAP15 | 2 BCDIN3D-AS1 | 2 C19orf45 | 2 CAMKK2 | 2 CD8A | 2 CLPTM1L |
| 2 ARHGAP30 | 2 BCL2 | 2 C19orf57 | 2 CAMP | 2 CDA | 2 CLSTN2 |
| 2 ARHGAP35 | 2 BCL2L1 | 2 C19orf60 | 2 CAMSAP1 | 2 CDAN1 | 2 CLTCL1 |
| 2 ARHGAP39 | 2 BCL2L11 | 2 C1QL1 | 2 CAP2 | 2 CDC42BPA | 2 CLVS2 |
| 2 ARHGAP6 | 2 BCL2L14 | 2 C1QTNF6 | 2 CAPN1 | 2 CDC42BPG | 2 CMC2 |
| 2 ARHGDIA | 2 BCL7A | 2 C1S | 2 CAPN2 | 2 CDC42EP5 | 2 CMTM4 |
| 2 ARHGDIB | 2 BCL9L | 2 C1orf123 | 2 CARNS1 | 2 CDCA2 | 2 CNEP1R1 |
| 2 ARHGEF12 | 2 BDH1 | 2 C1orf151-NBL1 | 2 CARS2 | 2 CDH13 | 2 CNGA1 |
| 2 ARHGEF15 | 2 BECN1 | 2 C1orf172 | 2 CASP3 | 2 CDH20 | 2 CNGB1 |
| 2 ARHGEF37 | 2 BEND5 | 2 C1orf174 | 2 CASP8 | 2 CDH22 | 2 CNIH |
| 2 ARHGEF7 | 2 BEND7 | 2 C1orf21 | 2 CASQ1 | 2 CDHR3 | 2 CNTD1 |
| 2 ARID1A | 2 BEST1 | 2 C1orf229 | 2 CATSPER2P1 | 2 CDK5R1 | 2 CNTD2 |
| 2 ARL10 | 2 BET3L | 2 C1orf50 | 2 CBFA2T2 | 2 CDK6 | 2 CNTN1 |
| 2 ARL13B | 2 BEX4 | 2 C1orf86 | 2 CBLL1 | 2 CDK9 | 2 CNTN4 |
| 2 ARL15 | 2 BEX5 | 2 C20orf151 | 2 CBLN2 | 2 CDKL2 | 2 CNTNAP3 |
| 2 ARL2BP | 2 BHLHA15 | 2 C20orf201 | 2 CBX1 | 2 CDKN1A | 2 COA3 |
| 2 ARMC9 | 2 BICC1 | 2 C20orf94 | 2 CBY1 | 2 CDKN1C | 2 COA5 |
| 2 ARMCX1 | 2 BIK | 2 C20orf96 | 2 CC2D1B | 2 CDO1 | 2 COBL |
| 2 ARR3 | 2 BLVRA | 2 C21orf33 | 2 CCAR1 | 2 CDPF1 | 2 COCH |
| 2 ARRB1 | 2 BMF | 2 C21orf49 | 2 CCBL2 | 2 CEACAM1 | 2 COL12A1 |
| 2 ARRDC5 | 2 BMI1 | 2 C21orf56 | 2 CCDC101 | 2 CEACAM6 | 2 COL13A1 |
| 2 ARSB | 2 BMP1 | 2 C21orf7 | 2 CCDC102A | 2 CEBPE | 2 COL15A1 |
| 2 ARSI | 2 BMP4 | 2 C22orf28 | 2 CCDC104 | 2 CEBPG | 2 COL19A1 |
| 2 ASAP1 | 2 BMPR1B | 2 C2CD2L | 2 CCDC105 | 2 CECR2 | 2 COL21A1 |
| 2 ASB1 | 2 BMX | 2 C2orf16 | 2 CCDC106 | 2 CELF5 | 2 COL25A1 |
| 2 ASB18 | 2 BNC1 | 2 C2orf42 | 2 CCDC111 | 2 CENPM | 2 COL3A1 |
| 2 ASB6 | 2 BNC2 | 2 C2orf43 | 2 CCDC124 | 2 CENPN | 2 COLQ |
| 2 ASCL4 | 2 BOK | 2 C2orf50 | 2 CCDC144A | 2 CEP164 | 2 COQ5 |
| 2 ASCL5 | 2 BOK-AS1 | 2 C2orf68 | 2 CCDC15 | 2 CEP55 | 2 CORO1A |
| 2 ASPA | 2 BOP1 | 2 C2orf81 | 2 CCDC150 | 2 CEP76 | 2 COTL1 |
| 2 ASS1 | 2 BRI3BP | 2 C3 | 2 CCDC152 | 2 CEP78 | 2 COX10 |
| 2 ASXL2 | 2 BTAF1 | 2 C3orf27 | 2 CCDC166 | 2 CERS2 | 2 COX10-AS1 |
| 2 ATAD3B | 2 BTBD16 | 2 C3orf36 | 2 CCDC167 | 2 CES3 | 2 COX15 |
| 2 ATAD3C | 2 BTBD6 | 2 C3orf78 | 2 CCDC19 | 2 CFH | 2 COX16 |
| 2 ATAD5 | 2 BTF3 | 2 C4orf21 | 2 CCDC24 | 2 CFLAR | 2 COX17 |
| 2 ATF5 | 2 BTG4 | 2 C4orf27 | 2 CCDC37 | 2 CFP | 2 COX19 |
| 2 ATF7 | 2 BTRC | 2 C5orf52 | 2 CCDC40 | 2 CGB2 | 2 COX6A2 |
| 2 ATG16L1 | 2 BUB3 | 2 C5orf56 | 2 CCDC42 | 2 CGREF1 | 2 CPA2 |
| 2 ATP10D | 2 BYSL | 2 C6orf1 | 2 CCDC42B | 2 CHADL | 2 CPEB4 |
| 2 ATP13A1 | 2 C10orf128 | 2 C6orf164 | 2 CCDC6 | 2 CHAMP1 | 2 CPLX3 |
| 2 ATP1B1 | 2 C10orf82 | 2 C6orf170 | 2 CCDC67 | 2 CHCHD4 | 2 CPNE2 |
| 2 ATP5L2 | 2 C11orf45 | 2 C7orf13 | 2 CCDC77 | 2 CHIC1 | 2 CPNE9 |
| 2 ATP5S | 2 C11orf53 | 2 C7orf26 | 2 CCDC78 | 2 CHML | 2 CPQ |
| 2 ATP6AP2 | 2 C11orf68 | 2 C7orf41 | 2 CCDC78 | 2 CHMP2A | 2 CPSF3 |
| 2 ATP6V1F | 2 C11orf75 | 2 C7orf65 | 2 CCDC9 | 2 CHMP3 | 2 CPSF4L |

TABLE 2-continued

Infertility Genes, Ranked

| | | | | | |
|---|---|---|---|---|---|
| 2 ATP8B3 | 2 C11orf88 | 2 C7orf69 | 2 CCDC90A | 2 CHRNA4 | 2 CPT2 |
| 2 ATP8B4 | 2 C12orf10 | 2 C8orf31 | 2 CCDC92 | 2 CHRNB1 | 2 CPVL |
| 2 CPXCR1 | 2 DGKA | 2 DYNLL1 | 2 ESM1 | 2 FAM83D | 2 FSCN2 |
| 2 CPXM2 | 2 DGKI | 2 DYNLRB2 | 2 ESR1 | 2 FAM83F | 2 FTO |
| 2 CPZ | 2 DGKQ | 2 DYRK1B | 2 ESR2 | 2 FAM98C | 2 FTX |
| 2 CRABP1 | 2 DHCR24 | 2 DYRK2 | 2 ESYT1 | 2 FASTKD3 | 2 FXN |
| 2 CRB2 | 2 DHDH | 2 E2F4 | 2 ESYT3 | 2 FASTKD5 | 2 FXYD6 |
| 2 CREB3L2 | 2 DHRS11 | 2 EARS2 | 2 ETNK1 | 2 FBF1 | 2 FYB |
| 2 CREBBP | 2 DHRS3 | 2 EBI3 | 2 ETS1 | 2 FBL | 2 FYN |
| 2 CREG2 | 2 DHRS7C | 2 ECH1 | 2 ETV1 | 2 FBLN2 | 2 GABARAPL1 |
| 2 CRHR1 | 2 DHX29 | 2 ECHDC3 | 2 EXOC6 | 2 FBN1 | 2 GABRG3 |
| 2 CRISP2 | 2 DHX35 | 2 ECT2L | 2 EXOSC10 | 2 FBXL14 | 2 GABRR1 |
| 2 CRISPLD1 | 2 DHX40 | 2 EDF1 | 2 EXT1 | 2 FBXO10 | 2 GABRR3 |
| 2 CRK | 2 DHX57 | 2 EDIL3 | 2 EXTL3 | 2 FBXO25 | 2 GADL1 |
| 2 CRTAM | 2 DIABLO | 2 EDN2 | 2 EYS | 2 FBXO27 | 2 GAGE13 |
| 2 CRYGD | 2 DIDO1 | 2 EDN3 | 2 F11R | 2 FBXO34 | 2 GAL |
| 2 CRYGN | 2 DIRAS2 | 2 EDNRA | 2 F3 | 2 FBXO4 | 2 GALC |
| 2 CRYZL1 | 2 DISP1 | 2 EEF1A2 | 2 F8 | 2 FBXW4 | 2 GALM |
| 2 CSF3R | 2 DIXDC1 | 2 EFCAB4A | 2 FAAH | 2 FBXW5 | 2 GALNT13 |
| 2 CSGALNACT2 | 2 DLG3 | 2 EFCAB4B | 2 FABP6 | 2 FBXW9 | 2 GALNT7 |
| 2 CSK | 2 DLGAP4 | 2 EFHB | 2 FAF2 | 2 FCER1G | 2 GALNT8 |
| 2 CSN1S2BP | 2 DLL4 | 2 EFHD2 | 2 FAIM2 | 2 FCHSD1 | 2 GALR2 |
| 2 CSNK1A1 | 2 DNAH5 | 2 EFNA4 | 2 FAM101A | 2 FCN3 | 2 GAP43 |
| 2 CSNK1D | 2 DNAH7 | 2 EFNB1 | 2 FAM108C1 | 2 FER | 2 GAPDHS |
| 2 CSNK1G1 | 2 DNAH9 | 2 EFR3A | 2 FAM110A | 2 FER1L4 | 2 GAS2L2 |
| 2 CSNK2A1 | 2 DNAI2 | 2 EHD1 | 2 FAM115A | 2 FGD1 | 2 GATA5 |
| 2 CSRNP1 | 2 DNAJB1 | 2 EHD3 | 2 FAM120B | 2 FGF11 | 2 GCAT |
| 2 CSRP3 | 2 DNAJB12 | 2 EHF | 2 FAM123A | 2 FGF22 | 2 GCFC1 |
| 2 CT47B1 | 2 DNAJB13 | 2 EIF2AK1 | 2 FAM123B | 2 FGF23 | 2 GCSAM |
| 2 CTBP1 | 2 DNAJC11 | 2 EIF2C2 | 2 FAM127C | 2 FGFBP2 | 2 GDA |
| 2 CTBP1-AS1 | 2 DNAJC18 | 2 EIF2S2 | 2 FAM131A | 2 FGFR3 | 2 GDI2 |
| 2 CTGF | 2 DNAJC2 | 2 EIF4EBP1 | 2 FAM131B | 2 FHDC1 | 2 GEMIN2 |
| 2 CTIF | 2 DNAJC8 | 2 EIF4G3 | 2 FAM133B | 2 FHL2 | 2 GEMIN4 |
| 2 CTSF | 2 DNER | 2 EIF5A2 | 2 FAM133DP | 2 FHL3 | 2 GEMIN6 |
| 2 CTSG | 2 DNTTIP1 | 2 ELAC1 | 2 FAM150B | 2 FIGNL2 | 2 GEMIN7 |
| 2 CTTNBP2NL | 2 DNTTIP2 | 2 ELF3 | 2 FAM157A | 2 FITM2 | 2 GFER |
| 2 CUL5 | 2 DOCK10 | 2 ELFN1 | 2 FAM159A | 2 FKBP1A | 2 GFPT2 |
| 2 CUTC | 2 DPF1 | 2 ELL3 | 2 FAM160B2 | 2 FKBP1A- | 2 GFRA1 |
| 2 CWC25 | 2 DPF2 | 2 ELN | 2 FAM163A | SDCBP2 | 2 GFRA2 |
| 2 CXADR | 2 DPH5 | 2 ELSPBP1 | 2 FAM171A1 | 2 FKBP9 | 2 GGA1 |
| 2 CXCL1 | 2 DPM2 | 2 EMBP1 | 2 FAM173A | 2 FLAD1 | 2 GGTLC2 |
| 2 CXCR4 | 2 DPP10 | 2 EMC7 | 2 FAM174B | 2 FLJ12825 | 2 GHRL |
| 2 CXorf65 | 2 DPPA3 | 2 EML2 | 2 FAM176B | 2 FLJ14107 | 2 GHRLOS |
| 2 CYB561D2 | 2 DPYSL2 | 2 EMP3 | 2 FAM176C | 2 FLJ16171 | 2 GINS3 |
| 2 CYBASC3 | 2 DPYSL3 | 2 ENDOG | 2 FAM178B | 2 FLJ35390 | 2 GIPC2 |
| 2 CYFIP2 | 2 DPYSL5 | 2 ENHO | 2 FAM185A | 2 FLJ41941 | 2 GJB2 |
| 2 CYP11A1 | 2 DRAP1 | 2 ENPP6 | 2 FAM188B | 2 FLJ42351 | 2 GJC2 |
| 2 CYP19A1 | 2 DRD2 | 2 ENPP7 | 2 FAM18B1 | 2 FLJ43663 | 2 GK5 |
| 2 CYP20A1 | 2 DRD4 | 2 ENSA | 2 FAM190B | 2 FLNC | 2 GLB1 |
| 2 CYP27C1 | 2 DSC2 | 2 ENTHD1 | 2 FAM192A | 2 FLOT1 | 2 GLB1L3 |
| 2 CYP2J2 | 2 DSCAML1 | 2 ENTPD2 | 2 FAM194A | 2 FLT1 | 2 GLCCI1 |
| 2 CYP2S1 | 2 DSCR3 | 2 ENTPD4 | 2 FAM198B | 2 FLT4 | 2 GLI1 |
| 2 CYP2W1 | 2 DSCR6 | 2 EPB41 | 2 FAM207A | 2 FLVCR2 | 2 GLIS3 |
| 2 CYP4F24P | 2 DSEL | 2 EPB41L1 | 2 FAM227A | 2 FLYWCH1 | 2 GLO1 |
| 2 DAPK2 | 2 DSP | 2 EPB49 | 2 FAM24B | 2 FMNL2 | 2 GLRX |
| 2 DARC | 2 DTNB | 2 EPC1 | 2 FAM24B- | 2 FNDC3B | 2 GLRX5 |
| 2 DAZAP1 | 2 DTNBP1 | 2 EPC2 | CUZD1 | 2 FNDC5 | 2 GLS2 |
| 2 DBIL5P | 2 DTX4 | 2 EPG5 | 2 FAM26D | 2 FNIP1 | 2 GLT1D1 |
| 2 DBNL | 2 DUOX2 | 2 EPHA2 | 2 FAM26E | 2 FNIP2 | 2 GLTSCR2 |
| 2 DBP | 2 DUOXA1 | 2 EPHA3 | 2 FAM27L | 2 FOXD2 | 2 GLUD2 |
| 2 DCAF12 | 2 DUOXA2 | 2 EPS8L2 | 2 FAM32A | 2 FOXD4L1 | 2 GLYR1 |
| 2 DCAF8L2 | 2 DUS1L | 2 EPSTI1 | 2 FAM40A | 2 FOXN2 | 2 GMIP |
| 2 DCBLD1 | 2 DUS3L | 2 EPT1 | 2 FAM47E | 2 FOXO3 | 2 GMPS |
| 2 DCHS2 | 2 DUSP22 | 2 ERAS | 2 FAM53B | 2 FOXO4 | 2 GNAI2 |
| 2 DCK | 2 DUSP26 | 2 ERBB2 | 2 FAM5B | 2 FOXP2 | 2 GNAL |
| 2 DCLRE1A | 2 DUSP5 | 2 ERC2 | 2 FAM69B | 2 FOXP4 | 2 GNB1 |
| 2 DCUN1D1 | 2 DYDC1 | 2 ERCC6L2 | 2 FAM72A | 2 FRG2 | 2 GNE |
| 2 DDIT3 | 2 DYDC2 | 2 ERF | 2 FAM73A | 2 FRG2B | 2 GNG11 |
| 2 DDX47 | 2 DYNC1H1 | 2 ERN2 | 2 FAM78A | 2 FRMD6 | 2 GNG5 |
| 2 DGCR8 | 2 DYNC1I1 | 2 ERP44 | 2 FAM78B | 2 FRRS1L | 2 GNGT2 |
| 2 GNMT | 2 HEXDC | 2 IL13RA2 | 2 KCNU1 | 2 LAPTM5 | 2 LOC100129858 |
| 2 GOLGA8B | 2 HEXIM1 | 2 IL17D | 2 KCP | 2 LARP1 | 2 LOC100130015 |
| 2 GON4L | 2 HEYL | 2 IL17RD | 2 KCTD1 | 2 LARP1B | 2 LOC100130238 |
| 2 GOT2 | 2 HHIPL2 | 2 IL1R2 | 2 KCTD11 | 2 LARP4B | 2 LOC100130417 |
| 2 GPATCH3 | 2 HIST1H2AJ | 2 IL1RAP | 2 KCTD15 | 2 LAT2 | 2 LOC100130557 |
| 2 GPC4 | 2 HIST1H2APS1 | 2 IL20RB | 2 KCTD16 | 2 LCE3A | 2 LOC100131289 |
| 2 GPC6 | 2 HIST1H2BO | 2 IL23A | 2 KCTD6 | 2 LCLAT1 | 2 LOC100131655 |
| 2 GPD2 | 2 HIST1H3I | 2 IL28A | 2 KCTD9 | 2 LCN12 | 2 LOC100131691 |

TABLE 2-continued

Infertility Genes, Ranked

| | | | | | |
|---|---|---|---|---|---|
| 2 GPKOW | 2 HIST1H3J | 2 IL2RG | 2 KDELC2 | 2 LCN8 | 2 LOC100131825 |
| 2 GPN2 | 2 HIST1H4L | 2 ILDR1 | 2 KDELR2 | 2 LDHAL6A | 2 LOC100133669 |
| 2 GPR1 | 2 HIST4H4 | 2 INE2 | 2 KDM1A | 2 LDLRAD3 | 2 LOC100134317 |
| 2 GPR111 | 2 HIVEP3 | 2 INHBA | 2 KDM3B | 2 LDLRAP1 | 2 LOC100134368 |
| 2 GPR113 | 2 HK1 | 2 INHBA-AS1 | 2 KDM5A | 2 LDOC1L | 2 LOC100188947 |
| 2 GPR135 | 2 HLA-DRB1 | 2 INHBE | 2 KDM5B | 2 LEFTY2 | 2 LOC100287482 |
| 2 GPR142 | 2 HLF | 2 INMT-FAM188B | 2 KDM5B-AS1 | 2 LENG9 | 2 LOC100288255 |
| 2 GPR144 | 2 HMBOX1 | 2 INO80 | 2 KEL | 2 LEP | 2 LOC100288911 |
| 2 GPR153 | 2 HMGB3P1 | 2 INPP1 | 2 KIAA0226L | 2 LEPR | 2 LOC100289511 |
| 2 GPR156 | 2 HN1 | 2 INS | 2 KIAA0232 | 2 LEPRE1 | 2 LOC100499227 |
| 2 GPR35 | 2 HNRNPCL1 | 2 INTS2 | 2 KIAA0247 | 2 LEPREL1 | 2 LOC100499484 |
| 2 GPR37 | 2 HNRNPF | 2 INTS9 | 2 KIAA0754 | 2 LEPROT | 2 |
| 2 GPR6 | 2 HNRNPH1 | 2 IQCD | 2 KIAA0930 | 2 LETMD1 | LOC100499484- |
| 2 GPR84 | 2 HOOK3 | 2 IQCH | 2 KIAA0947 | 2 LGALS12 | C9ORF174 |
| 2 GPRIN2 | 2 HORMAD2 | 2 IQCJ-SCHIP1 | 2 KIAA1191 | 2 LGALS4 | 2 LOC100505495 |
| 2 GPSM3 | 2 HOTAIR | 2 IQUB | 2 KIAA1199 | 2 LGALS7B | 2 LOC100505583 |
| 2 GPX7 | 2 HOTAIRM1 | 2 ISYNA1 | 2 KIAA1217 | 2 LGALS9B | 2 LOC100505666 |
| 2 GRAMD1B | 2 HOXA1 | 2 ITFG1 | 2 KIAA1467 | 2 LHFPL3-AS2 | 2 LOC100505875 |
| 2 GRID2 | 2 HOXB7 | 2 ITGA1 | 2 KIAA1683 | 2 LHFPL4 | 2 LOC100506082 |
| 2 GRIK1 | 2 HOXC11 | 2 ITGA11 | 2 KIAA1731 | 2 LHFPL5 | 2 LOC100506274 |
| 2 GRM1 | 2 HOXC9 | 2 ITGA2 | 2 KIF26A | 2 LHPP | 2 LOC100506585 |
| 2 GRM2 | 2 HPS4 | 2 ITGA5 | 2 KIF3A | 2 LHX3 | 2 LOC100506668 |
| 2 GRM3 | 2 HR | 2 ITGA8 | 2 KIFC3 | 2 LHX6 | 2 LOC100507066 |
| 2 GRM6 | 2 HS3ST6 | 2 ITGB1 | 2 KLB | 2 LIMK2 | 2 LOC100507299 |
| 2 GRM7 | 2 HSD11B1L | 2 ITGB1BP1 | 2 KLF14 | 2 LIN7B | 2 LOC100507373 |
| 2 GRN | 2 HSD17B1 | 2 ITGB3 | 2 KLF2 | 2 LINC00028 | 2 LOC100507443 |
| 2 GSG1L | 2 HSF4 | 2 ITGB7 | 2 KLHDC8A | 2 LINC00167 | 2 LOC100507564 |
| 2 GSN | 2 HSPA1B | 2 ITK | 2 KLHL22 | 2 LINC00242 | 2 LOC100507605 |
| 2 GSTM4 | 2 HSPA4L | 2 ITM2C | 2 KLHL31 | 2 LINC00264 | 2 LOC100507634 |
| 2 GTF2A1 | 2 HSPA9 | 2 ITPA | 2 KLK10 | 2 LINC00265 | 2 LOC100508120 |
| 2 GTF2IRD1 | 2 HSPB6 | 2 ITPK1-AS1 | 2 KLK11 | 2 LINC00299 | 2 LOC101055625 |
| 2 GTF2IRD1P1 | 2 HTR1B | 2 ITPR1 | 2 KLK12 | 2 LINC00307 | 2 LOC147670 |
| 2 GUSBP4 | 2 HTR4 | 2 ITPRIP | 2 KLK6 | 2 LINC00310 | 2 LOC148709 |
| 2 GXYLT2 | 2 HTR6 | 2 IVNS1ABP | 2 KPNA1 | 2 LINC00319 | 2 LOC150197 |
| 2 H1F0 | 2 HYAL2 | 2 IZUMO4 | 2 KRBA2 | 2 LINC00426 | 2 LOC154449 |
| 2 H2AFJ | 2 IBSP | 2 JAKMIP2 | 2 KREMEN1 | 2 LINC00466 | 2 LOC154822 |
| 2 H2AFY | 2 IDH2 | 2 JAKMIP2-AS1 | 2 KRIT1 | 2 LINC00471 | 2 LOC155060 |
| 2 H2BFM | 2 IDUA | 2 JMJD1C | 2 KRT1 | 2 LINC00475 | 2 LOC200772 |
| 2 H3F3A | 2 IER3 | 2 JOSD1 | 2 KRT2 | 2 LINC00476 | 2 LOC202781 |
| 2 H3F3AP4 | 2 IFFO1 | 2 JPH2 | 2 KRT3 | 2 LINC00478 | 2 LOC255130 |
| 2 HADH | 2 IFI16 | 2 JPX | 2 KRT7 | 2 LINC00574 | 2 LOC256021 |
| 2 HAGHL | 2 IFI27 | 2 JUNB | 2 KRT80 | 2 LINC00602 | 2 LOC283194 |
| 2 HARS | 2 IFI30 | 2 JUP | 2 KRT86 | 2 LINC00612 | 2 LOC284798 |
| 2 HARS2 | 2 IFI44L | 2 KARS | 2 KRT8P41 | 2 LINC00634 | 2 LOC284865 |
| 2 HAVCR1 | 2 IFI6 | 2 KAT2B | 2 KRTAP16-1 | 2 LINC00638 | 2 LOC284889 |
| 2 HBQ1 | 2 IFITM10 | 2 KATNB1 | 2 KRTAP20-1 | 2 LINC00675 | 2 LOC284950 |
| 2 HCAR1 | 2 IFITM3 | 2 KATNBL1 | 2 KRTAP20-4 | 2 LLGL1 | 2 LOC285626 |
| 2 HCG9 | 2 IFITM4P | 2 KAZN | 2 KRTAP5-6 | 2 LMAN2 | 2 LOC285696 |
| 2 HCLS1 | 2 IFNAR2 | 2 KBTBD11 | 2 KRTAP6-1 | 2 LMF1 | 2 LOC285972 |
| 2 HCN2 | 2 IFRD1 | 2 KCNA5 | 2 KRTCAP3 | 2 LMO7 | 2 LOC286059 |
| 2 HCRTR1 | 2 IFT88 | 2 KCNB1 | 2 KSR1 | 2 LOC100127888 | 2 LOC338963 |
| 2 HDAC11 | 2 IGF2BP2 | 2 KCNE4 | 2 KSR2 | 2 LOC100128071 | 2 LOC349160 |
| 2 HDAC2 | 2 IGFBP1 | 2 KCNG3 | 2 KYNU | 2 LOC100128076 | 2 LOC399815 |
| 2 HDAC9 | 2 IGLL1 | 2 KCNG4 | 2 L1TD1 | 2 LOC100128098 | 2 LOC400680 |
| 2 HDDC2 | 2 IGLON5 | 2 KCNH1 | 2 L2HGDH | 2 LOC100128338 | 2 LOC400940 |
| 2 HDDC3 | 2 IGSF3 | 2 KCNJ15 | 2 LAGE3 | 2 LOC100128568 | 2 LOC401164 |
| 2 HECTD2 | 2 IKZF1 | 2 KCNJ5 | 2 LAMA5 | 2 LOC100129046 | 2 LOC401320 |
| 2 HEG1 | 2 IKZF2 | 2 KCNJ8 | 2 LAMB2 | 2 LOC100129250 | 2 LOC402160 |
| 2 HELQ | 2 IKZF5 | 2 KCNQ4 | 2 LAMTOR4 | 2 LOC100129345 | 2 LOC440461 |
| 2 HEPACAM | 2 IL12B | 2 KCNT2 | 2 LAMTOR5 | 2 LOC100129636 | 2 LOC440563 |
| 2 LOC440600 | 2 MACC1 | 2 MGC39372 | 2 MLF1 | 2 MZF1 | 2 NMRAL1 |
| 2 LOC440944 | 2 MACROD1 | 2 MGC57346 | 2 MLIP | 2 MZT2B | 2 NNMT |
| 2 LOC441242 | 2 MAFF | 2 MICAL2 | 2 MLKL | 2 NAA10 | 2 NOL7 |
| 2 LOC442459 | 2 MAGEC1 | 2 MIER2 | 2 MLLT4 | 2 NAA16 | 2 NOLC1 |
| 2 LOC541473 | 2 MAGEC3 | 2 MIIP | 2 MLLT4-AS1 | 2 NAALAD2 | 2 NOM1 |
| 2 LOC574538 | 2 MAGEE1 | 2 MIR1184-1 | 2 MLLT6 | 2 NACC2 | 2 NOP14-AS1 |
| 2 LOC606724 | 2 MAGOH | 2 MIR1184-2 | 2 MLNR | 2 NADKD1 | 2 NOTCH1 |
| 2 LOC641746 | 2 MAK16 | 2 MIR1184-3 | 2 MMEL1 | 2 NAGA | 2 NOVA1 |
| 2 LOC643037 | 2 MAL | 2 MIR1245A | 2 MMP11 | 2 NANP | 2 NOXO1 |
| 2 LOC643529 | 2 MAMDC4 | 2 MIR1275 | 2 MMP17 | 2 NAP1L4 | 2 NPBWR2 |
| 2 LOC643542 | 2 MAN2B1 | 2 MIR1306 | 2 MNS1 | 2 NAP1L6 | 2 NPDC1 |
| 2 LOC644189 | 2 MAP1B | 2 MIR135A1 | 2 MOBP | 2 NAPB | 2 NPEPL1 |
| 2 LOC644554 | 2 MAP2K4P1 | 2 MIR142 | 2 MOCS1 | 2 NAPSB | 2 NPRL2 |
| 2 LOC644990 | 2 MAP3K13 | 2 MIR153-2 | 2 MOGAT3 | 2 NARFL | 2 NPTX2 |
| 2 LOC648809 | 2 MAP3K3 | 2 MIR181A2HG | 2 MON1A | 2 NARG2 | 2 NR1D2 |
| 2 LOC649330 | 2 MAP3K8 | 2 MIR205 | 2 MORN2 | 2 NAT9 | 2 NR1H3 |
| 2 LOC728012 | 2 MAP3K9 | 2 MIR205HG | 2 MORN4 | 2 NAV3 | 2 NR2E1 |
| 2 LOC728175 | 2 MAP4K1 | 2 MIR2861 | 2 MOS | 2 NBL1 | 2 NR2F1 |

TABLE 2-continued

Infertility Genes, Ranked

| | | | | | |
|---|---|---|---|---|---|
| 2 LOC728392 | 2 MAP4K2 | 2 MIR3187 | 2 MOXD1 | 2 NBPF3 | 2 NR5A1 |
| 2 LOC728431 | 2 MAP4K4 | 2 MIR320B1 | 2 MPC1 | 2 NCAM2 | 2 NR6A1 |
| 2 LOC728730 | 2 MAP6D1 | 2 MIR320C1 | 2 MPL | 2 NCF4 | 2 NRARP |
| 2 LOC729609 | 2 MAPK13 | 2 MIR339 | 2 MRAP2 | 2 NCKAP5L | 2 NRBP2 |
| 2 LOC729966 | 2 MAPK14 | 2 MIR34B | 2 MRFAP1 | 2 NCL | 2 NRD1 |
| 2 LOC730668 | 2 MAPK4 | 2 MIR34C | 2 MRPL16 | 2 NCR2 | 2 NRF1 |
| 2 LOC730811 | 2 MAPK7 | 2 MIR3618 | 2 MRPL19 | 2 NCR3 | 2 NRG3 |
| 2 LOC731275 | 2 MAPK8IP1 | 2 MIR3649 | 2 MRPL23 | 2 NCR3LG1 | 2 NRG4 |
| 2 LOC91450 | 2 MARCH8 | 2 MIR365A | 2 MRPL52 | 2 NDN | 2 NRN1L |
| 2 LONP2 | 2 MARCKS | 2 MIR3675 | 2 MRPS18C | 2 NDNL2 | 2 NRP2 |
| 2 LOXL1 | 2 MARCKSL1 | 2 MIR3680-1 | 2 MRPS2 | 2 NDRG4 | 2 NSD1 |
| 2 LOXL1-AS1 | 2 MARCO | 2 MIR3680-2 | 2 MRPS21 | 2 NDUFA13 | 2 NSRP1 |
| 2 LOXL2 | 2 MARS2 | 2 MIR3913-2 | 2 MRVI1 | 2 NDUFA4 | 2 NT5C |
| 2 LPHN1 | 2 MARVELD1 | 2 MIR3960 | 2 MSMO1 | 2 NDUFA7 | 2 NT5DC2 |
| 2 LPPR2 | 2 MAT2A | 2 MIR423 | 2 MST1P2 | 2 NDUFAF4 | 2 NTAN1 |
| 2 LPPR4 | 2 MAZ | 2 MIR4258 | 2 MSX2P1 | 2 NDUFB8 | 2 NTN5 |
| 2 LRAT | 2 MB21D2 | 2 MIR4289 | 2 MT1A | 2 NDUFS5 | 2 NTRK3 |
| 2 LRCH1 | 2 MBD2 | 2 MIR4298 | 2 MT1DP | 2 NDUFV1 | 2 NTSR1 |
| 2 LRIG3 | 2 MBD5 | 2 MIR4444-1 | 2 MT1L | 2 NEAT1 | 2 NUB1 |
| 2 LRIT1 | 2 MBD6 | 2 MIR4461 | 2 MTA3 | 2 NEBL | 2 NUDT1 |
| 2 LRP6 | 2 MBOAT7 | 2 MIR4468 | 2 MTCH1 | 2 NEK4 | 2 NUDT10 |
| 2 LRR1 | 2 MCAT | 2 MIR4479 | 2 MTERF | 2 NENF | 2 NUDT21 |
| 2 LRRC14 | 2 MCC | 2 MIR4489 | 2 MTERFD1 | 2 NET1 | 2 NUDT8 |
| 2 LRRC14B | 2 MCCD1 | 2 MIR4505 | 2 MTHFD1 | 2 NEURL | 2 NUP133 |
| 2 LRRC2 | 2 MCHR2 | 2 MIR4513 | 2 MTHFD1L | 2 NF1 | 2 NUP43 |
| 2 LRRC23 | 2 MCL1 | 2 MIR4520A | 2 MTHFD2L | 2 NFKB1 | 2 NUP62 |
| 2 LRRC32 | 2 MDFIC | 2 MIR4651 | 2 MTIF2 | 2 NFKBIE | 2 NUP98 |
| 2 LRRC34 | 2 MDM4 | 2 MIR4657 | 2 MTM1 | 2 NFKBIL1 | 2 NUPR1L |
| 2 LRRC37A6P | 2 ME1 | 2 MIR4669 | 2 MTPAP | 2 NFYB | 2 NUTF2 |
| 2 LRRC45 | 2 MED1 | 2 MIR4686 | 2 MTRR | 2 NFYC | 2 NXNL1 |
| 2 LRRC4C | 2 MED12L | 2 MIR4726 | 2 MTUS1 | 2 NGB | 2 NXPH2 |
| 2 LRRC66 | 2 MED15 | 2 MIR4727 | 2 MUM1 | 2 NGEF | 2 OCEL1 |
| 2 LRRC71 | 2 MED20 | 2 MIR4728 | 2 MX1 | 2 NHEJ1 | 2 OCSTAMP |
| 2 LRRC8B | 2 MED22 | 2 MIR4736 | 2 MXD3 | 2 NHLRC1 | 2 ODC1 |
| 2 LRRC8E | 2 MEF2A | 2 MIR4749 | 2 MYADM | 2 NHLRC2 | 2 ODF2 |
| 2 LRRCC1 | 2 MEFV | 2 MIR4751 | 2 MYCL1 | 2 NHLRC4 | 2 ODF3L1 |
| 2 LRRFIP1 | 2 MEGF10 | 2 MIR4786 | 2 MYEF2 | 2 NINJ1 | 2 OGFOD1 |
| 2 LRRIQ4 | 2 MEGF11 | 2 MIR5095 | 2 MYH16 | 2 NINL | 2 OPN3 |
| 2 LRRK1 | 2 MEIS2 | 2 MIR548AE2 | 2 MYNN | 2 NIPAL2 | 2 OPN5 |
| 2 LRRN4CL | 2 MESP1 | 2 MIR548AO | 2 MYO18A | 2 NIPSNAP3B | 2 OPRL1 |
| 2 LRRTM4 | 2 METTL10 | 2 MIR5580 | 2 MYO18B | 2 NKAPL | 2 OR2T12 |
| 2 LSM7 | 2 METTL17 | 2 MIR5584 | 2 MYO1B | 2 NKIRAS2 | 2 OR4N3P |
| 2 LTN1 | 2 MFGE8 | 2 MIR5691 | 2 MYO1D | 2 NLK | 2 OR5AP2 |
| 2 LTV1 | 2 MFSD10 | 2 MIR572 | 2 MYO3B | 2 NLRC3 | 2 OR7C1 |
| 2 LUC7L3 | 2 MFSD11 | 2 MIR636 | 2 MYO9A | 2 NLRP12 | 2 OR7E2P |
| 2 LYPD1 | 2 MFSD2B | 2 MIR641 | 2 MYOCD | 2 NLRP2 | 2 ORAI2 |
| 2 LYPD6 | 2 MGAT1 | 2 MIR7-2 | 2 MYOF | 2 NMB | 2 ORAOV1 |
| 2 LYRM2 | 2 MGC12916 | 2 MIR935 | 2 MYOM1 | 2 NMD3 | 2 OS9 |
| 2 LYSMD4 | 2 MGC16275 | 2 MKRN3 | 2 MYPOP | 2 NMI | 2 OSBPL10 |
| 2 LZTR1 | 2 MGC23284 | 2 MKRN9P | 2 MYSM1 | 2 NMNAT2 | 2 OSBPL6 |
| 2 OSCP1 | 2 PDZK1IP1 | 2 POLR3B | 2 PSCA | 2 RDH11 | 2 RPS15 |
| 2 OSGIN2 | 2 PDZRN3 | 2 POLR3GL | 2 PSMA1 | 2 RDH12 | 2 RPS18 |
| 2 OTOS | 2 PECAM1 | 2 POM121L10P | 2 PSMA4 | 2 RDH14 | 2 RPS20 |
| 2 OTUD7B | 2 PEF1 | 2 POM121L1P | 2 PSMB4 | 2 REEP3 | 2 RPS23 |
| 2 OXA1L | 2 PELO | 2 POMT1 | 2 PSMB9 | 2 RELT | 2 RPS26 |
| 2 OXSR1 | 2 PEX14 | 2 PON1 | 2 PSMC2 | 2 REM1 | 2 RPS4Y2 |
| 2 P2RX2 | 2 PEX19 | 2 POP7 | 2 PSMD14 | 2 RER1 | 2 RPS6KA2-IT1 |
| 2 P2RX7 | 2 PEX2 | 2 POR | 2 PSMG2 | 2 RFC3 | 2 RPS6KA3 |
| 2 P2RY13 | 2 PEX5 | 2 PORCN | 2 PTAFR | 2 RFFL | 2 RPS8 |
| 2 P2RY6 | 2 PFDN5 | 2 POU4F1-AS1 | 2 PTBP1 | 2 RFK | 2 RPSAP58 |
| 2 P4HB | 2 PGAM4 | 2 POU5F1B | 2 PTCD3 | 2 RFPL2 | 2 RPUSD1 |
| 2 PABPC1 | 2 PGAP2 | 2 PP12613 | 2 PTCH2 | 2 RFTN1 | 2 RPUSD3 |
| 2 PABPC5 | 2 PGBD4 | 2 PPAPDC1B | 2 PTGFRN | 2 RFTN2 | 2 RRAGD |
| 2 PADI2 | 2 PGD | 2 PPARG | 2 PTHLH | 2 RFX8 | 2 RRH |
| 2 PADI3 | 2 PGM3 | 2 PPFIA1 | 2 PTK7 | 2 RGAG1 | 2 RSBN1 |
| 2 PAEP | 2 PHACTR2 | 2 PPIA | 2 PTOV1 | 2 RGMA | 2 RSPH9 |
| 2 PAFAH1B3 | 2 PHF21A | 2 PPIE | 2 PTOV1-AS1 | 2 RGPD3 | 2 RSPO1 |
| 2 PAFAH2 | 2 PHF23 | 2 PPIH | 2 PTPN22 | 2 RGS22 | 2 RSPO3 |
| 2 PAGE1 | 2 PHKB | 2 PPP1R14B | 2 PTPN5 | 2 RGS3 | 2 RSPRY1 |
| 2 PAGE4 | 2 PHPT1 | 2 PPP1R15A | 2 PTPN7 | 2 RGS6 | 2 RTEL1 |
| 2 PAIP2 | 2 PI16 | 2 PPP1R37 | 2 PTPRCAP | 2 RHBDL1 | 2 RTEL1- |
| 2 PAK3 | 2 PIAS2 | 2 PPP1R3F | 2 PTPRG | 2 RHCG | TNFRSF6B |
| 2 PAN2 | 2 PICK1 | 2 PPP2CB | 2 PUF60 | 2 RHOG | 2 RTN4RL1 |
| 2 PANK2 | 2 PIEZO1 | 2 PPP2R3A | 2 PURB | 2 RHPN2 | 2 RTP1 |
| 2 PANK3 | 2 PIGQ | 2 PPP2R5A | 2 PURG | 2 RIF1 | 2 RUNDC3B |
| 2 PAPLN | 2 PIGR | 2 PPP2R5C | 2 PUSL1 | 2 RILP | 2 RWDD2A |
| 2 PAPSS2 | 2 PIGU | 2 PPP3CB | 2 PVR | 2 RIMS4 | 2 RWDD2B |
| 2 PAQR3 | 2 PIH1D1 | 2 PPP4C | 2 PVRL1 | 2 RINL | 2 RXFP3 |

TABLE 2-continued

Infertility Genes, Ranked

| | | | | | |
|---|---|---|---|---|---|
| 2 PAQR5 | 2 PIK3CD | 2 PPP5D1 | 2 PXMP2 | 2 RNASEK | 2 RXFP4 |
| 2 PAQR6 | 2 PIK3R1 | 2 PPP6C | 2 PXMP4 | 2 RNASEK-C17ORF49 | 2 SAAL1 |
| 2 PARD6B | 2 PILRA | 2 PRADC1 | 2 PYROXD1 | | 2 SAFB2 |
| 2 PARD6G | 2 PINK1 | 2 PRDM1 | 2 QRFPR | 2 RND2 | 2 SAMD3 |
| 2 PARD6G-AS1 | 2 PIP5K1C | 2 PRDM10 | 2 RAB12 | 2 RNF10 | 2 SAMD9L |
| 2 PARL | 2 PITPNM3 | 2 PREB | 2 RAB24 | 2 RNF126P1 | 2 SAP18 |
| 2 PASD1 | 2 PITRM1 | 2 PRELID2 | 2 RAB3B | 2 RNF13 | 2 SARM1 |
| 2 PATL2 | 2 PIWIL3 | 2 PREP | 2 RAB3D | 2 RNF130 | 2 SATL1 |
| 2 PAX5 | 2 PKD1L1 | 2 PRICKLE1 | 2 RAB4A | 2 RNF144A | 2 SBF1 |
| 2 PAX6 | 2 PKD2 | 2 PRICKLE2-AS1 | 2 RAB8B | 2 RNF144A-AS1 | 2 SBF2-AS1 |
| 2 PAX9 | 2 PKN3 | 2 PRICKLE2-AS2 | 2 RABL2B | 2 RNF145 | 2 SBSN |
| 2 PAXIP1 | 2 PKNOX1 | 2 PRICKLE3 | 2 RAC2 | 2 RNF170 | 2 SCAND2 |
| 2 PCBD2 | 2 PKP1 | 2 PRIM1 | 2 RAC3 | 2 RNF175 | 2 SCARF1 |
| 2 PCCA | 2 PKP3 | 2 PRKAR2B | 2 RAD18 | 2 RNF182 | 2 SCARNA13 |
| 2 PCDH20 | 2 PLCB3 | 2 PRKCA | 2 RAD23A | 2 RNF20 | 2 SCHIP1 |
| 2 PCDH9 | 2 PLCG1 | 2 PRKRIR | 2 RAD50 | 2 RNF208 | 2 SCIMP |
| 2 PCDHAC1 | 2 PLD4 | 2 PRLHR | 2 RAD51L3-RFFL | 2 RNF216 | 2 SCOC |
| 2 PCDHB1 | 2 PLD6 | 2 PROCA1 | 2 RAE1 | 2 RNF32 | 2 SCP2 |
| 2 PCDHB18 | 2 PLEK | 2 PROCR | 2 RAI14 | 2 RNF44 | 2 SCUBE2 |
| 2 PCDHGC3 | 2 PLEKHA2 | 2 PROSC | 2 RANBP3 | 2 RNU6-19 | 2 SCUBE3 |
| 2 PCED1B | 2 PLEKHG4 | 2 PRPF3 | 2 RANGRF | 2 RNU6-28 | 2 SDAD1 |
| 2 PCGF1 | 2 PLEKHG4B | 2 PRPF40B | 2 RAP2B | 2 ROPN1B | 2 SDC4 |
| 2 PCID2 | 2 PLEKHG6 | 2 PRR18 | 2 RASA4CP | 2 RPAP1 | 2 SDCBP2 |
| 2 PCK2 | 2 PLEKHM3 | 2 PRR19 | 2 RASGRP4 | 2 RPF1 | 2 SDCBP2-AS1 |
| 2 PCMT1 | 2 PLK2 | 2 PRR20A | 2 RASL10B | 2 RPH3A | 2 SEC11C |
| 2 PCSK1N | 2 PLK3 | 2 PRR20B | 2 RASL11B | 2 RPL13A | 2 SEC14L4 |
| 2 PCYT1B | 2 PLLP | 2 PRR20C | 2 RASSF9 | 2 RPL13AP5 | 2 SEC1P |
| 2 PDCL3 | 2 PLS3 | 2 PRR20D | 2 RBFOX2 | 2 RPL23 | 2 SEC22A |
| 2 PDE12 | 2 PMS1 | 2 PRR20E | 2 RBL1 | 2 RPL23AP53 | 2 SEC22B |
| 2 PDE1C | 2 PMS2P4 | 2 PRR22 | 2 RBL2 | 2 RPL23AP82 | 2 SEMA4A |
| 2 PDE2A | 2 PNCK | 2 PRR23B | 2 RBM15 | 2 RPL27A | 2 SEMA4B |
| 2 PDE3B | 2 PNMA3 | 2 PRRC2C | 2 RBM17 | 2 RPL3 | 2 SENP8 |
| 2 PDIA3 | 2 PNMAL2 | 2 PRRG1 | 2 RBM20 | 2 RPL30 | 2 SEPT10 |
| 2 PDLIM1 | 2 PNMT | 2 PRRT2 | 2 RBM26 | 2 RPL36 | 2 SEPT14 |
| 2 PDLIM2 | 2 PNOC | 2 PRRT3 | 2 RBM4B | 2 RPL39L | 2 SEPT6 |
| 2 PDPK1 | 2 PNPLA2 | 2 PRRT3-AS1 | 2 RBM5 | 2 RPL4 | 2 SERBP1 |
| 2 PDPN | 2 POC5 | 2 PRSS16 | 2 RBMXL1 | 2 RPL7A | 2 SERF2 |
| 2 PDS5A | 2 POLE | 2 PRSS27 | 2 RBMY2FP | 2 RPP21 | 2 SERPINB6 |
| 2 PDSS1 | 2 POLR1A | 2 PRSS36 | 2 RBP7 | 2 RPS10 | 2 SERPINB8 |
| 2 PDXDC2P | 2 POLR2G | 2 PRTG | 2 RCC2 | 2 RPS10-NUDT3 | 2 SERPINB9 |
| 2 SERTM1 | 2 SLC41A3 | 2 SNORD24 | 2 SSR1 | 2 TBX10 | 2 TMEM2 |
| 2 SETD1A | 2 SLC43A3 | 2 SNORD32A | 2 SSTR1 | 2 TBX3 | 2 TMEM200A |
| 2 SETD5 | 2 SLC46A3 | 2 SNORD33 | 2 SSTR5 | 2 TBXA2R | 2 TMEM211 |
| 2 SETMAR | 2 SLC4A1AP | 2 SNORD34 | 2 SSX4 | 2 TC2N | 2 TMEM229A |
| 2 SF3B5 | 2 SLC4A7 | 2 SNORD35A | 2 SSX4B | 2 TCAP | 2 TMEM230 |
| 2 SFTPC | 2 SLC51B | 2 SNORD36A | 2 SSX5 | 2 TCEAL5 | 2 TMEM241 |
| 2 SGCD | 2 SLC5A8 | 2 SNORD36B | 2 ST3GAL1 | 2 TCEAL7 | 2 TMEM40 |
| 2 SGK1 | 2 SLC6A1 | 2 SNORD36C | 2 ST6GAL1 | 2 TCF15 | 2 TMEM43 |
| 2 SGMS2 | 2 SLC6A1-AS1 | 2 SNORD38A | 2 ST6GAL2 | 2 TCF3 | 2 TMEM44 |
| 2 SGSH | 2 SLC6A20 | 2 SNORD38B | 2 ST6GALNAC3 | 2 TCP1 | 2 TMEM52B |
| 2 SGSM1 | 2 SLC6A3 | 2 SNORD46 | 2 ST6GALNAC4 | 2 TDH | 2 TMEM53 |
| 2 SH3GL3 | 2 SLC7A5 | 2 SNORD54 | 2 ST6GALNAC6 | 2 TDRD9 | 2 TMEM61 |
| 2 SH3KBP1 | 2 SLC7A8 | 2 SNORD55 | 2 ST8SIA2 | 2 TDRG1 | 2 TMEM65 |
| 2 SH3PXD2B | 2 SLC9A1 | 2 SNORD83A | 2 ST8SIA4 | 2 TEFM | 2 TMEM72 |
| 2 SHANK1 | 2 SLC9A3R2 | 2 SNORD83B | 2 ST8SIA5 | 2 TENM1 | 2 TMEM79 |
| 2 SHC1 | 2 SLC9A4 | 2 SNORD87 | 2 STAC | 2 TEPP | 2 TMEM8A |
| 2 SHISA5 | 2 SLCO1B3 | 2 SNRNP27 | 2 STAG3L4 | 2 TERC | 2 TMEM95 |
| 2 SHISA6 | 2 SLCO4A1 | 2 SNRNP48 | 2 STAT4 | 2 TERF2IP | 2 TMPRSS12 |
| 2 SHROOM1 | 2 SLX4 | 2 SNRPB2 | 2 STC2 | 2 TERT | 2 TMPRSS13 |
| 2 SHROOM4 | 2 SMAD9 | 2 SNTB1 | 2 STEAP1B | 2 TEX13B | 2 TMPRSS3 |
| 2 SIDT2 | 2 SMAP2 | 2 SNX21 | 2 STEAP2 | 2 TFAP2A | 2 TNFAIP3 |
| 2 SIGLEC10 | 2 SMARCA4 | 2 SNX22 | 2 STIP1 | 2 TFR2 | 2 TNFRSF13B |
| 2 SIGLEC12 | 2 SMARCAD1 | 2 SNX4 | 2 STK11IP | 2 TGFBR2 | 2 TNFRSF6B |
| 2 SIK2 | 2 SMARCAL1 | 2 SNX6 | 2 STOML1 | 2 TGFBRAP1 | 2 TNFSF12 |
| 2 SIPA1 | 2 SMARCB1 | 2 SOCS1 | 2 STON2 | 2 TGIF2LY | 2 TNIP2 |
| 2 SIRT2 | 2 SMARCD2 | 2 SOCS2 | 2 STOX1 | 2 TGM6 | 2 TNN |
| 2 SIX4 | 2 SMC2 | 2 SOCS2-AS1 | 2 STOX2 | 2 TH | 2 TNNT1 |
| 2 SKAP1 | 2 SMC5 | 2 SOCS3 | 2 STPG2 | 2 THAP4 | 2 TNNT2 |
| 2 SKIV2L2 | 2 SMG5 | 2 SOD2 | 2 STRA6 | 2 THEM4 | 2 TNRC6A |
| 2 SLA2 | 2 SMG8 | 2 SOD3 | 2 STRBP | 2 THOC7 | 2 TNRC6B |
| 2 SLC11A1 | 2 SMG9 | 2 SOLH | 2 STUB1 | 2 THRB | 2 TNRC6C |
| 2 SLC11A2 | 2 SMOX | 2 SOWAHC | 2 STX16-NPEPL1 | 2 THY1 | 2 TOM1L1 |
| 2 SLC12A5 | 2 SMPD4 | 2 SOX11 | 2 STX7 | 2 TIAF1 | 2 TOP1P2 |
| 2 SLC16A1 | 2 SMPDL3A | 2 SOX8 | 2 STXBP5L | 2 TIAL1 | 2 TOPORS |
| 2 SLC16A12 | 2 SMTNL2 | 2 SOX9 | 2 STYK1 | 2 TIE1 | 2 TOX3 |
| 2 SLC16A4 | 2 SNAI2 | 2 SP3 | 2 SULF2 | 2 TIGD7 | 2 TP53BP1 |
| 2 SLC16A8 | 2 SNAI3 | 2 SP6 | 2 SULT1A1 | 2 TIMM8A | 2 TP53BP2 |
| 2 SLC19A2 | 2 SNAP91 | 2 SPAG11A | 2 SUPT16H | 2 TJP1 | 2 TPBG |

TABLE 2-continued

Infertility Genes, Ranked

| | | | | | |
|---|---|---|---|---|---|
| 2 SLC19A3 | 2 SNAPC5 | 2 SPARCL1 | 2 SUPT7L | 2 TJP2 | 2 TPH1 |
| 2 SLC1A1 | 2 SNAPIN | 2 SPATA22 | 2 SVOPL | 2 TK1 | 2 TPM2 |
| 2 SLC1A3 | 2 SNAR-C1 | 2 SPATA5 | 2 SYCP2 | 2 TK2 | 2 TPPP |
| 2 SLC1A6 | 2 SNAR-C2 | 2 SPDEF | 2 SYNDIG1 | 2 TLK2 | 2 TRA2A |
| 2 SLC20A1 | 2 SNAR-C5 | 2 SPDL1 | 2 SYNE3 | 2 TLR3 | 2 TRABD2B |
| 2 SLC23A1 | 2 SNAR-E | 2 SPEG | 2 SYNGAP1 | 2 TLR4 | 2 TRAF1 |
| 2 SLC25A14 | 2 SNAR-G1 | 2 SPEN | 2 SYNPO | 2 TM9SF1 | 2 TRAF2 |
| 2 SLC25A17 | 2 SNAR-G2 | 2 SPG11 | 2 SYPL1 | 2 TMA16 | 2 TRAF3 |
| 2 SLC25A30 | 2 SNHG10 | 2 SPHK2 | 2 SYT11 | 2 TMBIM1 | 2 TRAF5 |
| 2 SLC25A33 | 2 SNHG4 | 2 SPIRE1 | 2 SYT14 | 2 TMBIM6 | 2 TRAPPC1 |
| 2 SLC25A34 | 2 SNHG6 | 2 SPIRE2 | 2 SYT17 | 2 TMC4 | 2 TRIB3 |
| 2 SLC25A35 | 2 SNORA20 | 2 SPNS1 | 2 SYT2 | 2 TMCC1 | 2 TRIM16 |
| 2 SLC26A1 | 2 SNORA21 | 2 SPNS2 | 2 SYT5 | 2 TMCC3 | 2 TRIM26 |
| 2 SLC26A10 | 2 SNORA3 | 2 SPOCK2 | 2 SYT6 | 2 TMED1 | 2 TRIM38 |
| 2 SLC26A11 | 2 SNORA37 | 2 SPPL2B | 2 SYT7 | 2 TMED9 | 2 TRIM44 |
| 2 SLC26A8 | 2 SNORA45 | 2 SPSB1 | 2 SYT8 | 2 TMEM102 | 2 TRIM60 |
| 2 SLC27A2 | 2 SNORA72 | 2 SQLE | 2 SZRD1 | 2 TMEM130 | 2 TRIM69 |
| 2 SLC29A3 | 2 SNORA74A | 2 SQSTM1 | 2 TAF4B | 2 TMEM132E | 2 TRIM72 |
| 2 SLC2A1-AS1 | 2 SNORA80B | 2 SRGN | 2 TAF6L | 2 TMEM134 | 2 TRIM73 |
| 2 SLC2A10 | 2 SNORD114-14 | 2 SRL | 2 TAG | 2 TMEM138 | 2 TRIM74 |
| 2 SLC2A13 | 2 SNORD114-15 | 2 SRM | 2 TAP1 | 2 TMEM155 | 2 TRIML2 |
| 2 SLC35A4 | 2 SNORD114-16 | 2 SRMS | 2 TBC1D10C | 2 TMEM158 | 2 TRIP10 |
| 2 SLC35D2 | 2 SNORD114-17 | 2 SRP68 | 2 TBC1D13 | 2 TMEM168 | 2 TRIP4 |
| 2 SLC35F2 | 2 SNORD114-18 | 2 SRRD | 2 TBC1D15 | 2 TMEM171 | 2 TRMT10B |
| 2 SLC38A11 | 2 SNORD114-19 | 2 SRSF1 | 2 TBC1D24 | 2 TMEM177 | 2 TRMT44 |
| 2 SLC38A3 | 2 SNORD16 | 2 SRSF2 | 2 TBC1D5 | 2 TMEM179B | 2 TRMT61A |
| 2 SLC38A4 | 2 SNORD18A | 2 SRSF4 | 2 TBC1D8 | 2 TMEM181 | 2 TRNP1 |
| 2 SLC38A8 | 2 SNORD18B | 2 SSC5D | 2 TBK1 | 2 TMEM185B | 2 TRPC1 |
| 2 SLC39A14 | 2 SNORD18C | 2 SSH2 | 2 TBPL2 | 2 TMEM194B | 2 TRPC4 |
| 2 SLC41A1 | 2 SNORD2 | 2 SSPN | 2 TBRG4 | 2 TMEM196 | 2 TRPC7 |
| 2 TRPM1 | 2 USP43 | 2 YWHAQ | 2 ZNF548 | 1 AK3 | 1 BNIP1 |
| 2 TRPM6 | 2 USP46 | 2 YY2 | 2 ZNF569 | 1 AKR7A2 | 1 BPIFA4P |
| 2 TRPM8 | 2 USP47 | 2 ZBBX | 2 ZNF570 | 1 ALG9 | 1 BSG |
| 2 TRPV3 | 2 USP50 | 2 ZBED6 | 2 ZNF578 | 1 ALK | 1 BTD |
| 2 TSC1 | 2 USP8 | 2 ZBP1 | 2 ZNF596 | 1 ALKBH5 | 1 BTN3A3 |
| 2 TSC22D1 | 2 UST | 2 ZBTB1 | 2 ZNF598 | 1 ALKBH7 | 1 C10orf2 |
| 2 TSC22D1-AS1 | 2 UTP11L | 2 ZBTB25 | 2 ZNF615 | 1 ALMS1P | 1 C11orf73 |
| 2 TSC22D3 | 2 UTP23 | 2 ZBTB33 | 2 ZNF618 | 1 ALOX12B | 1 C12orf66 |
| 2 TSPAN14 | 2 VANGL1 | 2 ZBTB38 | 2 ZNF625 | 1 ALPI | 1 C12orf71 |
| 2 TSPAN15 | 2 VAX1 | 2 ZBTB4 | 2 ZNF625-ZNF20 | 1 AMBRA1 | 1 C14orf159 |
| 2 TSPY26P | 2 VBP1 | 2 ZBTB41 | 2 ZNF644 | 1 AMOT | 1 C14orf169 |
| 2 TSPY8 | 2 VCPIP1 | 2 ZBTB43 | 2 ZNF664- | 1 AMPH | 1 C15orf40 |
| 2 TSSC1 | 2 VCX3B | 2 ZBTB8A | FAM101A | 1 AMTN | 1 C15orf56 |
| 2 TSSK3 | 2 VDAC1 | 2 ZC2HC1C | 2 ZNF669 | 1 ANAPC1 | 1 C17orf50 |
| 2 TSSK6 | 2 VPS18 | 2 ZC3H4 | 2 ZNF670- | 1 ANKRD36 | 1 C17orf51 |
| 2 TTC14 | 2 VPS41 | 2 ZC4H2 | ZNF695 | 1 ANKRD65 | 1 C18orf42 |
| 2 TTC17 | 2 VPS52 | 2 ZCCHC3 | 2 ZNF671 | 1 ANO5 | 1 C18orf63 |
| 2 TTC23L | 2 VPS53 | 2 ZDHHC22 | 2 ZNF681 | 1 AP3S1 | 1 C19orf2 |
| 2 TTC25 | 2 VTN | 2 ZDHHC8P1 | 2 ZNF695 | 1 APBB1 | 1 C19orf40 |
| 2 TTC30A | 2 VTRNA1-2 | 2 ZEB1 | 2 ZNF703 | 1 APH1A | 1 C1orf194 |
| 2 TTC30B | 2 VWA2 | 2 ZEB1-AS1 | 2 ZNF710 | 1 APITD1 | 1 C1orf213 |
| 2 TTC7A | 2 VWA5B1 | 2 ZFAND2A | 2 ZNF728 | 1 APITD1-CORT | 1 C1orf54 |
| 2 TTC9B | 2 WAS | 2 ZFP14 | 2 ZNF738 | 1 APOC1 | 1 C20orf111 |
| 2 TTLL10 | 2 WASF2 | 2 ZFP161 | 2 ZNF75A | 1 AQR | 1 C2orf69 |
| 2 TTLL13 | 2 WBP11P1 | 2 ZFP41 | 2 ZNF783 | 1 ARC | 1 C2orf70 |
| 2 TTLL6 | 2 WDFY2 | 2 ZFP82 | 2 ZNF800 | 1 ARF5 | 1 C3AR1 |
| 2 TTPAL | 2 WDR1 | 2 ZFR2 | 2 ZNF827 | 1 ARHGAP44 | 1 C3orf18 |
| 2 TTYH2 | 2 WDR17 | 2 ZFYVE27 | 2 ZNF835 | 1 ARHGAP9 | 1 C3orf20 |
| 2 TUBA1A | 2 WDR26 | 2 ZHX2 | 2 ZNF836 | 1 ARHGEF6 | 1 C3orf62 |
| 2 TUBGCP3 | 2 WDR45 | 2 ZHX3 | 2 ZNF84 | 1 ARL3 | 1 C6orf70 |
| 2 TUSC3 | 2 WDR48 | 2 ZKSCAN1 | 2 ZNF878 | 1 ARL5A | 1 C7orf63 |
| 2 TUSC5 | 2 WDR54 | 2 ZKSCAN3 | 2 ZNHIT2 | 1 ARMC2 | 1 C7orf73 |
| 2 TYR | 2 WDR5B | 2 ZMAT2 | 2 ZNHIT3 | 1 ARMCX2 | 1 C9orf129 |
| 2 U2AF1 | 2 WDR67 | 2 ZMAT4 | 2 ZNRF3 | 1 ARPP19 | 1 C9orf131 |
| 2 UBAC1 | 2 WDR82 | 2 ZMAT5 | 2 ZRSR2 | 1 ARSF | 1 C9orf135 |
| 2 UBAC2-AS1 | 2 WDR86 | 2 ZNF136 | 2 ZSCAN1 | 1 ASAH2B | 1 C9orf171 |
| 2 UBAP2 | 2 WDTC1 | 2 ZNF140 | 2 ZSCAN23 | 1 ASB12 | 1 CACNA1G |
| 2 UBE2E2 | 2 WFDC3 | 2 ZNF17 | 2 ZSCAN30 | 1 ASB9 | 1 CACNB2 |
| 2 UBE2K | 2 WFS1 | 2 ZNF185 | 2 ZSCAN5B | 1 ASRGL1 | 1 CACTIN |
| 2 UBE2M | 2 WIBG | 2 ZNF204P | 2 ZWILCH | 1 ASTL | 1 CACYBP |
| 2 UBE2Z | 2 WIPF2 | 2 ZNF212 | 2 ZXDB | 1 ASTN1 | 1 CALCA |
| 2 UBFD1 | 2 WIPF3 | 2 ZNF221 | 2 ZXDC | 1 ATAD2B | 1 CAPN7 |
| 2 UBLCP1 | 2 WIPI1 | 2 ZNF222 | 1 AADAT | 1 ATF3 | 1 CASKIN2 |
| 2 UBN1 | 2 WIPI2 | 2 ZNF229 | 1 AAK1 | 1 ATP12A | 1 CCDC169 |
| 2 UBOX5 | 2 WISP1 | 2 ZNF235 | 1 AANAT | 1 ATP4A | 1 CCDC28B |
| 2 UBXN4 | 2 WISP2 | 2 ZNF236 | 1 AASDH | 1 ATP5SL | 1 CCDC47 |
| 2 UHMK1 | 2 WNK4 | 2 ZNF264 | 1 AASDHPPT | 1 ATP6AP1 | 1 CCDC60 |
| 2 UHRF1 | | 2 ZNF280B | 1 ABCA9 | 1 ATP6V0A2 | 1 CCDC88A |

TABLE 2-continued

Infertility Genes, Ranked

| | | | | | |
|---|---|---|---|---|---|
| 2 UHRF2 | 2 WNT16 | 2 ZNF280D | 1 ABCC13 | 1 ATP6V0E1 | 1 CCDC97 |
| 2 UIMC1 | 2 WRN | 2 ZNF292 | 1 ABCG1 | 1 ATP6V1G1 | 1 CCL1 |
| 2 ULK4 | 2 WSB1 | 2 ZNF324 | 1 ABHD11-AS1 | 1 ATP6V1G2- | 1 CCNT1 |
| 2 UNC119 | 2 WSCD2 | 2 ZNF331 | 1 ABI3BP | DDX39B | 1 CCR9 |
| 2 UNC45A | 2 WWC2-AS2 | 2 ZNF34 | 1 ACAT2 | 1 ATP8B5P | 1 CD160 |
| 2 UNC50 | 2 WWOX | 2 ZNF367 | 1 ACCS | 1 ATRNL1 | 1 CD276 |
| 2 UNC5C | 2 XAGE5 | 2 ZNF395 | 1 ACOT13 | 1 ATXN7L3B | 1 CD80 |
| 2 UNKL | 2 XPA | 2 ZNF414 | 1 ACOX1 | 1 AVPR2 | 1 CD84 |
| 2 UNQ6494 | 2 XPOT | 2 ZNF415 | 1 ACSBG2 | 1 AXIN1 | 1 CDC42 |
| 2 UPF1 | 2 XYLT1 | 2 ZNF425 | 1 ACSF2 | 1 B3GALT4 | 1 CDC42EP3 |
| 2 UPF3A | 2 YAE1D1 | 2 ZNF44 | 1 ACTC1 | 1 B3GAT1 | 1 CDK11B |
| 2 UPK2 | 2 YAF2 | 2 ZNF445 | 1 ADAM32 | 1 BAG4 | 1 CDK5R2 |
| 2 UQCRFS1 | 2 YBX2 | 2 ZNF497 | 1 ADAMTS13 | 1 BBS7 | 1 CEACAM5 |
| 2 USF2 | 2 YEATS2 | 2 ZNF507 | 1 ADAMTS15 | 1 BCKDHB | 1 CEL |
| 2 USH1C | 2 YIF1A | 2 ZNF511 | 1 ADCK3 | 1 BCL2L15 | 1 CELSR1 |
| 2 USP16 | 2 YLPM1 | 2 ZNF512 | 1 ADCYAP1 | 1 BCORP1 | 1 CENPA |
| 2 USP19 | 2 YPEL2 | 2 ZNF513 | 1 ADRA2B | 1 BEND3 | 1 CEP85 |
| 2 USP2 | 2 YPEL3 | 2 ZNF518A | 1 AGPAT3 | 1 BEST2 | 1 CEP89 |
| 2 USP24 | 2 YTHDC1 | 2 ZNF530 | 1 AIM1L | 1 BLNK | 1 CERKL |
| 2 USP39 | 2 YTHDF2 | 2 ZNF536 | 1 AIRE | 1 BMPR1A | 1 CERS6 |
| 1 CES1 | 1 DEFB121 | 1 FAM179A | 1 GNAT1 | 1 HYDIN | 1 LINC00487 |
| 1 CES2 | 1 DEFB133 | 1 FAM195B | 1 GNG4 | 1 IBTK | 1 LINC00578 |
| 1 CFB | 1 DENND5A | 1 FAM196A | 1 GNL1 | 1 IFITM1 | 1 LINC00582 |
| 1 CFHR5 | 1 DEPDC7 | 1 FAM196B | 1 GNL3 | 1 IFLTD1 | 1 LINC00605 |
| 1 CFI | 1 DERA | 1 FAM19A3 | 1 GOLGA2P5 | 1 IGF1R | 1 LINC00673 |
| 1 CFTR | 1 DGAT2L6 | 1 FAM19A4 | 1 GPATCH1 | 1 IGSF5 | 1 LNP1 |
| 1 CHAC1 | 1 DGCR10 | 1 FAM200B | 1 GPBAR1 | 1 IGSF6 | 1 LNX1 |
| 1 CHAD | 1 DHRS7 | 1 FAM211A | 1 GPC3 | 1 IKZF3 | 1 LNX1-AS1 |
| 1 CHD8 | 1 DHRS9 | 1 FAM212B | 1 GPD1 | 1 IL10RA | 1 LOC100128264 |
| 1 CHI3L2 | 1 DIO2 | 1 FAM214A | 1 GPR64 | 1 IL17B | 1 LOC100128292 |
| 1 CHMP2B | 1 DIO2-AS1 | 1 FAM222B | 1 GPR88 | 1 IL1R1 | 1 LOC100129518 |
| 1 CHRDL2 | 1 DIO3 | 1 FAM57A | 1 GPR98 | 1 IL1RL2 | 1 LOC100130476 |
| 1 CHRM2 | 1 DIO3OS | 1 FAM66A | 1 GPRASP1 | 1 ILDR2 | 1 LOC100130539 |
| 1 CHRM3 | 1 | 1 FAM91A1 | 1 GPRC5D | 1 IQCC | 1 LOC100130700 |
| 1 CHRNA6 | DKFZp686K1684 | 1 FAM92B | 1 GPX1 | 1 IQSEC2 | 1 LOC100131138 |
| 1 CHRND | 1 DKK3 | 1 FAM96B | 1 GPX5 | 1 IRF8 | 1 LOC100132078 |
| 1 CLDN11 | 1 DLL1 | 1 FANCI | 1 GREB1 | 1 IRX6 | 1 LOC100132354 |
| 1 CLEC12B | 1 DMBT1 | 1 FARP2 | 1 GRHL3 | 1 ISG20 | 1 LOC100132987 |
| 1 CLINT1 | 1 DNAJB5 | 1 FARS2 | 1 GRIA1 | 1 ITCH | 1 LOC100133985 |
| 1 CLRN1 | 1 DNAJC5 | 1 FBP1 | 1 GRIPAP1 | 1 ITFG2 | 1 LOC100134868 |
| 1 CMSS1 | 1 DNAJC5B | 1 FBXO11 | 1 GRM8 | 1 ITIH3 | 1 LOC100240735 |
| 1 CMTM7 | 1 DNPEP | 1 FBXO22 | 1 GSTM5 | 1 JOSD2 | 1 LOC100268168 |
| 1 CMTM8 | 1 DOCK2 | 1 FBXO3 | 1 GTF3A | 1 KCNA7 | 1 LOC100288346 |
| 1 CNPY1 | 1 DOK1 | 1 FBXO41 | 1 GZMB | 1 KCNAB2 | 1 LOC100289019 |
| 1 CNRIP1 | 1 DPEP1 | 1 FCRL5 | 1 GZMM | 1 KCNH3 | 1 LOC100302640 |
| 1 COG2 | 1 DPPA4 | 1 FEZF1 | 1 H2AFB1 | 1 KCNJ4 | 1 LOC100335030 |
| 1 COL11A1 | 1 DPY19L1 | 1 FEZF1-AS1 | 1 H2AFB3 | 1 KCNJ9 | 1 LOC100498859 |
| 1 COL1A2 | 1 DPYS | 1 FIBIN | 1 HACE1 | 1 KCNK15 | 1 LOC100505783 |
| 1 COL6A4P1 | 1 DSC3 | 1 FIBP | 1 HACL1 | 1 KCNK17 | 1 LOC100506746 |
| 1 COL8A2 | 1 DTNA | 1 FILIP1L | 1 HAT1 | 1 KDM2A | 1 LOC100616530 |
| 1 COLEC11 | 1 DUSP14 | 1 FIP1L1 | 1 HDC | 1 KDM4C | 1 LOC100652791 |
| 1 CORO2B | 1 DUSP27 | 1 FKBP7 | 1 HEATR4 | 1 KIAA0319 | 1 LOC146880 |
| 1 CPEB2 | 1 DUSP3 | 1 FLJ22184 | 1 HEMK1 | 1 KIF5C | 1 LOC151174 |
| 1 CPSF1 | 1 DUT | 1 FLJ33065 | 1 HERC2P2 | 1 KITLG | 1 LOC282997 |
| 1 CRADD | 1 EBF4 | 1 FLJ34208 | 1 HEXA | 1 KLHDC4 | 1 LOC283143 |
| 1 CREBZF | 1 ECM1 | 1 FLJ39051 | 1 HEXA-AS1 | 1 KLHL18 | 1 LOC283335 |
| 1 CREM | 1 EDC3 | 1 FLJ44635 | 1 HEY1 | 1 KLHL3 | 1 LOC286190 |
| 1 CRHBP | 1 EFCAB13 | 1 FN1 | 1 HHAT | 1 KLHL30 | 1 LOC338817 |
| 1 CRTC1 | 1 EFCAB2 | 1 FNDC3A | 1 HIATL1 | 1 KLHL32 | 1 LOC344595 |
| 1 CSRP1 | 1 EFNB2 | 1 FNTA | 1 HIC1 | 1 KRT12 | 1 LOC400456 |
| 1 CST7 | 1 EGF | 1 FOXN3 | 1 HIST1H2AL | 1 KRT27 | 1 LOC401127 |
| 1 CSTA | 1 EGFL6 | 1 FREM1 | 1 HIST1H2BF | 1 KRT8 | 1 LOC439990 |
| 1 CTDNEP1 | 1 EGOT | 1 FTSJD1 | 1 HIST2H2AB | 1 KRT84 | 1 LOC440028 |
| 1 CTTN | 1 EGR4 | 1 FUNDC2 | 1 HIST2H2BE | 1 KRTAP10-10 | 1 LOC494558 |
| 1 CTTNBP2 | 1 EI24 | 1 FXR2 | 1 HLA-B | 1 KRTAP10-2 | 1 LOC642852 |
| 1 CTXN1 | 1 EIF2C4 | 1 FZD9 | 1 HLA-C | 1 KRTAP5-5 | 1 LOC643387 |
| 1 CUL2 | 1 EIF3G | 1 GAL3ST2 | 1 HMGA2 | 1 KRTCAP2 | 1 LOC644961 |
| 1 CUL3 | 1 ELK3 | 1 GALK2 | 1 HMGXB3 | 1 LACE1 | 1 LOC646903 |
| 1 CWH43 | 1 ELMOD1 | 1 GALNS | 1 HNRNPUL1 | 1 LAMTOR3 | 1 LOC650226 |
| 1 CYBRD1 | 1 ELP5 | 1 GALNT4 | 1 HOPX | 1 LAPTM4B | 1 LOC728024 |
| 1 CYFIP1 | 1 EME1 | 1 GALNT6 | 1 HOXB4 | 1 LCA5L | 1 LOC728218 |
| 1 CYP1A1 | 1 EMILIN3 | 1 GALNTL6 | 1 HOXB9 | 1 LCE1E | 1 LOC728613 |
| 1 CYP2D7P1 | 1 EMP2 | 1 GBA3 | 1 HOXC-AS5 | 1 LCN15 | 1 LOC729020 |
| 1 CYP39A1 | 1 EPB41L3 | 1 GBP3 | 1 HOXC12 | 1 LCN2 | 1 LOC729059 |
| 1 CYP4F11 | 1 EPS8L1 | 1 GCC1 | 1 HOXC13 | 1 LCN6 | 1 LOC732275 |
| 1 CYP4F8 | 1 ERN1 | 1 GCHFR | 1 HOXC8 | 1 LGALS1 | 1 LOXL3 |
| 1 DACT3 | 1 ETV7 | 1 GDAP2 | 1 HOXD10 | 1 LGALS17A | 1 LOXL4 |
| 1 DAGLB | 1 F2RL1 | 1 GDF15 | 1 HPRT1 | 1 LGALS8 | 1 LPHN3 |

TABLE 2-continued

Infertility Genes, Ranked

| | | | | | |
|---|---|---|---|---|---|
| 1 DAK | 1 F8A1 | 1 GDI1 | 1 HPSE | 1 LGALS8-AS1 | 1 LPO |
| 1 DALRD3 | 1 F8A2 | 1 GFI1B | 1 HPSE2 | 1 LGI3 | 1 LRPAP1 |
| 1 DAP | 1 F8A3 | 1 GID8 | 1 HSD17B12 | 1 LHB | 1 LRRC3B |
| 1 DAPP1 | 1 F9 | 1 GIGYF2 | 1 HSPA12A | 1 LHFPL2 | 1 LRRC55 |
| 1 DCAF5 | 1 FAHD2B | 1 GIMAP2 | 1 HSPA1A | 1 LHX4 | 1 LRRN2 |
| 1 DCDC2B | 1 FAM100B | 1 GIMAP7 | 1 HSPA1L | 1 LIMS1 | 1 LSM1 |
| 1 DDX20 | 1 FAM105A | 1 GIPR | 1 HTR3D | 1 LINC00051 | 1 LYPD5 |
| 1 DDX39B | 1 FAM135B | 1 GLRA4 | 1 HTR5A | 1 LINC00189 | 1 MAML1 |
| 1 DDX42 | 1 FAM13B | 1 GLTPD2 | 1 HTRA3 | 1 LINC00304 | 1 MANBA |
| 1 DEFA10P | 1 FAM169B | 1 GNAI3 | 1 HUWE1 | 1 LINC00472 | 1 MAP2K1 |
| 1 MAP2K6 | 1 MRPL28 | 1 OR8K1 | 1 POFUT2 | 1 RNASE12 | 1 SLC47A1 |
| 1 MAPK11 | 1 MRPL43 | 1 OR8S1 | 1 POGLUT1 | 1 RNASE6 | 1 SLC48A1 |
| 1 MAPK15 | 1 MRPL45 | 1 OSBPL10-AS1 | 1 POGZ | 1 RNF126 | 1 SLC4A8 |
| 1 MASTL | 1 MS4A8B | 1 OSBPL11 | 1 POLA2 | 1 RNF128 | 1 SLC5A1 |
| 1 MAT2B | 1 MSH3 | 1 OTOF | 1 POLD3 | 1 RNF133 | 1 SLC5A7 |
| 1 MB | 1 MSH6 | 1 OTOP3 | 1 POLDIP3 | 1 RNF138P1 | 1 SLC6A18 |
| 1 MCM3 | 1 MSRB3 | 1 OTP | 1 POLK | 1 RNF144B | 1 SLC6A4 |
| 1 MCTP1 | 1 MSX2 | 1 OTUD7A | 1 POLR1B | 1 RNF148 | 1 SLC7A14 |
| 1 MEAF6 | 1 MT1E | 1 P2RY11 | 1 POLR2C | 1 RNF168 | 1 SMG7 |
| 1 MECOM | 1 MT2A | 1 P2RY12 | 1 POLR3H | 1 RNF7 | 1 SMG7-AS1 |
| 1 MED12 | 1 MTOR | 1 P2RY14 | 1 POU6F2 | 1 RP1L1 | 1 SNAR-C3 |
| 1 MED18 | 1 MUC15 | 1 P2RY2 | 1 PPFIBP1 | 1 RPL11 | 1 SNHG16 |
| 1 MEF2C | 1 MXD4 | 1 PABPC4L | 1 PPIL1 | 1 RPL24 | 1 SNHG3 |
| 1 MEIS1 | 1 MYB | 1 PADI1 | 1 PPIL2 | 1 RPL26 | 1 SNORA11B |
| 1 MEIS1-AS3 | 1 MYBPHL | 1 PAK1 | 1 PPIL4 | 1 RPL26L1 | 1 SNORA4 |
| 1 MEPCE | 1 MYF6 | 1 PAK4 | 1 PPM1B | 1 RPL8 | 1 SNORA63 |
| 1 METTL24 | 1 MYL10 | 1 PAK6 | 1 PPM1F | 1 RPRD2 | 1 SNORD19B |
| 1 METTL3 | 1 MYLK4 | 1 PAPPA2 | 1 PPM1J | 1 RRAS2 | 1 SNORD1A |
| 1 MFSD3 | 1 MYO15B | 1 PAQR8 | 1 PPP1CA | 1 RRP12 | 1 SNORD1B |
| 1 MFSD7 | 1 MYOC | 1 PARVB | 1 PPP1R27 | 1 RRP7B | 1 SNORD1C |
| 1 MGA | 1 MYRIP | 1 PBRM1 | 1 PPP2R5D | 1 RSAD1 | 1 SNORD69 |
| 1 MGP | 1 MYT1 | 1 PCDHB11 | 1 PQLC2 | 1 RSU1 | 1 SNORD84 |
| 1 MIAT | 1 MZB1 | 1 PCED1B-AS1 | 1 PRAF2 | 1 RUFY4 | 1 SNRPG |
| 1 MICB | 1 NANOS3 | 1 PCMTD1 | 1 PRDX1 | 1 RYBP | 1 SNX27 |
| 1 MID1 | 1 NAT8 | 1 PCMTD2 | 1 PRKCD | 1 S100A11 | 1 SNX9 |
| 1 MIR1207 | 1 NBLA00301 | 1 PCYT2 | 1 PRKD1 | 1 SACS | 1 SOCS6 |
| 1 MIR1307 | 1 NCBP1 | 1 PDCD11 | 1 PRKD3 | 1 SAFB | 1 SORD |
| 1 MIR1322 | 1 NCOA5 | 1 PDCD4 | 1 PROB1 | 1 SAMD12 | 1 SOX2-OT |
| 1 MIR193B | 1 NDST1 | 1 PDCL2 | 1 PROM1 | 1 SAMM50 | 1 SOX6 |
| 1 MIR196A | 1 NDUFA10 | 1 PDE7A | 1 PRPF18 | 1 SCAF8 | 1 SPACA7 |
| 1 MIR200A | 1 NDUFAF3 | 1 PDE8A | 1 PRR15L | 1 SCEL | 1 SPATS2 |
| 1 MIR218-2 | 1 NEDD9 | 1 PDGFRA | 1 PRR3 | 1 SCG5 | 1 SPEM1 |
| 1 MIR22 | 1 NEK5 | 1 PECR | 1 PRRX1 | 1 SCML2 | 1 SPHKAP |
| 1 MIR2276 | 1 NFIB | 1 PELI2 | 1 PRSS12 | 1 SDE2 | 1 SPINT1 |
| 1 MIR22HG | 1 NFKBIA | 1 PEX10 | 1 PRSS23 | 1 SDHAF1 | 1 SPOP |
| 1 MIR3127 | 1 NHP2L1 | 1 PEX6 | 1 PSMA3 | 1 SEC63 | 1 SPTBN1 |
| 1 MIR3142 | 1 NLGN4Y | 1 PFKL | 1 PSMD1 | 1 SECISBP2L | 1 SRD5A1P1 |
| 1 MIR3646 | 1 NMNAT1 | 1 PFN2 | 1 PSMF1 | 1 SEMA4D | 1 SRGAP1 |
| 1 MIR424 | 1 NODAL | 1 PGAP1 | 1 PTCHD2 | 1 SEMA6D | 1 ST3GAL4 |
| 1 MIR425 | 1 NOS1 | 1 PGAP3 | 1 PTCRA | 1 SEPP1 | 1 ST6GALNAC1 |
| 1 MIR429 | 1 NOTO | 1 PGLYRP4 | 1 PTEN | 1 SEPT8 | 1 ST8SIA1 |
| 1 MIR4314 | 1 NOTUM | 1 PGM1 | 1 PTGER1 | 1 SERPINA5 | 1 STARD9 |
| 1 MIR4500HG | 1 NOX1 | 1 PHACTR4 | 1 PTP4A3 | 1 SF3B1 | 1 STEAP1 |
| 1 MIR4508 | 1 NPAS2 | 1 PHF17 | 1 PTPN3 | 1 SFXN2 | 1 STIM1 |
| 1 MIR4632 | 1 NR2C2 | 1 PHOX2A | 1 PURA | 1 SH2D1A | 1 STK17A |
| 1 MIR4716 | 1 NR4A1 | 1 PHOX2B | 1 PXN | 1 SH2D2A | 1 STK39 |
| 1 MIR4795 | 1 NR4A2 | 1 PI4KB | 1 QPRT | 1 SH3BGR | 1 STMN2 |
| 1 MIR4800 | 1 NRBP1 | 1 PIGZ | 1 QSOX2 | 1 SH3BGRL3 | 1 STMN3 |
| 1 MIR503 | 1 NRCAM | 1 PIK3R5 | 1 RAPGEF4 | 1 SHBG | 1 STXBP6 |
| 1 MIR521-2 | 1 NRM | 1 PIWIL4 | 1 RAPGEF4-AS1 | 1 SHC2 | 1 SUCLA2 |
| 1 MIR548N | 1 NT5C2 | 1 PLAC2 | 1 RARRES2 | 1 SHISA8 | 1 SURF6 |
| 1 MIR567 | 1 NT5C3 | 1 PLAC8 | 1 RARRES3 | 1 SHQ1 | 1 SUV39H1 |
| 1 MIR592 | 1 NTN1 | 1 PLCB4 | 1 RBM12B | 1 SIK3 | 1 SYCP2L |
| 1 MIR600 | 1 NTRK1 | 1 PLCD1 | 1 RBM12B-AS1 | 1 SIRPA | 1 SYNE1 |
| 1 MIR600HG | 1 NUCB2 | 1 PLEK2 | 1 RBM38 | 1 SIRT7 | 1 TAAR6 |
| 1 MIR626 | 1 NUPL1 | 1 PLEKHA3 | 1 RBMY2EP | 1 SKA3 | 1 TAB2 |
| 1 MIR642A | 1 NXPH4 | 1 PLEKHG1 | 1 RBPMS2 | 1 SKIDA1 | 1 TAC3 |
| 1 MIR648 | 1 OAS3 | 1 PLK1 | 1 RCAN1 | 1 SLAMF8 | 1 TACC1 |
| 1 MIR9-1 | 1 OAZ1 | 1 PLSCR3 | 1 RESP18 | 1 SLC14A1 | 1 TANC1 |
| 1 MIR9-3 | 1 OIT3 | 1 PM20D1 | 1 RFX2 | 1 SLC17A3 | 1 TAS1R1 |
| 1 MITF | 1 OLFM4 | 1 PNLIPRP1 | 1 RFXAP | 1 SLC17A8 | 1 TBC1D2 |
| 1 MMP2 | 1 OLIG1 | 1 PNMAL1 | 1 RGAG4 | 1 SLC22A1 | 1 TBL1XR1 |
| 1 MMP3 | 1 OR1F1 | 1 PNN | 1 RGS17 | 1 SLC23A2 | 1 TBPL1 |
| 1 MMP7 | 1 OR2W3 | 1 PNPLA4 | 1 RGS2 | 1 SLC25A27 | 1 TBX20 |
| 1 MORC2-AS1 | 1 OR52B6 | 1 PNPLA7 | 1 RGS9 | 1 SLC25A52 | 1 TBX4 |
| 1 MPEG1 | 1 OR52K2 | 1 POC1B | 1 RIMBP2 | 1 SLC39A4 | 1 TBXAS1 |
| 1 MPP5 | 1 OR52N2 | 1 POC1B-GALNT4 | 1 RIMS2 | 1 SLC43A1 | 1 TCF7L2 |
| 1 MRO | 1 OR6P1 | | 1 RNASE11 | 1 SLC46A2 | 1 TDP2 |

TABLE 2-continued

Infertility Genes, Ranked

| | | | | | |
|---|---|---|---|---|---|
| 1 TENC1 | 1 TMEM206 | 1 TRIM55 | 1 UBE2N | 1 WNT11 | 1 ZNF148 |
| 1 TESC | 1 TMEM217 | 1 TRMT11 | 1 UBXN10 | 1 WNT4 | 1 ZNF234 |
| 1 TEX2 | 1 TMEM222 | 1 TSHR | 1 UGT3A2 | 1 WNT7B | 1 ZNF257 |
| 1 TEX22 | 1 TMEM31 | 1 TSNARE1 | 1 UHRF1BP1 | 1 WWP1 | 1 ZNF296 |
| 1 TEX33 | 1 TMEM39A | 1 TSPAN18 | 1 ULBP2 | 1 XIRP1 | 1 ZNF322 |
| 1 TFAP2B | 1 TMPRSS2 | 1 TSPEAR | 1 ULBP3 | 1 XKR5 | 1 ZNF385D |
| 1 TGFBR1 | 1 TMSB4Y | 1 TSTD2 | 1 ULK1 | 1 XPO6 | 1 ZNF436 |
| 1 TGFBR3 | 1 TMX1 | 1 TTBK1 | 1 UPF2 | 1 YEATS4 | 1 ZNF468 |
| 1 THSD4 | 1 TNFSF10 | 1 TTC32 | 1 USMG5 | 1 YME1L1 | 1 ZNF485 |
| 1 TIMM44 | 1 TNNI3K | 1 TTC4 | 1 USP14 | 1 ZAR1 | 1 ZNF518B |
| 1 TLR10 | 1 TNS4 | 1 TTC9 | 1 USP36 | 1 ZBED3 | 1 ZNF541 |
| 1 TLR8 | 1 TOMM70A | 1 TTF1 | 1 UTRN | 1 ZBED3-AS1 | 1 ZNF583 |
| 1 TLR8-AS1 | 1 TOP3B | 1 TTLL5 | 1 VAV1 | 1 ZBTB48 | 1 ZNF624 |
| 1 TLX2 | 1 TPH2 | 1 TTTY14 | 1 VAV2 | 1 ZCWPW1 | 1 ZNF704 |
| 1 TM4SF18 | 1 TPI1 | 1 TTYH1 | 1 VMA21 | 1 ZDHHC20 | 1 ZNF740 |
| 1 TMEM150B | 1 TPK1 | 1 TUBGCP4 | 1 VMO1 | 1 ZFAND1 | 1 ZNF793 |
| 1 TMEM169 | 1 TRAF3IP1 | 1 TUBGCP6 | 1 VTRNA1-3 | 1 ZIC2 | 1 ZNF80 |
| 1 TMEM17 | 1 TRAM1 | 1 TXK | 1 VWC2 | 1 ZKSCAN2 | 1 ZNF83 |
| 1 TMEM176A | 1 TRAPPC6B | 1 TXLNG | 1 WDR19 | 1 ZMYM4 | 1 ZPBP2 |
| 1 TMEM176B | 1 TRDN | 1 TXN2 | 1 WDR81 | 1 ZMYM5 | 1 ZSCAN12P1 |
| 1 TMEM182 | 1 TREM1 | 1 TXNRD1 | 1 WFIKKN2 | 1 ZMYND11 | 1 ZSCAN29 |
| 1 TMEM200C | 1 TRIM46 | 1 UAP1L1 | 1 WNT10A | 1 ZNF107 | |

TABLE 3

Poor Embryo-Quality Genes, Ranked

| | | | | | |
|---|---|---|---|---|---|
| 35 VIPR2 | 21 FAM53A | 20 SNRPN | 19 | 18 C6orf201 | 18 MCF2L2 |
| 34 NRXN2 | 21 FLJ36000 | 20 TMEM74 | LOC100287834 | 18 CCDC121 | 18 MDGA2 |
| 30 APOL6 | 21 HIST1H1T | 20 TRABD | 19 LOC653160 | 18 CEBPE | 18 MESTIT1 |
| 30 SMAP1 | 21 LINC00607 | 20 TRIM10 | 19 LRP4-AS1 | 18 CTNNB1 | 18 MRI1 |
| 28 SNTG2 | 21 LOC729121 | 20 TRIM15 | 19 LRRC7 | 18 CYB5D1 | 18 MTX2 |
| 27 KCNQ1 | 21 MEST | 20 ZC3H11A | 19 LY86 | 18 DDAH2 | 18 N6AMT2 |
| 27 TNXB | 21 PABPC1P2 | 20 ZFHX4 | 19 MAD1L1 | 18 DDX3Y | 18 NPRL3 |
| 27 ZBTB46 | 21 PCDHA5 | 19 ACE2 | 19 MAGEA12 | 18 DNHD1 | 18 NR5A2 |
| 26 HDAC4 | 21 PCDHA6 | 19 ADAMTS20 | 19 MAGEB2 | 18 FAM184B | 18 NT5C1B |
| 26 PDZD2 | 21 PLAGL1 | 19 ADRBK1 | 19 MDC1 | 18 FAM217A | 18 OPA1 |
| 26 RPTOR | 21 PRPS1L1 | 19 ARHGEF10 | 19 MREG | 18 FARP1 | 18 OR2AE1 |
| 25 C14orf79 | 21 PSMD14 | 19 BLCAP | 19 NAP1L5 | 18 FKBP6 | 18 PAGE2B |
| 25 HCG17 | 21 RABIF | 19 C13orf45 | 19 NCK2 | 18 FTHL17 | 18 PCDHA8 |
| 25 HCG18 | 21 RGPD4 | 19 C1QTNF7 | 19 NNAT | 18 GATA6 | 18 PCDHGA1 |
| 25 TBC1D1 | 21 STK19 | 19 CARD11 | 19 NSUN7 | 18 GPN1 | 18 PCDHGA10 |
| 25 TRIM39 | 21 TAF1C | 19 CCDC169- | 19 NT5C1B- | 18 GPR50 | 18 PCDHGA11 |
| 25 TRIM39-RPP21 | 21 XXYLT1<br>21 ZC3H12D | SOHLH2<br>19 CCDC79 | RDH14<br>19 OPRD1 | 18 GRIN2D<br>18 GZF1 | 18 PCDHGA2<br>18 PCDHGA3 |
| 24 CALHM1 | 20 ANK1 | 19 CNTROB | 19 OR10C1 | 18 HAPLN1 | 18 PCDHGA4 |
| 24 CSMD1 | 20 ANO3 | 19 COX8C | 19 PCDHA7 | 18 HDGFL1 | 18 PCDHGA5 |
| 24 TXNDC15 | 20 BEX1 | 19 CSAG1 | 19 PRDM16 | 18 HGC6.3 | 18 PCDHGA6 |
| 23 LRP4 | 20 DIP2C | 19 CTAGE1 | 19 PTPRD | 18 HIST1H1A | 18 PCDHGA7 |
| 23 PCDHA1 | 20 DYNC1LI1 | 19 CUX1 | 19 QRSL1 | 18 HIST1H3A | 18 PCDHGA8 |
| 23 PCDHA2 | 20 HOXA3 | 19 DLGAP2 | 19 RTN4IP1 | 18 HIST1H4A | 18 PCDHGA9 |
| 23 RNF220 | 20 HYMAI | 19 EIF2C1 | 19 S100A9 | 18 HS3ST1 | 18 PCDHGB1 |
| 22 DUSP21 | 20 ID3 | 19 EXOSC9 | 19 SLC9A3 | 18 HSPG2 | 18 PCDHGB2 |
| 22 ITGAE | 20 JARID2 | 19 FBXL20 | 19 SOHLH2 | 18 IL17RA | 18 PCDHGB3 |
| 22 LOC643406 | 20 LOC401242 | 19 FMN2 | 19 TCEB3B | 18 IL18 | 18 PCDHGB4 |
| 22 LRRC37BP1 | 20 LRBA | 19 FTMT | 19 TNFRSF18 | 18 INPP5A | 18 PCDHGB5 |
| 22 NFIC | 20 MAB21L2 | 19 GNG12-AS1 | 19 TUBB | 18 KCNH5 | 18 PCDHGB6 |
| 22 PCDHA3 | 20 MAGEB1 | 19 GPR123 | 19 UNC79 | 18 KDM6B | 18 PCDHGB7 |
| 22 PCDHA4 | 20 MAPK10 | 19 GPX6 | 18 ACVR1C | 18 KIAA1551 | 18 PDXDC1 |
| 22 POMT2 | 20 MIR148A | 19 HERC3 | 18 ADAMTS2 | 18 KIFC1 | 18 PPT2 |
| 22 SLAIN1 | 20 NGFRAP1 | 19 HLA-A | 18 AGAP1 | 18 LAMA2 | 18 PPT2-EGFL8 |
| 22 TRAPPC12 | 20 NOS3 | 19 HSPA7 | 18 ANTXR2 | 18 | 18 PRRT1 |
| 22 WFDC1 | 20 PACRG | 19 KATNAL2 | 18 BCYRN1 | LOC100506451 | 18 RAI1 |
| 21 ADAD2 | 20 PENK | 19 KCNAB3 | 18 BLOC1S5-<br>TXNDC5 | 18 LOC442028 | 18 RASSF8 |
| 21 C3orf24 | 20 RAD51B | 19 KIF26B | 18 BRDT | 18 LOC641367 | 18 RBCK1 |
| 21 CALD1 | 20 SKI | 19 LINC00340 | 18 C2orf47 | 18 LRFN1 | 18 RBFOX1 |
| 21 COL23A1 | 20 SMYD3 | | | 18 LY9 | 18 RELB |
| 18 RNU6-81 | 17 FAM9A | 17 NRSN1 | 17 ZFP64 | 16 DAB1 | 16 KLF8 |
| 18 SENP3 | 17 FAM9B | 17 PCDHGA12 | 17 ZGLP1 | 16 DACH1 | 16 KRBA1 |
| 18 SENP3-EIF4A1 | 17 FASTK | 17 PDP1 | 17 ZIC5 | 16 DAZL | 16 KRT28 |
| 18 SLMO1 | 17 FBXL18 | 17 PLEC | 17 ZNF219 | 16 DCAF4L1 | 16 L3MBTL4 |
| 18 SMAD6 | 17 FRMD1 | 17 PLEKHA5 | 17 ZNF354A | 16 DCAF4L2 | 16 LATS2 |
| 18 SPERT | 17 GAS7 | 17 PNLDC1 | 17 ZNF521 | 16 DDX53 | 16 LDHD |
| 18 SSTR5-AS1 | 17 GIMAP1 | 17 PNMA1 | 17 ZNF532 | 16 DEF6 | 16 LFNG |
| 18 STK3 | 17 GIMAP1- | 17 PPARA | 17 ZNF579 | 16 DIAPH2 | 16 LINC00473 |

TABLE 3-continued

Poor Embryo-Quality Genes, Ranked

| | | | | | |
|---|---|---|---|---|---|
| 18 SVIL | GIMAP5 | 17 PPP1R18 | 17 ZNF668 | 16 DIRAS3 | 16 LINC00668 |
| 18 TAPBP | 17 GLTSCR1 | 17 PRDM9 | 17 ZNF678 | 16 DMRTB1 | 16 LMF1 |
| 18 TEX12 | 17 GNAS | 17 PRELP | 17 ZNF714 | 16 DNAH12 | 16 LMTK3 |
| 18 TMEM88 | 17 GPR39 | 17 PSORS1C1 | 17 ZNF735 | 16 DNAJA4 | 16 |
| 18 TRIM50 | 17 GRIN2B | 17 PTPRCAP | 17 ZNF775 | 16 DVL3 | LOC100128750 |
| 18 TXLNA | 17 HLA-DQB2 | 17 PTPRN2 | 17 ZNF843 | 16 EFHC2 | 16 |
| 18 TYW5 | 17 HLTF | 17 QRICH2 | 17 ZNF865 | 16 EFNA2 | LOC100129794 |
| 18 WDR27 | 17 HLTF-AS1 | 17 RARG | 16 ABCA7 | 16 EHBP1 | 16 |
| 18 ZBTB22 | 17 HNRNPA1L2 | 17 RBPMS | 16 ABHD8 | 16 EHD4 | LOC100132215 |
| 18 ZNF100 | 17 HOXA4 | 17 REPIN1 | 16 ACOT4 | 16 EXOC4 | 16 |
| 18 ZNF696 | 17 HTR2C | 17 RFPL3 | 16 ACSL5 | 16 FAM13C | LOC100506713 |
| 18 ZNF74 | 17 INF2 | 17 RFX1 | 16 ADARB2 | 16 FAM151B | 16 |
| 17 ABR | 17 INPP5F | 17 RGS7 | 16 ADGB | 16 FAM172A | LOC100507266 |
| 17 ADAD1 | 17 ITPR1 | 17 RNF103- | 16 ALOX12P2 | 16 FAM189A1 | 16 |
| 17 ADCY10P1 | 17 KCNJ14 | CHMP3 | 16 ALOX5AP | 16 FAM197Y2 | LOC100507463 |
| 17 AGA | 17 KCNQ1OT1 | 17 RNF113B | 16 AMFR | 16 FAM197Y5 | 16 LOC116437 |
| 17 AGAP3 | 17 KEAP1 | 17 RNU6-71 | 16 ANKFY1 | 16 FAM204A | 16 LOC340094 |
| 17 AKAP12 | 17 KHDC1 | 17 RPL22L1 | 16 AP2M1 | 16 FAM47B | 16 LOC389641 |
| 17 AKT3 | 17 KIAA0146 | 17 RPS6KA2 | 16 APC | 16 FAM48B1 | 16 LOC401164 |
| 17 ANKRD20A9P | 17 KIAA2013 | 17 RPS6KA4 | 16 APCDD1L | 16 FAT3 | 16 LOC643441 |
| 17 ANKRD30A | 17 KIF16B | 17 SGK223 | 16 ARHGEF4 | 16 FHOD3 | 16 LOC654433 |
| 17 ANO1 | 17 KLHL13 | 17 SHCBP1L | 16 ATP10A | 16 FIZ1 | 16 LOC729177 |
| 17 APBA1 | 17 KLHL20 | 17 SLC12A6 | 16 BCL2L2- | 16 FLJ42875 | 16 LOC731789 |
| 17 AR | 17 KPRP | 17 SLC9C1 | PABPN1 | 16 FPGT | 16 LPCAT1 |
| 17 ARHGAP27 | 17 LINC00221 | 17 SORCS2 | 16 BCOR | 16 FPGT-TNNI3K | 16 LRFN3 |
| 17 ARHGEF17 | 17 LINC00359 | 17 SOX30 | 16 BMP3 | 16 GALNT9 | 16 LRRC38 |
| 17 ARID3A | 17 LINC00482 | 17 SPDYC | 16 BTBD19 | 16 GDF1 | 16 LRRIQ3 |
| 17 ASIC4 | 17 | 17 SPRED3 | 16 C10orf32- | 16 GGN | 16 LRRTM3 |
| 17 ATP11A | LOC100128714 | 17 SRGAP3 | AS3MT | 16 GHRL | 16 LUZP4 |
| 17 BEND2 | 17 | 17 STAU2 | 16 C10orf71 | 16 GLI2 | 16 MAGEB6 |
| 17 BEX2 | LOC100133612 | 17 STK31 | 16 C11orf21 | 16 GML | 16 MCCC1 |
| 17 BHMT | 17 | 17 TBC1D16 | 16 C11orf52 | 16 GNA12 | 16 MCF2L |
| 17 BOLL | LOC100286922 | 17 TCTN1 | 16 C17orf98 | 16 GNAS-AS1 | 16 MEG3 |
| 17 BRCA1 | 17 | 17 TECTA | 16 C1orf146 | 16 GNG7 | 16 MINK1 |
| 17 BRD9 | LOC100873065 | 17 TEX28 | 16 C1orf228 | 16 GRASP | 16 MIR1237 |
| 17 C10orf47 | 17 LOC153684 | 17 TFAP2E | 16 C22orf45 | 16 GRB10 | 16 MIR143HG |
| 17 C12orf40 | 17 LOC219731 | 17 TKTL1 | 16 C2orf65 | 16 GRWD1 | 16 MIR145 |
| 17 C1orf61 | 17 LOC285768 | 17 TMEM237 | 16 C4orf22 | 16 GSPT1 | 16 MIR4648 |
| 17 C3orf77 | 17 LOC339822 | 17 TMUB1 | 16 C7orf72 | 16 GSTCD | 16 MKX |
| 17 C6orf147 | 17 LOC401010 | 17 TNRC18 | 16 C9orf156 | 16 HIPK2 | 16 MMP28 |
| 17 C7orf50 | 17 LST1 | 17 TRERF1 | 16 CALN1 | 16 HIST1H2BH | 16 MORC1 |
| 17 C8orf22 | 17 LTB | 17 TRIO | 16 CAPS2 | 16 HIST1H4G | 16 MRPL34 |
| 17 CACNA1I | 17 MAEL | 17 TRIP13 | 16 CASP7 | 16 HLA-DPA1 | 16 MYLK-AS1 |
| 17 CAMTA1 | 17 MAGEA10 | 17 TTYH3 | 16 CCDC117 | 16 HLA-DPB1 | 16 MYO7B |
| 17 CBFA2T3 | 17 MAGEA10- | 17 TUBA3C | 16 CCKBR | 16 HSPB2- | 16 NBR2 |
| 17 CCER1 | MAGEA5 | 17 TUSC5 | 16 CCSAP | C11orf52 | 16 NEDD4L |
| 17 CLEC17A | 17 MAGEC2 | 17 UBE4B | 16 CD58 | 16 IFITM2 | 16 NSUN4 |
| 17 COL9A1 | 17 MAP7D1 | 17 UGT1A1 | 16 CDK2AP1 | 16 INTS12 | 16 NTM |
| 17 CSNK1A1P1 | 17 MAT2A | 17 UGT1A10 | 16 CECR1 | 16 ITFG3 | 16 NUDT9P1 |
| 17 CXorf61 | 17 MBD3 | 17 UGT1A3 | 16 CERS1 | 16 ITIH5 | 16 OCA2 |
| 17 DCAF4 | 17 MGAT4C | 17 UGT1A4 | 16 CGNL1 | 16 ITPKB | 16 OPHN1 |
| 17 DLG2 | 17 MIR223 | 17 UGT1A5 | 16 CHD7 | 16 ITSN2 | 16 OXCT1 |
| 17 DSCR4 | 17 MIR335 | 17 UGT1A6 | 16 CHMP3 | 16 KCNB2 | 16 OXR1 |
| 17 DSCR8 | 17 MIR378D2 | 17 UGT1A7 | 16 CLEC4C | 16 KCNG2 | 16 PABPC3 |
| 17 EGFR | 17 MYT1L | 17 UGT1A8 | 16 COL22A1 | 16 KCNJ16 | 16 PABPN1 |
| 17 ELMSAN1 | 17 NDUFA11 | 17 UGT1A9 | 16 CRYL1 | 16 KCNQ5 | 16 PAGE1 |
| 17 EXOC2 | 17 NEURL1B | 17 UNC5B | 16 CT45A1 | 16 KDM5B | 16 PARK2 |
| 17 FAM107B | 17 NFYA | 17 VPS51 | 16 CTNNA3 | 16 KDM5B-AS1 | 16 PAX8 |
| 17 FAM47A | 17 NOBOX | 17 WIPF1 | 16 CXorf36 | 16 KIAA2022 | 16 PCDH15 |
| 17 FAM58BP | 17 NOS1AP | 17 ZBTB7A | 16 CYB5R2 | 16 KIF2B | 16 PDE11A |
| 16 PDHA2 | 16 TAF7 | 15 ANO9 | 15 CTBP2 | 15 GPR146 | 15 |
| 16 PER3 | 16 TAP2 | 15 APOA5 | 15 CTCFL | 15 GPR25 | LOC100507384 |
| 16 PFKFB2 | 16 TBCB | 15 ARHGAP22 | 15 CTNNA2 | 15 GPR75 | 15 |
| 16 PGGT1B | 16 TCTEX1D4 | 15 ARHGEF18 | 15 CWC22 | 15 GPR75-ASB3 | LOC100507584 |
| 16 PGK2 | 16 TDRD12 | 15 ARHGEF25 | 15 CYTH1 | 15 GPRC5C | 15 |
| 16 PGPEP1L | 16 TM7SF2 | 15 ARHGEF28 | 15 DCP1B | 15 GPSM2 | LOC100861402 |
| 16 PHLPP1 | 16 TMEM14C | 15 ATF6 | 15 DENND1C | 15 GRIN3B | 15 LOC253039 |
| 16 PIK3R6 | 16 TMEM247 | 15 ATF6B | 15 | 15 GRK5 | 15 LOC255025 |
| 16 PKHD1L1 | 16 TNFRSF10A | 15 ATOH7 | DKFZp566F0947 | 15 GSE1 | 15 LOC284100 |
| 16 PLA2G4E | 16 TNFRSF1A | 15 ATP2C1 | 15 | 15 GTSF1 | 15 LOC285441 |
| 16 PLEKHF1 | 16 TNFSF12- | 15 ATP8A2 | DKFZp686O1327 | 15 HEXIM2 | 15 LOC285577 |
| 16 POM121L12 | TNFSF13 | 15 B3GALT6 | 15 DLC1 | 15 HEY2 | 15 LOC407835 |
| 16 PPP1R2P9 | 16 TRIM27 | 15 BCL11A | 15 DMRTC2 | 15 HLA-DPB2 | 15 LOC440356 |
| 16 PPP4R1L | 16 TRIM36 | 15 BCL2L12 | 15 DNAJB3 | 15 HMG20B | 15 LOC441601 |
| 16 PRKAR1B | 16 TRPV2 | 15 BCL3 | 15 DND1 | 15 HMGN3 | 15 LOC646762 |
| 16 PROKR1 | 16 TRPV4 | 15 BFAR | 15 DNMT3A | 15 HNRPDL | 15 LOC649395 |
| 16 PRR5 | 16 TSPAN32 | 15 BHLHB9 | 15 DOCK4 | 15 HPCAL1 | 15 LOC729176 |
| 16 PSD3 | 16 TSPY1 | 15 BHLHE40 | 15 DOK2 | 15 HSF2BP | 15 LOC84856 |

TABLE 3-continued

Poor Embryo-Quality Genes, Ranked

| | | | | | |
|---|---|---|---|---|---|
| 16 PSMB5 | 16 TSPY4 | 15 BMS1P4 | 15 DOK7 | 15 ICA1 | 15 LPGAT1 |
| 16 PSORS1C2 | 16 TTC33 | 15 BOD1L2 | 15 DPP6 | 15 IL21R | 15 LRP1B |
| 16 PTAR1 | 16 TTC40 | 15 BST2 | 15 DPP9 | 15 IL21R-AS1 | 15 LTC4S |
| 16 PTPLB | 16 TUBA3D | 15 BTBD11 | 15 DPPA5 | 15 IL22 | 15 LY6K |
| 16 PTRF | 16 TUBA3E | 15 C10orf32 | 15 DYNC1H1 | 15 ING1 | 15 LYPD4 |
| 16 PVRL4 | 16 TYK2 | 15 C11orf53 | 15 DYNC1LI2 | 15 INPP5D | 15 MAGEA4 |
| 16 PXDNL | 16 UBAP1L | 15 C12orf5 | 15 DZIP1 | 15 INSL6 | 15 MAGEA8 |
| 16 RAB22A | 16 UNC5D | 15 C16orf90 | 15 E2F2 | 15 IQCA1 | 15 MAGEB10 |
| 16 RAB32 | 16 UPB1 | 15 C19orf25 | 15 EBPL | 15 IRAK4 | 15 MAGIX |
| 16 RAB5A | 16 VASH1 | 15 C2 | 15 EEF1DP3 | 15 IRF3 | 15 MANBAL |
| 16 RASGEF1C | 16 VSIG2 | 15 C2orf27A | 15 EEPD1 | 15 IRS2 | 15 MCM3AP |
| 16 RBM11 | 16 WDR69 | 15 C3orf45 | 15 EGR1 | 15 ITGAX | 15 MCM5 |
| 16 RBMS1 | 16 WDR88 | 15 C5orf47 | 15 EHD2 | 15 KCND2 | 15 MCMDC2 |
| 16 RCCD1 | 16 WLS | 15 C5orf58 | 15 EHMT2 | 15 KCNG1 | 15 MCPH1 |
| 16 RFPL3-AS1 | 16 WSB1 | 15 C9orf170 | 15 EIF2AK4 | 15 KCNH8 | 15 METTL5 |
| 16 RIPK4 | 16 XKR4 | 15 CACNA2D1 | 15 ELAVL4 | 15 KCNK3 | 15 MGC72080 |
| 16 RNF166 | 16 YBX1 | 15 CACNG2 | 15 ELK2AP | 15 KCNT1 | 15 MGST1 |
| 16 RNF39 | 16 YOD1 | 15 CARD14 | 15 ENOPH1 | 15 KCTD15 | 15 MGST2 |
| 16 RP1 | 16 ZBTB17 | 15 CARHSP1 | 15 ERRFI1 | 15 KDM2B | 15 MIR3065 |
| 16 RPH3AL | 16 ZBTB7C | 15 CASZ1 | 15 ESRRG | 15 KHDC3L | 15 MIR4785 |
| 16 RPL13 | 16 ZMIZ1 | 15 CAV1 | 15 FAM124A | 15 KIAA0513 | 15 MIR548AP |
| 16 RREB1 | 16 ZNF19 | 15 CCDC130 | 15 FAM160B2 | 15 KIDINS220 | 15 MIR548H4 |
| 16 RRP1B | 16 ZNF282 | 15 CCDC141 | 15 FAM170B | 15 KIF13B | 15 MKRN2 |
| 16 RTN1 | 16 ZNF354B | 15 CCDC162P | 15 FAM20B | 15 KIF3B | 15 MLC1 |
| 16 RUFY1 | 16 ZNF611 | 15 CCDC173 | 15 FAM214A | 15 KLF11 | 15 MOB3A |
| 16 RYR1 | 16 ZNF784 | 15 CCDC71L | 15 FAM217B | 15 KLHDC7B | 15 MOV10L1 |
| 16 SALL3 | 16 ZNF787 | 15 CCDC80 | 15 FAM221A | 15 KLHL6 | 15 MPDU1 |
| 16 SARS | 16 ZNF98 | 15 CCND3 | 15 FANCF | 15 KRAS | 15 MPHOSPH6 |
| 16 SBF1P1 | 16 ZSCAN10 | 15 CCRL2 | 15 FGF17 | 15 KRT18P55 | 15 MPST |
| 16 SBNO2 | 16 ZSWIM4 | 15 CCZ1B | 15 FKBP5 | 15 L3MBTL1 | 15 MTSS1L |
| 16 SDPR | 16 ZYG11A | 15 CDH11 | 15 FLII | 15 LBX2 | 15 MXI1 |
| 16 SH3BP5L | 15 AATK | 15 CDH23 | 15 FLJ42289 | 15 LCOR | 15 MYADML |
| 16 SIVA1 | 15 ABCB6 | 15 CDH5 | 15 FLRT2 | 15 LEMD2 | 15 MYEOV2 |
| 16 SLC22A18 | 15 ABT1 | 15 CDIPT | 15 FMNL1 | 15 LIG1 | 15 MYO15A |
| 16 SLC25A21 | 15 ACER2 | 15 CDKL2 | 15 FRMPD4 | 15 LIMCH1 | 15 MYO5C |
| 16 SLC30A8 | 15 ACOT11 | 15 CDKN3 | 15 FTLP10 | 15 LINC00351 | 15 NAF1 |
| 16 SLC43A2 | 15 ACRC | 15 CDX1 | 15 GAB2 | 15 LINC00460 | 15 NCOR2 |
| 16 SLC44A2 | 15 ADAM18 | 15 CETN1 | 15 GABRB1 | 15 LINC00461 | 15 NDUFA13 |
| 16 SLC8A3 | 15 ADAM8 | 15 CHDH | 15 GABRB3 | 15 LOC100130581 | 15 NEIL3 |
| 16 SLC9B2 | 15 ADAMTS12 | 15 CKLF-CMTM1 | 15 GAGE10 | 15 LOC100131094 | 15 NEURL3 |
| 16 SLCO5A1 | 15 AFF3 | 15 CLCN6 | 15 GAGE2E | 15 LOC100132831 | 15 NFATC2 |
| 16 SNURF | 15 AGAP2 | 15 CLK2P | 15 GAGE8 | 15 LOC100288198 | 15 NHSL2 |
| 16 SPG21 | 15 AGTR1 | 15 CLUAP1 | 15 GALNTL5 | 15 LOC100294145 | 15 NICN1 |
| 16 SPRED2 | 15 AIPL1 | 15 CMTM1 | 15 GEMIN8P4 | 15 LOC100506733 | 15 NOSIP |
| 16 SSBP2 | 15 AKAP10 | 15 CMTM6 | 15 GFM1 | 14 C3orf14 | 15 NOSTRIN |
| 16 SSBP3 | 15 AMT | 15 CNTN1 | 15 GGT7 | 14 C3orf30 | 15 NOTCH3 |
| 16 SSX3 | 15 ANKRD11 | 15 COL18A1 | 15 GJA8 | 14 C3orf52 | 15 NPAS1 |
| 16 SSX7 | 15 ANKRD2 | 15 COL9A2 | 15 GK2 | 14 C3orf67 | 15 NR1D2 |
| 16 ST14 | 15 ANKRD33B | 15 CSGALNACT1 | 15 GLUD1P3 | 14 C4orf36 | 15 NRXN1 |
| 16 STK11 | 15 ANKRD9 | 15 CT45A6 | 15 GPATCH8 | 14 C5orf56 | 15 NUBPL |
| 15 OBFC1 | 15 SAAL1 | 15 TMEM161A | 14 ACVR1B | 14 C8orf40 | 14 CYP4X1 |
| 15 OR10Q1 | 15 SAGE1 | 15 TMEM72-AS1 | 14 ACYP2 | 14 C8orf73 | 14 CYSTM1 |
| 15 OSBP2 | 15 SALL4 | 15 TNFSF13 | 14 ADAM11 | 14 C9orf43 | 14 DAB2 |
| 15 OSMR | 15 SAP25 | 15 TNNT3 | 14 ADAM2 | 14 CACNA2D4 | 14 DACT1 |
| 15 OTUD6A | 15 SBK2 | 15 TNPO3 | 14 ADAMTS1 | 14 CALB1 | 14 DACT2 |
| 15 P2RX4 | 15 SDCCAG8 | 15 TOMM20L | 14 ADAMTS10 | 14 CAMK1D | 14 DBT |
| 15 PAGE2 | 15 SDF4 | 15 TOR4A | 14 ADAMTS17 | 14 CANX | 14 DCAF8L1 |
| 15 PARD3B | 15 SEC22A | 15 TRAM1L1 | 14 ADAMTSL1 | 14 CAPNS1 | 14 DDX1 |
| 15 PARN | 15 SEMA3B | 15 TREX1 | 14 ADCY9 | 14 CATSPER2 | 14 DDX43 |
| 15 PBX1 | 15 SEMA5A | 15 TRIM2 | 14 ADHFE1 | 14 CBX6 | 14 DDX4 |
| 15 PBX2 | 15 SEMA6A | 15 TRIM29 | 14 AEBP1 | 14 CCDC142 | 14 DDX49 |
| 15 PCDHA9 | 15 SH2B2 | 15 TRIM41 | 14 AEBP2 | 14 CCDC164 | 14 DFFB |
| 15 PCSK4 | 15 SH2B3 | 15 TRIM68 | 14 AFAP1 | 14 CCDC166 | 14 DGKZ |
| 15 PEG10 | 15 SH2D4B | 15 TRIM71 | 14 AGBL4 | 14 CCDC73 | 14 DHX58 |
| 15 PELI1 | 15 SH3TC1 | 15 TRPM2 | 14 AHDC1 | 14 CCNB3 | 14 DIS3L2 |
| 15 PGRMC1 | 15 SHANK2 | 15 TRPM4 | 14 AHRR | 14 CCNC | 14 DLEU2 |
| 15 PHLDB3 | 15 SHMT1 | 15 TSPAN17 | 14 AKAP13 | 14 CCP110 | 14 DLGAP1 |
| 15 PHOSPHO2 | 15 SIGIRR | 15 TSSK6 | 14 ALDH5A1 | 14 CCR6 | 14 DLGAP1-AS3 |
| 15 PHOSPHO2-KLHL23 | 15 SIPA1L3 | 15 TST | 14 ALOX12 | 14 CD151 | 14 DMD |
| 15 PIN1P1 | 15 SLAIN2 | 15 TTC21B | 14 ALPK1 | 14 CD59 | 14 DMGDH |
| 15 PIWIL2 | 15 SLC10A7 | 15 TUBB8 | 14 ALS2CL | 14 CDH10 | 14 DNM1L |
| 15 PKN1 | 15 SLC17A9 | 15 TUBGCP2 | 14 ALS2CR11 | 14 CDH6 | 14 DOK6 |
| 15 PLEKHB1 | 15 SLC1A1 | 15 UBR3 | 14 AMDHD2 | 14 CCP110 | 14 DPPA2 |
| 15 PLEKHH1 | 15 SLC20A2 | 15 UBXN2B | 14 AMMECR1L | 14 CCR6 | 14 DPPA3 |
| 15 PNMA5 | 15 SLC22A18AS | 15 UHRF1BP1L | 14 AMPD3 | 14 CD151 | 14 DUS3L |
| 15 PODXL2 | 15 SLC28A2 | 15 UNC13A | 14 ANKRD26P1 | 14 CD59 | 14 DYX1C1 |
| 15 PON2 | 15 SLC2A5 | 15 UNC80 | 14 ANO10 | 14 CDH10 | 14 DYX1C1-CCPG1 |
| | 15 SLC35D1 | 15 UNC93B1 | 14 AP3B2 | 14 CDH6 | |

TABLE 3-continued

Poor Embryo-Quality Genes, Ranked

| | | | | | |
|---|---|---|---|---|---|
| 15 POU5F2 | 15 SLC39A10 | 15 USP42 | 14 APBB2 | 14 CDHR5 | 14 EBAG9 |
| 15 PPFIA3 | 15 SLC6A16 | 15 USP49 | 14 ARHGAP12 | 14 CDK18 | 14 EDNRB |
| 15 PRNP | 15 SNAPIN | 15 VAMP3 | 14 ARHGAP30 | 14 CDK6 | 14 EGFLAM |
| 15 PRR23C | 15 SNED1 | 15 VHL | 14 ARL13B | 14 CELSR3 | 14 EIF4G1 |
| 15 PRSS3 | 15 SNORD58A | 15 WDR60 | 14 ARL4C | 14 CEP104 | 14 ELAC1 |
| 15 PRSS35 | 15 SNORD58B | 15 WNT7A | 14 ART3 | 14 CEP78 | 14 ELF5 |
| 15 PRSS42 | 15 SNORD58C | 15 WTAPP1 | 14 ATG9A | 14 CEP85L | 14 ELOVL7 |
| 15 PSMD5 | 15 SNX20 | 15 XAGE3 | 14 ATP6V0C | 14 CFH | 14 ELTD1 |
| 15 PSTPIP1 | 15 SOAT2 | 15 XIST | 14 AUTS2 | 14 CHMP2B | 14 EN2 |
| 15 PTDSS2 | 15 SOHLH1 | 15 YBEY | 14 B3GNTL1 | 14 CHORDC1 | 14 ENO4 |
| 15 PTPN6 | 15 SORBS2 | 15 ZADH2 | 14 B4GALT7 | 14 CHSY3 | 14 EPHX4 |
| 15 PTPRE | 15 SPATA16 | 15 ZBTB12 | 14 BAG2 | 14 CHURC1- | 14 ERLIN2 |
| 15 PUS7L | 15 SPON1 | 15 ZBTB47 | 14 BAIAP2 | FNTB | 14 ERO1L |
| 15 PXDN | 15 SSX1 | 15 ZFHX2 | 14 BASP1 | 14 CKLF | 14 ESRRB |
| 15 RAB27A | 15 ST20 | 15 ZFP57 | 14 BATF | 14 CLASRP | 14 EVPLL |
| 15 RADIL | 15 ST20-MTHFS | 15 ZFPM1 | 14 BCLAF1 | 14 CLCN7 | 14 EYA3 |
| 15 RALBP1 | 15 STK10 | 15 ZNF143 | 14 BHMT2 | 14 CLEC2L | 14 F2RL3 |
| 15 RASGRF2 | 15 SUN1 | 15 ZNF217 | 14 BID | 14 CLHC1 | 14 FAM163A |
| 15 RB1 | 15 SUV420H1 | 15 ZNF259 | 14 BMP2 | 14 CLMN | 14 FAM171A2 |
| 15 RBM24 | 15 SYCP2 | 15 ZNF264 | 14 BMP8A | 14 CMAHP | 14 FAM206A |
| 15 RBM44 | 15 SYCP3 | 15 ZNF311 | 14 BNIPL | 14 CNDP2 | 14 FAM46D |
| 15 RBM45 | 15 SYNJ2BP- | 15 ZNF326 | 14 BOLA3 | 14 CNNM1 | 14 FAM50B |
| 15 RBM46 | COX16 | 15 ZNF385A | 14 BOLA3-AS1 | 14 CNP | 14 FAM83B |
| 15 RBM47 | 15 SYNPO2 | 15 ZNF438 | 14 BRE | 14 COPE | 14 FAM96A |
| 15 RCC1 | 15 TAF5 | 15 ZNF467 | 14 BRE-AS1 | 14 CORO1B | 14 FBXL19 |
| 15 RELL1 | 15 TAF8 | 15 ZNF599 | 14 BRSK1 | 14 CPA1 | 14 FBXL7 |
| 15 REXO1L2P | 15 TBC1D17 | 15 ZNF622 | 14 C11orf20 | 14 CPE | 14 FECH |
| 15 RFESD | 15 TCP11 | 15 ZNF665 | 14 C11orf63 | 14 CPT1A | 14 FER |
| 15 RFPL4B | 15 TDRD6 | 15 ZNF701 | 14 C11orf80 | 14 CRTAC1 | 14 FEZ1 |
| 15 RGS14 | 15 TECR | 15 ZNF831 | 14 C12orf56 | 14 CRYBG3 | 14 FIGLA |
| 15 RIN3 | 15 TENM2 | 15 ZNF853 | 14 C15orf38 | 14 CRYZL1 | 14 FKBPL |
| 15 RNU5F-1 | 15 TENM3 | 15 ZNRD1-AS1 | 14 C15orf38- | 14 CSDE1 | 14 FKRP |
| 15 ROBO2 | 15 TEX14 | 15 ZPBP | AP3S2 | 14 CSMD2 | 14 FMN1 |
| 15 RPL17 | 15 TFAP4 | 15 ZSCAN5A | 14 C15orf43 | 14 CTPS1 | 14 FNTB |
| 15 RPL17- | 15 THBS4 | 14 AAED1 | 14 C15orf60 | 14 CTU1 | 14 FOLH1 |
| C18ORF32 | 15 THTPA | 14 ABCA1 | 14 C1orf114 | 14 CXCL9 | 14 FOPNL |
| 15 RPS7 | 15 TLR6 | 14 ABCA13 | 14 C1orf56 | 14 CXXC1 | 14 FOXR1 |
| 15 RRP1 | 15 TMC1 | 14 ABHD16B | 14 C1orf87 | 14 CYB561 | 14 FOXRED2 |
| 15 RYR2 | 15 TMEM132D | 14 ACSF3 | 14 C2orf42 | 14 CYB5R3 | 14 FRAS1 |
| 15 S100A10 | 15 TMEM160 | 14 ACTL7B | 14 C2orf61 | 14 CYP25C1 | 14 FRMD4A |
| 14 FRMD8 | 14 KANK2 | 14 LOC644649 | 14 NPFFR2 | 14 PRR20D | 14 SLC25A16 |
| 14 FSTL1 | 14 KAT6B | 14 LOC650226 | 14 NPHP3 | 14 PRR20E | 14 SLC25A22 |
| 14 FTCD | 14 KAZN | 14 LOC728613 | 14 NPHP3- | 14 PRR5- | 14 SLC25A45 |
| 14 FUNDC2P2 | 14 KBTBD5 | 14 LOXHD1 | ACAD11 | ARHGAP8 | 14 SLC25A48 |
| 14 FUT4 | 14 KCNC2 | 14 LOXL1 | 14 NPHP3-AS1 | 14 PRRC2A | 14 SLC25A51P1 |
| 14 FZD5 | 14 KCND3 | 14 LPAR5 | 14 NPR2 | 14 PRSS22 | 14 SLC34A2 |
| 14 GAB1 | 14 KCNK4 | 14 LPCAT2 | 14 NPTN | 14 PRSS50 | 14 SLC35C1 |
| 14 GAB4 | 14 KCNMA1 | 14 LRCH4 | 14 NR3C1 | 14 PRSS55 | 14 SLC37A4 |
| 14 GAGE2A | 14 KCNV2 | 14 LRRC4 | 14 NRG1 | 14 PSMA8 | 14 SLC6A6 |
| 14 GATM | 14 KCTD12 | 14 LRRC56 | 14 NSA2 | 14 PTPN21 | 14 SLC6A8 |
| 14 GDE1 | 14 KDM5C | 14 LRRK1 | 14 NUP133 | 14 PURG | 14 SLC9A4 |
| 14 GDF10 | 14 KIAA0664 | 14 LSM6 | 14 NUS1 | 14 PUS10 | 14 SMAD3 |
| 14 GEMIN8 | 14 KIAA1211L | 14 LY86-AS1 | 14 NXT2 | 14 PYROXD2 | 14 SMARCA2 |
| 14 GFM2 | 14 KIAA1383 | 14 MACROD2 | 14 OOEP | 14 R3HDM4 | 14 SMARCA5 |
| 14 GFPT1 | 14 KIAA1522 | 14 MAFK | 14 OPRK1 | 14 RABL6 | 14 SMCR7 |
| 14 GFRA3 | 14 KIAA1875 | 14 MAGEB18 | 14 ORAI3 | 14 RAP1GAP2 | 14 SMG6 |
| 14 GINS4 | 14 KIAA1984 | 14 MAML1 | 14 OSBPL7 | 14 RARA | 14 SMOC2 |
| 14 GLB1L2 | 14 KIAA1984-AS1 | 14 MAN1C1 | 14 OTX1 | 14 RARB | 14 SMTNL2 |
| 14 GLOD4 | 14 KLF15 | 14 MAP2K3 | 14 P2RY1 | 14 RASA3 | 14 SNAR-I |
| 14 GLRX2 | 14 KLF17 | 14 MBP | 14 PACSIN1 | 14 RASAL3 | 14 SND1 |
| 14 GLT25D1 | 14 KLHDC7A | 14 MBTPS2 | 14 PAG1 | 14 RBKS | 14 SNTG1 |
| 14 GNAL | 14 KRBOX1 | 14 METTL16 | 14 PAGE3 | 14 RBM15B | 14 SNX1 |
| 14 GNG13 | 14 KRT85 | 14 MEX3B | 14 PAOX | 14 RBM33 | 14 SNX8 |
| 14 GPLD1 | 14 KRTAP19-5 | 14 MGC2752 | 14 PAQR9 | 14 RDH11 | 14 SOCS5 |
| 14 GPR158 | 14 KTI12 | 14 MIA3 | 14 PCBD1 | 14 RDH14 | 14 SPESP1 |
| 14 GPR45 | 14 L3MBTL3 | 14 MIMT1 | 14 PCDHA10 | 14 RGPD3 | 14 SPN |
| 14 GPR97 | 14 LAMA4 | 14 MIR130B | 14 PCDHA11 | 14 RGS10 | 14 SPTB |
| 14 GREM2 | 14 LAT2 | 14 MIR23A | 14 PCDHA12 | 14 RGS12 | 14 SPTBN5 |
| 14 GRHL2 | 14 LCK | 14 MIR24-2 | 14 PCDHA13 | 14 RHOBTB1 | 14 SREBF1 |
| 14 GUCY2D | 14 LDB3 | 14 MIR27A | 14 PCDHB8 | 14 RIN2 | 14 SRGN |
| 14 GUCY2GP | 14 LDHAL6A | 14 MIR301B | 14 PCGF3 | 14 RIT2 | 14 SRRM2 |
| 14 GUSBP11 | 14 LEPREL1 | 14 MIR3136 | 14 PCSK1N | 14 RLN1 | 14 SRRM2-AS1 |
| 14 H1FNT | 14 LHPP | 14 MIR320E | 14 PCSK2 | 14 RNF17 | 14 SSX2IP |
| 14 HAS1 | 14 LINC00242 | 14 MIR4426 | 14 PDE9A | 14 RNF2 | 14 ST6GALNAC3 |
| 14 HCN1 | 14 LINC00301 | 14 MIR4795 | 14 PDZD7 | 14 RNMTL1 | 14 STAB1 |
| 14 HEATR2 | 14 LINC00379 | 14 MIR548W | 14 PEG3 | 14 RNPEP | 14 STARD8 |
| 14 HEXDC | 14 LINC00574 | 14 MLLT1 | 14 PEMT | 14 RPA4 | 14 STEAP3 |
| 14 HIBADH | 14 LINC00588 | 14 MMADHC | 14 PFN3 | 14 RPL31 | 14 STK32A |

TABLE 3-continued

Poor Embryo-Quality Genes, Ranked

| | | | | | |
|---|---|---|---|---|---|
| 14 HIVEP2 | 14 LINC00640 | 14 MMP13 | 14 PGAM2 | 14 RPL6 | 14 STRA8 |
| 14 HLA-F | 14 | 14 MMP9 | 14 PHF19 | 14 RPS27A | 14 SYCE1L |
| 14 HLA-G | LOC100129138 | 14 MNS1 | 14 PICK1 | 14 RPS4X | 14 SYNJ2BP |
| 14 HLA-J | 14 | 14 MOB3C | 14 PION | 14 RRP15 | 14 SYTL1 |
| 14 HLA-L | LOC100131089 | 14 MON1B | 14 PITPNM1 | 14 RUNX1 | 14 TAG |
| 14 HLCS | 14 | 14 MORC2 | 14 PLA2G16 | 14 RXRA | 14 TAGAP |
| 14 HMHA1 | LOC100131496 | 14 MRC2 | 14 PLCB2 | 14 S100Z | 14 TCEAL4 |
| 14 HOOK2 | 14 | 14 MRGPRE | 14 PLD1 | 14 S1PR4 | 14 TCEAL6 |
| 14 HOXA2 | LOC100287704 | 14 MRPL53 | 14 PLEKHG5 | 14 SCRN2 | 14 TEF |
| 14 HRAS | 14 | 14 MRPS14 | 14 PLEKHG6 | 14 SCT | 14 TES |
| 14 ICA1L | LOC100289187 | 14 MRPS17 | 14 PLEKHH3 | 14 SCUBE3 | 14 TEX101 |
| 14 IDS | 14 | 14 MRPS9 | 14 PNPLA6 | 14 SEL1L2 | 14 TEX264 |
| 14 IDUA | LOC100289673 | 14 MSGN1 | 14 POLE3 | 14 SEMA5B | 14 TEX30 |
| 14 IGLL1 | 14 | 14 MTHFR | 14 POLE4 | 14 SEPT1 | 14 TFPT |
| 14 IGSF11 | LOC100506122 | 14 MTMR3 | 14 POLG | 14 SEPT9 | 14 TGIF2LY |
| 14 IKBKAP | 14 | 14 MYO16 | 14 PPAP2C | 14 SERPINE1 | 14 THSD7A |
| 14 IL16 | LOC100506994 | 14 MYO1H | 14 PPP1R16B | 14 SETBP1 | 14 TIAL1 |
| 14 IL6 | 14 | 14 NAGLU | 14 PPP3CC | 14 SFRP2 | 14 TIPIN |
| 14 INPP5B | LOC100507377 | 14 NAPEPLD | 14 PRDM1 | 14 SFXN3 | 14 TKTL2 |
| 14 INTS2 | 14 LOC145663 | 14 NAV1 | 14 PRDM10 | 14 SH3BP5 | 14 TLL2 |
| 14 IQCE | 14 LOC148696 | 14 NECAB1 | 14 PRDM2 | 14 SH3GL3 | 14 TMEM132C |
| 14 IQCG | 14 LOC150568 | 14 NEK3 | 14 PRKAG2 | 14 SH3PXD2A | 14 TMEM140 |
| 14 IQSEC3 | 14 LOC154822 | 14 NFATC4 | 14 PRKCZ | 14 SHANK3 | 14 TMEM151A |
| 14 IRAK2 | 14 LOC283692 | 14 NHP2 | 14 PRKD2 | 14 SHROOM3 | 14 TMEM229B |
| 14 IRGQ | 14 LOC284023 | 14 NHSL1 | 14 PRMT8 | 14 SIAH3 | 14 TMEM242 |
| 14 IRS1 | 14 LOC284454 | 14 NID1 | 14 PRPF31 | 14 SIM1 | 14 TMEM26 |
| 14 ITGB2 | 14 LOC284798 | 14 NINJ2 | 14 PRR12 | 14 SIPA1 | 14 TMF1 |
| 14 ITGB2-AS1 | 14 LOC285501 | 14 NKX6-3 | 14 PRR20A | 14 SLC15A1 | 14 TNFAIP8 |
| 14 ITSN1 | 14 LOC285972 | 14 NMUR2 | 14 PRR20B | 14 SLC16A14 | 14 TOX |
| 14 JPH3 | 14 LOC339894 | 14 NOX5 | 14 PRR20C | 14 SLC22A31 | 14 TPCN1 |
| 14 TPD52L2 | 14 ZNF746 | 13 BCAR3 | 13 CIT | 13 EXOC6B | 13 HBQ1 |
| 14 TRAF3IP2 | 14 ZNF766 | 13 BCMO1 | 13 CLCA4 | 13 EXOSC3 | 13 HIBCH |
| 14 TRAF3IP2-AS1 | 14 ZNF777 | 13 BMP1 | 13 CLDN18 | 13 EZH1 | 13 HIST1H2AA |
| 14 TRIM61 | 14 ZNF837 | 13 BOK-AS1 | 13 CLIC6 | 13 FA2H | 13 HIST1H2BA |
| 14 TRIM62 | 14 ZNF839 | 13 BRCA2 | 13 CLN3 | 13 FAM109B | 13 HIST1H3E |
| 14 TRIML1 | 14 ZNRD1 | 13 BRF1 | 13 CLTB | 13 FAM111A | 13 HIST3H3 |
| 14 TRPS1 | 14 ZRANB2 | 13 BRI3 | 13 COASY | 13 FAM122C | 13 HIVEP3 |
| 14 TSKS | 14 ZRANB2-AS2 | 13 BTK | 13 COL5A1 | 13 FAM125B | 13 HMGCL |
| 14 TSNAX | 13 A1BG | 13 C10orf128 | 13 COL6A4P2 | 13 FAM170A | 13 HMGCLL1 |
| 14 TSNAX-DISC1 | 13 ABHD12 | 13 C15orf62 | 13 COL6A6 | 13 FAM174B | 13 HMOX2 |
| 14 TSPAN31 | 13 ABHD14A | 13 C15orf63 | 13 COX6A2 | 13 FAM188A | 13 HNRNPC |
| 14 TSPYL2 | 13 ABHD14A- | 13 C17orf28 | 13 COX7B2 | 13 FAM24B | 13 HOMER3 |
| 14 TSPYL5 | ACY1 | 13 C17orf61 | 13 CPEB1 | 13 FAM24B- | 13 HOXC4 |
| 14 TTC22 | 13 ABHD14B | 13 C17orf61- | 13 CPLX1 | CUZD1 | 13 HPS4 |
| 14 TTTY23 | 13 ACAP3 | PLSCR3 | 13 CPN1 | 13 FAM83A | 13 HSH2D |
| 14 TTTY23B | 13 ACBD3 | 13 C17orf64 | 13 CR1L | 13 FAM83H | 13 HYAL2 |
| 14 TUG1 | 13 ACER3 | 13 C19orf35 | 13 CRBN | 13 FBF1 | 13 IDO2 |
| 14 TXNDC12 | 13 ACTRT3 | 13 C19orf66 | 13 CRH | 13 FBLN7 | 13 IFITM5 |
| 14 UNC13B | 13 ADAM5 | 13 C1orf65 | 13 CRTAM | 13 FBN1 | 13 IFNAR2 |
| 14 USP29 | 13 ADCY3 | 13 C20orf151 | 13 CSF2 | 13 FBN2 | 13 IGDCC3 |
| 14 USP43 | 13 ADCY5 | 13 C20orf96 | 13 CSGALNACT2 | 13 FBRSL1 | 13 IGSF3 |
| 14 UTP11L | 13 ADCY8 | 13 C22orf28 | 13 CSNK1A1L | 13 FBXW8 | 13 IL12B |
| 14 VAT1L | 13 ADRA1D | 13 C2CD2L | 13 CTAG2 | 13 FCER1G | 13 IL17D |
| 14 VCL | 13 ADRA2C | 13 C2orf74 | 13 CTAGE7P | 13 FFAR1 | 13 IL1RAPL2 |
| 14 VCX3B | 13 ADSS | 13 C5orf42 | 13 CUX2 | 13 FGFR1 | 13 INCENP |
| 14 VENTXP7 | 13 AGER | 13 C5orf52 | 13 CXCL1 | 13 FHIT | 13 INSR |
| 14 VGLL4 | 13 AGMO | 13 C5orf63 | 13 CYFIP2 | 13 FHL2 | 13 INTS1 |
| 14 VPREB1 | 13 AHNAK2 | 13 C6orf25 | 13 CYP2E1 | 13 FITM2 | 13 IQSEC1 |
| 14 VPS13B | 13 AIP | 13 C7orf13 | 13 CYR61 | 13 FLJ25363 | 13 IRF5 |
| 14 VWA1 | 13 AKIP1 | 13 C7orf45 | 13 CYTH4 | 13 FLJ46906 | 13 ISM1 |
| 14 VWA7 | 13 AKR1B1 | 13 C8orf86 | 13 DCC | 13 FLNA | 13 ITGA4 |
| 14 WDR13 | 13 ALDH3B1 | 13 C9orf47 | 13 DCLK1 | 13 FNDC5 | 13 ITPKA |
| 14 WDR43 | 13 ALOXE3 | 13 CABLES2 | 13 DCUN1D1 | 13 FOXC2 | 13 ITPRIPL2 |
| 14 WFIKKN1 | 13 ALPK3 | 13 CACNA1S | 13 DDAH1 | 13 FOXK1 | 13 JAK2 |
| 14 WNT5B | 13 AMIGO2 | 13 CACNB1 | 13 DHRS7C | 13 FOXN2 | 13 JAKMIP1 |
| 14 WRN | 13 AMMECR1 | 13 CACNG6 | 13 DHX35 | 13 FRMD6-AS2 | 13 JRKL |
| 14 YPEL4 | 13 ANKRD13B | 13 CACTIN-AS1 | 13 DLK1 | 13 FUT6 | 13 KCNA1 |
| 14 ZBTB2 | 13 | 13 CADM4 | 13 DNAH8 | 13 FXN | 13 KCNE4 |
| 14 ZBTB20 | ANKRD20A11P | 13 CALML3 | 13 DNAH9 | 13 FZD1 | 13 KCNIP2 |
| 14 ZBTB7B | 13 ANKRD30BL | 13 CALML5 | 13 DNAI2 | 13 GABARAPL3 | 13 KCNQ1DN |
| 14 ZC3H8 | 13 ANO8 | 13 CAMTA2 | 13 DNAJB6 | 13 GAL | 13 KCNT2 |
| 14 ZC3HC1 | 13 APOB | 13 CAPZB | 13 DNAJC17 | 13 GAL3ST1 | 13 KIAA0226 |
| 14 ZDHHC14 | 13 APOBR | 13 CASP5 | 13 DNAJC27 | 13 GEMIN5 | 13 KIAA0319L |
| 14 ZEB2 | 13 APOOL | 13 CCDC102B | 13 DNAJC27-AS1 | 13 GFOD1 | 13 KIAA0391 |
| 14 ZFYVE28 | 13 AQP11 | 13 CCDC116 | 13 DNAJC5G | 13 GFPT2 | 13 KIAA0528 |
| 14 ZIM2 | 13 ARHGEF19 | 13 CCDC152 | 13 DNASE1L1 | 13 GJA9 | 13 KIAA1549 |
| 14 ZMYND8 | 13 ARMC9 | 13 CCDC17 | 13 DOCK10 | 13 GJA9-MYCBP | 13 KIF23 |
| 14 ZNF18 | 13 ARMCX1 | 13 CCDC25 | 13 DOK3 | 13 GJD3 | 13 KIF3C |

TABLE 3-continued

Poor Embryo-Quality Genes, Ranked

| | | | | | |
|---|---|---|---|---|---|
| 14 ZNF232 | 13 ARPC2 | 13 CCDC82 | 13 DPY19L2P3 | 13 GLO1 | 13 KIRREL3 |
| 14 ZNF236 | 13 ARSD | 13 CCDC85A | 13 DRD4 | 13 GNPDA1 | 13 KLF14 |
| 14 ZNF267 | 13 ARVCF | 13 CCDC90B | 13 E2F7 | 13 GPC2 | 13 KLHDC1 |
| 14 ZNF275 | 13 ASB4 | 13 CCDC96 | 13 EBF3 | 13 GPR111 | 13 KLHDC5 |
| 14 ZNF286A | 13 ASCL2 | 13 CCNB1 | 13 EFHA1 | 13 GPR12 | 13 KLHL17 |
| 14 ZNF330 | 13 ASGR1 | 13 CCZ1 | 13 EHBP1L1 | 13 GPR133 | 13 KLHL22 |
| 14 ZNF341 | 13 ASPDH | 13 CD177 | 13 EHMT1 | 13 GPR135 | 13 KLHL36 |
| 14 ZNF350 | 13 ASPH | 13 CD1D | 13 ELFN1 | 13 GPR143 | 13 KLK4 |
| 14 ZNF428 | 13 ASPHD1 | 13 CD47 | 13 ELK4 | 13 GPR160 | 13 KRT83 |
| 14 ZNF48 | 13 ATF7IP2 | 13 CDH24 | 13 ELOVL2 | 13 GPR20 | 13 LAMC2 |
| 14 ZNF517 | 13 ATG5 | 13 CDK12 | 13 ELOVL2-AS1 | 13 GPR4 | 13 LBX2-AS1 |
| 14 ZNF556 | 13 ATP6V0CP3 | 13 CDKN1A | 13 EMD | 13 GPR89B | 13 LDLRAD2 |
| 14 ZNF576 | 13 ATP6V0D1 | 13 CELF6 | 13 EMP1 | 13 GPRIN1 | 13 LHCGR |
| 14 ZNF598 | 13 ATP7A | 13 CENPJ | 13 EP400NL | 13 GPRIN2 | 13 LHFPL5 |
| 14 ZNF643 | 13 AURKAIP1 | 13 CENPM | 13 EPHA1-AS1 | 13 GRK7 | 13 LIMK1 |
| 14 ZNF679 | 13 AXIN2 | 13 CERS3 | 13 ERC2 | 13 GRTP1 | 13 LINC00167 |
| 14 ZNF688 | 13 B3GNT6 | 13 CGREF1 | 13 ERG | 13 GSDMD | 13 LINC00310 |
| 14 ZNF689 | 13 B4GALNT3 | 13 CHCHD6 | 13 ESCO2 | 13 GTF2IRD1 | 13 LINC00332 |
| 14 ZNF697 | 13 BAIAP2L2 | 13 CHST6 | 13 ETV6 | 13 GTPBP3 | 13 LINC00634 |
| 14 ZNF718 | 13 BCAR1 | 13 CIITA | 13 EVPL | 13 H2BFM | 13 LIPK |
| 13 LOC100129636 | 13 MEX3D | 13 NLRP4 | 13 PRAM1 | 13 SHISA2 | 13 TAZ |
| 13 LOC100129931 | 13 MFI2 | 13 NME8 | 13 PRICKLE3 | 13 SIGLEC15 | 13 TBC1D10C |
| 13 LOC100131691 | 13 MFSD2B | 13 NMRAL1 | 13 PRKACA | 13 SIM2 | 13 TBC1D7 |
| 13 LOC100131726 | 13 MGAT3 | 13 NOC2L | 13 PRKCA | 13 SLC16A8 | 13 TBPL2 |
| 13 LOC100144597 | 13 MGC3771 | 13 NOVA2 | 13 PRKCH | 13 SLC16A9 | 13 TCEAL2 |
| 13 LOC100499194 | 13 MGMT | 13 NPAP1 | 13 PRSS36 | 13 SLC22A3 | 13 TCEAL3 |
| 13 LOC100506082 | 13 MICAL2 | 13 NR1H3 | 13 PRSS41 | 13 SLC23A2 | 13 TCN2 |
| 13 LOC100507547 | 13 MIR100HG | 13 NR6A1 | 13 PSD | 13 SLC25A14 | 13 TDRG1 |
| 13 LOC100507605 | 13 MIR1225 | 13 NRBF2 | 13 PSMB9 | 13 SLC25A29 | 13 TERC |
| 13 LOC100996291 | 13 MIR1256 | 13 NRXN3 | 13 PSORS1C3 | 13 SLC25A31 | 13 TEX13A |
| 13 LOC284998 | 13 MIR125B1 | 13 NT5DC1 | 13 PTK6 | 13 SLC25A33 | 13 TEX13B |
| 13 LOC285626 | 13 MIR141 | 13 NUP210L | 13 PTPRU | 13 SLC25A3P1 | 13 TFDP2 |
| 13 LOC286467 | 13 MIR153-2 | 13 NXPH2 | 13 PWWP2B | 13 SLC26A1 | 13 TFEB |
| 13 LOC339529 | 13 MIR181A2HG | 13 NYAP2 | 13 QPCT | 13 SLC26A8 | 13 TFF2 |
| 13 LOC339803 | 13 MIR195 | 13 OASL | 13 RAB13 | 13 SLC37A1 | 13 THRB |
| 13 LOC349160 | 13 MIR196A1 | 13 ODC1 | 13 RAB3D | 13 SLC41A1 | 13 TIE1 |
| 13 LOC387723 | 13 MIR200C | 13 ODF2 | 13 RAB40B | 13 SLC47A2 | 13 TIGD3 |
| 13 LOC399815 | 13 MIR320B1 | 13 OPCML | 13 RAC1 | 13 SLC5A3 | 13 TMC8 |
| 13 LOC400043 | 13 MIR3684 | 13 ORAI1 | 13 RAD51C | 13 SLC7A5 | 13 TMEM151B |
| 13 LOC440900 | 13 MIR371B | 13 OSBPL5 | 13 RANBP17 | 13 SLCO3A1 | 13 TMEM173 |
| 13 LOC493754 | 13 MIR372 | 13 OSBPL6 | 13 RAP1A | 13 SLMO2 | 13 TMEM175 |
| 13 LOC63930 | 13 MIR373 | 13 OSCAR | 13 RAPGEF1 | 13 SLMO2-ATP5E | 13 TMEM209 |
| 13 LOC644990 | 13 MIR4750 | 13 OSM | 13 RASGEF1B | 13 SMARCAL1 | 13 TMPRSS9 |
| 13 LOC653486 | 13 MIR497 | 13 OTOP2 | 13 RASL11B | 13 SMC1B | 13 TMX3 |
| 13 LOC728012 | 13 MIR497HG | 13 P2RX7 | 13 RAVER2 | 13 SNAR-H | 13 TNFAIP8L2-SCNM1 |
| 13 LOC728743 | 13 MIR550A3 | 13 PACS2 | 13 RBM25 | 13 SNORA14B | 13 TNFRSF1B |
| 13 LPIN1 | 13 MIR5584 | 13 PAGE4 | 13 RBM6 | 13 SNORA38 | 13 TNFRSF25 |
| 13 LPPR3 | 13 MIR589 | 13 PAPOLB | 13 RBP4 | 13 SNORA80B | 13 TNK1 |
| 13 LRP5 | 13 MLX | 13 PARD3 | 13 RFC1 | 13 SNX16 | 13 TOMM20 |
| 13 LRRC4B | 13 MPC1L | 13 PARP4 | 13 RGAG1 | 13 SNX25 | 13 TPI1P2 |
| 13 LRRC66 | 13 MRPL19 | 13 PART1 | 13 RHBDF1 | 13 SNX29 | 13 TPM1 |
| 13 LRRC72 | 13 MRPL22 | 13 PASD1 | 13 RHOXF1 | 13 SNX4 | 13 TPTE2P5 |
| 13 LRRIQ4 | 13 MRPL39 | 13 PBK | 13 RIBC2 | 13 SOX10 | 13 TRIM38 |
| 13 LRRN4CL | 13 MRPS22 | 13 PCDHB16 | 13 RNF175 | 13 SPAG7 | 13 TRIM43 |
| 13 LSP1P3 | 13 MRPS6 | 13 PCDHB17 | 13 RNF32 | 13 SPARCL1 | 13 TRIM60 |
| 13 LTBP4 | 13 MSH4 | 13 PCDHB18 | 13 RNF44 | 13 SPECC1 | 13 TRIM65 |
| 13 LUC7L | 13 MSRA | 13 PCDHB6 | 13 ROBO1 | 13 SPI1 | 13 TRIM7 |
| 13 LY6G6C | 13 MSTO2P | 13 PCSK6 | 13 RORA | 13 SPSB4 | 13 TRMT61A |
| 13 LYSMD1 | 13 MTSS1 | 13 PDE1A | 13 RPL13AP3 | 13 SPTBN4 | 13 TRPC3 |
| 13 MAGED2 | 13 MXRA7 | 13 PDE4D | 13 RPRM | 13 SRD5A1P1 | 13 TSC22D1 |
| 13 MAGEE1 | 13 MXRA8 | 13 PDLIM7 | 13 RPS27 | 13 SRRD | 13 TSC22D1-AS1 |
| 13 MAGEL2 | 13 MYCBP | 13 PDXDC2P | 13 RPUSD3 | 13 SRSF5 | 13 TSC22D4 |
| 13 MAK16 | 13 MYEF2 | 13 PDXK | 13 RSPH1 | 13 SSX5 | 13 TSPAN16 |
| 13 MALL | 13 MYNN | 13 PEBP4 | 13 RTEL1 | 13 ST5 | 13 TSPY2 |
| 13 MAML3 | 13 MYO10 | 13 PES1 | 13 RTEL1-TNFRSF6B | 13 ST6GALNAC6 | 13 TSPYL6 |
| 13 MAP3K6 | 13 MYO18A | 13 PIH1D1 | 13 S100B | 13 ST8SIA5 | 13 TTC39B |
| 13 MAPK14 | 13 MYO18B | 13 PIK3CG | 13 S1PR1 | 13 STAG3 | 13 TTLL13 |
| 13 MARK4 | 13 MYO9B | 13 PIM1 | 13 S1PR3 | 13 STARD13 | 13 TUBA8 |
| | 13 MZF1 | 13 PITRM1 | 13 SATL1 | 13 STARD3NL | 13 TYROBP |
| | 13 N4BP1 | 13 PKD1 | 13 SCARA5 | 13 STK32C | 13 UBE2K |
| | 13 NAA11 | 13 PKP1 | 13 SCGB1C1 | 13 STON1-GTF2A1L | 13 UBE2Z |
| | 13 NAGA | 13 PLCD3 | 13 SCNM1 | 13 STOX1 | 13 UBXN4 |
| | 13 NAPSB | 13 PLCL2 | 13 SEC14L4 | 13 STX16-NPEPL1 | 13 UHMK1 |
| | 13 NCAM1 | 13 PLEKHA2 | 13 SEL1L3 | 13 SUGT1P3 | 13 UNC13D |
| | 13 NCF4 | 13 PLIN5 | 13 SELM | | 13 USB1 |
| | 13 NDNF | 13 PNCK | 13 SELT | 13 SUMO3 | 13 USF2 |
| | 13 NDUFA12 | 13 POLE2 | 13 SEMA3G | 13 SYCE1 | 13 USH1G |
| | 13 NDUFS2 | 13 POLR2G | | | |

TABLE 3-continued

Poor Embryo-Quality Genes, Ranked

| | | | | | |
|---|---|---|---|---|---|
| 13 MARS | 13 NEIL2 | 13 POLRMT | 13 SENP5 | 13 SYDE1 | 13 USP18 |
| 13 MARVELD1 | 13 NEU1 | 13 POM121L9P | 13 SERF2-C15ORF63 | 13 SYN1 | 13 USP53 |
| 13 MAST4 | 13 NFATC1 | 13 PON3 | 13 SERHL2 | 13 SYNE2 | 13 USP7 |
| 13 MBTPS1 | 13 NFYB | 13 POTEA | 13 SERINC4 | 13 SYS1 | 13 UTS2D |
| 13 MCHR2 | 13 NIPA1 | 13 PP2D1 | 13 SEZ6L2 | 13 SYS1-DBNDD2 | 13 UXS1 |
| 13 MCOLN1 | 13 NIPSNAP3B | 13 PPIE | 13 SH3GL1 | 13 SYT2 | 13 VENTXP1 |
| 13 MDGA1 | 13 NKAIN4 | 13 PPM1H | 13 SH3RF3 | 13 TADA2B | 13 VIPR1 |
| 13 MEGF10 | 13 NLGN2 | 13 PPP1R13L | 13 SH3RF3-AS1 | 13 TAF3 | 13 VPS37B |
| 13 MERTK | 13 NLRP11 | 13 PPP1R2P3 | 13 SHANK1 | 13 TAF4 | 13 VWA5B2 |
| 13 METAP1 | 13 NLRP2 | 13 PPP2R3C | 12 CUTC | 13 TAP1 | 13 VWF |
| 13 WARS2 | 12 ANKRD24 | 12 CAD | 12 CWF19L1 | 12 FCHO2 | 12 HTR7P1 |
| 13 WDR24 | 12 ANKRD31 | 12 CAMSAP3 | 12 CYP21A1P | 12 FCN3 | 12 IBA57 |
| 13 WDR35 | 12 ANKRD7 | 12 CAPG | 12 CYP21A2 | 12 FERMT3 | 12 ICAM3 |
| 13 WHSC2 | 12 AP2A1 | 12 CARD9 | 12 CYP2J2 | 12 FGF11 | 12 IFFO1 |
| 13 WIF1 | 12 APBA2 | 12 CARS2 | 12 DAZAP2 | 12 FHOD1 | 12 IFT140 |
| 13 WIZ | 12 APLNR | 12 CBR4 | 12 DCTN2 | 12 FKBP9 | 12 IKZF4 |
| 13 WRAP73 | 12 APOE | 12 CBX4 | 12 DCTN4 | 12 FLJ42627 | 12 IL4I1 |
| 13 WWC2 | 12 APTX | 12 CCBP2 | 12 DDX11 | 12 FNDC1 | 12 ILDR1 |
| 13 XAF1 | 12 ARAP1 | 12 CCDC104 | 12 DDX11-AS1 | 12 FNIP1 | 12 IMP4 |
| 13 XYLT1 | 12 ARHGAP25 | 12 CCDC115 | 12 DENND2D | 12 FOXO3B | 12 IRF2BPL |
| 13 YDJC | 12 ARHGAP39 | 12 CCDC177 | 12 DGKD | 12 G3BP2 | 12 ITGA1 |
| 13 YJEFN3 | 12 ARL2BP | 12 CCDC27 | 12 DIABLO | 12 GABBR1 | 12 ITGA6 |
| 13 ZAR1L | 12 ASAP3 | 12 CCDC74B-AS1 | 12 DIEXF | 12 GABRA5 | 12 ITGA7 |
| 13 ZBTB16 | 12 ASCL5 | 12 CCDC88B | 12 DLG4 | 12 GADL1 | 12 ITGAL |
| 13 ZBTB20-AS1 | 12 ASIC1 | 12 CCNI2 | 12 DNAJB1 | 12 GAGE12B | 12 ITIH1 |
| 13 ZC3H12A | 12 ATF7IP | 12 CCNL1 | 12 DNAJC13 | 12 GAGE12C | 12 ITM2C |
| 13 ZCCHC3 | 12 ATG7 | 12 CCT6A | 12 DNAJC15 | 12 GAGE12D | 12 KAZALD1 |
| 13 ZFPM2 | 12 ATP2A3 | 12 CD300LF | 12 DNLZ | 12 GAGE12E | 12 KBTBD8 |
| 13 ZFYVE26 | 12 ATP6AP1L | 12 CD79B | 12 DOCK9 | 12 GAGE12F | 12 KCNJ15 |
| 13 ZNF136 | 12 ATP6V1C1 | 12 CDA | 12 DOHH | 12 GAGE12G | 12 KCNQ4 |
| 13 ZNF205 | 12 ATPBD4 | 12 CDC37 | 12 DPEP3 | 12 GAGE12H | 12 KCNU1 |
| 13 ZNF212 | 12 ATPBD4-AS1 | 12 CDC5L | 12 DPM1 | 12 GAGE12I | 12 KCTD5 |
| 13 ZNF229 | 12 ATRAID | 12 CDHR1 | 12 DRAP1 | 12 GAGE2C | 12 KCTD6 |
| 13 ZNF235 | 12 ATXN1 | 12 CDKN2C | 12 DSCAM | 12 GAGE2D | 12 KDM6A |
| 13 ZNF280A | 12 ATXN3 | 12 CDR2 | 12 DSEL | 12 GAGE4 | 12 KIAA1614 |
| 13 ZNF280D | 12 ATXN7L1 | 12 CDR2L | 12 DTX1 | 12 GAGE5 | 12 KIAA1731 |
| 13 ZNF319 | 12 ATXN8OS | 12 CENPF | 12 DUOX1 | 12 GAGE7 | 12 KIF5A |
| 13 ZNF358 | 12 AURKC | 12 CENPW | 12 DUS4L | 12 GALC | 12 KIF5B |
| 13 ZNF396 | 12 B4GALNT4 | 12 CEP120 | 12 DUSP2 | 12 GALE | 12 KLF6 |
| 13 ZNF423 | 12 BAI2 | 12 CERK | 12 DYM | 12 GAN | 12 KLHL1 |
| 13 ZNF444 | 12 BAIAP2-AS1 | 12 CERS2 | 12 EBF1 | 12 GCK | 12 KREMEN2 |
| 13 ZNF497 | 12 BCL11B | 12 CFDP1 | 12 EBNA1BP2 | 12 GCSAML-AS1 | 12 KRTAP17-1 |
| 13 ZNF524 | 12 BEND4 | 12 CFP | 12 ECE1 | 12 GDF9 | 12 LAGE3 |
| 13 ZNF625 | 12 BLOC1S1 | 12 CHAF1B | 12 EIF3M | 12 GHRLOS | 12 LAPTM5 |
| 13 ZNF625-ZNF20 | 12 BLOC1S1-RDH5 | 12 CHCHD4 | 12 ELF2 | 12 GJA3 | 12 LDLRAP1 |
| 13 ZNF629 | 12 BNIP2 | 12 CHMP6 | 12 ELF4 | 12 GJA5 | 12 LGALS12 |
| 13 ZNF644 | 12 BNIP3 | 12 CHODL | 12 ELL | 12 GLUL | 12 LGALS9 |
| 13 ZNF645 | 12 BOK | 12 CHRNB3 | 12 EMILIN1 | 12 GNA14 | 12 LILRB1 |
| 13 ZNF648 | 12 BOLA1 | 12 CHST11 | 12 EML2 | 12 GNB4 | 12 LIMS2 |
| 13 ZNF682 | 12 BRAF | 12 CHST12 | 12 ENSA | 12 GPR112 | 12 LINC00029 |
| 13 ZNF764 | 12 BTBD2 | 12 CHST15 | 12 EPB49 | 12 GPR132 | 12 LINC00032 |
| 13 ZNF768 | 12 BTBD6 | 12 CHST8 | 12 EPHA3 | 12 GPR6 | 12 LINC00200 |
| 13 ZNF77 | 12 BVES | 12 CILP2 | 12 EPHB3 | 12 GPR68 | 12 LINC00426 |
| 13 ZNF774 | 12 BVES-AS1 | 12 CLCC1 | 12 ESD | 12 GPSM3 | 12 LINC00535 |
| 13 ZNF782 | 12 BZRAP1 | 12 CLCF1 | 12 EXOC8 | 12 GSN | 12 LINC00643 |
| 13 ZNF785 | 12 BZRAP1-AS1 | 12 CLP1 | 12 F10 | 12 GSPT2 | 12 LMO2 |
| 13 ZNF786 | 12 C10orf118 | 12 CLSTN2 | 12 FAM100A | 12 GTDC1 | 12 LOC100128993 |
| 13 ZNF835 | 12 C11orf68 | 12 CMIP | 12 FAM110B | 12 GYS1 | 12 LOC100129520 |
| 13 ZNF84 | 12 C12orf75 | 12 CNTD1 | 12 FAM115A | 12 HAPLN4 | 12 LOC100130015 |
| 13 ZNHIT3 | 12 C14orf162 | 12 CNTNAP1 | 12 FAM165B | 12 HCG4B | 12 LOC100130987 |
| 12 ABCC1 | 12 C14orf28 | 12 COA3 | 12 FAM178B | 12 HCN3 | 12 LOC100293534 |
| 12 ACAP1 | 12 C16orf70 | 12 COG5 | 12 FAM207A | 12 HEATR7A | 12 LOC100505806 |
| 12 ACTN2 | 12 C17orf101 | 12 COL16A1 | 12 FAM3A | 12 HEBP1 | 12 LOC100507424 |
| 12 ADAM19 | 12 C17orf49 | 12 COL2A1 | 12 FAM46C | 12 HELZ2 | 12 LOC282980 |
| 12 ADAM30 | 12 C17orf97 | 12 COL4A1 | 12 FAM47C | 12 HERC2 | 12 LOC283050 |
| 12 ADNP2 | 12 C18orf34 | 12 COL4A2 | 12 FAM53B | 12 HHIPL1 | 12 LOC284661 |
| 12 ADORA1 | 12 C1QL3 | 12 COL9A3 | 12 FAM57B | 12 HIVEP1 | 12 LOC284688 |
| 12 ADORA3 | 12 C1orf106 | 12 COX15 | 12 FAM98C | 12 HLA-DRB1 | 12 LOC400680 |
| 12 AFF1 | 12 C1orf145 | 12 CPLX2 | 12 FAM9C | 12 HMHB1 | 12 LOC400940 |
| 12 AFMID | 12 C1orf204 | 12 CPNE4 | 12 FANCC | 12 HNF4A | 12 LOC619207 |
| 12 AGBL5 | 12 C21orf91 | 12 CPPED1 | 12 FANK1 | 12 HOXA-AS3 | 12 LOC643037 |
| 12 AGFG1 | 12 C2orf16 | 12 CRISP2 | 12 FASTKD5 | 12 HOXA5 | |
| 12 AGRN | 12 C4A | 12 CROCC | 12 FAT1 | 12 HOXB6 | |
| 12 AICDA | 12 C4B | 12 CSN1S2BP | 12 FBXL16 | 12 HOXB7 | |
| 12 AIF1 | 12 C4orf47 | 12 CSNK1G1 | 12 FBXO21 | 12 HOXC-AS5 | |
| 12 AIFM1 | 12 C8orf44-SGK3 | 12 CSNK2A1 | 12 FBXO46 | 12 HOXC13 | |
| 12 AKR1E2 | 12 C9orf123 | 12 CTU2 | 12 FCAMR | 12 HS6ST1 | |
| 12 ALOX5 | | 12 CUL4B | | 12 HSPA1B | |

TABLE 3-continued

Poor Embryo-Quality Genes, Ranked

| | | | | | |
|---|---|---|---|---|---|
| 12 LOC643542 | 12 NFIX | 12 PRR25 | 12 SMIM1 | 12 UBQLN1 | 11 ALDH1L1 |
| 12 LOC728431 | 12 NGDN | 12 PRSS21 | 12 SMURF1 | 12 UBXN1 | 11 ALDH4A1 |
| 12 LOC729080 | 12 NGFR | 12 PSMB7 | 12 SNF8 | 12 UCHL1 | 11 ANG |
| 12 LOC730101 | 12 NGLY1 | 12 PSMD6 | 12 SNORA37 | 12 UCK2 | 11 ANGPT2 |
| 12 LOC731275 | 12 NIPAL2 | 12 PSRC1 | 12 SNORD123 | 12 UCKL1 | 11 ANKAR |
| 12 LONRF1 | 12 NR5A1 | 12 PTBP1 | 12 SNRPD1 | 12 UFSP2 | 11 ANKRD13D |
| 12 LOXL1-AS1 | 12 NRG3 | 12 PTHLH | 12 SNX18 | 12 UGT8 | 11 ANKRD45 |
| 12 LRFN2 | 12 NRIP2 | 12 PTK7 | 12 SOGA3 | 12 UHRF1 | 11 ANO4 |
| 12 LRP12 | 12 NT5C | 12 PTPN23 | 12 SPACA1 | 12 UNC5A | 11 ANP32B |
| 12 LRP8 | 12 NTRK3 | 12 PTPRA | 12 SPATA13 | 12 UNC5C | 11 AP2A2 |
| 12 LRRC34 | 12 NTSR2 | 12 PUF60 | 12 SPATC1 | 12 UQCRQ | 11 AP2B1 |
| 12 LSP1 | 12 NXN | 12 PVT1 | 12 SPHK2 | 12 USP12 | 11 AP4S1 |
| 12 LTBP3 | 12 OBSCN | 12 PXMP2 | 12 SPRTN | 12 USP13 | 11 APCDD1 |
| 12 LYNX1 | 12 OLA1 | 12 QRFP | 12 SRRM4 | 12 USP2 | 11 APOBEC3A_B |
| 12 MACROD1 | 12 OR2C3 | 12 QRFPR | 12 SSTR1 | 12 USP35 | 11 AQP9 |
| 12 MAFF | 12 OXSM | 12 RAB15 | 12 STEAP2 | 12 USP45 | 11 ARHGEF33 |
| 12 MAGEA1 | 12 PAGE5 | 12 RAB33A | 12 STYX | 12 UTY | 11 ARL2 |
| 12 MAGEB16 | 12 PALD1 | 12 RAB37 | 12 SUMF2 | 12 VDAC3 | 11 ARL2-SNX15 |
| 12 MAGI2 | 12 PALLD | 12 RAB3C | 12 SV2B | 12 VPS13D | 11 ARPP21 |
| 12 MAGI2-AS3 | 12 PANK3 | 12 RAB40AL | 12 SYNGAP1 | 12 VRK2 | 11 ASAP1 |
| 12 MAMDC2 | 12 PAQR4 | 12 RAD51L3- | 12 SYNJ2 | 12 VSIG8 | 11 ASB8 |
| 12 MAP1B | 12 PARVG | RFFL | 12 TARSL2 | 12 VTI1A | 11 ASNA1 |
| 12 MAP1LC3A | 12 PATL1 | 12 RAD52 | 12 TBCD | 12 WDR65 | 11 ASPSCR1 |
| 12 MAP3K11 | 12 PCDHB19P | 12 RAE1 | 12 TBX6 | 12 WNT10B | 11 ATMIN |
| 12 MAP7 | 12 PDE7B | 12 RAN | 12 TDRD1 | 12 WTIP | 11 ATP5D |
| 12 MARCKS | 12 PDE8B | 12 RAP2A | 12 TENM4 | 12 WWC2-AS2 | 11 ATP8B4 |
| 12 MATN4 | 12 PELO | 12 RASGRP2 | 12 TERT | 12 XPO4 | 11 ATRIP |
| 12 MBD2 | 12 PEX19 | 12 RBFOX3 | 12 TEX22 | 12 XPOT | 11 AVPR1B |
| 12 MC1R | 12 PFKFB3 | 12 RBM20 | 12 TGFBR1 | 12 XRCC5 | 11 B3GNT8 |
| 12 MCHR1 | 12 PGLYRP2 | 12 RBP7 | 12 TGIF2LX | 12 YLPM1 | 11 BCCIP |
| 12 MED1 | 12 PHACTR1 | 12 RBPJ | 12 THEM4 | 12 YPEL3 | 11 BCDIN3D |
| 12 MED15 | 12 PHAX | 12 RDH5 | 12 TIMM8A | 12 ZC3H3 | 11 BCKDK |
| 12 MEI1 | 12 PHF14 | 12 RECQL5 | 12 TK1 | 12 ZCCHC13 | 11 BCL2L11 |
| 12 MELK | 12 PHF16 | 12 REM2 | 12 TLR5 | 12 ZCCHC14 | 11 BDKRB1 |
| 12 METTL22 | 12 PHF23 | 12 RFFL | 12 TMC6 | 12 ZFP92 | 11 BICD1 |
| 12 MEX3A | 12 PHYHIP | 12 RGMA | 12 TMEM102 | 12 ZKSCAN3 | 11 BIN2 |
| 12 MFSD12 | 12 PIP5K1C | 12 RNASEK | 12 TMEM132A | 12 ZNF213 | 11 BLK |
| 12 MGARP | 12 PIP5K1P1 | 12 RNASEK- | 12 TMEM163 | 12 ZNF277 | 11 BRAT1 |
| 12 MGRN1 | 12 PITPNC1 | C17ORF49 | 12 TMEM204 | 12 ZNF286B | 11 BRSK2 |
| 12 MIR1224 | 12 PITPNM2 | 12 RPS6KA1 | 12 TMEM43 | 12 ZNF324 | 11 C10orf105 |
| 12 MIR137HG | 12 PITPNM3 | 12 RRAD | 12 TMEM52B | 12 ZNF331 | 11 C10orf76 |
| 12 MIR219-2 | 12 PKD2 | 12 S100A2 | 12 TNFRSF11A | 12 ZNF354C | 11 C11orf75 |
| 12 MIR2964A | 12 PKD2L2 | 12 SATB2 | 12 TNFRSF6B | 12 ZNF366 | 11 C11orf88 |
| 12 MIR3187 | 12 PKDREJ | 12 SATB2-AS1 | 12 TNFRSF8 | 12 ZNF367 | 11 C16orf54 |
| 12 MIR3680-1 | 12 PKIA | 12 SDR16C5 | 12 TNFSF12 | 12 ZNF414 | 11 C19orf43 |
| 12 MIR3680-2 | 12 PKNOX2 | 12 SECTM1 | 12 TNXA | 12 ZNF461 | 11 C1QTNF3- |
| 12 MIR371A | 12 PLEKHA6 | 12 SELPLG | 12 TOP1 | 12 ZNF490 | AMACR |
| 12 MIR5093 | 12 PLP2 | 12 SEPT14 | 12 TOP1MT | 12 ZNF512 | 11 C1orf21 |
| 12 MIR5095 | 12 PMEPA1 | 12 SGCE | 12 TP73-AS1 | 12 ZNF542 | 11 C20orf197 |
| 12 MIR548AO | 12 PML | 12 SGCZ | 12 TPBG | 12 ZNF618 | 11 C20orf26 |
| 12 MIR5703 | 12 PNPT1 | 12 SH2D3C | 12 TRAF3 | 12 ZNHIT6 | 11 C2CD4C |
| 12 MMP21 | 12 POLE | 12 SH3D21 | 12 TRAPPC10 | 12 ZSCAN1 | 11 C7orf65 |
| 12 MOCS3 | 12 POMC | 12 SHARPIN | 12 TRIM43B | 11 AARS | 11 C8orf42 |
| 12 MRPL15 | 12 POTEF | 12 SHFM1 | 12 TRIML2 | 11 ABCA4 | 11 C8orf76 |
| 12 MSI2 | 12 POU2AF1 | 12 SHROOM1 | 12 TRMT10A | 11 ABHD13 | 11 C8orf82 |
| 12 MTMR14 | 12 PPCDC | 12 SIRPB2 | 12 TRPC2 | 11 ABLIM3 | 11 C9orf40 |
| 12 MTTP | 12 PPDPF | 12 SLA2 | 12 TTC23L | 11 ABP1 | 11 C9orf69 |
| 12 MYL7 | 12 PPIH | 12 SLC10A4 | 12 TTC24 | 11 ACAA2 | 11 CACNA1C |
| 12 MYO1G | 12 PPP1CC | 12 SLC13A4 | 12 TTC38 | 11 ACOX3 | 11 CALHM3 |
| 12 MYO7A | 12 PPP1R36 | 12 SLC22A4 | 12 TTC39A | 11 ACSL1 | 11 CCDC33 |
| 12 MYOM3 | 12 PPP6C | 12 SLC25A37 | 12 TTLL7 | 11 ADAMTS4 | 11 CCND2 |
| 12 NAP1L4 | 12 PRDM8 | 12 SLC4A3 | 12 TUBB3 | 11 ADD2 | 11 CD48 |
| 12 NCDN | 12 PRKRIR | 12 SLC5A6 | 12 TXLNB | 11 AGRP | 11 CD6 |
| 12 NCKAP5 | 12 PRMT2 | 12 SLC6A11 | 12 UBAC2 | 11 AGXT2L1 | 11 CD7 |
| 12 NCL | 12 PROSAPIP1 | 12 SLC6A7 | 12 UBAP2 | 11 AIM1 | 11 CDC14C |
| 12 NDUFV1 | 12 PROX1 | 12 SLC7A7 | 12 UBE2D1 | 11 AJAP1 | 11 CDC42EP1 |
| 12 NECAP1 | 12 PRPF3 | 12 SMARCAD1 | 12 UBE2H | 11 AK7 | 11 CDH9 |
| 12 NET1 | 12 PRR22 | 12 SMARCD1 | 12 UBOX5 | 11 AKIRIN2 | 11 CDHR3 |
| 11 CDKL1 | 11 FOXP1 | 11 LINC00299 | 11 MYOM1 | 11 RBPMS2 | 11 TBC1D4 |
| 11 CELF4 | 11 FRG2 | 11 LINC00477 | 11 N4BP2L1 | 11 RDH12 | 11 TBC1D9 |
| 11 CENPT | 11 FRG2B | 11 LITAF | 11 NADK | 11 RELT | 11 TCIRG1 |
| 11 CHD6 | 11 FRG2C | 11 LMO4 | 11 NAT14 | 11 RGMB | 11 TEKT4 |
| 11 CHST3 | 11 GALNT2 | 11 | 11 NAT2 | 11 RLTPR | 11 TERF2IP |
| 11 CIRBP | 11 GALNT5 | LOC100128164 | 11 NCALD | 11 RNASE4 | 11 TFDP1 |
| 11 CIRBP-AS1 | 11 GBF1 | 11 | 11 NDUFB6 | 11 RNF103 | 11 TG |
| 11 CKAP2 | 11 GGTLC1 | LOC100131551 | 11 NDUFS8 | 11 RNF157 | 11 TGFB1 |
| 11 CLASP2 | 11 GHDC | 11 | 11 NEU3 | 11 RNF182 | 11 TGFB1I1 |
| 11 CLDN9 | 11 GLT1D1 | LOC100288255 | 11 NEURL4 | 11 RNU6-19 | 11 TGM5 |

TABLE 3-continued

Poor Embryo-Quality Genes, Ranked

| | | | | | |
|---|---|---|---|---|---|
| 11 CLEC3B | 11 GMFG | 11 | 11 NFAM1 | 11 RPL10L | 11 THAP11 |
| 11 CLIC1 | 11 GORASP2 | LOC100506585 | 11 NIPA2 | 11 RPL30 | 11 TIMP2 |
| 11 CLYBL | 11 GPR108 | 11 | 11 NLRC4 | 11 RPP21 | 11 TIPARP |
| 11 CNNM4 | 11 GRAMD2 | LOC100507373 | 11 NLRP12 | 11 RPS4Y2 | 11 TIPARP-AS1 |
| 11 CPLX3 | 11 GRM4 | 11 | 11 NLRP3 | 11 RUNX1T1 | 11 TKT |
| 11 CRNKL1 | 11 GTF2B | LOC100507634 | 11 NMB | 11 S100A4 | 11 TMEM120A |
| 11 CRTC3 | 11 GXYLT2 | 11 | 11 NOMO1 | 11 S100A5 | 11 TMEM196 |
| 11 CSF3R | 11 HAUS3 | LOC100653515 | 11 NOX4 | 11 S100A8 | 11 TNF |
| 11 CSMD3 | 11 HCAR1 | 11 LOC200772 | 11 NPY1R | 11 SASH3 | 11 TNFSF11 |
| 11 CTBP1 | 11 HCLS1 | 11 LOC283663 | 11 NR2E1 | 11 SBF2 | 11 TPD52L3 |
| 11 CXXC5 | 11 HDAC9 | 11 LOC286177 | 11 NR2F1 | 11 SBF2-AS1 | 11 TPM4 |
| 11 CYFIP1 | 11 HDGFRP2 | 11 LOC339166 | 11 NRD1 | 11 SCML4 | 11 TRAF3IP3 |
| 11 CYP4F2 | 11 HECW1 | 11 LOC339975 | 11 NSMCE1 | 11 SCNN1A | 11 TRAPPC9 |
| 11 DAXX | 11 HIST1H1D | 11 LOC375196 | 11 NSRP1 | 11 SCNN1D | 11 TRIM14 |
| 11 DDO | 11 HIST1H2AE | 11 LOC389247 | 11 NUCB1 | 11 SCYL1 | 11 TRIP6 |
| 11 DDX19B | 11 HIST1H4F | 11 LOC400794 | 11 NUDT10 | 11 SEC31B | 11 TRMT44 |
| 11 DDX25 | 11 HK1 | 11 LOC643401 | 11 OCSTAMP | 11 SEC62 | 11 TRNP1 |
| 11 DEF8 | 11 HLA-DOA | 11 LOC646278 | 11 OSGIN2 | 11 SEMA4B | 11 TRPM6 |
| 11 DENND3 | 11 HLA-DQA2 | 11 LOC730668 | 11 OXT | 11 SEPT10 | 11 TSHZ1 |
| 11 DLEU7 | 11 HNRNPH1 | 11 LPAR3 | 11 P2RY6 | 11 SERPINE2 | 11 TSPAN11 |
| 11 DLEU7-AS1 | 11 HOMER1 | 11 LPHN1 | 11 PCDHB5 | 11 SFRP4 | 11 TTLL10 |
| 11 DLL3 | 11 HSF5 | 11 LPPR4 | 11 PCGF1 | 11 SGK3 | 11 TTLL11 |
| 11 DOM3Z | 11 HSPA4L | 11 LRPPRC | 11 PDE3B | 11 SGMS2 | 11 TULP2 |
| 11 DSG3 | 11 HTR1B | 11 LRRC24 | 11 PDE6B | 11 SIX2 | 11 TXNRD2 |
| 11 DUPD1 | 11 HUS1B | 11 LYRM2 | 11 PDLIM1 | 11 SLA | 11 UBAC1 |
| 11 DYNC2H1 | 11 HYLS1 | 11 LYSMD4 | 11 PDLIM2 | 11 SLC12A4 | 11 UBASH3B |
| 11 EBF2 | 11 IKZF1 | 11 MAP3K5 | 11 PDS5B | 11 SLC12A7 | 11 UBE2DNL |
| 11 EHHADH | 11 IL28A | 11 MAPK13 | 11 PDZRN4 | 11 SLC12A9 | 11 UBE2U |
| 11 EIF4A3 | 11 IL28B | 11 MAPKAPK2 | 11 PET112 | 11 SLC18A2 | 11 UBN2 |
| 11 ELP6 | 11 IL2RG | 11 MARCH1 | 11 PID1 | 11 SLC19A1 | 11 UNC119B |
| 11 ELSPBP1 | 11 ING2 | 11 MARCH8 | 11 PIGH | 11 SLC22A20 | 11 UROS |
| 11 EMC10 | 11 IQUB | 11 MARK2 | 11 PITX2 | 11 SLC25A24 | 11 USP24 |
| 11 EML4 | 11 ISOC1 | 11 MC3R | 11 PITX3 | 11 SLC2A14 | 11 VPS28 |
| 11 ENPEP | 11 ITGB5 | 11 MCM3 | 11 PIWIL1 | 11 SLC38A10 | 11 VPS36 |
| 11 EPDR1 | 11 ITPK1 | 11 MESDC1 | 11 PLEKHF2 | 11 SLC3A1 | 11 VPS39 |
| 11 EPRS | 11 ITPRIP | 11 MFAP1 | 11 PLOD1 | 11 SLC45A2 | 11 VWC2L |
| 11 ERCC2 | 11 JAK1 | 11 MIDN | 11 PLXND1 | 11 SLC6A2 | 11 WARS |
| 11 ESYT2 | 11 JPH1 | 11 MIPEPP3 | 11 PNPLA1 | 11 SLC9A9 | 11 WAS |
| 11 ETS1 | 11 KARS | 11 MIR142 | 11 PNPLA2 | 11 SLCO4A1 | 11 WBP1L |
| 11 EXOC3 | 11 KATNB1 | 11 MIR1976 | 11 POLR1A | 11 SLITRK5 | 11 WDFY4 |
| 11 EXOSC6 | 11 KCNIP1 | 11 MIR423 | 11 PPP1R11 | 11 SMAP2 | 11 WDR17 |
| 11 FABP7 | 11 KCNJ11 | 11 MIR4468 | 11 PPP1R12B | 11 SMEK3P | 11 WDR25 |
| 11 FAM171A1 | 11 KCNQ2 | 11 MIR4534 | 11 PRELID2 | 11 SNORA72 | 11 WDR73 |
| 11 FAM19A2 | 11 KDELC2 | 11 MIR4633 | 11 PRRC2C | 11 SOGA1 | 11 WDR76 |
| 11 FAM228A | 11 KDM4B | 11 MIR5680 | 11 PRTN3 | 11 SOWAHC | 11 WDR86 |
| 11 FAM71E1 | 11 KIAA1210 | 11 MIR596 | 11 PSKH2 | 11 SPEG | 11 WIPF3 |
| 11 FAM83F | 11 KIAA1211 | 11 MMRN2 | 11 PSMA1 | 11 SPIRE2 | 11 WIPI2 |
| 11 FAM8A1 | 11 KLHL25 | 11 MOB2 | 11 PSMB4 | 11 SPOCK3 | 11 WT1 |
| 11 FCGBP | 11 KRT1 | 11 MOK | 11 PTCD3 | 11 SPTSSB | 11 WWC3 |
| 11 FEZ2 | 11 KRT81 | 11 MS4A13 | 11 PTCHD3 | 11 SQSTM1 | 11 WWTR1 |
| 11 FGR | 11 KRTAP5-6 | 11 MSH5 | 11 PTGDR2 | 11 SRPK3 | 11 ZC3H12C |
| 11 FLJ20518 | 11 KRTCAP3 | 11 MSH5-SAPCD1 | 11 PTPRJ | 11 SRSF4 | 11 ZC3H4 |
| 11 FLJ35946 | 11 KSR2 | 11 MST1P2 | 11 PUS3 | 11 STRA6 | 11 ZCCHC2 |
| 11 FLJ39653 | 11 LAT | 11 MTUS1 | 11 RAB25 | 11 STRN3 | 11 ZCCHC7 |
| 11 FLJ45974 | 11 LDOC1L | 11 MUC4 | 11 RAB7A | 11 SWAP70 | 11 ZFHX3 |
| 11 FOXF1 | 11 LGALS9C | 11 MYH13 | 11 RAB8B | 11 TACR1 | 11 ZFX |
| 11 FOXF1-AS1 | 11 LIG4 | 11 MYH9 | 11 RASSF2 | 11 TAOK3 | 11 ZFX-AS1 |
| 11 FOXN4 | 11 LIN9 | | 11 RBM8A | 11 TBC1D14 | |
| 11 ZHX1-C8ORF76 | 10 C1S | 10 DEDD2 | 10 GFI1 | 10 LINC00478 | 10 MTIF2 |
| 11 ZMAT5 | 10 C1orf101 | 10 DFNA5 | 10 GFRA1 | 10 LINC00577 | 10 MTMR2 |
| 11 ZNF101 | 10 C1orf177 | 10 DISP1 | 10 GIMAP8 | 10 LINC00602 | 10 MXD3 |
| 11 ZNF131 | 10 C2CD2 | 10 DNAH5 | 10 GIPC1 | 10 LINC00637 | 10 NAIF1 |
| 11 ZNF251 | 10 C3 | 10 DNAJB13 | 10 GLUD2 | 10 LLGL1 | 10 NANP |
| 11 ZNF32 | 10 C3orf38 | 10 DNER | 10 GNA15 | 10 LMNA | 10 NAT8 |
| 11 ZNF32-AS3 | 10 C3orf55 | 10 DNM3 | 10 GNAI2 | 10 LMNB2 | 10 NAT8L |
| 11 ZNF324B | 10 C3orf78 | 10 DNM3OS | 10 GNE | 10 | 10 NCR3LG1 |
| 11 ZNF549 | 10 C6orf123 | 10 DOCK1 | 10 GNG5 | LOC100129046 | 10 NFKBIE |
| 11 ZNF57 | 10 C6orf170 | 10 EDNRA | 10 GPR1 | 10 | 10 NKAIN3 |
| 11 ZNF610 | 10 C9orf116 | 10 EIF2C2 | 10 GPR157 | LOC100129620 | 10 NKIRAS2 |
| 11 ZNF628 | 10 C9orf131 | 10 EIF3J | 10 GRAMD3 | 10 | 10 NME7 |
| 11 ZNF710 | 10 CACTIN | 10 EMC7 | 10 GRIA3 | LOC100130417 | 10 NOD2 |
| 11 ZSCAN20 | 10 CALCB | 10 EML1 | 10 GRIK4 | 10 | 10 NOVA1 |
| 11 ZSCAN21 | 10 CAMSAP1 | 10 ENG | 10 GRK6 | LOC100133669 | 10 NT5DC2 |
| 10 AATF | 10 CANT1 | 10 EPG5 | 10 GRN | 10 | 10 NTAN1 |
| 10 ABLIM2 | 10 CAPN2 | 10 ERBB2 | 10 GSTM4 | LOC100134317 | 10 NTPCR |
| 10 ACRBP | 10 CAPN8 | 10 ERGIC1 | 10 GTF3C3 | 10 | 10 NYX |
| 10 ADORA2A | 10 CARTPT | 10 ERN2 | 10 GYG2 | LOC100499227 | 10 OGT |
| | 10 CBX7 | 10 ESM1 | 10 HADH | 10 | 10 ONECUT3 |

TABLE 3-continued

Poor Embryo-Quality Genes, Ranked

| | | | | | |
|---|---|---|---|---|---|
| 10 ADRA1B | 10 CCDC101 | 10 ESPNL | 10 HARS | LOC100506274 | 10 OSBPL9 |
| 10 ADRA2A | 10 CCDC144NL | 10 EZR | 10 HIF3A | 10 LOC283683 | 10 P2RX1 |
| 10 ADSSL1 | 10 CCDC172 | 10 F11R | 10 HIST1H3I | 10 LOC283688 | 10 P2RX2 |
| 10 AGPAT4 | 10 CCDC19 | 10 FAM131A | 10 HIST1H4L | 10 LOC441242 | 10 PADI4 |
| 10 AHCYL2 | 10 CCDC36 | 10 FAM136A | 10 HMCN1 | 10 LOC643339 | 10 PAN2 |
| 10 ALMS1P | 10 CCDC50 | 10 FAM157A | 10 HNRNPF | 10 LOC644669 | 10 PANX2 |
| 10 AMN1 | 10 CCL3 | 10 FAM176A | 10 HORMAD1 | 10 LOC645212 | 10 PAX7 |
| 10 ANK3 | 10 CCR1 | 10 FAM190B | 10 HOTAIR | 10 LOC727982 | 10 PC |
| 10 ANKLE1 | 10 CCT4 | 10 FAM194A | 10 HOTAIRM1 | 10 LPP | 10 PCDHAC1 |
| 10 ANKRD17 | 10 CD244 | 10 FAM208A | 10 HOXA1 | 10 LPPR5 | 10 PCDHB1 |
| 10 ANKRD27 | 10 CD37 | 10 FAM222A | 10 HOXC11 | 10 LRRC14B | 10 PCDHB15 |
| 10 ANO2 | 10 CD4 | 10 FAM222A-AS1 | 10 HS3ST3B1 | 10 LRRC15 | 10 PCDHB4 |
| 10 ARHGAP10 | 10 CDC42BPB | 10 FAM227B | 10 HSD11B1L | 10 LRTOMT | 10 PCDHB7 |
| 10 ARHGAP26 | 10 CDK11B | 10 FAM27L | 10 HSD17B7 | 10 LTBR | 10 PDCL3 |
| 10 ARHGAP31 | 10 CDK19 | 10 FAM49B | 10 HSPA6 | 10 LUC7L3 | 10 PDE12 |
| 10 ARHGEF9 | 10 CECR2 | 10 FAM59B | 10 HTR4 | 10 LYPD6 | 10 PDE1C |
| 10 ARID1A | 10 CGGBP1 | 10 FAM5C | 10 IER3 | 10 LYPD8 | 10 PDGFD |
| 10 ARNT2 | 10 CHEK1 | 10 FAM73A | 10 IFRD1 | 10 MAN2B1 | 10 PDLIM4 |
| 10 ARR3 | 10 CHSY1 | 10 FAM78A | 10 IKBKG | 10 MBD5 | 10 PDZD4 |
| 10 ARRB2 | 10 CLDN2 | 10 FANCG | 10 IL17RE | 10 MCAT | 10 PECAM1 |
| 10 ARSI | 10 CLDN4 | 10 FAP | 10 IL1RN | 10 MEFV | 10 PEX14 |
| 10 AS3MT | 10 CLIP2 | 10 FBLIM1 | 10 IL23A | 10 MFSD6 | 10 PGBD4 |
| 10 ASB16 | 10 CLNK | 10 FBLN2 | 10 IL2RB | 10 MFSD7 | 10 PI16 |
| 10 ATG16L2 | 10 CLVS2 | 10 FBXO17 | 10 INPP4A | 10 MGC12916 | 10 PILRA |
| 10 ATL2 | 10 CMTM2 | 10 FBXO4 | 10 IQCD | 10 MIR1297 | 10 PLCH1 |
| 10 ATP5F1 | 10 CNGB1 | 10 FCER2 | 10 IRF2 | 10 MIR199A2 | 10 PLD4 |
| 10 ATP6V1H | 10 CNNM2 | 10 FGD1 | 10 ISCU | 10 MIR2110 | 10 PLEK |
| 10 AUH | 10 CNTN4 | 10 FGF23 | 10 ITGA11 | 10 MIR3545 | 10 PLEKHG4B |
| 10 AURKB | 10 COA5 | 10 FIBCD1 | 10 JAKMIP3 | 10 MIR369 | 10 PLVAP |
| 10 B3GNT9 | 10 COL27A1 | 10 FIGNL1 | 10 JAZF1 | 10 MIR409 | 10 POP7 |
| 10 BAHCC1 | 10 COX10 | 10 FLJ16171 | 10 KCNH2 | 10 MIR410 | 10 PPIA |
| 10 BANP | 10 COX10-AS1 | 10 FLJ25758 | 10 KCNJ5 | 10 MIR412 | 10 PPIG |
| 10 BCL2L1 | 10 CPT1C | 10 FLOT1 | 10 KHDRBS1 | 10 MIR541 | 10 PPP1R13B |
| 10 BCL2L14 | 10 CPT2 | 10 FLYWCH2 | 10 KIAA0930 | 10 MIR548AA2 | 10 PPP1R1B |
| 10 BIN1 | 10 CRB3 | 10 FMR1NB | 10 KIAA1598 | 10 MIR548AN | 10 PPP1R9A |
| 10 BIRC8 | 10 CSRP3 | 10 FXYD1 | 10 KIF1B | 10 MIR548D2 | 10 PPP2R2C |
| 10 BPGM | 10 CTSF | 10 FXYD7 | 10 KIF21B | 10 MIR656 | 10 PRAP1 |
| 10 C10orf90 | 10 CTTN | 10 G6PD | 10 KIF6 | 10 MMP11 | 10 PRDM15 |
| 10 C11orf45 | 10 CUL1 | 10 GABARAPL1 | 10 KRT7 | 10 MMP17 | 10 PRH1-PRR4 |
| 10 C11orf54 | 10 CUL3 | 10 GABRD | 10 KRT80 | 10 MPL | 10 PRICKLE1 |
| 10 C11orf67 | 10 CX3CR1 | 10 GABRR3 | 10 LAIR1 | 10 MRPL23 | 10 PRL |
| 10 C12orf29 | 10 CXorf65 | 10 GALNS | 10 LEPR | 10 MRPL4 | 10 PRRT3 |
| 10 C15orf53 | 10 CYP20A1 | 10 GALNT12 | 10 LGI4 | 10 MRPL52 | 10 PRRT3-AS1 |
| 10 C16orf11 | 10 CYP27C1 | 10 GAPDH | 10 LGR6 | 10 MRPS2 | 10 PSMA4 |
| 10 C16orf74 | 10 DAZAP1 | 10 GAS2L2 | 10 LHX3 | 10 MRPS21 | 10 PTAFR |
| 10 C17orf65 | 10 DCBLD1 | 10 GATA2 | 10 LIMK2 | 10 MT1A | 10 PTPN4 |
| 10 C17orf96 | 10 DDI1 | 10 GATA5 | 10 LINC00226 | 10 MT1DP | 10 PTPN7 |
| 10 C19orf38 | 10 DDR1 | 10 GBA | 10 LINC00466 | 10 MT1L | 10 PYGO1 |
| 10 RAB11FIP1 | 10 SPNS2 | 10 ZNF527 | 9 CLDN15 | 9 GDI2 | 9 KRTAP2-1 |
| 10 RAB24 | 10 SRL | 10 ZNF589 | 9 CLEC16A | 9 GGA3 | 9 LAMTOR1 |
| 10 RAB41 | 10 SRPRB | 10 ZXDC | 9 CLEC5A | 9 GGACT | 9 LARS2 |
| 10 RAI14 | 10 ST6GAL1 | 9 AARD | 9 CLK2 | 9 GLB1L3 | 9 LCA5 |
| 10 RAPGEFL1 | 10 ST6GALNAC2 | 9 ABCA2 | 9 CLPB | 9 GLUD1 | 9 LEFTY2 |
| 10 RASGRF1 | 10 ST8SIA2 | 9 ABHD11 | 9 CMYA5 | 9 GMDS | 9 LETMD1 |
| 10 RASIP1 | 10 STARD10 | 9 ACOXL | 9 COQ5 | 9 GP9 | 9 LIN7A |
| 10 RASSF5 | 10 STARD3 | 9 ADAMTS7 | 9 CORO1C | 9 GPR153 | 9 LINC00475 |
| 10 RASSF9 | 10 STX16 | 9 ADAMTSL3 | 9 COTL1 | 9 GPR21 | 9 LINC00628 |
| 10 RBPJL | 10 SULF1 | 9 ADAP1 | 9 COX17 | 9 GPR84 | 9 LIPT1 |
| 10 RCBTB2 | 10 SULF2 | 9 ADCY7 | 9 CPEB3 | 9 GPSM1 | 9 LOC100128076 |
| 10 RERE | 10 SUMF1 | 9 AIG1 | 9 CRABP1 | 9 GPX3 | 9 LOC100128568 |
| 10 RFTN1 | 10 SVOPL | 9 AKAP7 | 9 CRELD2 | 9 GPX7 | 9 LOC100130950 |
| 10 RGS9BP | 10 SYT14 | 9 ALDH3A1 | 9 CRISPLD2 | 9 GRAMD4 | 9 LOC100132111 |
| 10 RHOG | 10 TAF1D | 9 AMACR | 9 CRSP8P | 9 GRAP2 | 9 LOC100271702 |
| 10 RHPN2 | 10 TAF4B | 9 AMIGO3 | 9 CSNK1G3 | 9 GTF2A1 | 9 LOC100630923 |
| 10 RIN1 | 10 TBRG4 | 9 AMZ1 | 9 CTAGE11P | 9 GTF2H4 | 9 LOC254312 |
| 10 RINL | 10 TET1 | 9 AP1M2 | 9 CTSO | 9 GTF3C4 | 9 LOC257358 |
| 10 RNU6-66 | 10 THBS1 | 9 AQP10 | 9 CXorf21 | 9 H2BFWT | 9 LOC284276 |
| 10 RORC | 10 THEGL | 9 ARF4 | 9 CYB5B | 9 HAS2 | 9 LOC339524 |
| 10 RPL36 | 10 THRAP3 | 9 ARFRP1 | 9 CYP46A1 | 9 HAS2-AS1 | 9 LRAT |
| 10 RPS19BP1 | 10 THY1 | 9 ARHGAP4 | 9 DAAM2 | 9 HAVCR1 | 9 LRIG1 |
| 10 RPS3A | 10 TIAF1 | 9 ARHGDIA | 9 DCDC2 | 9 HBEGF | 9 LRRC27 |
| 10 RPS6KA2-IT1 | 10 TMCC1 | 9 ARHGEF2 | 9 DDX31 | 9 HDDC3 | 9 LRRC32 |
| 10 RPS6KA3 | 10 TMEM108 | 9 ASCC2 | 9 DEDD | 9 HDGF | 9 LRRC4C |
| 10 RRAGD | 10 TMEM176A | 9 ATOH8 | 9 DEPDC7 | 9 HELLS | 9 LRRC8C |
| 10 RSF1 | 10 TMEM176B | 9 ATP8B2 | 9 DERL1 | 9 HEXB | 9 LRTM2 |
| 10 S100A1 | 10 TMEM249 | 9 AZU1 | 9 DEXI | 9 HIST1H2APS1 | 9 MAEA |
| 10 S100A13 | 10 TMEM72 | 9 B3GAT1 | 9 DLL4 | 9 HLA-DMB | 9 MAF |
| 10 SAP30BP | 10 TNFRSF4 | 9 BECN1 | 9 DNAI1 | 9 HLA-H | 9 MAFG |

TABLE 3-continued

Poor Embryo-Quality Genes, Ranked

| | | | | | |
|---|---|---|---|---|---|
| 10 SART3 | 10 TNN | 9 BST1 | 9 DPP10 | 9 HLX | 9 MAFG-AS1 |
| 10 SCARB1 | 10 TNNT2 | 9 BTBD18 | 9 DSC2 | 9 HNRNPM | 9 MAP1LC3B2 |
| 10 SCARF1 | 10 TNS3 | 9 BTG4 | 9 DTL | 9 HOXC5 | 9 MAP3K10 |
| 10 SCARF2 | 10 TOR3A | 9 C10orf107 | 9 DTX4 | 9 HOXC6 | 9 MAP4K2 |
| 10 SCN1A | 10 TPH1 | 9 C11orf49 | 9 EFCAB10 | 9 HRASLS | 9 MAPK8IP1 |
| 10 SDC4 | 10 TRIM72 | 9 C11orf92 | 9 EFEMP2 | 9 HRH1 | 9 MAPK8IP3 |
| 10 SEC14L1 | 10 TRIP4 | 9 C11orf93 | 9 EFR3A | 9 HSBP1 | 9 MDFIC |
| 10 SERBP1 | 10 TRPV3 | 9 C16orf91 | 9 ELL3 | 9 HTRA3 | 9 MEGF11 |
| 10 SERPINA1 | 10 TSPAN14 | 9 C19orf53 | 9 ELMO1 | 9 HUS1 | 9 MEGF6 |
| 10 SERPINB9 | 10 TTC25 | 9 C22orf13 | 9 EPHA4 | 9 ICMT | 9 MESP1 |
| 10 SESN2 | 10 TUB | 9 C2orf18 | 9 FAM120B | 9 IFFO2 | 9 MESP2 |
| 10 SIDT2 | 10 ULK2 | 9 C2orf27B | 9 FAM131B | 9 IGF1R | 9 MGAT4B |
| 10 SLC11A2 | 10 UNC50 | 9 C5orf55 | 9 FAM155A | 9 IGFBP1 | 9 MGC2889 |
| 10 SLC17A7 | 10 UPF2 | 9 C8orf46 | 9 FAM183B | 9 IGFLR1 | 9 MGLL |
| 10 SLC22A16 | 10 USP22 | 9 C9orf139 | 9 FAM18B1 | 9 IL20RB | 9 MIR138-2 |
| 10 SLC25A18 | 10 USP9X | 9 CA7 | 9 FAM18B2 | 9 INCA1 | 9 MIR1468 |
| 10 SLC25A25 | 10 UST | 9 CACNA1C-IT3 | 9 FAM18B2-CDRT4 | 9 INPP1 | 9 MIR150 |
| 10 SLC25A44 | 10 VCX | 9 CACNA1H | | 9 INTS7 | 9 MIR34B |
| 10 SLC27A1 | 10 VKORC1 | 9 CADM2 | 9 FAM195A | 9 IPCEF1 | 9 MIR34C |
| 10 SLC27A2 | 10 WDR1 | 9 CALR | 9 FAM219B | 9 IQGAP3 | 9 MIR4489 |
| 10 SLC2A13 | 10 WDR67 | 9 CASKIN1 | 9 FAM40A | 9 IRF7 | 9 MIR615 |
| 10 SLC35F3 | 10 WDR77 | 9 CCDC112 | 9 FAM60A | 9 ITGA2B | 9 MIR618 |
| 10 SLC4A7 | 10 WSCD2 | 9 CCDC67 | 9 FAM81A | 9 ITGB3 | 9 MLIP |
| 10 SLC52A2 | 10 WWOX | 9 CCDC81 | 9 FBXL8 | 9 ITPK1-AS1 | 9 MOB3B |
| 10 SLC6A20 | 10 YY2 | 9 CCM2 | 9 FCRL6 | 9 IVNS1ABP | 9 MON1A |
| 10 SLCO6A1 | 10 ZBTB43 | 9 CCNJL | 9 FHL3 | 9 IZUMO4 | 9 MPO |
| 10 SLIT1 | 10 ZC3H14 | 9 CCR10 | 9 FLI1 | 9 JUNB | 9 MR1 |
| 10 SMAD9 | 10 ZC4H2 | 9 CD28 | 9 FLJ27354 | 9 KCNE1 | 9 MRGPRF |
| 10 SMTN | 10 ZFR | 9 CDC25A | 9 FOLR3 | 9 KCNIP3 | 9 MTL5 |
| 10 SMYD4 | 10 ZG16B | 9 CDC42EP4 | 9 FOXA2 | 9 KCNMB3 | 9 MUM1 |
| 10 SNORD73A | 10 ZNF185 | 9 CDH1 | 9 FRMD4B | 9 KIAA0319 | 9 MYH14 |
| 10 SNORD93 | 10 ZNF200 | 9 CDH2 | 9 FSD1L | 9 KIAA0947 | 9 MYL9 |
| 10 SNRNP27 | 10 ZNF26 | 9 CDK20 | 9 FUT7 | 9 KIAA1199 | 9 MYLK2 |
| 10 SNX6 | 10 ZNF280B | 9 CEACAM21 | 9 GABRQ | 9 KIF1C | 9 MYO1A |
| 10 SORL1 | 10 ZNF284 | 9 CHD2 | 9 GAGE12J | 9 KLHL21 | 9 MYO1C |
| 10 SP110 | 10 ZNF343 | 9 CHD9 | 9 GALNT14 | 9 KLHL31 | 9 MYO3A |
| 10 SP140 | 10 ZNF44 | 9 CHST2 | 9 GCNT2 | 9 KRT16P3 | 9 N4BP3 |
| 10 SPATA5 | 10 ZNF507 | 9 CIAO1 | 9 GCOM1 | 9 KRT3 | 9 NAALADL2 |
| 9 NACA2 | 9 RNF216 | 9 TMX2-CTNND1 | 8 C11orf95 | 8 FFAR2 | 8 MINPP1 |
| 9 NACAP1 | 9 RP1-177G6.2 | 9 TNFAIP2 | 8 C16orf45 | 8 FLJ13197 | 8 MIR3202-2 |
| 9 NBEAL2 | 9 RPF1 | 9 TNIK | 8 C1orf173 | 8 FNIP2 | 8 MIR365A |
| 9 NCF2 | 9 RPL31P11 | 9 TNNI2 | 8 C1orf98 | 8 FOXJ2 | 8 MIR4444-1 |
| 9 NCKAP5L | 9 RPS6KL1 | 9 TOMM7 | 8 C2orf70 | 8 FOXK2 | 8 MIR4456 |
| 9 NCLN | 9 RRN3P2 | 9 TP53BP2 | 8 C5orf49 | 8 FTX | 8 MIR516B2 |
| 9 NDRG3 | 9 RRP12 | 9 TP73 | 8 CA5A | 8 FXR1 | 8 MIR520G |
| 9 NDRG4 | 9 RTN2 | 9 TPO | 8 CA6 | 8 GARS | 8 MKI67IP |
| 9 NEK6 | 9 S100P | 9 TRADD | 8 CABIN1 | 8 GGT1 | 8 MKS1 |
| 9 NGB | 9 SAE1 | 9 TRAF5 | 8 CACNA1A | 8 GJB1 | 8 MSRB1 |
| 9 NIM1 | 9 SCD | 9 TRANK1 | 8 CACNA1D | 8 GLB1 | 8 MST1R |
| 9 NIPSNAP1 | 9 SCIMP | 9 TRMT10C | 8 CAMKK2 | 8 GLCCI1 | 8 MT1IP |
| 9 NLRC3 | 9 SERF2 | 9 TSGA10 | 8 CAMKMT | 8 GLRA2 | 8 MTFMT |
| 9 NLRP14 | 9 SERPINB6 | 9 UBE2E1 | 8 CASS4 | 8 GPIHBP1 | 8 MUC15 |
| 9 NMD3 | 9 SERPINB8 | 9 UBE2MP1 | 8 CCAR1 | 8 GPR114 | 8 MYO1F |
| 9 NOL4 | 9 SERTAD2 | 9 UBXN11 | 8 CCDC11 | 8 GRIA4 | 8 MZB1 |
| 9 NPEPL1 | 9 SETD1A | 9 UCHL3 | 8 CCDC144B | 8 GRIN3A | 8 NECAB2 |
| 9 NRGN | 9 SGCB | 9 UNC45A | 8 CCDC155 | 8 GSDMB | 8 NEDD1 |
| 9 NUB1 | 9 SH3BP2 | 9 USP1 | 8 CCDC9 | 8 HENMT1 | 8 NIT2 |
| 9 OR9Q2 | 9 SIAE | 9 UTP23 | 8 CCL24 | 8 HK3 | 8 NOD1 |
| 9 OSBPL10 | 9 SKIL | 9 UVRAG | 8 CCL25 | 8 HNF1A-AS1 | 8 NOLC1 |
| 9 OTUD3 | 9 SLC22A8 | 9 VARS2 | 8 CCNB1IP1 | 8 HTR3A | 8 NOP14 |
| 9 OXA1L | 9 SLC25A17 | 9 VGLL3 | 8 CD22 | 8 IL17RC | 8 NSUN5 |
| 9 PACS1 | 9 SLC26A6 | 9 VWA3B | 8 CD300C | 8 ISPD | 8 OPLAH |
| 9 PARP11 | 9 SLC2A1 | 9 WDR90 | 8 CD33 | 8 ITGAM | 8 ORMDL3 |
| 9 PCNXL2 | 9 SLC2A6 | 9 XKR6 | 8 CD5 | 8 ITK | 8 OTOF |
| 9 PDE3A | 9 SLC35C2 | 9 YTHDC1 | 8 CD83 | 8 IZUMO1 | 8 OVOL1 |
| 9 PDGFB | 9 SLC35E2B | 9 ZBBX | 8 CDC26 | 8 JPX | 8 PACRG-AS1 |
| 9 PGAM1 | 9 SLC38A9 | 9 ZGPAT | 8 CDH12 | 8 KCNA3 | 8 PACSIN2 |
| 9 PGAM4 | 9 SLC39A12 | 9 ZHX1 | 8 CDK3 | 8 KCNH3 | 8 PADI3 |
| 9 PIEZO1 | 9 SLC43A3 | 9 ZNF329 | 8 CDYL | 8 KCNN3 | 8 PAPSS2 |
| 9 PIK3CD | 9 SLC8A2 | 9 ZNF385C | 8 CFHR5 | 8 KIAA0895L | 8 PAQR3 |
| 9 PINX1 | 9 SLFN5 | 9 ZNF446 | 8 CHRNA10 | 8 KIF1A | 8 PCCA |
| 9 PKIG | 9 SOCS3 | 9 ZNF530 | 8 CLDN10 | 8 KLF3 | 8 PCDH9 |
| 9 PLEKHO2 | 9 SPA17 | 9 ZNF555 | 8 CLPSL2 | 8 KLHL29 | 8 PCDHB9 |
| 9 PNMA2 | 9 SPAG16 | 9 ZNF564 | 8 CLRN1 | 8 KRT2 | 8 PCDHGB8P |
| 9 PNMAL2 | 9 SPG7 | 9 ZNF578 | 8 CNTD2 | 8 LASP1 | 8 PDE1B |
| 9 POLR2M | 9 SPOCD1 | 9 ZNF672 | 8 CORO1A | 8 LDLRAD3 | 8 PGBD5 |
| 9 PPFIA1 | 9 SRM | 9 ZNF716 | 8 COX7A1 | 8 LILRB3 | 8 PHF8 |
| 9 PPM1N | 9 SRPK2 | 9 ZNF747 | 8 CPM | 8 LINC00652 | 8 PIK3R2 |

TABLE 3-continued

Poor Embryo-Quality Genes, Ranked

| | | | | | |
|---|---|---|---|---|---|
| 9 PPP5D1 | 9 STRAP | 9 ZNF772 | 8 CRCP | 8 LINC00674 | 8 PITPNA |
| 9 PRIM1 | 9 STXBP5L | 9 ZNRF1 | 8 CROCCP3 | 8 LMO1 | 8 PKP3 |
| 9 PRKCDBP | 9 SUSD5 | 9 ZSCAN18 | 8 CYP26B1 | 8 LOC100216546 | 8 PLEKHA7 |
| 9 PRKRIP1 | 9 SYN2 | 9 ZSCAN30 | 8 DBNDD1 | 8 LOC100270804 | 8 PLEKHG3 |
| 9 PRMT7 | 9 SYNGR3 | 8 ABCG1 | 8 DEFB1 | 8 LOC100499489 | 8 PMS1 |
| 9 PRR23A | 9 SYNPO | 8 ACLY | 8 DEGS2 | 8 LOC100506207 | 8 PNKD |
| 9 PRRT4 | 9 TADA3 | 8 ADAMTS19 | 8 DGAT2L6 | 8 LOC255512 | 8 POLR3G |
| 9 PSEN2 | 9 TBC1D20 | 8 AGPAT3 | 8 DNAH14 | 8 LOC340357 | 8 PPAP2A |
| 9 PSENEN | 9 TBR1 | 8 AHNAK | 8 DNAJC5 | 8 LOC348761 | 8 PPP1CA |
| 9 PSTK | 9 TBX22 | 8 AKTIP | 8 DSE | 8 LOC374443 | 8 PPP3R2 |
| 9 PTP4A2 | 9 TCEAL5 | 8 AMPD2 | 8 EAF1 | 8 LOC606724 | 8 PREPL |
| 9 PTPRH | 9 TCF7L1 | 8 ANKLE2 | 8 EEF1A1 | 8 LOC641746 | 8 PROS1 |
| 9 R3HCC1L | 9 TEAD1 | 8 ANO5 | 8 EFHD2 | 8 LOC731223 | 8 PRPF4 |
| 9 RAB3IL1 | 9 TFDP3 | 8 AP2S1 | 8 EGFL7 | 8 LPO | 8 PRPF8 |
| 9 RABGAP1 | 9 TGFA | 8 APOBEC3B | 8 EHD1 | 8 LRCH1 | 8 PSD4 |
| 9 RAD54L2 | 9 TGFBR2 | 8 APOBEC3H | 8 EMID1 | 8 LRG1 | 8 PTH2R |
| 9 RANBP3 | 9 TGFBRAP1 | 8 ARHGEF26 | 8 ERBB2IP | 8 LRP6 | 8 PTPLAD1 |
| 9 RASGEF1A | 9 THSD1 | 8 ARHGEF26- | 8 ERBB4 | 8 LRRC73 | 8 PTPN18 |
| 9 RASL10A | 9 TIMP4 | AS1 | 8 EVL | 8 LZTFL1 | 8 PTPRO |
| 9 RBMY2EP | 9 TM4SF19 | 8 ARID5A | 8 EXOC3L1 | 8 MADCAM1 | 8 PTX4 |
| 9 RCSD1 | 9 TM4SF19- | 8 AVP | 8 EXOC3L2 | 8 MAP3K1 | 8 RAD23A |
| 9 RFPL2 | TCTEX1D2 | 8 BAHD1 | 8 EYS | 8 MAP3K14 | 8 RAD50 |
| 9 RGS2 | 9 TMEM105 | 8 BCL10 | 8 FAM63A | 8 MAPKAPK3 | 8 RAMP2 |
| 9 RHOB | 9 TMEM127 | 8 BCL2L10 | 8 FANCA | 8 MAST1 | 8 RAMP2-AS1 |
| 9 RIF1 | 9 TMEM184A | 8 BICD2 | 8 FARS2 | 8 MB21D2 | 8 RAPGEF4-AS1 |
| 9 RNF10 | 9 TMEM200B | 8 BIN3 | 8 FBXO41 | 8 MBD1 | 8 RBMXL2 |
| 9 RNF123 | 9 TMEM44-AS1 | 8 BNC2 | 8 FCHO1 | 8 MBLAC2 | 8 REEP4 |
| 9 RNF213 | 9 TMEM45B | 8 C11orf87 | 8 FEM1A | 8 MCRS1 | 8 RFWD3 |
| 8 RNASE2 | 8 VSIG4 | 7 DNMT3B | 7 LINC00629 | 7 PTCRA | 7 VPS18 |
| 8 RNF138P1 | 8 WDR52 | 7 DNPEP | 7 LMAN2L | 7 PTPRQ | 7 WBSCR17 |
| 8 RNF167 | 8 WNK1 | 7 DRP2 | 7 LOC100128881 | 7 PXMP4 | 7 WDR26 |
| 8 RNF6 | 8 XCR1 | 7 DYRK2 | 7 LOC100130776 | 7 RAB40C | 7 WDR81 |
| 8 ROPN1L | 8 YTHDF2 | 7 EFCAB9 | 7 LOC100288748 | 7 RAB44 | 7 WNK2 |
| 8 RP9P | 8 ZCCHC16 | 7 EIF3G | 7 LOC100507443 | 7 RAD18 | 7 ZCCHC5 |
| 8 RPP25 | 8 ZFP36L1 | 7 ESRP1 | 7 LOC283403 | 7 RBM38 | 7 ZFAND2B |
| 8 RRM2 | 8 ZFP42 | 7 ETV1 | 7 LOC344967 | 7 RBM5 | 7 ZFAT |
| 8 SAMD14 | 8 ZNF148 | 7 ETV3L | 7 LRIG3 | 7 REPS2 | 7 ZNF124 |
| 8 SCAF1 | 8 ZNF239 | 7 EXOC3L4 | 7 LRRC20 | 7 RGL4 | 7 ZNF204P |
| 8 SCAMP2 | 8 ZNF451 | 7 EXTL3 | 7 LRRC43 | 7 RLF | 7 ZNF398 |
| 8 SCRN1 | 7 ABCG4 | 7 FAAH | 7 LSM7 | 7 RNF126 | 7 ZNF415 |
| 8 SEMA6B | 7 ABI3 | 7 FAM129C | 7 LURAP1 | 7 RNF19B | 7 ZNF503 |
| 8 SETDB1 | 7 ACTN1 | 7 FAM173A | 7 LY6H | 7 RPL39L | 7 ZNF503-AS2 |
| 8 SLC11A1 | 7 ADCK3 | 7 FAM173B | 7 MAG | 7 SAFB | 7 ZNF512B |
| 8 SLC25A11 | 7 AMICA1 | 7 FAM48B2 | 7 MAP3K14-AS1 | 7 SEC61A2 | 7 ZNF548 |
| 8 SLC25A4 | 7 ANKIB1 | 7 FAM71F1 | 7 MAPT | 7 SEMA7A | 6 ACAT2 |
| 8 SLC25A42 | 7 ANKRD44 | 7 FCGR3B | 7 ME1 | 7 SERPINB13 | 6 ADAMTS3 |
| 8 SLC34A1 | 7 APLP2 | 7 FERMT2 | 7 MEIOB | 7 SGK110 | 6 ADARB1 |
| 8 SLC35B3 | 7 ARHGAP9 | 7 FLT1 | 7 MFSD6L | 7 SHKBP1 | 6 ADI1 |
| 8 SLC9A3R2 | 7 ARHGEF1 | 7 FOXN3 | 7 MGC16121 | 7 SLAMF8 | 6 ALOX15P1 |
| 8 SLIT3 | 7 ATF7 | 7 FRMD6 | 7 MGC34034 | 7 SLC1A3 | 6 APOLD1 |
| 8 SMOX | 7 ATG2A | 7 FSD1 | 7 MIR1204 | 7 SLC25A2 | 6 AQP8 |
| 8 SNORA30 | 7 BACH2 | 7 FTSJD1 | 7 MIR182 | 7 SMCHD1 | 6 ARHGAP6 |
| 8 SNRK | 7 BDH1 | 7 GAGE13 | 7 MIR1915 | 7 SNCG | 6 ARL15 |
| 8 SNX22 | 7 BMP8B | 7 GAK | 7 MIR192 | 7 SP8 | 6 ARPC1B |
| 8 SOX15 | 7 BSCL2 | 7 GMCL1P1 | 7 MIR194-2 | 7 SPPL2B | 6 ATP1B1 |
| 8 SPATA3 | 7 BTBD8 | 7 GNG3 | 7 MIR1973 | 7 SPTBN1 | 6 ATP5G2 |
| 8 SPO11 | 7 C10orf114 | 7 GNGT2 | 7 MIR3124 | 7 SRD5A2 | 6 BAIAP3 |
| 8 SRCAP | 7 C15orf52 | 7 GOLIM4 | 7 MIR3186 | 7 STAT3 | 6 BCL6B |
| 8 SRSF1 | 7 C16orf7 | 7 GP1BA | 7 MIR4673 | 7 STK17B | 6 BCL7A |
| 8 STAC | 7 C18orf26 | 7 GPR128 | 7 MIR542 | 7 STON2 | 6 BFSP2 |
| 8 STAT5A | 7 C19orf71 | 7 GRM8 | 7 MIR548N | 7 SUGT1P1 | 6 BIRC7 |
| 8 SUV39H1 | 7 C1orf200 | 7 GYPC | 7 MS4A6A | 7 SYNGR1 | 6 C12orf23 |
| 8 SUZ12P1 | 7 C1orf86 | 7 HAUS5 | 7 MTHFD1L | 7 TAGLN2 | 6 C12orf60 |
| 8 SYNM | 7 C20orf201 | 7 HBS1L | 7 MYCL1 | 7 TDGF1 | 6 C16orf93 |
| 8 TAF2 | 7 C2orf68 | 7 HCG11 | 7 MYL6B | 7 TERF1 | 6 C17orf75 |
| 8 TBXA2R | 7 CAMK2G | 7 HCN2 | 7 MYO3B | 7 TESC | 6 C18orf1 |
| 8 TCEA2 | 7 CARNS1 | 7 HIST1H2BO | 7 MYSM1 | 7 TEX26 | 6 C19orf55 |
| 8 TCEB3C | 7 CBX2 | 7 HIST1H3J | 7 NELF | 7 TFAP2A | 6 C19orf60 |
| 8 TCERG1L | 7 CBX3P2 | 7 HNRNPUL2- | 7 NFKBIL1 | 7 TINAGL1 | 6 C1QTNF4 |
| 8 TCF3 | 7 CCDC12 | BSCL2 | 7 NOL7 | 7 TJP2 | 6 C1QTNF9 |
| 8 TCFL5 | 7 CCDC167 | 7 HOXA10 | 7 NOP14-AS1 | 7 TMEM169 | 6 C1orf159 |
| 8 TCTN3 | 7 CCDC69 | 7 HOXA10- | 7 NOTCH1 | 7 TMEM63A | 6 C5orf43 |
| 8 TELO2 | 7 CCND1 | HOXA9 | 7 NPLOC4 | 7 TMIGD2 | 6 C9orf41 |
| 8 TEN1 | 7 CCT5 | 7 HSD17B12 | 7 NTHL1 | 7 TMPRSS13 | 6 CA14 |
| 8 TEN1-CDK3 | 7 CD36 | 7 HTR6 | 7 NUDT14 | 7 TNPO2 | 6 CACNG8 |
| 8 TEX26-AS1 | 7 CDC42EP3 | 7 IGF2BP1 | 7 OPRL1 | 7 TONSL | 6 CALM1 |
| 8 THBS2 | 7 CDCA3 | 7 IGSF9 | 7 OR8U8 | 7 TPT1-AS1 | 6 CAPN3 |
| 8 TLR9 | 7 CDKN1C | 7 IL27 | 7 OS9 | 7 TREML2 | 6 CARD8 |

TABLE 3-continued

Poor Embryo-Quality Genes, Ranked

| | | | | | |
|---|---|---|---|---|---|
| 8 TM2D3 | 7 CES1 | 7 IRF2BP1 | 7 PADI2 | 7 TRIM42 | 6 CASP10 |
| 8 TMEM187 | 7 CHD3 | 7 ITGA5 | 7 PAPD5 | 7 TRPC7 | 6 CBLC |
| 8 TMEM246 | 7 CLIC3 | 7 KAAG1 | 7 PARVB | 7 TSC2 | 6 CBLL1 |
| 8 TOLLIP | 7 COA1 | 7 KANK3 | 7 PCED1B | 7 TSNARE1 | 6 CCDC144A |
| 8 TOM1L1 | 7 COG8 | 7 KATNBL1 | 7 PDF | 7 TSPAN9 | 6 CCDC148 |
| 8 TRAM2 | 7 COX16 | 7 KBTBD13 | 7 PECR | 7 TSPO | 6 CCDC150 |
| 8 TRIM26 | 7 CPNE2 | 7 KCNAB2 | 7 PHC1 | 7 TSSC1 | 6 CCDC64B |
| 8 TRNT1 | 7 CPNE9 | 7 KCNN4 | 7 PHF15 | 7 TTN | 6 CCNK |
| 8 TRPC5 | 7 CPZ | 7 KIAA0195 | 7 PIK3R1 | 7 TTN-AS1 | 6 CD82 |
| 8 TRPM5 | 7 CRYGD | 7 KIAA1683 | 7 PILRB | 7 TUBB1 | 6 CDC14B |
| 8 TSHR | 7 CUL2 | 7 KLHDC4 | 7 PLA2G4D | 7 TUSC2 | 6 CDCA2 |
| 8 TSPY3 | 7 CUL5 | 7 KLHDC8A | 7 PLEKHM2 | 7 U2AF2 | 6 CDKAL1 |
| 8 TSPYL1 | 7 DCAF6 | 7 KLHL24 | 7 PNP | 7 UBE2M | 6 CDT1 |
| 8 TTC7A | 7 DECR1 | 7 KPNA1 | 7 POMGNT1 | 7 UROC1 | 6 CHN2 |
| 8 UBR4 | 7 DEFB132 | 7 KRIT1 | 7 PPP6R2 | 7 USP20 | 6 CLDN23 |
| 8 UMODL1 | 7 DHCR24 | 7 LEFTY1 | 7 PRCC | 7 USP39 | 6 CLDND1 |
| 8 UNCX | 7 DHRS11 | 7 LINC00324 | 7 PRKCD | 7 USP5 | 6 CLEC2B |
| 8 VAX2 | 7 DKFZP434A062 | 7 LINC00592 | 7 PRKG2 | 7 VAV2 | 6 CLEC4A |
| 6 CNR2 | 6 HNRNPU | 6 MYOF | 6 SPAM1 | 5 AQP1 | 6 CLSTN3 |
| 6 COL6A1 | 6 HSPB6 | 6 MYOM2 | 6 SPEN | 5 ARHGEF10L | 5 CNGA4 |
| 6 COL7A1 | 6 HSPBP1 | 6 NAPA | 6 SPIN2A | 5 ARHGEF12 | 5 COG2 |
| 6 CPSF6 | 6 IER5 | 6 NAPA-AS1 | 6 SPON2 | 5 ARMCX4 | 5 COL19A1 |
| 6 CPXM2 | 6 IFI30 | 6 NCAM2 | 6 SRSF2 | 5 ARRDC1 | 5 CPNE5 |
| 6 CSF1R | 6 IL13RA2 | 6 NCOA2 | 6 ST18 | 5 ASB18 | 5 CPSF1 |
| 6 CSNK1D | 6 IST1 | 6 NDE1 | 6 SUFU | 5 ASB2 | 5 CRIP2 |
| 6 CWH43 | 6 JAK3 | 6 NFKBIZ | 6 TACC1 | 5 ASGR2 | 5 CSNK1G2 |
| 6 D2HGDH | 6 KCNC1 | 6 NHLRC1 | 6 TAF1A | 5 ASZ1 | 5 CT47B1 |
| 6 DBF4B | 6 KCNMB2 | 6 NLRP1 | 6 TAS2R40 | 5 ATAD3C | 5 CTBP1-AS1 |
| 6 DCHS1 | 6 KCTD10 | 6 NPHP4 | 6 TBC1D15 | 5 ATP2C2 | 5 CTBS |
| 6 DDX54 | 6 KCTD11 | 6 NQO2 | 6 TBKBP1 | 5 ATP5L2 | 5 CTDNEP1 |
| 6 DGKA | 6 KCTD7 | 6 NR4A3 | 6 TCF15 | 5 ATP8B3 | 5 CTGF |
| 6 DHRS7 | 6 KCTD9 | 6 NSD1 | 6 TEX10 | 5 ATP9B | 5 CTSG |
| 6 DHX40 | 6 KDELR2 | 6 NTN5 | 6 TEX11 | 5 ATPIF1 | 5 CYP2D7P1 |
| 6 DNAJB12 | 6 KDM3A | 6 NUP188 | 6 TIGD1 | 5 ATXN7 | 5 CYP2W1 |
| 6 DOK4 | 6 KIAA1715 | 6 OGFR | 6 TIPRL | 5 AVPR2 | 5 DCAF12L2 |
| 6 DOLK | 6 KIF13A | 6 OPA3 | 6 TMCC3 | 5 AXDND1 | 5 DDX50 |
| 6 DRD5 | 6 KIF7 | 6 OR2L13 | 6 TMEM131 | 5 B3GALNT1 | 5 DHRS9 |
| 6 DSCAML1 | 6 KLHL26 | 6 OR8H2 | 6 TMEM135 | 5 B3GNT7 | 5 DHX16 |
| 6 DUOX2 | 6 KPTN | 6 OXER1 | 6 TMEM154 | 5 B4GALT3 | 5 DHX37 |
| 6 DUOXA1 | 6 KRCC1 | 6 PAX3 | 6 TMEM57 | 5 BCAS3 | 5 DMKN |
| 6 DUOXA2 | 6 LAMB3 | 6 PDZRN3 | 6 TMEM79 | 5 BCAT1 | 5 DNAJC8 |
| 6 DYNC1I2 | 6 LAMTOR3 | 6 PHKG2 | 6 TMEM95 | 5 BMP7 | 5 DUSP6 |
| 6 EFS | 6 LAMTOR4 | 6 PKP4 | 6 TNFAIP8L1 | 5 BNIP3L | 5 DYNC1I1 |
| 6 EIF4E2 | 6 LARP1B | 6 PMF1-BGLAP | 6 TNFAIP8L3 | 5 BPI | 5 DYNLL1 |
| 6 ELANE | 6 LINC00264 | 6 PNMA3 | 6 TNFRSF19 | 5 BRI3BP | 5 ECHDC1 |
| 6 EML6 | 6 LINC00441 | 6 PNOC | 6 TNFRSF21 | 5 C11orf58 | 5 EDAR |
| 6 EPHA7 | 6 LINC00476 | 6 POMT1 | 6 TOM1 | 5 C12orf44 | 5 EEF1D |
| 6 ERCC6L2 | 6 LINGO3 | 6 PPAP2B | 6 TOPORS | 5 C15orf55 | 5 EFHB |
| 6 ERF | 6 LIPH | 6 PPM1G | 6 TPRA1 | 5 C16orf5 | 5 ELAVL3 |
| 6 ETNK1 | 6 LMAN2 | 6 PPP2R5C | 6 TRIT1 | 5 C16orf58 | 5 ELF1 |
| 6 EXOC6 | 6 LOC100128071 | 6 PRMT6 | 6 TSSK3 | 5 C19orf10 | 5 ELP5 |
| 6 FAM127B | 6 LOC100128338 | 6 PROCR | 6 TTYH2 | 5 C1QL4 | 5 EML5 |
| 6 FAM133B | 6 LOC100128770 | 6 PRSS57 | 6 TUBA1A | 5 C1QTNF8 | 5 ENTHD1 |
| 6 FAM133DP | 6 LOC100129250 | 6 PSMC1 | 6 TYMP | 5 C1orf127 | 5 EP400 |
| 6 FAM159A | 6 LOC100129345 | 6 PTGES | 6 UCN2 | 5 C1orf174 | 5 EPAS1 |
| 6 FAM174A | 6 LOC100129518 | 6 PTPRG | 6 UNG | 5 C2orf29 | 5 EPB41 |
| 6 FAM18A | 6 LOC285696 | 6 RALA | 6 UPP1 | 5 C7orf26 | 5 EPCAM |
| 6 FAM83D | 6 LOC494141 | 6 RALGPS2 | 6 VRK1 | 5 CAMKK1 | 5 EPN1 |
| 6 FBN3 | 6 LOC574538 | 6 RAVER1 | 6 WBP11 | 5 CAP2 | 5 EPN3 |
| 6 FBXL6 | 6 LRCH2 | 6 RBFOX2 | 6 WRNIP1 | 5 CARS | 5 ERICH1 |
| 6 FBXO44 | 6 LRRC71 | 6 RBMXL3 | 6 XPO6 | 5 CASP2 | 5 EXD3 |
| 6 FBXO6 | 6 LRRFIP1 | 6 RFNG | 6 ZBTB8A | 5 CAV2 | 5 EXOSC1 |
| 6 FER1L4 | 6 MACF1 | 6 RGL3 | 6 ZFAND2A | 5 CCDC137 | 5 EXOSC7 |
| 6 FER1L5 | 6 MANBA | 6 RGS22 | 6 ZFP14 | 5 CCDC140 | 5 F8 |
| 6 FGFR3 | 6 MAP3K12 | 6 RHBDL3 | 6 ZFR2 | 5 CCDC146 | 5 F8A1 |
| 6 FLJ30403 | 6 MAP3K13 | 6 RNF185 | 6 ZHX2 | 5 CCDC15 | 5 F8A2 |
| 6 FNDC3B | 6 MAPKBP1 | 6 RNF19A | 6 ZMYND11 | 5 CCDC24 | 5 F8A3 |
| 6 FOXD4L1 | 6 MED12L | 6 RNF40 | 6 ZNF300P1 | 5 CCDC42 | 5 FAM169B |
| 6 FOXP2 | 6 MED25 | 6 RTDR1 | 6 ZNF7 | 5 CCDC88C | 5 FAM22F |
| 6 FRRS1L | 6 METTL17 | 6 RTKN | 6 ZNF862 | 5 CCDC92 | 5 FBXO15 |
| 6 FUOM | 6 METTL9 | 6 SCO2 | 5 ABCC3 | 5 CCIN | 5 FBXO47 |
| 6 FUZ | 6 MFNG | 6 SCTR | 5 ABHD3 | 5 CCT3 | 5 FKBP4 |
| 6 GDNF | 6 MFSD11 | 6 SDK1 | 5 ACADS | 5 CD300LG | 5 FLAD1 |
| 6 GEMIN4 | 6 MGC16275 | 6 SEC1P | 5 ACADSB | 5 CD44 | 5 FLT4 |
| 6 GFRA2 | 6 MIAT | 6 SEPT4 | 5 ACOT13 | 5 CDAN1 | 5 FOXD2 |
| 6 GGA1 | 6 MIR3196 | 6 SERPINB5 | 5 ACTL9 | 5 CDC16 | 5 FTSJ3 |
| 6 GPHN | 6 MIR4664 | 6 SETD3 | 5 ADAMTS18 | 5 CDH22 | 5 FZR1 |
| 6 GPR37 | 6 MIR5001 | 6 SFTPA1 | 5 AKNA | 5 CDK14 | 5 GALR2 |

TABLE 3-continued

Poor Embryo-Quality Genes, Ranked

| | | | | | |
|---|---|---|---|---|---|
| 6 GPR77 | 6 MIR636 | 6 SGK1 | 5 ALG1L | 5 CDO1 | 5 GCAT |
| 6 GPS1 | 6 MLK7-AS1 | 6 SGSM1 | 5 ANGEL2 | 5 CECR5 | 5 GCFC2 |
| 6 GPX1 | 6 MOGAT3 | 6 SGTA | 5 ANKRD30BP2 | 5 CECR5-AS1 | 5 GJB2 |
| 6 GRID2IP | 6 MORF4L2 | 6 SLAMF1 | 5 ANKRD33 | 5 CECR7 | 5 GJC2 |
| 6 GRM3 | 6 MORF4L2-AS1 | 6 SLC38A2 | 5 ANXA2R | 5 CELF2 | 5 GLIS1 |
| 6 HELZ | 6 MRPS7 | 6 SMG5 | 5 ANXA9 | 5 CEP170 | 5 GNPNAT1 |
| 6 HEPH | 6 MTNR1A | 6 SOWAHD | 5 AOAH | 5 CHST13 | 5 GPR137B |
| 6 HIP1 | 6 MYBPC3 | 6 SP1 | 5 AP1S2 | 5 CIDEB | 5 GPR78 |
| 5 GPRC5A | 5 MIR4520B | 5 SFMBT2 | 5 ULK4 | 4 ATP9A | 4 CMTM8 |
| 5 GRIK3 | 5 MIR4710 | 5 SFSWAP | 5 VENTX | 4 AVPI1 | 4 CNGA1 |
| 5 GRIPAP1 | 5 MIR4801 | 5 SH2D3A | 5 WAC | 4 B4GALT1 | 4 CNR1 |
| 5 GSG1L | 5 MLLT4 | 5 SH3TC2 | 5 WDFY3 | 4 BCAP31 | 4 COL15A1 |
| 5 GSTA4 | 5 MLLT4-AS1 | 5 SHROOM2 | 5 WDFY3-AS2 | 4 BEX4 | 4 COL25A1 |
| 5 H1F0 | 5 MRVI1 | 5 SIGLEC9 | 5 ZAP70 | 4 BGLAP | 4 COL4A5 |
| 5 H2AFB1 | 5 MXRA5 | 5 SLC1A7 | 5 ZDHHC16 | 4 BMP4 | 4 COL4A6 |
| 5 H2AFB3 | 5 NAA60 | 5 SLC25A52 | 5 ZDHHC17 | 4 BMP6 | 4 COMT |
| 5 HCRTR1 | 5 NAGK | 5 SLC35A3 | 5 ZDHHC3 | 4 BMPER | 4 COX19 |
| 5 HMGXB3 | 5 NAP1L6 | 5 SLC46A1 | 5 ZIC2 | 4 BRD4 | 4 COX4I2 |
| 5 HNRNPCL1 | 5 NAT9 | 5 SLC52A3 | 5 ZMAT2 | 4 BTAF1 | 4 CPEB4 |
| 5 HNRNPK | 5 NCR2 | 5 SLC5A2 | 5 ZNF222 | 4 BTBD16 | 4 CPQ |
| 5 HOXB-AS3 | 5 NDOR1 | 5 SLC5A8 | 5 ZNF34 | 4 BTBD17 | 4 CPSF4L |
| 5 HOXC8 | 5 NDUFAF4 | 5 SLC6A19 | 5 ZNF365 | 4 BTRC | 4 CPT1B |
| 5 HRASLS2 | 5 NDUFB4 | 5 SLC9A1 | 5 ZNF470 | 4 BUB1B | 4 CREB3L1 |
| 5 HS3ST2 | 5 NECAB3 | 5 SLITRK2 | 5 ZNF518A | 4 C10orf11 | 4 CREBBP |
| 5 HSPA2 | 5 NEU4 | 5 SLX4 | 5 ZNF536 | 4 C17orf10 | 4 CRK |
| 5 HTR3E | 5 NFE2L2 | 5 SMC2 | 5 ZNF574 | 4 C17orf62 | 4 CRYM |
| 5 ICAM2 | 5 NFIA | 5 SOCS2 | 5 ZNF615 | 4 C19orf12 | 4 CRYM-AS1 |
| 5 IGDCC4 | 5 NKAPL | 5 SOCS2-AS1 | 5 ZNF653 | 4 C19orf47 | 4 CSDC2 |
| 5 IKZF5 | 5 NOM1 | 5 SOD2 | 5 ZNF738 | 4 C1QTNF3 | 4 CSNK1A1 |
| 5 IL11RA | 5 NOP10 | 5 SOX11 | 5 ZNF80 | 4 C1QTNF6 | 4 CSRNP1 |
| 5 IL17REL | 5 NUDT4 | 5 SPATS2L | 5 ZNHIT1 | 4 C1orf50 | 4 CTNNBIP1 |
| 5 INTS6 | 5 NUDT4P1 | 5 SPDL1 | 5 ZNRF2 | 4 C3orf74 | 4 CTR9 |
| 5 ISLR2 | 5 NUPL1 | 5 SPSB1 | 5 ZSCAN23 | 4 C5orf45 | 4 CUEDC1 |
| 5 ITGBL1 | 5 OLFM2 | 5 SRCIN1 | 4 A1BG-AS1 | 4 C6orf136 | 4 CUL4A |
| 5 ITIH3 | 5 OR5AP2 | 5 SRP68 | 4 ABAT | 4 C6orf195 | 4 CWC25 |
| 5 JMJD8 | 5 OR6B2 | 5 SSTR5 | 4 ABCB4 | 4 C6orf89 | 4 CXCR2 |
| 5 KBTBD11 | 5 ORC2 | 5 ST8SIA6 | 4 ABCB9 | 4 C9orf3 | 4 CYB561D2 |
| 5 KCNE1L | 5 OTOP3 | 5 STAMBP | 4 ABCD1 | 4 C9orf66 | 4 DAPK3 |
| 5 KIAA0754 | 5 OXLD1 | 5 STK24 | 4 ABCF3 | 4 CACNA1F | 4 DARC |
| 5 KIAA0922 | 5 PAK3 | 5 STX11 | 4 ABHD15 | 4 CALML6 | 4 DBIL5P |
| 5 KIAA1239 | 5 PARD6G | 5 STXBP2 | 4 ACIN1 | 4 CAMK2B | 4 DBNL |
| 5 KLRG1 | 5 PCDHGC3 | 5 SUCLG2 | 4 ACOT7 | 4 CAPN1 | 4 DCAF16 |
| 5 KSR1 | 5 PEAR1 | 5 SYPL1 | 4 ACOT9 | 4 CASP8 | 4 DCSTAMP |
| 5 LANCL2 | 5 PER1 | 5 TC2N | 4 ACTL8 | 4 CBY1 | 4 DDC |
| 5 LILRA1 | 5 PIP5K1A | 5 TCF7 | 4 ACTN4 | 4 CCBL2 | 4 DGKI |
| 5 LINC00511 | 5 PIR | 5 TDP2 | 4 ADAMTS5 | 4 CCDC106 | 4 DGKQ |
| 5 LINC00606 | 5 PIR-FIGF | 5 TDRD5 | 4 ADAMTS9 | 4 CCDC22 | 4 DGUOK |
| 5 LMAN1L | 5 PIWIL3 | 5 TDRD9 | 4 ADCY2 | 4 CCDC57 | 4 DIRAS2 |
| 5 LOC100128098 | 5 PKNOX1 | 5 TECPR1 | 4 AEN | 4 CCDC8 | 4 DIRC3 |
| 5 LOC100130539 | 5 PLCG1 | 5 TEPP | 4 AFG3L1P | 4 CCNG2 | 4 DNAH6 |
| 5 LOC100130872 | 5 PLOD3 | 5 TFE3 | 4 AGBL3 | 4 CD247 | 4 DNAJA2 |
| 5 LOC100131655 | 5 PLXNB1 | 5 TGM2 | 4 AGT | 4 CD68 | 4 DNALI1 |
| 5 LOC100132077 | 5 PLXNC1 | 5 THEMIS2 | 4 AIFM3 | 4 CD8A | 4 DOCK6 |
| 5 LOC100132987 | 5 PMF1 | 5 TICRR | 4 AK4 | 4 CDH18 | 4 DOCK8 |
| 5 LOC100498859 | 5 POGZ | 5 TLE2 | 4 ALDH1A3 | 4 CDH20 | 4 DPYSL3 |
| 5 LOC100505495 | 5 PORCN | 5 TMEFF2 | 4 AMOTL1 | 4 CDH7 | 4 DPYSL4 |
| 5 LOC100506668 | 5 POU5F1P3 | 5 TMEM139 | 4 ANK2 | 4 CDK4 | 4 DRAXIN |
| 5 LOC147670 | 5 PPARD | 5 TMEM171 | 4 ANKRD34B | 4 CDPF1 | 4 DSCR6 |
| 5 LOC150185 | 5 PPM1B | 5 TMEM181 | 4 ANKRD63 | 4 CDSN | 4 DUSP22 |
| 5 LOC220906 | 5 PSMC5 | 5 TMEM190 | 4 ANKS1A | 4 CEACAM1 | 4 DVL1 |
| 5 LOC283731 | 5 RAB36 | 5 TMEM241 | 4 ANKS3 | 4 CEACAM6 | 4 DYSF |
| 5 LOC339442 | 5 RASSF1 | 5 TMEM56- | 4 ANXA11 | 4 CENPBD1 | 4 ECEL1P2 |
| 5 LOC643529 | 5 RBP5 | RWDD3 | 4 APBB3 | 4 CEP55 | 4 ECT2L |
| 5 LOC649330 | 5 REREP3 | 5 TMPRSS4 | 4 APC2 | 4 CES1P1 | 4 EFCAB4A |
| 5 LOH12CR1 | 5 RGS19 | 5 TMPRSS4-AS1 | 4 ARFIP2 | 4 CFLAR | 4 EFCAB4B |
| 5 LRRN4 | 5 RGS20 | 5 TMSB15A | 4 ARL10 | 4 CHADL | 4 EFCAB5 |
| 5 LTB4R | 5 RHOH | 5 TOP1P2 | 4 ARMCX5- | 4 CHGA | 4 EIF5 |
| 5 MAGOHB | 5 RHOF2 | 5 TPM2 | GPRASP2 | 4 CHKB-CPT1B | 4 ELOVL4 |
| 5 MAP3K9 | 5 RHOXF2B | 5 TPM3 | 4 ASB1 | 4 CHML | 4 EME2 |
| 5 MAP4K4 | 5 RMI1 | 5 TRIM16 | 4 ASIC2 | 4 CHMP4C | 4 EMP3 |
| 5 MARCKSL1 | 5 RNF111 | 5 TSACC | 4 ASPG | 4 CHRM5 | 4 ENTPD3 |
| 5 MED29 | 5 RPS15A | 5 TSPY8 | 4 ATAD3B | 4 CHRNB2 | 4 EPHA8 |
| 5 MED31 | 5 RWDD3 | 5 UBAC2-AS1 | 4 ATAT1 | 4 CKB | 4 EPM2AIP1 |
| 5 MFF | 5 SAMD4A | 5 UBE2D2 | 4 ATP5J2 | 4 CLDN5 | 4 ERI1 |
| 5 MIER2 | 5 SELK | 5 UBE2E2 | 4 ATP5J2-PTCD1 | 4 CLIP1 | 4 ERO1LB |
| 5 MIR320C1 | 5 SEPHS2 | 5 ULK1 | 4 ATP5S | 4 CMBL | 4 ESYT3 |
| 4 EXOSC2 | 4 HHAT | 4 LOC100130992 | 4 MIR3917 | 4 PAFAH1B3 | 4 RNF11 |
| 4 F12 | 4 HHIPL2 | 4 LOC100131060 | 4 MIR4505 | 4 PARP10 | 4 RNF13 |

TABLE 3-continued

Poor Embryo-Quality Genes, Ranked

| | | | | | |
|---|---|---|---|---|---|
| 4 FAIM2 | 4 HIGD1A | 4 LOC100131626 | 4 MIR4657 | 4 PAWR | 4 RNF212 |
| 4 FAM101A | 4 HILPDA | 4 LOC100131825 | 4 MIR4727 | 4 PAXIP1 | 4 RNF222 |
| 4 FAM102B | 4 HMG20A | 4 LOC100144603 | 4 MIR4728 | 4 PCDH11X | 4 ROBO4 |
| 4 FAM171B | 4 HMGA2 | 4 LOC100188947 | 4 MIR548F5 | 4 PCDHB14 | 4 ROR2 |
| 4 FAM200B | 4 HOXA11-AS | 4 LOC100287944 | 4 MIR5580 | 4 PCID2 | 4 RPL22 |
| 4 FAM219A | 4 HOXB2 | 4 | 4 MIR561 | 4 PCMT1 | 4 RPL36A |
| 4 FAM227A | 4 HOXB3 | LOC100499484- | 4 MIR5691 | 4 PDE2A | 4 RPL36A- |
| 4 FAM5B | 4 HOXB5 | C9ORF174 | 4 MIR602 | 4 PDGFRB | HNRNPH2 |
| 4 FAM78B | 4 HSD3B7 | 4 LOC100505583 | 4 MIR609 | 4 PEAK1 | 4 RPS15 |
| 4 FARP2 | 4 HSF4 | 4 LOC100505875 | 4 MIR675 | 4 PER2 | 4 RPS26 |
| 4 FBXO25 | 4 HSPB9 | 4 LOC100506229 | 4 MIR935 | 4 PF4V1 | 4 RPSAP58 |
| 4 FGF14 | 4 IFITM10 | 4 LOC100507066 | 4 MKNK1 | 4 PGAP2 | 4 RRAGA |
| 4 FGF14-AS2 | 4 IFITM4P | 4 LOC100507564 | 4 MKRN9P | 4 PHC2 | 4 RSBN1 |
| 4 FGF14-IT1 | 4 IFT88 | 4 LOC100996307 | 4 MLH1 | 4 PHKB | 4 RSPH3 |
| 4 FIGNL2 | 4 IGSF9B | 4 LOC150197 | 4 MOCS1 | 4 PIPSL | 4 RTN4 |
| 4 FLJ22184 | 4 IL17RD | 4 LOC151171 | 4 MORF4L1 | 4 PLD3 | 4 RUSC1 |
| 4 FLJ33534 | 4 IL19 | 4 LOC202781 | 4 MPRIP | 4 PLEKHM3 | 4 RUSC1-AS1 |
| 4 FLJ35390 | 4 INHBE | 4 LOC255130 | 4 MPZ | 4 PLXNB3 | 4 RYK |
| 4 FLJ46257 | 4 ITFG1 | 4 LOC283194 | 4 MRPL16 | 4 PODNL1 | 4 SAFB2 |
| 4 FLNC | 4 ITGA3 | 4 LOC284837 | 4 MRPL55 | 4 PP12613 | 4 SAP18 |
| 4 FOXN3-AS1 | 4 JAKMIP2 | 4 LOC284865 | 4 MRPS28 | 4 PPAN-P2RY11 | 4 SBK1 |
| 4 FXC1 | 4 JAKMIP2-AS1 | 4 LOC344887 | 4 MRPS34 | 4 PPP1R3D | 4 SCAND2 |
| 4 FXR2 | 4 JTB | 4 LOC348120 | 4 MS4A15 | 4 PPP1R3G | 4 SCARNA13 |
| 4 FXYD6 | 4 JUP | 4 LOC400685 | 4 MSX2P1 | 4 PPP2CA | 4 SCN4B |
| 4 FXYD6-FXYD2 | 4 KALRN | 4 LOC401109 | 4 MTF1 | 4 PPP2R5A | 4 SCN9A |
| 4 GABRG3 | 4 KANK4 | 4 LOC440563 | 4 MX2 | 4 PPP3CB | 4 SCP2 |
| 4 GATSL3 | 4 KAT2A | 4 LOC440944 | 4 MYBPC2 | 4 PRAME | 4 SCUBE2 |
| 4 GBX1 | 4 KCNAB1 | 4 LOC541473 | 4 MYH11 | 4 PREP | 4 SDC1 |
| 4 GDAP1 | 4 KCNB1 | 4 LOC644189 | 4 MYO1D | 4 PRKAR2B | 4 SDHC |
| 4 GDPD5 | 4 KCNJ8 | 4 LOC648691 | 4 MYO1E | 4 PROB1 | 4 SEC23B |
| 4 GEMIN7 | 4 KCTD16 | 4 L00648809 | 4 MZT2B | 4 PROCA1 | 4 SENP7 |
| 4 GIP | 4 KDM1A | 4 LOC728392 | 4 NACC2 | 4 PRR19 | 4 SERTM1 |
| 4 GLI3 | 4 KHK | 4 LONRF2 | 4 NAV3 | 4 PRR23B | 4 SETD5 |
| 4 GLRA1 | 4 KIAA0247 | 4 LRGUK | 4 NCAPG | 4 PRRT2 | 4 SFT2D3 |
| 4 GLRX5 | 4 KIAA1191 | 4 LRRC14 | 4 NDST4 | 4 PRSS16 | 4 SGCD |
| 4 GLS2 | 4 KIAA1462 | 4 LRRC2 | 4 NDUFAF5 | 4 PRSS27 | 4 SGOL1 |
| 4 GLYATL3 | 4 KIF19 | 4 LRRC45 | 4 NEAT1 | 4 PSMG2 | 4 SGSM3 |
| 4 GNB1 | 4 KLF13 | 4 LRRC8B | 4 NEK9 | 4 PSTPIP2 | 4 SH2D7 |
| 4 GNG11 | 4 KLF2 | 4 LTB4R2 | 4 NEURL | 4 PTGIS | 4 SH3RF1 |
| 4 GP6 | 4 KLHDC2 | 4 LYPLA1 | 4 NEXN | 4 PTPRC | 4 SHBG |
| 4 GPATCH3 | 4 KLK1 | 4 LYSMD2 | 4 NF1 | 4 PTPRN | 4 SHE |
| 4 GPD2 | 4 KLK15 | 4 LZTR1 | 4 NFYC | 4 PTPRR | 4 SHISA6 |
| 4 GPN2 | 4 KLK6 | 4 MAGEA2 | 4 NHEJ1 | 4 PURB | 4 SHROOM4 |
| 4 GPR124 | 4 KNDC1 | 4 MAGEA2B | 4 NKD1 | 4 PUSL1 | 4 SIK2 |
| 4 GPRASP2 | 4 KRT17 | 4 MAGI1 | 4 NME3 | 4 PXDC1 | 4 SKAP1 |
| 4 GPS2 | 4 KRT36 | 4 MAGOH | 4 NMS | 4 PYY | 4 SLC16A3 |
| 4 GRIN2A | 4 KRT8 | 4 MAL | 4 NODAL | 4 QSER1 | 4 SLC1A5 |
| 4 GRINA | 4 KRT86 | 4 MAOB | 4 NOTCH4 | 4 QSOX2 | 4 SLC1A6 |
| 4 GRK4 | 4 KRT8P41 | 4 MAP3K3 | 4 NPAS3 | 4 RAB12 | 4 SLC23A1 |
| 4 GRM6 | 4 L2HGDH | 4 MAP4K1 | 4 NPRL2 | 4 RAB4A | 4 SLC25A23 |
| 4 GTF2A1L | 4 LAMA5 | 4 MAP7D2 | 4 NRL | 4 RAC3 | 4 SLC25A3 |
| 4 GTPBP1 | 4 LAMB2 | 4 MARCH10 | 4 NTF3 | 4 RALGPS1 | 4 SLC25A30 |
| 4 GUCY1B2 | 4 LDHAL6B | 4 MARCH9 | 4 NUDT1 | 4 RASA4CP | 4 SLC26A10 |
| 4 GUCY2C | 4 LDHC | 4 MARCO | 4 NUMA1 | 4 RASAL1 | 4 SLC2A1-AS1 |
| 4 GULP1 | 4 LEPRE1 | 4 MARS2 | 4 NUP43 | 4 RBM4B | 4 SLC35A4 |
| 4 GXYLT1 | 4 LEPROT | 4 MATR3 | 4 NUP98 | 4 RBMXL1 | 4 SLC35G1 |
| 4 H19 | 4 LGALS3BP | 4 MAZ | 4 NXF3 | 4 RBMY1F | 4 SLC38A11 |
| 4 H3F3B | 4 LHX6 | 4 MBOAT7 | 4 OAT | 4 RELL2 | 4 SLC38A7 |
| 4 HDAC11 | 4 LIN7B | 4 MDM1 | 4 ODF2L | 4 REM1 | 4 SLC39A11 |
| 4 HDAC3 | 4 LINC00028 | 4 MEDAG | 4 OPN3 | 4 REXO2 | 4 SLC39A14 |
| 4 HDAC7 | 4 LINC00163 | 4 METTL10 | 4 OR7G3 | 4 RFX4 | 4 SLC39A4 |
| 4 HECTD2 | 4 LINC00273 | 4 METTL14 | 4 ORAOV1 | 4 RGN | 4 SLC4A11 |
| 4 HECW2 | 4 LINC00523 | 4 MFAP4 | 4 OSBPL3 | 4 RGS6 | 4 SLC5A11 |
| 4 HEPHL1 | 4 LMLN | 4 MFI2-AS1 | 4 OSR1 | 4 RHCG | 4 SLC9A3R1 |
| 4 HEXIM1 | 4 LOC100129917 | 4 MGAT1 | 4 PABPC5 | 4 RLIM | 4 SLCO1C1 |
| 4 HEYL | 4 LOC100130557 | 4 MIR3649 | 4 PADI1 | 4 RND2 | 4 SLMAP |
| 4 SLPI | 4 TRIM74 | 3 ADAMTSL5 | 3 C19orf26 | 3 COL20A1 | 3 FAIM3 |
| 4 SMG9 | 4 TRPM8 | 3 ADCY4 | 3 C19orf45 | 3 COL8A1 | 3 FAM111B |
| 4 SMPD4 | 4 TSHZ3 | 3 ADO | 3 C19orf6 | 3 COLQ | 3 FAM127C |
| 4 SMPDL3A | 4 TSPAN10 | 3 AFAP1L1 | 3 C1QTNF2 | 3 COMMD3-BMI1 | 3 FAM134A |
| 4 SNAR-C1 | 4 TSPAN15 | 3 AGXT2L2 | 3 C1orf123 | 3 COMMD7 | 3 FAM134B |
| 4 SNAR-C2 | 4 TTC30B | 3 ANCTF1 | 3 C1orf170 | 3 COX7C | 3 FAM150B |
| 4 SNAR-C5 | 4 TTC34 | 3 AKR7L | 3 C1orf210 | 3 CPA2 | 3 FAM175B |
| 4 SNHG10 | 4 TTC9B | 3 AKT2 | 3 C1orf52 | 3 CPNE7 | 3 FAM176B |
| 4 SNHG16 | 4 TTLL4 | 3 ALKBH5 | 3 C20orf112 | 3 CPSF3 | 3 FAM176C |
| 4 SNIP1 | 4 TTPAL | 3 ALPPL2 | 3 C21orf33 | 3 CREB3L3 | 3 FAM182B |
| 4 SNORD1A | 4 TUSC3 | 3 ALS2CR8 | 3 C22orf26 | 3 CREB5 | 3 FAM188B |
| 4 SNORD1B | 4 TYR | 3 AMDHD1 | 3 C2orf50 | 3 CRHR1 | 3 FAM193B |

TABLE 3-continued

Poor Embryo-Quality Genes, Ranked

| | | | | | |
|---|---|---|---|---|---|
| 4 SNORD1C | 4 UBA7 | 3 ANGPTL2 | 3 C3orf62 | 3 CRX | 3 FAM82A1 |
| 4 SNRPE | 4 UCN | 3 ANGPTL6 | 3 C3orf72 | 3 CS | 3 FAM83G |
| 4 SNX10 | 4 UCN3 | 3 ANKH | 3 C6orf1 | 3 CSF3 | 3 FAM98B |
| 4 SOCS1 | 4 UMOD | 3 ANKMY1 | 3 C6orf120 | 3 CTDSPL | 3 FASTKD3 |
| 4 SOCS7 | 4 UNK | 3 ANKRD34A | 3 C7orf10 | 3 CXADR | 3 FBXL14 |
| 4 SOX18 | 4 UNQ6494 | 3 ANKRD39 | 3 C7orf41 | 3 CXCL12 | 3 FBXO27 |
| 4 SP3 | 4 UPF3A | 3 ANP32C | 3 C7orf55- | 3 CYB561D1 | 3 FBXW4 |
| 4 SP6 | 4 UQCRFS1 | 3 ANXA6 | LUC7L2 | 3 CYC1 | 3 FCHSD1 |
| 4 SPAG11A | 4 USP19 | 3 AOX2P | 3 C8orf44 | 3 CYLD | 3 FERMT1 |
| 4 SPAG9 | 4 USP6 | 3 AP4E1 | 3 C8orf48 | 3 CYP11A1 | 3 FEZF2 |
| 4 SPINK13 | 4 VAC14 | 3 AP5S1 | 3 C9orf171 | 3 CYP2D6 | 3 FGD2 |
| 4 SPNS1 | 4 VAT1 | 3 APOA2 | 3 C9orf174 | 3 DAPK2 | 3 FGFBP2 |
| 4 SPNS3 | 4 VCX3A | 3 APOBEC3A | 3 CA11 | 3 DBP | 3 FHDC1 |
| 4 SRY | 4 WDR45 | 3 APOBEC3C | 3 CACNA1B | 3 DCAF12 | 3 FIBIN |
| 4 SSR4P1 | 4 WDR96 | 3 APOF | 3 CACNA2D3 | 3 DCAF12L1 | 3 FITM1 |
| 4 SSX6 | 4 WIBG | 3 AQP2 | 3 CALHM2 | 3 DCAF8L2 | 3 FKBP1A- |
| 4 ST6GAL2 | 4 WISP3 | 3 AQP5 | 3 CAPN12 | 3 DDX11L10 | SDCBP2 |
| 4 STARD5 | 4 WNT5A | 3 ARHGAP15 | 3 CARD10 | 3 DIO2 | 3 FLJ23152 |
| 4 STMN1 | 4 XK | 3 ARHGEF16 | 3 CASP3 | 3 DIO2-AS1 | 3 FLJ30679 |
| 4 STOML1 | 4 XRCC3 | 3 ARID5B | 3 CASR | 3 DISP2 | 3 FLJ43663 |
| 4 STRBP | 4 YIF1B | 3 ARL3 | 3 CAV3 | 3 DLX6-AS1 | 3 FLJ43860 |
| 4 STX1A | 4 ZBTB1 | 3 ARL4A | 3 CBFA2T2 | 3 DMAP1 | 3 FLVCR2 |
| 4 SUSD3 | 4 ZBTB25 | 3 ARRDC5 | 3 CBX5 | 3 DNAH7 | 3 FOXL2 |
| 4 SYBU | 4 ZBTB9 | 3 ASB13 | 3 CCDC107 | 3 DNAJC11 | 3 FSD2 |
| 4 SYCN | 4 ZEB1 | 3 ASIC3 | 3 CCDC111 | 3 DOC2GP | 3 FUCA2 |
| 4 SYNE1 | 4 ZEB1-AS1 | 3 ASS1 | 3 CCDC53 | 3 DOCK5 | 3 FUT3 |
| 4 TAF7L | 4 ZFAND4 | 3 ATL1 | 3 CCDC77 | 3 DOT1L | 3 FXYD2 |
| 4 TARM1 | 4 ZFP82 | 3 ATL3 | 3 CCDC83 | 3 DSP | 3 FYB |
| 4 TBC1D9B | 4 ZMIZ2 | 3 ATP6V0A2 | 3 CCDC86 | 3 DUSP14 | 3 GALNT13 |
| 4 TCEB3CL | 4 ZNF221 | 3 ATP6V1B1 | 3 CCT7 | 3 DUSP5 | 3 GAP43 |
| 4 TDRD10 | 4 ZNF238 | 3 ATP6V1F | 3 CD180 | 3 DUSP8 | 3 GAS2 |
| 4 TDRKH | 4 ZNF280C | 3 AXL | 3 CD320 | 3 E2F6 | 3 GEMIN6 |
| 4 TFB1M | 4 ZNF425 | 3 B3GALTL | 3 CD52 | 3 ECE2 | 3 GFER |
| 4 THAP4 | 4 ZNF516 | 3 B3GAT2 | 3 CD55 | 3 EDF1 | 3 GGNBP1 |
| 4 THG1L | 4 ZNF575 | 3 B3GNT3 | 3 CD72 | 3 EHD3 | 3 GIPC3 |
| 4 TIMM13 | 4 ZNF583 | 3 B9D1 | 3 CD79A | 3 EIF2B3 | 3 GLB1L |
| 4 TLK2 | 4 ZNF586 | 3 BAK1 | 3 CDCP2 | 3 EIF5A2 | 3 GLI1 |
| 4 TLR3 | 4 ZNF664- | 3 BATF2 | 3 CDHR2 | 3 ELFN2 | 3 GLOD5 |
| 4 TM9SF1 | FAM101A | 3 BBX | 3 CDK5 | 3 ELN | 3 GNA11 |
| 4 TMA16 | 4 ZNF681 | 3 BCL2A1 | 3 CDK5R1 | 3 ELOVL5 | 3 GNA13 |
| 4 TMC4 | 4 ZNF71 | 3 BCORL1 | 3 CDK9 | 3 EMBP1 | 3 GNL3 |
| 4 TMEM101 | 4 ZNF728 | 3 BIK | 3 CDON | 3 ENDOG | 3 GP1BB |
| 4 TMEM130 | 4 ZNF850 | 3 BLOC1S4 | 3 CEP164 | 3 ENOSF1 | 3 GPKOW |
| 4 TMEM155 | 4 ZNF878 | 3 BMI1 | 3 CHAMP1 | 3 EPB41L1 | 3 GPR142 |
| 4 TMEM158 | 3 A2M-AS1 | 3 BOC | 3 CHD5 | 3 EPB41L3 | 3 GPR35 |
| 4 TMEM177 | 3 AARS2 | 3 BOD1 | 3 CHMP2A | 3 EPB41L5 | 3 GPR56 |
| 4 TMEM40 | 3 ABCB7 | 3 BRD1 | 3 CHRNA4 | 3 EPC2 | 3 GPT2 |
| 4 TMEM5 | 3 ABCB8 | 3 BTBD1 | 3 CHRNB1 | 3 EPHA10 | 3 GRIK5 |
| 4 TMEM51 | 3 ABI1 | 3 BTG2 | 3 CILP | 3 EPS15L1 | 3 GRM2 |
| 4 TMEM61 | 3 ACBD5 | 3 BTLA | 3 CLCN1 | 3 EPS8L2 | 3 H3F3A |
| 4 TMEM9 | 3 ACP6 | 3 C14orf182 | 3 CLDN6 | 3 ERI3 | 3 H3F3AP4 |
| 4 TMIE | 3 ACTB | 3 C15orf27 | 3 CLMP | 3 ESPNP | 3 H6PD |
| 4 TNFRSF13B | 3 ACVR2B | 3 C16orf46 | 3 CMPK1 | 3 ESR1 | 3 HAMP |
| 4 TPCN2 | 3 ACVR2B-AS1 | 3 C17orf103 | 3 CMTM4 | 3 ESRP2 | 3 HARS2 |
| 4 TRAF1 | 3 ADAM22 | 3 C17orf109 | 3 CNFN | 3 EXO1 | 3 HCAR2 |
| 4 TRIM73 | 3 ADAM33 | 3 C17orf53 | 3 COIL | 3 EYA4 | 3 HCG22 |
| 3 HDDC2 | 3 LOC100292680 | 3 MIXL1 | 3 PBRM1 | 3 RPL27A | 3 SSPN |
| 3 HEG1 | 3 LOC100499484 | 3 MKLN1 | 3 PCSK9 | 3 RPL3 | 3 SSPO |
| 3 HIC2 | 3 LOC100505549 | 3 MLF1 | 3 PCTP | 3 RPS20 | 3 SSTR4 |
| 3 HIF1A-AS2 | 3 LOC100505622 | 3 MLKL | 3 PDLIM5 | 3 RSPH9 | 3 ST3GAL1 |
| 3 HKR1 | 3 LOC100506178 | 3 MLNR | 3 PDP2 | 3 RSPO1 | 3 ST6GALNAC4 |
| 3 HLA-DRB5 | 3 LOC100506710 | 3 MMP23A | 3 PDYN | 3 RSPO3 | 3 STAP2 |
| 3 HLA-F-AS1 | 3 LOC100507299 | 3 MORN1 | 3 PEX11G | 3 RUNX3 | 3 STAT2 |
| 3 HNRNPA1 | 3 LOC100652768 | 3 MPHOSPH8 | 3 PEX5 | 3 RWDD2B | 3 STC2 |
| 3 HNRNPA1P10 | 3 LOC150381 | 3 MPND | 3 PHLDA2 | 3 RXFP4 | 3 STIP1 |
| 3 HS1BP3 | 3 LOC155060 | 3 MPP2 | 3 PIGQ | 3 SAMD12 | 3 STK16 |
| 3 HS6ST3 | 3 LOC255167 | 3 MPPED2 | 3 PINLYP | 3 SARM1 | 3 STPG2 |
| 3 HSD17B7P2 | 3 LOC339505 | 3 MRFAP1 | 3 PKN3 | 3 SASH1 | 3 STUB1 |
| 3 HTRA1 | 3 LOC375295 | 3 MRPL23-AS1 | 3 PLA2G3 | 3 SCMH1 | 3 STX1B |
| 3 IFITM3 | 3 LOC389705 | 3 MRPL28 | 3 PLXNB2 | 3 SDCBP2 | 3 SUB1 |
| 3 IKZF2 | 3 LOC401320 | 3 MRPS15 | 3 POLR3GL | 3 SDCBP2-AS1 | 3 SULT1A1 |
| 3 IL17C | 3 LOC644248 | 3 MRRF | 3 POM121 | 3 SDF2 | 3 SUPT6H |
| 3 IL18BP | 3 LOC644554 | 3 MS4A3 | 3 POM121C | 3 SEPHS1 | 3 SYN3 |
| 3 IL20RA | 3 LOC728175 | 3 MSH3 | 3 POU2F2 | 3 SEPT5 | 3 SYNC |
| 3 IL4R | 3 LOC730227 | 3 MTA3 | 3 POU5F1B | 3 SEPT5-GP1BB | 3 SYNCRIP |
| 3 INMT-FAM188B | 3 LOC730811 | 3 MTCH1 | 3 PPAN | 3 SERP2 | 3 SYNGR2 |
| 3 INPPL1 | 3 LOC90834 | 3 MTHFD1 | 3 PPFIA4 | 3 SERPINA10 | 3 SYT17 |
| 3 ISYNA1 | 3 LOXL2 | 3 MTHFD2 | 3 PPFIBP2 | 3 SET | 3 SYT3 |

TABLE 3-continued

Poor Embryo-Quality Genes, Ranked

| | | | | | |
|---|---|---|---|---|---|
| 3 ITGB1 | 3 LPIN2 | 3 MTHFSD | 3 PPIL6 | 3 SFTA3 | 3 SYT8 |
| 3 ITGB1BP1 | 3 LRFN4 | 3 MTMR7 | 3 PPP1R26 | 3 SGMS1 | 3 SYTL3 |
| 3 JAM3 | 3 LRIT1 | 3 MTPAP | 3 PPP1R7 | 3 SH3BP4 | 3 TAGLN |
| 3 JMJD1C | 3 LRRC33 | 3 MTRR | 3 PPP2R5B | 3 SIGLEC10 | 3 TARS |
| 3 KCNG3 | 3 LSAMP | 3 MUC2 | 3 PRADC1 | 3 SIGLEC12 | 3 TBC1D13 |
| 3 KCNG4 | 3 LSM3 | 3 MUC5B | 3 PRDX2 | 3 SIRT1 | 3 TBC1D2B |
| 3 KCNK10 | 3 LTBP2 | 3 MYF5 | 3 PRKDC | 3 SIRT7 | 3 TBK1 |
| 3 KCP | 3 LTK | 3 MYO1B | 3 PROSC | 3 SKP1 | 3 TCEA3 |
| 3 KDM5A | 3 LUC7L2 | 3 MYZAP | 3 PRR15 | 3 SLC15A4 | 3 TCL1A |
| 3 KIAA0226L | 3 LYPD6B | 3 NAV2 | 3 PSMB2 | 3 SLC19A3 | 3 TCL1B |
| 3 KIAA0284 | 3 MAB21L1 | 3 NBEA | 3 PSME1 | 3 SLC26A11 | 3 TEAD3 |
| 3 KIAA1161 | 3 MAGEC1 | 3 NCAPH | 3 PTCH1 | 3 SLC26A9 | 3 TFR2 |
| 3 KIAA1217 | 3 MAGEC3 | 3 NEBL | 3 PTCH2 | 3 SLC38A8 | 3 THUMPD1 |
| 3 KIAA1467 | 3 MAGT1 | 3 NEK10 | 3 PTGFRN | 3 SLC44A4 | 3 TIAM2 |
| 3 KIAA1671 | 3 MAL2 | 3 NEK8 | 3 RABGAP1L | 3 SLC4A2 | 3 TK2 |
| 3 KIAA1804 | 3 MANEAL | 3 NFKB1 | 3 RABL2B | 3 SLC51B | 3 TMBIM1 |
| 3 KIF2A | 3 MAP4K5 | 3 NHLRC4 | 3 RABL5 | 3 SLC5A10 | 3 TMBIM6 |
| 3 KIF3A | 3 MAPK4 | 3 NISCH | 3 RAC2 | 3 SLC6A12 | 3 TMEM119 |
| 3 KLK11 | 3 MDFI | 3 NONO | 3 RAD21 | 3 SLC7A4 | 3 TMEM179 |
| 3 KLK12 | 3 MEF2A | 3 NOXO1 | 3 RAD21-AS1 | 3 SMAD7 | 3 TMEM185B |
| 3 KRT77 | 3 MEF2B | 3 NPM2 | 3 RAMP1 | 3 SMC5 | 3 TMEM27 |
| 3 L1TD1 | 3 MEF2BNB-MEF2B | 3 NPTX2 | 3 RBBP6 | 3 SMPD2 | 3 TMEM30B |
| 3 LAG3 | | 3 NR2F6 | 3 RBL1 | 3 SNCA | 3 TMEM44 |
| 3 LAMC1 | 3 METTL8 | 3 NRF1 | 3 RBL2 | 3 SNORA21 | 3 TMEM45A |
| 3 LAMC3 | 3 MFSD1 | 3 NRP1 | 3 RBM18 | 3 SNORA3 | 3 TMEM53 |
| 3 LAMP3 | 3 MFSD10 | 3 NRP2 | 3 RBMY1J | 3 SNORA45 | 3 TMPRSS3 |
| 3 LAX1 | 3 MGC57346 | 3 NUCKS1 | 3 RBMY2FP | 3 SNORD105 | 3 TNFRSF12A |
| 3 LCN8 | 3 MICALL2 | 3 NUP210 | 3 RFX7 | 3 SNORD19B | 3 TNIP2 |
| 3 LCP1 | 3 MIER1 | 3 NXNL1 | 3 RGAG4 | 3 SNORD54 | 3 TNK2 |
| 3 LEF1 | 3 MIIP | 3 OCEL1 | 3 RGR | 3 SNORD69 | 3 TNRC6A |
| 3 LEF1-AS1 | 3 MINA | 3 OLFML2B | 3 RGS3 | 3 SNORD83A | 3 TNS1 |
| 3 LENG8 | 3 MIR1234 | 3 OMA1 | 3 RHBDL1 | 3 SNORD83B | 3 TOMM40L |
| 3 LGALS7B | 3 MIR1275 | 3 OR7C1 | 3 RHOF | 3 SNRNP48 | 3 TOR1B |
| 3 LGMN | 3 MIR2861 | 3 OSCP1 | 3 RHOU | 3 SNRPB2 | 3 TP53BP1 |
| 3 LILRA4 | 3 MIR3150B | 3 OSTCP1 | 3 RILP | 3 SOBP | 3 TPTE |
| 3 LINC00202 | 3 MIR3607 | 3 P2RY10 | 3 RIMS1 | 3 SOX5 | 3 TRAF2 |
| 3 LINC00240 | 3 MIR3615 | 3 P2RY2 | 3 RNASEH2A | 3 SOX7 | 3 TRAF4 |
| 3 LINC00265 | 3 MIR3960 | 3 PABPC1 | 3 RNF138 | 3 SP140L | 3 TRAPPC1 |
| 3 LINC00313 | 3 MIR4285 | 3 PAEP | 3 RNLS | 3 SPATA18 | 3 TRDMT1 |
| 3 LINC00319 | 3 MIR4298 | 3 PAFAH2 | 3 RNU5D-1 | 3 SPATA2 | 3 TREH |
| 3 LINC00612 | 3 MIR4520A | 3 PAK7 | 3 RNU5E-1 | 3 SPIRE1 | 3 TRIM5 |
| 3 LIPJ | 3 MIR4669 | 3 PALM | 3 RNU6-28 | 3 SPOCK2 | 3 TRMT1L |
| 3 LMTK2 | 3 MIR5187 | 3 PAQR5 | 3 RPH3A | 3 SPTBN2 | 3 TRPM1 |
| 3 LMX1B | 3 MIR548G | 3 PARP12 | 3 RPL23 | 3 SQLE | 3 TTC7B |
| 3 LOC100009676 | 3 MIR641 | 3 PASK | 3 RPL23AP53 | 3 SRC | 3 TTC9 |
| 3 LOC100132354 | 3 MIR661 | 3 PAX5 | 3 RPL23AP82 | 3 SRMS | 3 TTLL6 |
| 3 UBLCP1 | 2 ACVR2A | 2 ATP6V1G1 | 2 C2CD4B | 2 CEP85 | 2 CSRNP3 |
| 3 UHRF2 | 2 ACVRL1 | 2 ATP6V1G2-DDX39B | 2 C2orf40 | 2 CERKL | 2 CST6 |
| 3 UNC119 | 2 ACYP1 | | 2 C2orf54 | 2 CES3 | 2 CTIF |
| 3 UPF1 | 2 ADAM15 | 2 ATPAF1 | 2 C3orf17 | 2 CFD | 2 CTSC |
| 3 UPK1B | 2 ADAMTS14 | 2 ATPAF1-AS1 | 2 C3orf27 | 2 CGB2 | 2 CTSW |
| 3 UPK2 | 2 ADAT3 | 2 AZIN1 | 2 C3orf32 | 2 CHAD | 2 CTTNBP2NL |
| 3 UQCC | 2 ADCK5 | 2 B3GALT5 | 2 C3orf36 | 2 CHD4 | 2 CTXN1 |
| 3 USP16 | 2 ADD3 | 2 B3GNT5 | 2 C3orf37 | 2 CHI3L1 | 2 CXCL10 |
| 3 USP47 | 2 ADNP | 2 BACE2 | 2 C4orf21 | 2 CHIC1 | 2 CXCL5 |
| 3 VAMP8 | 2 ADORA2B | 2 BACH1 | 2 C4orf27 | 2 CHRD | 2 CXCR1 |
| 3 VANGL2 | 2 ADRA2B | 2 BARHL2 | 2 C5AR1 | 2 CHRNA5 | 2 CXCR5 |
| 3 VDAC1 | 2 AGBL2 | 2 BCAM | 2 C5orf24 | 2 CHRND | 2 CYBASC3 |
| 3 VOPP1 | 2 AGK | 2 BCDIN3D-AS1 | 2 C6orf10 | 2 CHRNE | 2 CYP19A1 |
| 3 VSTM5 | 2 AGXT | 2 BCL9 | 2 C6orf15 | 2 CHST10 | 2 CYP1B1 |
| 3 VTN | 2 AK8 | 2 BCL9L | 2 C6orf164 | 2 CHST9 | 2 CYP1B1-AS1 |
| 3 VTRNA2-1 | 2 AKR7A2 | 2 BEAN1 | 2 C7orf55 | 2 CHTF18 | 2 CYP2F1 |
| 3 VWCE | 2 ALDH1L1-AS2 | 2 BEND7 | 2 C7orf69 | 2 CKAP2L | 2 CYP2S1 |
| 3 WBP2NL | 2 ALDH1L2 | 2 BEST1 | 2 C8orf31 | 2 CKS1B | 2 CYP4F24P |
| 3 WBSCR27 | 2 ALDH2 | 2 BET3L | 2 C8orf34 | 2 CLCN4 | 2 CYTH3 |
| 3 WDR12 | 2 ALG13 | 2 BEX5 | 2 C9orf169 | 2 CLCN5 | 2 DAGLA |
| 3 WDR18 | 2 ALG14 | 2 BGN | 2 C9orf50 | 2 CLCNKB | 2 DAGLB |
| 3 WDR78 | 2 ALG6 | 2 BHLHA15 | 2 C9orf9 | 2 CLDN7 | 2 DAP3 |
| 3 WDTC1 | 2 ALPL | 2 BHLHE41 | 2 CA12 | 2 CLDN8 | 2 DCAF17 |
| 3 WFS1 | 2 ALS2 | 2 BLVRA | 2 CABLES1 | 2 CLEC12B | 2 DCAF5 |
| 3 WHAMM | 2 AMN | 2 BLZF1 | 2 CACNA2D2 | 2 CLEC14A | 2 DCDC2B |
| 3 WISP1 | 2 AMPH | 2 BMF | 2 CACNB3 | 2 CLEC1A | 2 DCLRE1A |
| 3 XAGE5 | 2 ANAPC16 | 2 BMPR1B | 2 CACYBP | 2 CLK3 | 2 DCTPP1 |
| 3 XPC | 2 ANKK1 | 2 BMPR2 | 2 CADM1 | 2 CLN5 | 2 DDIT3 |
| 3 XRCC1 | 2 ANTXR1 | 2 BMX | 2 CALCOCO2 | 2 CLTCL1 | 2 DDX11L2 |
| 3 YBX2 | 2 ANXA1 | 2 BOP1 | 2 CAMP | 2 CMC1 | 2 DDX27 |
| 3 YEATS2 | 2 AP1B1 | 2 BRF2 | 2 CAPN14 | 2 CMC2 | 2 DDX39B |
| 3 YWHAQ | 2 AP1S3 | 2 BSN | 2 CARD6 | 2 CMSS1 | 2 DEFA4 |

TABLE 3-continued

Poor Embryo-Quality Genes, Ranked

| | | | | | |
|---|---|---|---|---|---|
| 3 ZAK | 2 AP3M2 | 2 BTBD3 | 2 CASKIN2 | 2 CMTM7 | 2 DENND1A |
| 3 ZBED3 | 2 AP4B1-AS1 | 2 BTC | 2 CASP4 | 2 CNEP1R1 | 2 DES |
| 3 ZBED3-AS1 | 2 AP5Z1 | 2 BTN3A3 | 2 CBX1 | 2 CNIH | 2 DGKG |
| 3 ZBTB11 | 2 APBB1IP | 2 BUB3 | 2 CCDC102A | 2 CNIH3 | 2 DHX15 |
| 3 ZBTB38 | 2 APMAP | 2 C10orf131 | 2 CCDC105 | 2 CNKSR2 | 2 DHX29 |
| 3 ZC3H7A | 2 APOL4 | 2 C10orf54 | 2 CCDC136 | 2 CNKSR3 | 2 DHX57 |
| 3 ZFP1 | 2 APP | 2 C10orf88 | 2 CCDC144C | 2 CNOT6 | 2 DIDO1 |
| 3 ZIM3 | 2 APPL2 | 2 C10orf91 | 2 CCDC151 | 2 CNTFR | 2 DIXDC1 |
| 3 ZNF169 | 2 ARC | 2 C10orf95 | 2 CCDC28B | 2 CNTNAP3 | 2 DLG5 |
| 3 ZNF274 | 2 ARHGAP18 | 2 C12orf10 | 2 CCDC40 | 2 COBL | 2 DLGAP4 |
| 3 ZNF292 | 2 ARHGAP21 | 2 C12orf65 | 2 CCDC42B | 2 COBRA1 | 2 DMPK |
| 3 ZNF37A | 2 ARHGAP29 | 2 C14orf64 | 2 CCDC71 | 2 COCH | 2 DMTF1 |
| 3 ZNF395 | 2 ARHGAP35 | 2 C15orf41 | 2 CCDC85C | 2 COL12A1 | 2 DMXL2 |
| 3 ZNF496 | 2 ARHGDIB | 2 C15orf56 | 2 CCDC90A | 2 COL21A1 | 2 DNAH11 |
| 3 ZNF513 | 2 ARHGEF37 | 2 C16orf55 | 2 CCNA1 | 2 COL3A1 | 2 DNAH17 |
| 3 ZNF554 | 2 ARHGEF7 | 2 C16orf78 | 2 CCNDBP1 | 2 COL8A2 | 2 DNAJB14 |
| 3 ZNF596 | 2 ARL5C | 2 C16orf86 | 2 CCT2 | 2 COMMD10 | 2 DNAJB2 |
| 3 ZNF609 | 2 ARL9 | 2 C17orf107 | 2 CD101 | 2 COMMD3 | 2 DNAJB5 |
| 3 ZNF703 | 2 ARMC4 | 2 C17orf59 | 2 CD163L1 | 2 COMMD6 | 2 DNAJC18 |
| 3 ZNF704 | 2 ARMCX2 | 2 C17orf79 | 2 CD19 | 2 COMP | 2 DNAJC2 |
| 3 ZNF706 | 2 ASB6 | 2 C18orf63 | 2 CD248 | 2 COPG1 | 2 DNM1 |
| 3 ZXDB | 2 ASCC1 | 2 C19orf24 | 2 CD300A | 2 COX6C | 2 DNMBP |
| 2 AAMP | 2 ASCL4 | 2 C19orf57 | 2 CD300LB | 2 CPA3 | 2 DNTTIP1 |
| 2 AASDH | 2 ASNS | 2 C1QTNF1 | 2 CD34 | 2 CPVL | 2 DNTTIP2 |
| 2 ABCA17P | 2 ASPA | 2 C1orf105 | 2 CD3G | 2 CRB1 | 2 DOCK11 |
| 2 ABCA3 | 2 ASXL2 | 2 C1orf151-NBL1 | 2 CD81 | 2 CRB2 | 2 DOCK3 |
| 2 ABL1 | 2 ATAD3A | 2 C1orf172 | 2 CDC42BPG | 2 CREB3L2 | 2 DPM2 |
| 2 ABLIM1 | 2 ATF5 | 2 C1orf213 | 2 CDC42EP5 | 2 CRELD1 | 2 DPP4 |
| 2 ACADM | 2 ATP10D | 2 C1orf229 | 2 CDCP1 | 2 CRHBP | 2 DPYS |
| 2 ACBD4 | 2 ATP12A | 2 C1orf233 | 2 CDH15 | 2 CRISPLD1 | 2 DPYSL2 |
| 2 ACD | 2 ATP13A1 | 2 C1orf53 | 2 CDH4 | 2 CRYBA2 | 2 DPYSL5 |
| 2 ACOT8 | 2 ATP1A1OS | 2 C20orf94 | 2 CDS1 | 2 CRYBA4 | 2 DRG1 |
| 2 ACSF2 | 2 ATP2B2 | 2 C21orf128 | 2 CEACAM4 | 2 CRYBB1 | 2 DSCR3 |
| 2 ACSL6 | 2 ATP4A | 2 C21orf7 | 2 CENPB | 2 CSK | 2 DSCR9 |
| 2 ACTR1A | 2 ATP6AP2 | 2 C22orf32 | 2 CENPN | 2 CSNK2B | 2 DSTN |
| 2 ACTR8 | 2 ATP6V1E2 | 2 C22orf39 | 2 CEP76 | 2 CSPG4 | 2 DTNBP1 |
| 2 DTX3 | 2 FAM26D | 2 GLTSCR2 | 2 HMGA1 | 2 KLHDC9 | 2 LOC100505761 |
| 2 DTYMK | 2 FAM26E | 2 GLYR1 | 2 HMGB3P1 | 2 KLHL12 | 2 LOC100505933 |
| 2 DUS1L | 2 FAM45B | 2 GMCL1 | 2 HMSD | 2 KLHL15 | 2 LOC100507433 |
| 2 DYNLRB2 | 2 FAM47E | 2 GMIP | 2 HN1 | 2 KLHL2 | 2 LOC100507557 |
| 2 DYNLT3 | 2 FAM69A | 2 GNAQ | 2 HNF1B | 2 KLHL33 | 2 LOC100508120 |
| 2 DYRK1B | 2 FAM89A | 2 GNAT1 | 2 HNRNPA0 | 2 KLHL35 | 2 LOC100652739 |
| 2 EARS2 | 2 FARSA | 2 GNG12 | 2 HOMER2 | 2 KLK2 | 2 LOC100652791 |
| 2 EBI3 | 2 FBL | 2 GNMT | 2 HORMAD2 | 2 KLK8 | 2 LOC148709 |
| 2 ECHS1 | 2 FBLN1 | 2 GNPTAB | 2 HOXB-AS5 | 2 KLK9 | 2 LOC149086 |
| 2 EDN3 | 2 FBP1 | 2 GOLGA3 | 2 HOXC9 | 2 KPNA5 | 2 LOC151174 |
| 2 EEF1A2 | 2 FBXL4 | 2 GOLGA7B | 2 HOXD4 | 2 KPNA6 | 2 LOC154449 |
| 2 EFCAB2 | 2 FBXL5 | 2 GOLGA8B | 2 HPS1 | 2 KRBA2 | 2 LOC158435 |
| 2 EFNA4 | 2 FBXO22 | 2 GON4L | 2 HSD17B10 | 2 KREMEN1 | 2 LOC202181 |
| 2 EFNB1 | 2 FBXO34 | 2 GPANK1 | 2 HSD17B13 | 2 KRT15 | 2 LOC254099 |
| 2 EGFL6 | 2 FBXO39 | 2 GPI | 2 HSD17B8 | 2 KRT25 | 2 LOC256880 |
| 2 EHF | 2 FCRL5 | 2 GPR113 | 2 HSD52 | 2 KRTAP5-8 | 2 LOC283335 |
| 2 EIF2AK1 | 2 FEV | 2 GPR125 | 2 HSPA12B | 2 KTN1 | 2 LOC284412 |
| 2 EIF2C4 | 2 FGF9 | 2 GPR144 | 2 HSPA9 | 2 KTN1-AS1 | 2 LOC284889 |
| 2 EIF2S2 | 2 FGFR2 | 2 GPR162 | 2 HTRA4 | 2 KYNU | 2 LOC284950 |
| 2 EIF4A2 | 2 FGGY | 2 GPR19 | 2 HVCN1 | 2 LACE1 | 2 LOC285033 |
| 2 EIF4E3 | 2 FHAD1 | 2 GPRIN3 | 2 IBSP | 2 LAMTOR5 | 2 LOC285484 |
| 2 EIF4H | 2 FILIP1L | 2 GPT | 2 IBTK | 2 LARP4 | 2 LOC286189 |
| 2 ELF3 | 2 FIS1 | 2 GRAMD1B | 2 IGF2 | 2 LARP4B | 2 LOC286190 |
| 2 ELK1 | 2 FLJ12334 | 2 GRAP | 2 IGF2BP3 | 2 LBH | 2 LOC338817 |
| 2 ELL2 | 2 FLJ12825 | 2 GRB14 | 2 IGLON5 | 2 LCE3A | 2 LOC400558 |
| 2 ELMO3 | 2 FLJ14107 | 2 GRB2 | 2 IKBKE | 2 LCLAT1 | 2 LOC400927 |
| 2 ELOVL3 | 2 FLJ37453 | 2 GREB1 | 2 IKZF3 | 2 LCN10 | 2 LOC402160 |
| 2 EMB | 2 FLOT2 | 2 GRID1 | 2 IL1RAP | 2 LEKR1 | 2 LOC440600 |
| 2 EMID2 | 2 FLVCR1 | 2 GRIK1 | 2 IL1RL2 | 2 LENG9 | 2 LOC554223 |
| 2 ENDOD1 | 2 FLVCR1-AS1 | 2 GSC | 2 IL6R | 2 LEP | 2 LOC643387 |
| 2 ENGASE | 2 FLYWCH1 | 2 GTDC2 | 2 IMMT | 2 LEPROTL1 | 2 LOC646626 |
| 2 ENPP6 | 2 FMNL2 | 2 GTF2IRD1P1 | 2 IMPACT | 2 LETM1 | 2 LOC646903 |
| 2 ENPP7 | 2 FN3K | 2 GTF3C5 | 2 INE2 | 2 LGALS9B | 2 LOC728024 |
| 2 ENTPD2 | 2 FN3KRP | 2 GTPBP4 | 2 INHA | 2 LHFPL2 | 2 LOC728558 |
| 2 ENTPD4 | 2 FOLR1 | 2 GUCA1C | 2 INHBA | 2 LIG3 | 2 LOC729059 |
| 2 EOGT | 2 FOS | 2 GUCY1A2 | 2 INHBA-AS1 | 2 LIMA1 | 2 LOC729506 |
| 2 EPC1 | 2 FOSL1 | 2 GUCY1B3 | 2 INIP | 2 LINC00051 | 2 LOC729609 |
| 2 EPHA1 | 2 FOXD4L5 | 2 H2AFY | 2 INS-IGF2 | 2 LINC00092 | 2 LOC729732 |
| 2 EPHA2 | 2 FOXE3 | 2 H2AFY2 | 2 IQCC | 2 LINC00189 | 2 LOC729966 |
| 2 EPHB1 | 2 FOXI1 | 2 HADHA | 2 IRX4 | 2 LINC00307 | 2 LOC84989 |
| 2 EPM2A | 2 FOXS1 | 2 HADHB | 2 ISCA1 | 2 LINC00346 | 2 LOC91450 |
| 2 EPS8L1 | 2 FPR3 | 2 HAUS4 | 2 ITCH | 2 LINC00467 | 2 LOH12CR2 |

TABLE 3-continued

Poor Embryo-Quality Genes, Ranked

| | | | | | |
|---|---|---|---|---|---|
| 2 EPT1 | 2 FRS2 | 2 HAUS7 | 2 ITGB7 | 2 LINC00469 | 2 LOX |
| 2 ERAS | 2 FSCN2 | 2 HCAR3 | 2 ITPA | 2 LINC00488 | 2 LOXL4 |
| 2 ERCC4 | 2 FSTL4 | 2 HCFC1 | 2 JOSD1 | 2 LINC00605 | 2 LPP-AS2 |
| 2 EREG | 2 FUBP1 | 2 HCG4 | 2 JPH2 | 2 LINC00620 | 2 LPXN |
| 2 ERN1 | 2 FUT2 | 2 HCG9 | 2 KANSL1L | 2 LINC00638 | 2 LRP11 |
| 2 ESR2 | 2 FYN | 2 HDLBP | 2 KAT6A | 2 LINC00642 | 2 LRR1 |
| 2 EVI2A | 2 FZD8 | 2 HEATR6 | 2 KCNA5 | 2 LINC00654 | 2 LRRC25 |
| 2 EXOSC10 | 2 GABRR1 | 2 HEATR8 | 2 KCNC4 | 2 LIPE | 2 LRRC30 |
| 2 EXOSC4 | 2 GAL3ST3 | 2 HEATR8-TTC4 | 2 KCNE3 | 2 LIPN | 2 LRRC37A6P |
| 2 EYA2 | 2 GALM | 2 HEPACAM | 2 KCNH1 | 2 LLGL2 | 2 LRRC40 |
| 2 F3 | 2 GALNT8 | 2 HERC1 | 2 KCNJ1 | 2 LMNB1 | 2 LRRC55 |
| 2 FABP6 | 2 GALNTL2 | 2 HES6 | 2 KCNJ3 | 2 LNX1 | 2 LRRC6 |
| 2 FAF2 | 2 GALNTL4 | 2 HEXA | 2 KCNK15 | 2 LNX1-AS1 | 2 LRRCC1 |
| 2 FAM105B | 2 GAS2L1 | 2 HEXA-AS1 | 2 KCNK9 | 2 LOC100128593 | 2 LRRTM4 |
| 2 FAM114A1 | 2 GAS2L3 | 2 HEY1 | 2 KDM3B | 2 LOC100129858 | 2 LTBP1 |
| 2 FAM118A | 2 GBE1 | 2 HINFP | 2 KDM8 | 2 LOC100129924 | 2 LTN1 |
| 2 FAM123B | 2 GBX2 | 2 HIP1R | 2 KIAA0586 | 2 LOC100130238 | 2 LY6G5B |
| 2 FAM124B | 2 GCSAM | 2 HIST1H2AC | 2 KIAA1586 | 2 LOC100130700 | 2 LYN |
| 2 FAM129A | 2 GDF5 | 2 HIST1H2AL | 2 KIAA1609 | 2 LOC100131635 | 2 LYPD3 |
| 2 FAM131C | 2 GDPD2 | 2 HIST1H2BC | 2 KIAA1755 | 2 LOC100134868 | 2 MAB21L3 |
| 2 FAM155B | 2 GET4 | 2 HIST1H2BF | 2 KIF12 | 2 LOC100268168 | 2 MAD2L2 |
| 2 FAM185A | 2 GINS2 | 2 HIST1H2BK | 2 KIF25 | 2 LOC100288974 | 2 MAGI3 |
| 2 FAM186A | 2 GINS3 | 2 HIST1H4I | 2 KIRREL | 2 LOC100289019 | 2 MAMDC4 |
| 2 FAM196A | 2 GIPC2 | 2 HLA-C | 2 KL | 2 LOC100289511 | 2 MAML2 |
| 2 FAM19A3 | 2 GK5 | 2 HLA-DQB1 | 2 KLB | 2 LOC100505666 | 2 MAP2K1 |
| 2 FAM19A5 | 2 GLT8D2 | 2 HLA-DRB6 | 2 KLF16 | 2 LOC100505738 | 2 MAP2K4P1 |
| 2 MAP3K8 | 2 MIR4736 | 2 NEFH | 2 PCDHB10 | 2 PPP1R14A | 2 RD3 |
| 2 MAP6D1 | 2 MIR4749 | 2 NEK4 | 2 PCDHB3 | 2 PPP1R14B | 2 REC8 |
| 2 MAPK1 | 2 MIR4751 | 2 NEK7 | 2 PCNXL3 | 2 PPP1R15A | 2 RFX2 |
| 2 MAPK6 | 2 MIR4761 | 2 NENF | 2 PCYT1B | 2 PPP1R37 | 2 RFX8 |
| 2 MAPK7 | 2 MIR4779 | 2 NEO1 | 2 PCYT2 | 2 PPP1R3F | 2 RGS5 |
| 2 MAPK8IP2 | 2 MIR4786 | 2 NFE2 | 2 PDCD1 | 2 PPP2CB | 2 RHBDF2 |
| 2 MAPRE2 | 2 MIR503 | 2 NHLRC2 | 2 PDCL2 | 2 PPP5C | 2 RHOD |
| 2 MARCH11 | 2 MIR5188 | 2 NHP2L1 | 2 PDE7A | 2 PPP6R1 | 2 RIMS4 |
| 2 MBD6 | 2 MIR548O2 | 2 NINJ1 | 2 PDSS1 | 2 PQLC2 | 2 RLBP1 |
| 2 MBL1P | 2 MIR5702 | 2 NKAIN1 | 2 PDZK1IP1 | 2 PRAF2 | 2 RNASEH2B |
| 2 MBNL2 | 2 MIR608 | 2 NLGN4Y | 2 PEF1 | 2 PRDM11 | 2 RNF126P1 |
| 2 MCMBP | 2 MKRN1 | 2 NME1-NME2 | 2 PELI2 | 2 PRF1 | 2 RNF144A |
| 2 MCTP1 | 2 MKRN3 | 2 NME2 | 2 PEX7 | 2 PRHOXNB | 2 RNF150 |
| 2 MDH2 | 2 MLLT6 | 2 NOL12 | 2 PFDN5 | 2 PRKCE | 2 RNF168 |
| 2 ME3 | 2 MMAB | 2 NPAS2 | 2 PFKFB4 | 2 PRLHR | 2 RNF208 |
| 2 MECOM | 2 MMEL1 | 2 NPDC1 | 2 PFKP | 2 PROP1 | 2 RNF224 |
| 2 MED12 | 2 MMP23B | 2 NPFFR1 | 2 PFN2 | 2 PRPF40B | 2 RNF7 |
| 2 MED22 | 2 MOCOS | 2 NPHS2 | 2 PGF | 2 PRRG1 | 2 ROBO3 |
| 2 MED7 | 2 MORN2 | 2 NPPA-AS1 | 2 PGM3 | 2 PRSS23 | 2 RPL11 |
| 2 MEF2D | 2 MORN4 | 2 NPSR1 | 2 PHF20 | 2 PRSS33 | 2 RPL13A |
| 2 MEIS2 | 2 MOS | 2 NPTXR | 2 PHGR1 | 2 PRTG | 2 RPL13AP5 |
| 2 MEIS3 | 2 MPP5 | 2 NR4A2 | 2 PHOSPHO1 | 2 PRUNE | 2 RPL26L1 |
| 2 MEPCE | 2 MRPL35 | 2 NRBP1 | 2 PHPT1 | 2 PSMB8 | 2 RPL3L |
| 2 METTL24 | 2 MRPL48 | 2 NRN1L | 2 PHYHD1 | 2 PSMC2 | 2 RPL4 |
| 2 METTL2A | 2 MRPL9 | 2 NTN1 | 2 PI4KB | 2 PSMD12 | 2 RPL5 |
| 2 MFHAS1 | 2 MSL3 | 2 NTNG1 | 2 PIAS2 | 2 PSMD8 | 2 RPL7A |
| 2 MFSD3 | 2 MSRB2 | 2 NTSR1 | 2 PIGC | 2 PSMF1 | 2 RPS10 |
| 2 MGAT5B | 2 MT2A | 2 NUAK2 | 2 PIGU | 2 PTCHD2 | 2 RPS10-NUDT3 |
| 2 MGC23284 | 2 MTERF | 2 NUDT21 | 2 PIK3R5 | 2 PTDSS1 | 2 RPS18 |
| 2 MIB2 | 2 MTERFD1 | 2 NUP35 | 2 PKD1L1 | 2 PTGER1 | 2 RPS24 |
| 2 MIR1182 | 2 MTMR6 | 2 NUP62 | 2 PKD1L2 | 2 PTGES3L | 2 RPS8 |
| 2 MIR1184-1 | 2 MUC21 | 2 NUPR1L | 2 PKDCC | 2 PTGES3L- | 2 RPUSD1 |
| 2 MIR1184-2 | 2 MUL1 | 2 NUTF2 | 2 PKMYT1 | AARSD1 | 2 RRM2B |
| 2 MIR1184-3 | 2 MVK | 2 NXF4 | 2 PLA2G2D | 2 PTK2B | 2 RSAD2 |
| 2 MIR1245A | 2 MX1 | 2 O3FAR1 | 2 PLA2G4A | 2 PTOV1 | 2 RTN4RL1 |
| 2 MIR1248 | 2 MYBPHL | 2 OAZ1 | 2 PLAC9 | 2 PTOV1-AS1 | 2 RTP2 |
| 2 MIR1284 | 2 MYCBPAP | 2 OAZ3 | 2 PLBD1 | 2 PTP4A3 | 2 RUNDC1 |
| 2 MIR135A1 | 2 MYH16 | 2 OBSL1 | 2 PLBD2 | 2 PTPN11 | 2 RUNX1-IT1 |
| 2 MIR143 | 2 MYH6 | 2 OCLN | 2 PLCB3 | 2 PTPN2 | 2 RWDD2A |
| 2 MIR181C | 2 MYLK | 2 ODF3L1 | 2 PLCE1 | 2 PTPN22 | 2 RXRB |
| 2 MIR181D | 2 MYO5A | 2 OGFOD1 | 2 PLCH2 | 2 PUS7 | 2 RXRG |
| 2 MIR199B | 2 MYO9A | 2 OGFRL1 | 2 PLEKHN1 | 2 PVR | 2 RYBP |
| 2 MIR200B | 2 MYOCD | 2 OLIG1 | 2 PLK2 | 2 PVRL1 | 2 SAC3D1 |
| 2 MIR205 | 2 MYOZ1 | 2 OR10H2 | 2 PLLP | 2 PYCR2 | 2 SAMD3 |
| 2 MIR205HG | 2 NAA10 | 2 OR2T12 | 2 PLN | 2 PYROXD1 | 2 SASS6 |
| 2 MIR208A | 2 NACA | 2 OXSR1 | 2 PLS3 | 2 R3HDML | 2 SATB1 |
| 2 MIR21 | 2 NADKD1 | 2 OXTR | 2 PLSCR3 | 2 RAB20 | 2 SCAMP4 |
| 2 MIR2276 | 2 NALCN-AS1 | 2 P2RX5 | 2 PLXDC1 | 2 RAB3A | 2 SCAND3 |
| 2 MIR3154 | 2 NANOGNB | 2 P2RX5- | 2 PM20D1 | 2 RAB9B | 2 SCGB1D2 |
| 2 MIR339 | 2 NANOS3 | TAX1BP3 | 2 PMAIP1 | 2 RABEP1 | 2 SCML2 |
| 2 MIR3646 | 2 NARFL | 2 P2RY11 | 2 PMVK | 2 RAD51AP2 | 2 SCOC |
| 2 MIR3675 | 2 NAT8B | 2 P2RY12 | 2 PNLIPRP2 | 2 RAD9B | 2 SCUBE1 |

TABLE 3-continued

Poor Embryo-Quality Genes, Ranked

| | | | | | |
|---|---|---|---|---|---|
| 2 MIR3913-2 | 2 NBL1 | 2 PABPN1L | 2 POC5 | 2 RALGDS | 2 SDAD1 |
| 2 MIR3944 | 2 NBN | 2 PAK6 | 2 POLN | 2 RAPGEF4 | 2 SDC2 |
| 2 MIR424 | 2 NBPF3 | 2 PAMR1 | 2 POLR3A | 2 RARRES2 | 2 SDK2 |
| 2 MIR4258 | 2 NCKAP1L | 2 PANK2 | 2 POLR3B | 2 RASAL2 | 2 SDS |
| 2 MIR4284 | 2 NCOA5 | 2 PAPD7 | 2 PON1 | 2 RASAL2-AS1 | 2 SDSL |
| 2 MIR4316 | 2 NCOA7 | 2 PAQR8 | 2 POU4F1-AS1 | 2 RASEF | 2 SEC11C |
| 2 MIR4458 | 2 NCR3 | 2 PARD6A | 2 POU6F1 | 2 RASGRP4 | 2 SEC22B |
| 2 MIR4479 | 2 NDN | 2 PARD6B | 2 POU6F2 | 2 RASL10B | 2 SEC31A |
| 2 MIR4499 | 2 NDNL2 | 2 PARD6G-AS1 | 2 PPAPDC1B | 2 RBM12B | 2 SEMA3E |
| 2 MIR4508 | 2 NDUFA3 | 2 PARL | 2 PPARG | 2 RBM15 | 2 SEMA4A |
| 2 MIR4513 | 2 NDUFA4 | 2 PAX1 | 2 PPARGC1B | 2 RBM17 | 2 SEMA4G |
| 2 MIR4656 | 2 NDUFB10 | 2 PAX9 | 2 PPBPP2 | 2 RBM26 | 2 SENP8 |
| 2 MIR4667 | 2 NDUFB2 | 2 PBX3 | 2 PPIL1 | 2 RBM28 | 2 SEPT6 |
| 2 MIR4686 | 2 NDUFB2-AS1 | 2 PCBP1 | 2 PPIL2 | 2 RBMS2 | 2 SERGEF |
| 2 MIR4707 | 2 NDUFB8 | 2 PCBP1-AS1 | 2 PPM1E | 2 RBMX | 2 SERINC5 |
| 2 MIR4726 | 2 NDUFS5 | 2 PCDH20 | 2 PPM1J | 2 RCC2 | 2 SERPINF2 |
| 2 SERPING1 | 2 SNHG6 | 2 TARBP1 | 2 TNNT1 | 2 VPS29 | 2 ZNF630 |
| 2 SERTAD4 | 2 SNORA74A | 2 TARP | 2 TNR | 2 VPS45 | 2 ZNF642 |
| 2 SERTAD4-AS1 | 2 SNORA81 | 2 TBC1D12 | 2 TNRC6C | 2 VPS52 | 2 ZNF670- |
| 2 SETMAR | 2 SNORD105B | 2 TBC1D24 | 2 TOM1L2 | 2 VSTM2L | ZNF695 |
| 2 SGK494 | 2 SNORD16 | 2 TBCA | 2 TP53 | 2 VTI1B | 2 ZNF671 |
| 2 SGSH | 2 SNORD18A | 2 TBL1X | 2 TP53I11 | 2 VWA2 | 2 ZNF687 |
| 2 SH3BGRL3 | 2 SNORD18B | 2 TBX1 | 2 TP53I13 | 2 VWC2 | 2 ZNF695 |
| 2 SHC1 | 2 SNORD18C | 2 TBX15 | 2 TPBGL | 2 WBP11P1 | 2 ZNF708 |
| 2 SHISA9 | 2 SNORD2 | 2 TBX3 | 2 TPK1 | 2 WDR5B | 2 ZNF75A |
| 2 SIGLEC17P | 2 SNORD24 | 2 TBX5 | 2 TPST2 | 2 WDR85 | 2 ZNF783 |
| 2 SIRPA | 2 SNORD32A | 2 TBXAS1 | 2 TRA2A | 2 WFDC3 | 2 ZNF790 |
| 2 SIRPB1 | 2 SNORD33 | 2 TCEAL7 | 2 TRAK2 | 2 WFDC5 | 2 ZNF827 |
| 2 SIRT2 | 2 SNORD34 | 2 TCF12 | 2 TRAM1 | 2 WHSC1L1 | 2 ZNRF3 |
| 2 SIRT6 | 2 SNORD35A | 2 TCF7L2 | 2 TRH | 2 WIPF2 | 2 ZPBP2 |
| 2 SIX4 | 2 SNORD36A | 2 TDH | 2 TRIB1 | 2 WISP2 | 2 ZRSR2 |
| 2 SIX5 | 2 SNORD36B | 2 TEFM | 2 TRIB3 | 2 WNT11 | 2 ZSCAN12P1 |
| 2 SKAP2 | 2 SNORD36C | 2 TENC1 | 2 TRIM40 | 2 WNT6 | 2 ZSWIM6 |
| 2 SKIV2L2 | 2 SNORD38A | 2 TESK1 | 2 TRIM44 | 2 WRAP53 | 2 ZUFSP |
| 2 SLC12A5 | 2 SNORD38B | 2 TESPA1 | 2 TRIM67 | 2 WRB | 2 ZWILCH |
| 2 SLC12A8 | 2 SNORD46 | 2 TET2 | 2 TRIM69 | 2 WWP2 | 1 AACSP1 |
| 2 SLC16A12 | 2 SNORD55 | 2 TEX2 | 2 TRIP10 | 2 XKR5 | 1 AANAT |
| 2 SLC19A2 | 2 SNORD61 | 2 TGFBR3 | 2 TRMT10B | 2 XPA | 1 ABCC4 |
| 2 SLC22A1 | 2 SNORD84 | 2 TGIF1 | 2 TRMT13 | 2 XRCC2 | 1 ABCC8 |
| 2 SLC22A23 | 2 SNORD87 | 2 TH | 2 TRPA1 | 2 YAE1D1 | 1 ABHD10 |
| 2 SLC23A3 | 2 SNX21 | 2 THNSL2 | 2 TRPC6 | 2 YAF2 | 1 ABHD12B |
| 2 SLC25A10 | 2 SNX9 | 2 THPO | 2 TSC1 | 2 YIF1A | 1 ABL2 |
| 2 SLC25A34 | 2 SORCS1 | 2 THRA | 2 TSC22D3 | 2 YIPF4 | 1 ACADVL |
| 2 SLC25A51 | 2 SOS1 | 2 THSD4 | 2 TSLP | 2 YPEL2 | 1 ACAP2 |
| 2 SLC26A5 | 2 SPAG5-AS1 | 2 TIGD2 | 2 TSPAN1 | 2 YWHAG | 1 ACOX1 |
| 2 SLC27A5 | 2 SPATA20 | 2 TIGD7 | 2 TSPAN2 | 2 YY1AP1 | 1 ACOX2 |
| 2 SLC29A3 | 2 SPATA22 | 2 TIMM21 | 2 TSPAN4 | 2 ZBED6 | 1 ACP5 |
| 2 SLC2A10 | 2 SPEF1 | 2 TIMM44 | 2 TSPAN6 | 2 ZBP1 | 1 ACPP |
| 2 SLC2A2 | 2 SPHK1 | 2 TIMM9 | 2 TSPEAR | 2 ZBTB40 | 1 ACSL3 |
| 2 SLC30A10 | 2 SPIB | 2 TJP1 | 2 TSPO2 | 2 ZBTB41 | 1 ACSL4 |
| 2 SLC30A5 | 2 SRRM3 | 2 TM4SF5 | 2 TTC12 | 2 ZBTB45 | 1 ACTBL2 |
| 2 SLC34A3 | 2 SRSF11 | 2 TM9SF4 | 2 TTC14 | 2 ZC2HC1C | 1 ACTG1 |
| 2 SLC35D2 | 2 SRSF12 | 2 TMC7 | 2 TTC17 | 2 ZCCHC6 | 1 ACTL6B |
| 2 SLC35E2 | 2 SSC5D | 2 TMED1 | 2 TTC32 | 2 ZCWPW1 | 1 ACTR3 |
| 2 SLC35E4 | 2 ST7 | 2 TMED9 | 2 TUBGCP3 | 2 ZDHHC2 | 1 ACTR3C |
| 2 SLC36A3 | 2 ST7-AS1 | 2 TMEM104 | 2 TXN2 | 2 ZDHHC23 | 1 ADAM12 |
| 2 SLC38A5 | 2 ST7-OT4 | 2 TMEM106C | 2 TXNDC5 | 2 ZDHHC8P1 | 1 ADAMTS13 |
| 2 SLC39A7 | 2 ST8SIA4 | 2 TMEM120B | 2 TXNL4A | 2 ZFP41 | 1 ADAMTS15 |
| 2 SLC41A3 | 2 STARD7 | 2 TMEM132B | 2 U2AF1L4 | 2 ZFP91 | 1 ADCK4 |
| 2 SLC43A1 | 2 STAT5B | 2 TMEM134 | 2 UBC | 2 ZFP91-CNTF | 1 ADM |
| 2 SLC44A3 | 2 STEAP1B | 2 TMEM138 | 2 UBE2G1 | 2 ZFYVE27 | 1 ADM2 |
| 2 SLC46A2 | 2 STK11IP | 2 TMEM145 | 2 UBE2I | 2 ZIK1 | 1 ADPGK-AS1 |
| 2 SLC46A3 | 2 STOX2 | 2 TMEM168 | 2 UBE2N | 2 ZKSCAN1 | 1 AGTPBP1 |
| 2 SLC4A1AP | 2 STRADB | 2 TMEM170A | 2 UBFD1 | 2 ZKSCAN4 | 1 AGTR2 |
| 2 SLC5A7 | 2 STX7 | 2 TMEM178B | 2 UBN1 | 2 ZMAT4 | 1 AIM1L |
| 2 SLC6A15 | 2 STXBP5-AS1 | 2 TMEM179B | 2 UBXN10 | 2 ZNF135 | 1 AIM2 |
| 2 SLC7A10 | 2 STYXL1 | 2 TMEM180 | 2 UGP2 | 2 ZNF137P | 1 AKAP8 |
| 2 SLC7A2 | 2 SULT1C4 | 2 TMEM184B | 2 ULK3 | 2 ZNF140 | 1 AKIRIN1 |
| 2 SLCO2B1 | 2 SULT2B1 | 2 TMEM194B | 2 UNC5CL | 2 ZNF167 | 1 ALAD |
| 2 SMAGP | 2 SUN2 | 2 TMEM2 | 2 UPK3B | 2 ZNF17 | 1 ALAS1 |
| 2 SMARCA1 | 2 SUPT7L | 2 TMEM200A | 2 URGCP | 2 ZNF184 | 1 ALDH3B2 |
| 2 SMARCB1 | 2 SYCE3 | 2 TMEM211 | 2 URGCP- | 2 ZNF202 | 1 ALG1 |
| 2 SMARCD2 | 2 SYNDIG1 | 2 TMEM230 | MRPS24 | 2 ZNF266 | 1 ALK |
| 2 SMG8 | 2 SYNPO2L | 2 TMEM38B | 2 USP6NL | 2 ZNF268 | 1 ALKBH7 |
| 2 SMOC1 | 2 SYT11 | 2 TMEM62 | 2 USP8 | 2 ZNF37BP | 1 ALLC |
| 2 SMPD3 | 2 SYT5 | 2 TMEM71 | 2 UTF1 | 2 ZNF416 | 1 ALPI |
| 2 SMURF2 | 2 SYT6 | 2 TMEM74B | 2 UTS2R | 2 ZNF436 | 1 ALX4 |
| 2 SMYD5 | 2 SYT9 | 2 TMOD2 | 2 VANGL1 | 2 ZNF469 | 1 AMBRA1 |

TABLE 3-continued

Poor Embryo-Quality Genes, Ranked

| | | | | | |
|---|---|---|---|---|---|
| 2 SNAI2 | 2 SZRD1 | 2 TMOD3 | 2 VAX1 | 2 ZNF487P | 1 AMOT |
| 2 SNAI3 | 2 TAAR6 | 2 TMPRSS12 | 2 VCAM1 | 2 ZNF511 | 1 AMTN |
| 2 SNAP91 | 2 TACC2 | 2 TMSB4Y | 2 VCPIP1 | 2 ZNF518B | 1 ANAPC13 |
| 2 SNAR-G1 | 2 TACSTD2 | 2 TNFAIP3 | 2 VMP1 | 2 ZNF540 | 1 ANAPC1P1 |
| 2 SNAR-G2 | 2 TAF6L | 2 TNFSF13B | 2 VNN1 | 2 ZNF594 | 1 ANKDD1A |
| 2 SNHG4 | 2 TANC1 | 2 TNFSF14 | 2 VNN2 | 2 ZNF605 | 1 ANKDD1B |
| 1 ANKRD10 | 1 C2orf81 | 1 CLPTM1 | 1 EDN2 | 1 FOXR2 | 1 HERC2P2 |
| 1 ANKRD20A5P | 1 C3orf18 | 1 CNGA3 | 1 EEF2K | 1 FSCN1 | 1 HFE |
| 1 ANKRD53 | 1 C4orf29 | 1 CNPY1 | 1 EFCAB12 | 1 FSCN3 | 1 HFE2 |
| 1 ANKRD6 | 1 C4orf32 | 1 CNRIP1 | 1 EFNA5 | 1 FSTL5 | 1 HHIP |
| 1 ANKS1B | 1 C5orf27 | 1 CNTN6 | 1 EFNB2 | 1 FTL | 1 HHIP-AS1 |
| 1 ANXA2P2 | 1 C6orf62 | 1 COG1 | 1 EGR4 | 1 FUBP3 | 1 HIST1H1B |
| 1 AP1G2 | 1 C6orf7 | 1 COL13A1 | 1 EIF2C3 | 1 FUCA1 | 1 HIST1H2BN |
| 1 APOL1 | 1 C7orf23 | 1 COL1A2 | 1 ELMOD3 | 1 FUNDC2 | 1 HIST1H4K |
| 1 APOL2 | 1 C7orf49 | 1 COLEC11 | 1 ENAH | 1 FZD7 | 1 HIST2H2BF |
| 1 APRT | 1 C7orf73 | 1 COMTD1 | 1 ENOX1 | 1 GAA | 1 HIST4H4 |
| 1 AQP12B | 1 C8orf37 | 1 COPS2 | 1 EPHX2 | 1 GABBR2 | 1 HMGA1P7 |
| 1 AQPEP | 1 C8orf74 | 1 CPOX | 1 EPSTI1 | 1 GALNT6 | 1 HMGN4 |
| 1 ARF1 | 1 C9orf129 | 1 CR1 | 1 ERP44 | 1 GALNT7 | 1 HNMT |
| 1 ARF5 | 1 CA5BP1 | 1 CRADD | 1 ESYT1 | 1 GALNTL1 | 1 HNRNPUL1 |
| 1 ARFGEF2 | 1 CAB39L | 1 CRIM1 | 1 ETS2 | 1 GAPDHS | 1 HOOK3 |
| 1 ARHGAP23 | 1 CACNA1E | 1 CRY2 | 1 EXT1 | 1 GAS8 | 1 HOTTIP |
| 1 ARHGAP5 | 1 CALML4 | 1 CRYGN | 1 F2RL2 | 1 GATAD2B | 1 HOXA13 |
| 1 ARHGEF15 | 1 CATSPER2P1 | 1 CRYZ | 1 F5 | 1 GBGT1 | 1 HOXA6 |
| 1 ARHGEF3 | 1 CBLN1 | 1 CSF2RB | 1 FAM104B | 1 GBP1 | 1 HOXD10 |
| 1 ARMC1 | 1 CBLN2 | 1 CSTA | 1 FAM108A1 | 1 GCFC1 | 1 HPCAL4 |
| 1 ARMC7 | 1 CC2D1B | 1 CTC1 | 1 FAM123A | 1 GDF15 | 1 HPD |
| 1 ARPP19 | 1 CCDC124 | 1 CTDP1 | 1 FAM129B | 1 GDF7 | 1 HR |
| 1 ARRB1 | 1 CCDC135 | 1 CTSA | 1 FAM135A | 1 GEM | 1 HSD17B1 |
| 1 ARSG | 1 CCDC37 | 1 CX3CL1 | 1 FAM135B | 1 GEMIN2 | 1 HSPA12A |
| 1 ARX | 1 CCDC48 | 1 CXCR4 | 1 FAM157B | 1 GGT5 | 1 HSPA14 |
| 1 ASAH2B | 1 CCDC60 | 1 CXorf48 | 1 FAM162B | 1 GHRHR | 1 HSPBAP1 |
| 1 ASAP1-IT1 | 1 CCDC68 | 1 CYP26A1 | 1 FAM168A | 1 GIGYF2 | 1 HTR5A |
| 1 ASRGL1 | 1 CCDC78 | 1 CYP39A1 | 1 FAM172BP | 1 GIMAP2 | 1 HUWE1 |
| 1 ATF3 | 1 CCL1 | 1 CYP4F8 | 1 FAM195B | 1 GJD4 | 1 IDH2 |
| 1 ATG10 | 1 CCL8 | 1 CYTH2 | 1 FAM198A | 1 GLIS3 | 1 IFI27 |
| 1 ATP2B4 | 1 CCNY | 1 DAP | 1 FAM198B | 1 GLRA4 | 1 IFI44L |
| 1 ATP5C1 | 1 CCR2 | 1 DCDC1 | 1 FAM208B | 1 GMPS | 1 IFI6 |
| 1 ATP5E | 1 CCR7 | 1 DCHS2 | 1 FAM210B | 1 GNB5 | 1 IGF2BP2 |
| 1 ATP6V0E1 | 1 CCR9 | 1 DCLK2 | 1 FAM211A | 1 GPBAR1 | 1 IGFBP6 |
| 1 ATP8B5P | 1 CD109 | 1 DCLRE1C | 1 FAM49A | 1 GPC4 | 1 IGFBP7 |
| 1 AVEN | 1 CD160 | 1 DCUN1D3 | 1 FAM59A | 1 GPC5 | 1 IGFN1 |
| 1 AVIL | 1 CD164 | 1 DDX21 | 1 FAM72A | 1 GPR126 | 1 IGSF21 |
| 1 B3GALNT2 | 1 CD209 | 1 DDX47 | 1 FAM76A | 1 GPR156 | 1 IL12RB1 |
| 1 B3GALT4 | 1 CD86 | 1 DEFB121 | 1 FAM91A1 | 1 GPR180 | 1 IL1A |
| 1 B4GALT2 | 1 CD8B | 1 DEFB133 | 1 FBXL13 | 1 GPR62 | 1 IL1R1 |
| 1 BAIAP2L1 | 1 CD9 | 1 DENND1B | 1 FBXO10 | 1 GPR85 | 1 IL1R2 |
| 1 BBS7 | 1 CDC14A | 1 DEPTOR | 1 FBXO3 | 1 GPR98 | 1 IL32 |
| 1 BCL2 | 1 CDCA4 | 1 DGKE | 1 FBXO31 | 1 GPX5 | 1 ILDR2 |
| 1 BEST2 | 1 CDH3 | 1 DHDH | 1 FBXO36 | 1 GRAMD1C | 1 IMMP2L |
| 1 BLNK | 1 CDK13 | 1 DHX36 | 1 FBXO9 | 1 GRHL3 | 1 INO80C |
| 1 BPHL | 1 CDNF | 1 DIO3 | 1 FBXW9 | 1 GRID2 | 1 INPP5K |
| 1 BYSL | 1 CDX2 | 1 DIRC2 | 1 FEZF1 | 1 GRM1 | 1 INTS3 |
| 1 C12orf43 | 1 CDX4 | 1 DLGAP3 | 1 FEZF1-AS1 | 1 GRM7 | 1 IQCJ-SCHIP1 |
| 1 C12orf70 | 1 CEACAM5 | 1 DLL1 | 1 FFAR3 | 1 GSTA5 | 1 IQGAP2 |
| 1 C14orf23 | 1 CENPA | 1 DNAJC24 | 1 FGA | 1 GSTM3 | 1 ITGA8 |
| 1 C14orf93 | 1 CEP63 | 1 DNM2 | 1 FGF19 | 1 GTF2E2 | 1 ITGB4 |
| 1 C15orf54 | 1 CEP70 | 1 DNMBP-AS1 | 1 FGF20 | 1 GUCA2A | 1 ITPKC |
| 1 C16orf53 | 1 CETP | 1 DPEP1 | 1 FGL1 | 1 GUSBP10 | 1 JMY |
| 1 C16orf71 | 1 CFB | 1 DPF1 | 1 FIBP | 1 GUSBP4 | 1 JPH4 |
| 1 C17orf67 | 1 CFTR | 1 DPRXP4 | 1 FIGN | 1 GYLTL1B | 1 KANSL3 |
| 1 C18orf32 | 1 CHAT | 1 DRD2 | 1 FIP1L1 | 1 H2AFJ | 1 KAT5 |
| 1 C1QL1 | 1 CHCHD5 | 1 DROSHA | 1 FLJ21408 | 1 H3F3C | 1 KBTBD7 |
| 1 C1QTNF9B-AS1 | 1 CHERP | 1 DSC3 | 1 FLJ33065 | 1 HAGHL | 1 KCNA6 |
| 1 C1orf85 | 1 CHL1 | 1 DTNB | 1 FLJ42351 | 1 HAVCR2 | 1 KCNA7 |
| 1 C1orf94 | 1 CHRM1 | 1 DUSP26 | 1 FMOD | 1 HCG27 | 1 KCNJ4 |
| 1 C20orf160 | 1 CHRM4 | 1 DUSP28 | 1 FNBP1 | 1 HCRTR2 | 1 KCNJ9 |
| 1 C20orf166 | 1 CHRNG | 1 E2F3 | 1 FNDC9 | 1 HCST | 1 KCHMB1 |
| 1 C21orf49 | 1 CHST1 | 1 E2F4 | 1 FOLR2 | 1 HEATR5A | 1 KCNQ3 |
| 1 C21orf56 | 1 CHUK | 1 E2F5 | 1 FOXD4 | 1 HECTD3 | 1 KCNS1 |
| 1 C21orf62 | 1 CIB3 | 1 EBF4 | 1 FOXI2 | 1 HECTD4 | 1 KCNS3 |
| 1 C2orf43 | 1 CLDN11 | 1 ECH1 | 1 FOXO1 | 1 HELQ | 1 KEL |
| 1 C2orf69 | 1 CLINT1 | 1 EDC3 | 1 FOXO3 | 1 HEMK1 | 1 KHDC1L |
| | 1 CLN6 | 1 EDIL3 | 1 FOXP3 | 1 HERC2P10 | 1 KIAA0232 |
| 1 KIAA1324 | 1 LOC440028 | 1 MIR550A1 | 1 NUDT8 | 1 POR | 1 RNASEH1 |
| 1 KIAA1430 | 1 LOC440461 | 1 MIR572 | 1 NUPL2 | 1 POSTN | 1 RND3 |
| 1 KIF17 | 1 LOC442459 | 1 MIR802 | 1 NUSAP1 | 1 PPEF2 | 1 RNF112 |
| 1 KIFC3 | 1 LOC554206 | 1 MIR938 | 1 NWD1 | 1 PPIEL | 1 RNF128 |

TABLE 3-continued

Poor Embryo-Quality Genes, Ranked

| | | | | | |
|---|---|---|---|---|---|
| 1 KIN | 1 LOC643802 | 1 MIS18BP1 | 1 NXPH1 | 1 PPP1R12C | 1 RNF135 |
| 1 KITLG | 1 LOC646329 | 1 MITF | 1 ODF3L2 | 1 PPP1R27 | 1 RNF14 |
| 1 KLHL32 | 1 LOC728218 | 1 MKNK2 | 1 OIP5 | 1 PPP1R35 | 1 RNF145 |
| 1 KLRC2 | 1 LOC728730 | 1 MN1 | 1 OIP5-AS1 | 1 PPP1R3C | 1 RNF170 |
| 1 KNTC1 | 1 LOC729852 | 1 MOBP | 1 OPN5 | 1 PPP1R9B | 1 RNF5P1 |
| 1 KPNA4 | 1 LOC730102 | 1 MOG | 1 OPRM1 | 1 PPP2R1A | 1 ROPN1B |
| 1 KRT12 | 1 LOC93622 | 1 MORC2-AS1 | 1 OR1F1 | 1 PPP2R2B | 1 RPA3 |
| 1 KRT23 | 1 LPHN3 | 1 MPP3 | 1 OR2J3 | 1 PPP2R3A | 1 RPL8 |
| 1 KRT73 | 1 LPPR1 | 1 MPZL2 | 1 OR6K2 | 1 PQLC3 | 1 RPN1 |
| 1 KRTAP10-10 | 1 LRP2 | 1 MRAP2 | 1 OR7E2P | 1 PRDM12 | 1 RRAS2 |
| 1 KRTAP10-6 | 1 LRP2BP | 1 MRAS | 1 OSBPL10-AS1 | 1 PRDX6 | 1 RRBP1 |
| 1 KRTAP2-2 | 1 LRPAP1 | 1 MRGPRG | 1 OSGIN1 | 1 PREX1 | 1 RSAD1 |
| 1 KRTAP2-3 | 1 LRRC17 | 1 MRGPRX3 | 1 OTUD7B | 1 PRICKLE2 | 1 RSRC2 |
| 1 KRTAP5-5 | 1 LRRC23 | 1 MRO | 1 P2RY13 | 1 PRICKLE2-AS1 | 1 RXFP3 |
| 1 KY | 1 LRRC52 | 1 MRPL3 | 1 P2RY14 | 1 PRICKLE2-AS2 | 1 SAA1 |
| 1 LAMA3 | 1 LRRC61 | 1 MRPS10 | 1 PACSIN3 | 1 PRICKLE4 | 1 SAMD13 |
| 1 LAMP1 | 1 LRRC8D | 1 MRPS18C | 1 PAK2 | 1 PRKCB | 1 SAMD9L |
| 1 LCN2 | 1 LTV1 | 1 MS4A4A | 1 PANK1 | 1 PRKD1 | 1 SAMM50 |
| 1 LCN6 | 1 LY6D | 1 MSLN | 1 PAPLN | 1 PRPF39 | 1 SAT2 |
| 1 LGALS2 | 1 LYL1 | 1 MSRB3 | 1 PAQR7 | 1 PRR11 | 1 SBSN |
| 1 LGALS4 | 1 LYPD1 | 1 MSX1 | 1 PAX6 | 1 PRR3 | 1 SBSPON |
| 1 LHFP | 1 LYPD5 | 1 MSX2 | 1 PCDH12 | 1 PRRX1 | 1 SCAI |
| 1 LHFPL3-AS2 | 1 LYRM1 | 1 MTA1 | 1 PCED1B-AS1 | 1 PSCA | 1 SCG5 |
| 1 LHX9 | 1 MACC1 | 1 MTG1 | 1 PCK2 | 1 PSEN1 | 1 SCGB2A2 |
| 1 LILRA3 | 1 MAGED1 | 1 MTM1 | 1 PCYOX1L | 1 PSKH1 | 1 SCHIP1 |
| 1 LILRA6 | 1 MAP2K2 | 1 MTMR11 | 1 PDCD10 | 1 PSMB6 | 1 SDHAF1 |
| 1 LILRB5 | 1 MAP2K6 | 1 MTOR | 1 PDIA3 | 1 PSMD13 | 1 SEC14L3 |
| 1 LIMD1 | 1 MAP6 | 1 MVP | 1 PDK2 | 1 PTBP2 | 1 SEC16A |
| 1 LINC00471 | 1 MARCH3 | 1 MYL10 | 1 PDPN | 1 PTGER4 | 1 SEC22C |
| 1 LINC00521 | 1 MARCH4 | 1 MYPOP | 1 PEA15 | 1 PTGFR | 1 SEL1L |
| 1 LINC00617 | 1 MAST3 | 1 MYRIP | 1 PEX13 | 1 PTGR1 | 1 SELO |
| 1 LINC00673 | 1 MATN1 | 1 MYT1 | 1 PEX16 | 1 PTH1R | 1 SELP |
| 1 LINC00675 | 1 MATN1-AS1 | 1 NAALAD2 | 1 PFDN2 | 1 PTPN5 | 1 SEMA4C |
| 1 LINGO2 | 1 MATN2 | 1 NACAD | 1 PFKL | 1 PTPRS | 1 SENP2 |
| 1 LMO7 | 1 MATN3 | 1 NADSYN1 | 1 PGPEP1 | 1 PTPRT | 1 SERINC1 |
| 1 LOC100127888 | 1 MCCD1 | 1 NAGPA | 1 PHF17 | 1 PURA | 1 SERPINI1 |
| 1 LOC100128264 | 1 MCM10 | 1 NAGPA-AS1 | 1 PHF21A | 1 RAB17 | 1 SERTAD3 |
| 1 LOC100131067 | 1 MED13L | 1 NANOS2 | 1 PHGDH | 1 RAB8A | 1 SEZ6 |
| 1 LOC100131138 | 1 MED20 | 1 NARS | 1 PHKG1 | 1 RALB | 1 SF3A3 |
| 1 LOC100131289 | 1 MEF2C | 1 NCAPG2 | 1 PHOX2B | 1 RAMP3 | 1 SF3B4 |
| 1 LOC100132078 | 1 MEIG1 | 1 NCCRP1 | 1 PHYH | 1 RAP1GAP | 1 SF3B5 |
| 1 LOC100272217 | 1 MEOX1 | 1 NDRG1 | 1 PIK3R3 | 1 RARRES3 | 1 SFXN2 |
| 1 LOC100288911 | 1 METTL20 | 1 NECAP2 | 1 PIM2 | 1 RASD1 | 1 SGK2 |
| 1 LOC100335030 | 1 METTL3 | 1 NEURL2 | 1 PINK1 | 1 RASD2 | 1 SGPP2 |
| 1 LOC100422737 | 1 MFSD8 | 1 NF2 | 1 PITPNB | 1 RASSF4 | 1 SH2D1A |
| 1 LOC100505876 | 1 MGP | 1 NFASC | 1 PIWIL4 | 1 RBBP9 | 1 SH3KBP1 |
| 1 LOC100506023 | 1 MICAL3 | 1 NFIB | 1 PKIB | 1 RC3H2 | 1 SHC2 |
| 1 LOC100506054 | 1 MID1IP1 | 1 NFKBIA | 1 PKM | 1 RCAN3 | 1 SHC4 |
| 1 LOC100506388 | 1 MIOX | 1 NFKBID | 1 PLA2G2E | 1 RCVRN | 1 SHISA5 |
| 1 LOC100506804 | 1 MIPEP | 1 NHLH2 | 1 PLA2G4C | 1 RDM1 | 1 SHISA7 |
| 1 LOC100506810 | 1 MIR1207 | 1 NIT1 | 1 PLAT | 1 RDX | 1 SIAH1 |
| 1 LOC100616530 | 1 MIR1247 | 1 NKAIN2 | 1 PLAUR | 1 REEP3 | 1 SIK1 |
| 1 LOC146513 | 1 MIR1250 | 1 NKPD1 | 1 PLEKHG4 | 1 REN | 1 SIRPG |
| 1 LOC150622 | 1 MIR1276 | 1 NLGN3 | 1 PLSCR4 | 1 RESP18 | 1 SIRT3 |
| 1 LOC221122 | 1 MIR133A2 | 1 NMNAT2 | 1 PLXNA4 | 1 RETSAT | 1 SIX3 |
| 1 LOC254559 | 1 MIR135B | 1 NR2F2 | 1 PMS2P4 | 1 REXO4 | 1 SKIDA1 |
| 1 LOC338963 | 1 MIR196A2 | 1 NR4A1 | 1 PNMT | 1 RFC3 | 1 SLC10A3 |
| 1 LOC387647 | 1 MIR4269 | 1 NRARP | 1 PNPO | 1 RFTN2 | 1 SLC13A3 |
| 1 LOC387895 | 1 MIR4500HG | 1 NRCAM | 1 POF1B | 1 RGCC | 1 SLC17A3 |
| 1 LOC389906 | 1 MIR450A2 | 1 NRG2 | 1 POGLUT1 | 1 RHBDD2 | 1 SLC20A1 |
| 1 LOC399708 | 1 MIR4632 | 1 NRK | 1 POLA1 | 1 RHOA | 1 SLC25A27 |
| 1 LOC400456 | 1 MIR4651 | 1 NRM | 1 POLR2I | 1 RHOJ | 1 SLC25A39 |
| 1 LOC401127 | 1 MIR4655 | 1 NTRK1 | 1 POLR3H | 1 RIMKLA | 1 SLC25A5 |
| 1 LOC439990 | 1 MIR548AE2 | 1 NUDT13 | 1 POM121L10P | 1 RNASE7 | 1 SLC25A5-AS1 |
| 1 SLC26A7 | 1 SPATA21 | 1 TBC1D8 | 1 TNNI3K | 1 TUBA4A | 1 WDR45L |
| 1 SLC2A8 | 1 SPATS2 | 1 TBL1XR1 | 1 TNRC6B | 1 TUBA4B | 1 WDR54 |
| 1 SLC2A9 | 1 SPDEF | 1 TBL2 | 1 TOMM6 | 1 TUBB2B | 1 WDR72 |
| 1 SLC35B1 | 1 SPG11 | 1 TBX10 | 1 TOP3B | 1 TULP1 | 1 WNK4 |
| 1 SLC35G2 | 1 SPICE1 | 1 TBX4 | 1 TOR2A | 1 TXLNG | 1 WNT7B |
| 1 SLC37A3 | 1 SPINT1 | 1 TCAIM | 1 TOX2 | 1 TXNRD1 | 1 XIRP1 |
| 1 SLC38A3 | 1 SPRY4 | 1 TCAP | 1 TOX3 | 1 TYW3 | 1 ZBTB6 |
| 1 SLC38A4 | 1 SPTLC3 | 1 TCTA | 1 TP53I3 | 1 U2AF1 | 1 ZCCHC8 |
| 1 SLC45A3 | 1 SS18L2 | 1 TEX33 | 1 TPD52 | 1 UBE2C | 1 ZCCHC9 |
| 1 SLC45A4 | 1 SSRP1 | 1 TFAP2D | 1 TPGSI | 1 UBE2F | 1 ZDHHC13 |
| 1 SLC4A4 | 1 SSX4 | 1 THOC2 | 1 TPI1 | 1 UBE2F-SCLY | 1 ZDHHC20 |
| 1 SLC4A8 | 1 SSX4B | 1 THOC7 | 1 TPPP | 1 UBE3B | 1 ZNF107 |

TABLE 3-continued

Poor Embryo-Quality Genes, Ranked

| | | | | | |
|---|---|---|---|---|---|
| 1 SLC4A9 | 1 ST6GALNAC1 | 1 THSD7B | 1 TPRX1 | 1 UBL4A | 1 ZNF385D |
| 1 SLC6A1 | 1 STAG3L4 | 1 TIMM17A | 1 TRABD2B | 1 UBR5 | 1 ZNF394 |
| 1 SLC6A1-AS1 | 1 STAMBPL1 | 1 TM4SF1 | 1 TRAIP | 1 UCA1 | 1 ZNF418 |
| 1 SLC6A18 | 1 STAP1 | 1 TMEM114 | 1 TRAK1 | 1 UGT2B4 | 1 ZNF445 |
| 1 SLC6A4 | 1 STARD4 | 1 TMEM132E | 1 TREX2 | 1 UNKL | 1 ZNF485 |
| 1 SLCO2A1 | 1 STARD4-AS1 | 1 TMEM170B | 1 TRIL | 1 UROD | 1 ZNF502 |
| 1 SLCO4C1 | 1 STK25 | 1 TMEM201 | 1 TRIM22 | 1 USH1C | 1 ZNF541 |
| 1 SLFN13 | 1 STK40 | 1 TMEM229A | 1 TRIM31 | 1 USP21 | 1 ZNF569 |
| 1 SMPDL3B | 1 STXBP6 | 1 TMEM240 | 1 TRIM34 | 1 USP4 | 1 ZNF570 |
| 1 SNAP47 | 1 STYK1 | 1 TMEM30A | 1 TRIM4 | 1 USP50 | 1 ZNF585B |
| 1 SNAR-F | 1 SULT1E1 | 1 TMEM31 | 1 TRIM59 | 1 UVSSA | 1 ZNF608 |
| 1 SNCAIP | 1 SUZ12 | 1 TMEM33 | 1 TRIM6-TRIM34 | 1 VAMP5 | 1 ZNF619 |
| 1 SNORD53 | 1 SVEP1 | 1 TMEM39A | 1 TRIM8 | 1 VARS | 1 ZNF740 |
| 1 SNTB1 | 1 SYNE3 | 1 TMEM41A | 1 TRMU | 1 VASH2 | 1 ZNF776 |
| 1 SNUPN | 1 SYT12 | 1 TMEM65 | 1 TRO | 1 VMA21 | 1 ZNRF2P2 |
| 1 SNX27 | 1 SYT7 | 1 TMEM67 | 1 TRPC4AP | 1 VPS53 | 1 ZSCAN5B |
| 1 SOD3 | 1 TACC3 | 1 TMEM98 | 1 TSPAN18 | 1 VSX1 | 1 ZXDA |
| 1 SORT1 | 1 TAF11 | 1 TMPRSS2 | 1 TSTD1 | 1 VTRNA1-2 | |
| 1 SOWAHA | 1 TAF13 | 1 TMX1 | 1 TTBK1 | 1 VWA5B1 | |
| 1 SOX17 | 1 TAF1B | 1 TNFAIP8L2 | 1 TTC30A | 1 WASF2 | |
| 1 SPAG4 | 1 TAPBPL | 1 TNFRSF10C | 1 TTF1 | 1 WDFY2 | |
| 1 SPATA12 | 1 TBC1D2 | 1 TNKS1BP1 | 1 TTTY14 | 1 WDR34 | |

EXAMPLES

To further illustrate these embodiments, the following examples are provided. These examples are not intended to limit the scope of the claimed invention, which should be determined solely on the basis of the attached claims.

Example 1

Semen samples were from the University of Utah tissue bank following informed consent according to IRB-approved protocols. Individuals were asked to adhere to general semen collection instructions, which included 2-5 days of abstinence prior to collection. Collected samples were mixed in a 1:1 ratio with Test Yolk Buffer (Irvine Scientific, Santa Ana, Calif.) and stored in liquid nitrogen prior to utilization herein. Control samples (n=54) were collected from normozoospermic men with proven fertility. The majority of control samples were composed of whole ejaculate (n=36), while 12 were prepared by density gradient centrifugation prior to cryopreservation, and the preparation was not recorded for 6 of the samples. In vitro fertilization (IVF) samples were selected from 292 IVF patients based on embryo quality and pregnancy outcome (see Table 4).

TABLE 4

General composition of the study groups including semen parameters and IVF embryo quality.

| | Good embryos, pregnant | | Poor embryos, not pregnant | | Poor embryos, pregnant | | |
|---|---|---|---|---|---|---|---|
| | Mean | Std. Dev. | Mean | Std. Dev. | Mean | Std. Dev. | ANOVA P |
| Male age | 33.08 | 5.97 | 32.98 | 4.29 | 33.15 | 5.03 | 0.9913 |
| Sperm concentration (M/ml) | 58.58 | 62.78 | 69.31 | 77.13 | 76.26 | 71.60 | 0.4527 |
| Progressively motile sperm (%) | 45.00 | 20.15 | 42.64 | 18.29 | 43.44 | 24.86 | 0.8867 |
| Female age | 30.93 | 4.52 | 32.60 | 5.12 | 30.98 | 4.51 | 0.242 |
| # eggs retrieved | 14.07 | 5.91 | 10.47 | 4.13 | 12.98 | 4.72 | 0.0103 |
| # MII eggs | 12.09 | 5.15 | 8.87 | 3.89 | 11.29 | 3.83 | 0.0073 |
| # eggs fertilized normally | 10.74 | 4.82 | 7.23 | 3.33 | 9.26 | 4.00 | 0.0019 |
| # embryos cryopreserved | 4.21 | 3.10 | 0.26 | 1.16 | 0.81 | 1.55 | <0.0001 |
| % fertilized eggs ≥ level 2-6-cell on day 3 | 0.73 | 0.23 | 0.37 | 0.30 | 0.45 | 0.30 | <0.0001 |
| % fertilized eggs ≥ level 2-early blast on day 5/6 | 0.44 | 0.18 | 0.07 | 0.09 | 0.13 | 0.15 | <0.0001 |
| # embryos transferred | 2.04 | 0.55 | 2.17 | 0.80 | 2.34 | 0.53 | 0.0596 |

Couples presenting with moderate to severe female factor infertility, including advanced maternal age and severe endometriosis or polycystic ovarian syndrome, were excluded from the study. A total of 55 patients were selected based on a high blastulation rate and confirmed pregnancy. Seventy-two patients were selected that displayed generally poor embryogenesis. Of these, 42 achieved a pregnancy, and 30 did not. A separate experiment was performed on a subset of the samples from IVF patients. For samples that contained >5×10$^6$ progressively motile sperm (n=44), DNA methylation was assessed on the whole ejaculate, and separately a portion of the sample was purified using a 45%/90% discontinuous Isolate gradient, and the 90% fraction was also subjected to methylation analysis.

Table 5 illustrates the frequency of male factor infertility (defined as being below the WHO threshold in at least one of the semen parameters), female factor infertility, the presence of both male and female factors, and the designation of idiopathic infertility among both partners. Also displayed are the natures of the various mild female factors within each group of IVF patients. The frequencies of all factors are statistically similar between groups (p>0.05 by chi-squared analysis).

TABLE 5

Frequency of male and mild female factors in 127 IVF patient-couples tested (no significant differences were observed between groups).

| Factor | Good embryogenesis, positive pregnancy (n = 53) | Poor embryogenesis, negative pregnancy (n = 31) | Poor embryogenesis, positive pregnancy (n = 42) |
|---|---|---|---|
| Male Factor Only | 15 | 12 | 14 |
| Female Factor Only | 16 | 13 | 17 |
| Male & Female Factor | 16 | 3 | 6 |
| Idiopathic (Unexplained) | 6 | 3 | 5 |
| Endometriosis | 10 | 3 | 10 |
| Diminished Ovarian Reserve | 2 | 5 | 3 |
| Polycystic Ovary Syndrome | 8 | 3 | 3 |

Example 2

Sperm samples were thawed simultaneously and were subjected to a column-based DNA extraction protocol with sperm-specific modification to the DNeasy kit (Qiagen, Valencia, Calif.). Prior to DNA extraction, somatic cell lysis was performed by incubation in somatic cell lysis buffer (0.1% SDS, 0.5% Triton X-100 in DEPC $H_2O$) for 20 minutes on ice to eliminate white blood cell contamination. Next, somatic cell lysis sperm were pelleted, and a visual inspection of each sample was performed to ensure the absence of all potentially contaminating cells before proceeding. Extracted sperm DNA was bisulfite converted with EZ-96 DNA Methylation-Gold kit (Zymo Research, Irvine, Calif.) according to the manufacturer's recommendations specifically for use with array platforms. Converted DNA was then delivered to the University of Utah Genomics Core Facility and hybridized to Infinium HumanMethylation450 BeadChip microarrays (Illumina) and analyzed according to Illumina protocols.

Example 3

Following the hybridization protocol, as discussed above, arrays were scanned and β-values were generated for each CpG by using the minfi package (see Aryee M J et al. Bioinformatics. 2014; 30(10):1363-9, which is incorporated by reference herein in its entirety) to extract methylation levels (β-values), which were adjusted using SWAN normalization (see Maksimovic J et al. Genome biology. 2012; 13(6):R44, which is incorporated by reference herein in its entirety). Statistical comparisons were made between: 1) all patients versus controls; and 2) IVF patients with good embryogenesis versus patients with poor embryogenesis. Hierarchical clustering was applied using Euclidean distance between methylation profiles. For the construction of discriminative models to differentiate IVF patient samples from fertile donor samples, and good from poor embryo-quality samples, two types of features were explored to describe each sample: the Euclidean distance between the sample and all other samples in the training set, and a subset of the individual CpG methylation values for each sample. In the latter case, to select the subset, the 500 most discriminative loci were first identified using a Wilcoxon rank sum test (i.e., the 500 loci with the lowest β-values).

All models were constructed (including feature selection steps) and evaluated using ten-fold cross validation. Briefly, the samples are split into 10 stratified folds (10 disjoint sets where the proportion of factor levels in each set approximates, as closely as possible, the proportion in the full dataset). Ten rounds of testing are conducted where, for each round, one of the ten folds is held out of the complete dataset as testing data and the remaining nine folds are used to train the model. After model training is complete, the held-out testing data is classified, and the number of true/false positives and true/false negatives is recorded. This is repeated for all ten folds of the data, such that every sample is tested (classified) exactly once, and every sample is unknown to the model that classifies it.

For GO analysis, genes were ranked by the number of differentially methylated CpGs (p<0.05, Wilcoxon rank sum test). For grouping genes into differentially methylated and not differentially methylated sets, individual p-values were combined for the CpGs within the promoter region (+/−5 kb) of each gene using Stouffer's method (see Stouffer S A et al. Adjustment during Army Life. Princeton: Princeton University Press; 1949, which is incorporated by reference herein in its entirety). Unless otherwise stated, all p-values are corrected for multiple hypothesis testing using Benjamini and Hochberg's method (see Benjamini Y and Hochberg Y. Journal of the Royal Statistical Society, Series B. 1995; 57(1):289-300, which is incorporated by reference herein in its entirety).

Example 4

To establish a baseline for comparison, two non-informative models were used that make no use of the features in each sample: ZeroR and Random. The first of these, ZeroR, always predicts the majority class when classifying samples (the class which appears most often in the training data). The second, Random, assigns a class to each sample based on a Bernoulli trial with success probability of 0.5.

Example 5

For classifying samples based on Euclidean distance to other samples, a decision stump classifier was used. Briefly, this is a rule of the form 'if distance is greater than X, classify the sample as class A else classify it as class B,' where A and B depend on the comparison (for example, good and poor embryo quality). The value of X is learned by exhaustive enumeration of discriminative thresholds, and the one with the lowest relative cost is selected. The trade-off between sensitivity and specificity was modulated in this learning process by adjusting the relative cost of false positives to false negatives.

Example 6

For classifying samples based on the p-values from a subset of selected CpGs, the decision stump classifier, as described above, was used. More complex models and learning algorithms are also explored: a support vector machine (see Platt J C. Sequential Minimal Optimization: A Fast Algorithm for Training Support Vector Machines.

Advances in kernel methods—support vector learning. 1998, which is incorporated by reference herein in its entirety), a nearest neighbor classifier, a decision tree, and naïve Bayes; WEKA (see Hall M et al. The WEKA Data Mining Software: An Update. SIGKDD Explorations. 2009; 11(1), which is incorporated by reference herein in its entirety) was used for its implementation of these, run with default parameters unless specified. Further, a number of these were augmented with adaptive boosting (AdaBoost), with bootstrap aggregating (bagging), and by weighting training data to effect a cost-sensitive training scheme (always favoring high specificity).

Example 7

A hierarchical clustering of all 163 neat samples was performed, based on the methylation level of all 485,000+ CpGs interrogated by the array for each sample. This clustering (see FIG. 1A) revealed an out-group composed exclusively of IVF-patient samples (labeled in FIG. 1A as the patient-only cluster), which contained within it a subgroup almost exclusively composed of samples which lead to poor embryo quality (labeled in FIG. 1A as the poor embryo-quality cluster). However, the majority of IVF-patient samples and poor embryo-quality samples were distributed evenly amongst fertile donor samples and good embryo-quality samples outside of this group.

Figures 1B, 1C:
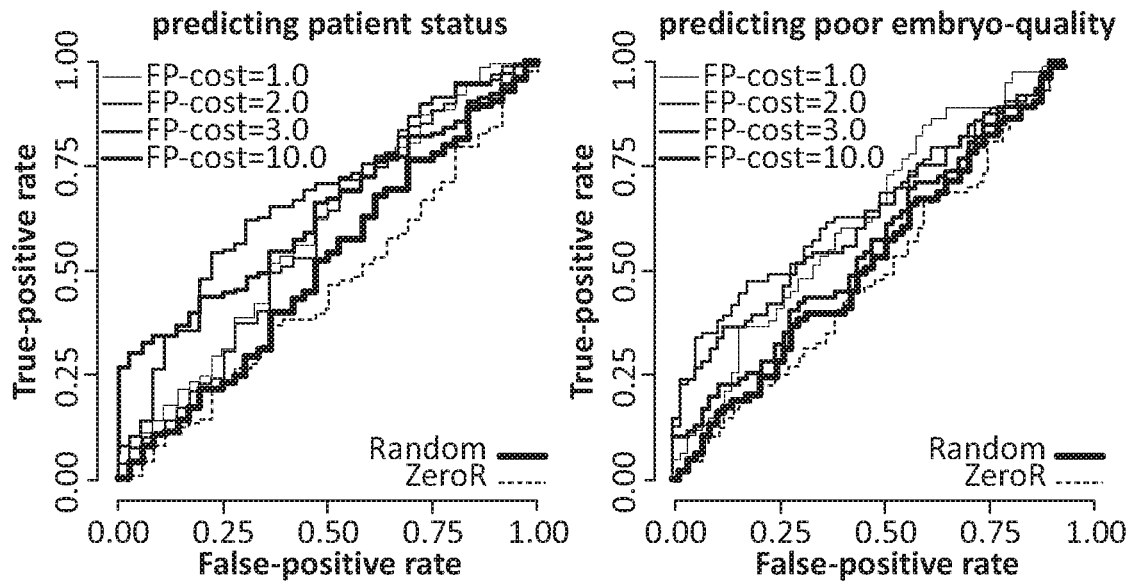
FIG. 1B depicts the ROC curve for prediction of patient status (in vitro fertilization (IVF) patient or fertile donor, left panel). Classification was performed by building a one-level decision tree based on Euclidean distance between samples. Training and testing were performed using ten-fold cross-validation. The right panel depicts the ROC curve for prediction of embryo quality. In both cases, high confidence predictions (bottom right of plots) can have a high probability of being correct.
FIG. 1C depicts classification statistics for the ROC curves of FIG. 1B. Samples were predicted as positive (i.e., a patient sample or a poor embryo-quality sample) when the probability exceeded 50%. In both cases, high specificity and positive predictive value can be achieved.

Without being bound by theory, the above results suggest two modalities of infertility: large-scale methylation aberrations that are identifiable at the full-genome resolution employed herein, and subtler methylation changes that might affect a smaller number of critical loci. To assess the predictive power of the genome-scale methylation differences observed from the clustering, a simple decision-stump classifier was trained (as described above) using ten-fold cross-validation wherein each sample was described by the Euclidean distance to each of the samples in the training set. The false positive cost of the training algorithm was adjusted (as described above) from 1 (i.e., a false positive was considered as costly as a false negative when training) to 10 (i.e., a false positive was considered 10 times more costly than a false negative when training). It was observed that with high false-positive costs, the classifier could achieve close to perfect specificity while identifying between a quarter and a third of the IVF-patient or poor embryo-quality samples (see FIGS. 1B and 1C).

Figure 2A:
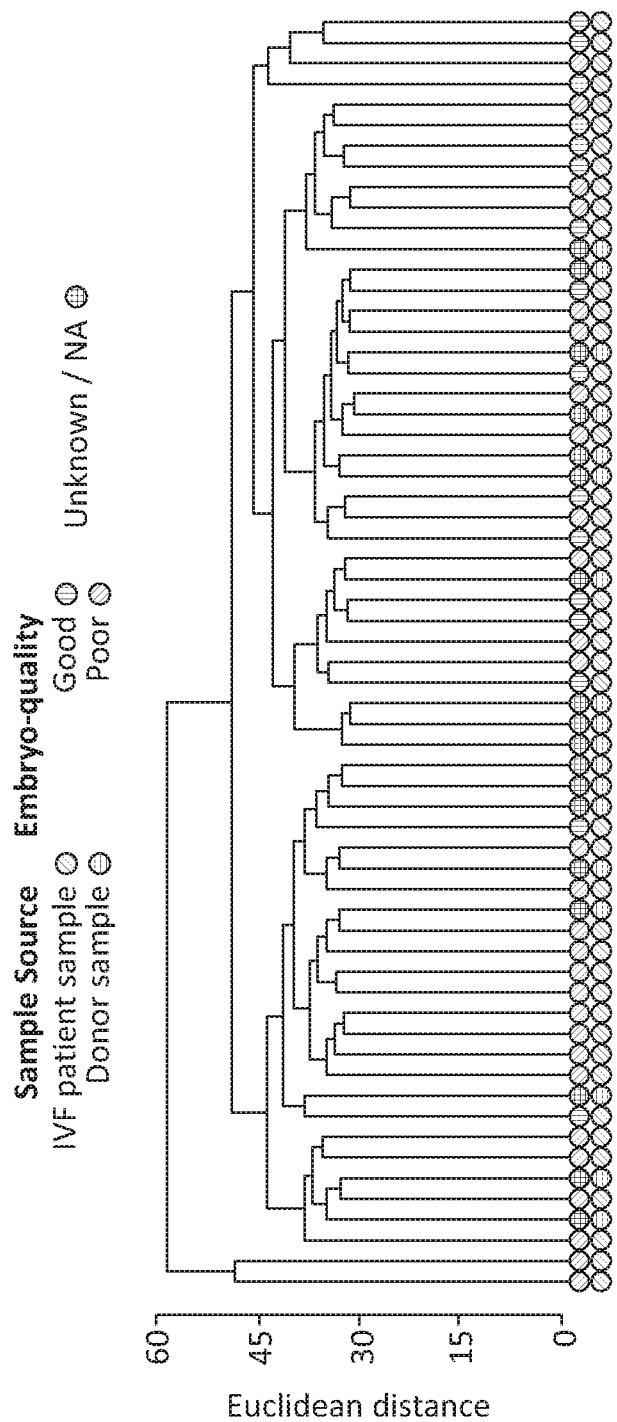
FIG. 2A depicts hierarchical clustering of 62 gradient-purified sperm samples based on global methylation profile. Two clear clusters are apparent, one of which contains almost exclusively poor embryo-quality samples.
Figures 2B, 2C:
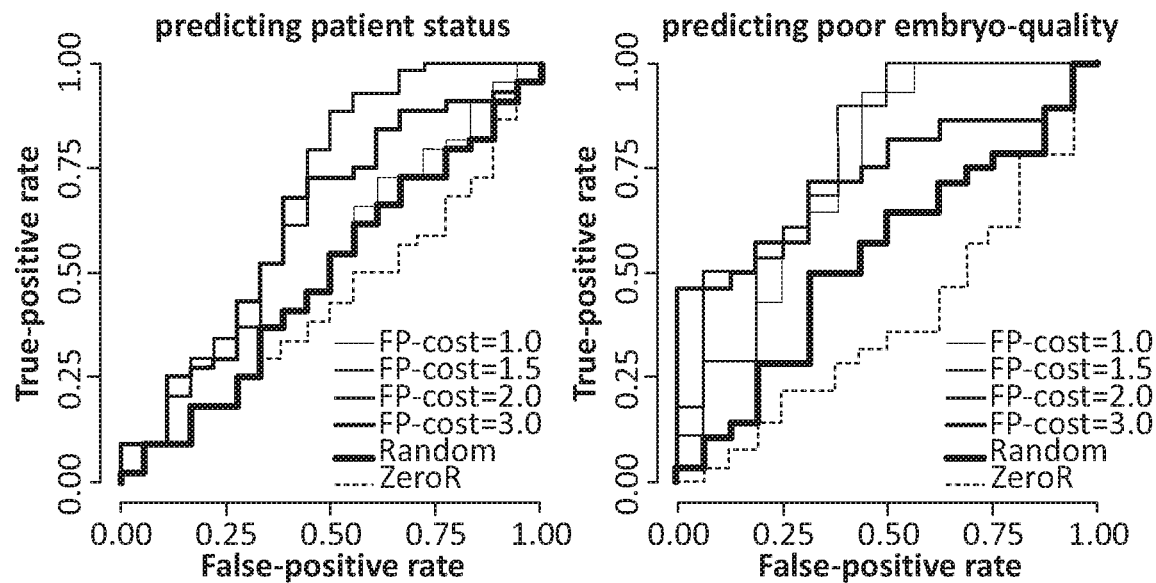
FIG. 2B depicts the ROC curve for prediction of patient status (IVF patient or fertile donor) from the 62 gradient purified samples (left panel). Classification was performed by building a one-level decision tree based on Euclidean distance between samples. Training and testing were performed using ten-fold cross-validation. The right panel depicts the ROC curve for prediction of embryo quality from the subset of 45 samples for which this information is known. Although classification of patient status is degraded from that with unpurified samples, the ability to predict poor embryo-quality is markedly improved.
FIG. 2C depicts classification statistics for the ROC curves of FIG. 2B. Samples were predicted as positive (i.e., a patient sample or a poor embryo-quality sample) when the probability exceeded 50%. In the case of predicting poor embryo-quality, very high specificity and positive predictive value can be achieved.

The above-described analysis was replicated on the density gradient-purified samples, and an even more stark separation of good and poor embryo-quality samples was observed, although little discernible separation of IVF-patient and donor samples was observed, possibly due to the small number of purified donor samples (see FIG. 2A). This was reflected in the classification results from these samples, which showed even greater ability to identify poor embryo-quality samples, with just under half of the poor embryo-quality patients recovered with zero false positives, while the ability to differentiate between IVF-patient and donor samples was largely eliminated (see FIGS. 2B and 2C).

Example 8

Figure 3A:
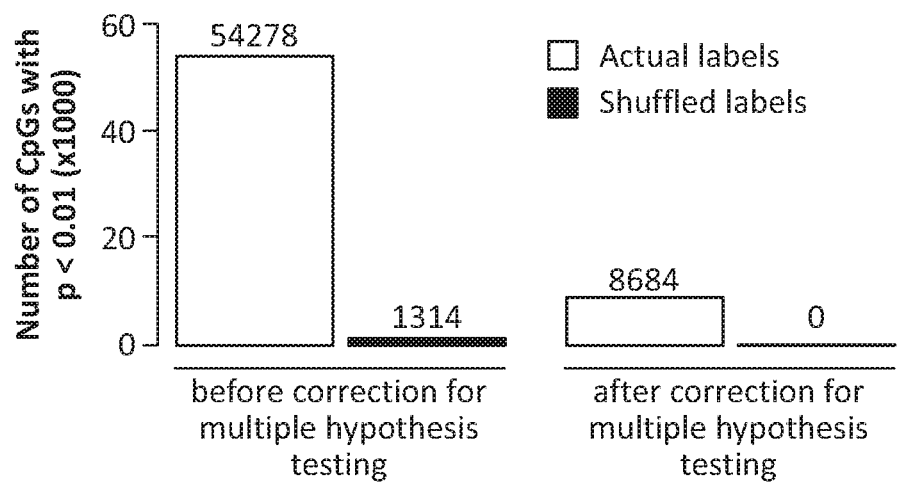
FIG. 3A depicts the number of differentially methylated CpGs between unpurified donor and IVF patient samples before and after correction for multiple hypothesis testing using both the actual donor/patient labels and randomly shuffled donor/patient labels as a control.
Figure 3B:
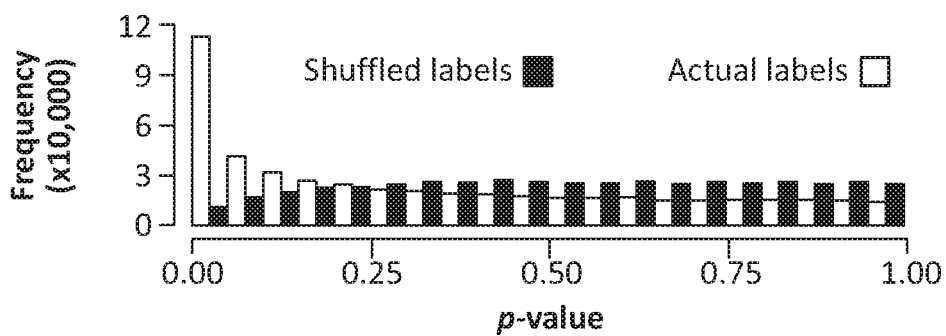
FIG. 3B depicts the distribution of p-values for all profiled CpGs from tests of differential methylation between donor and IVF-patient samples using both actual labels and randomly shuffled donor/patient labels as a control.
Figure 3C:
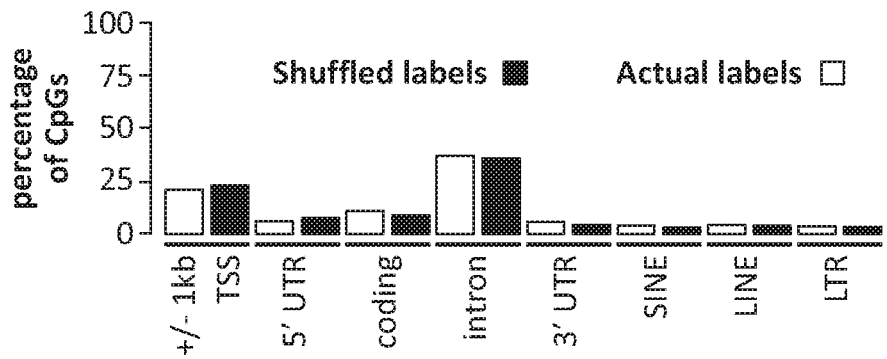
FIG. 3C depicts the proportion of differentially methylated CpGs (before correction for multiple hypothesis testing) that fall within regions annotated as shown, for both actual donor/IVF-patient labels and randomly permuted labels.
Figure 3D:
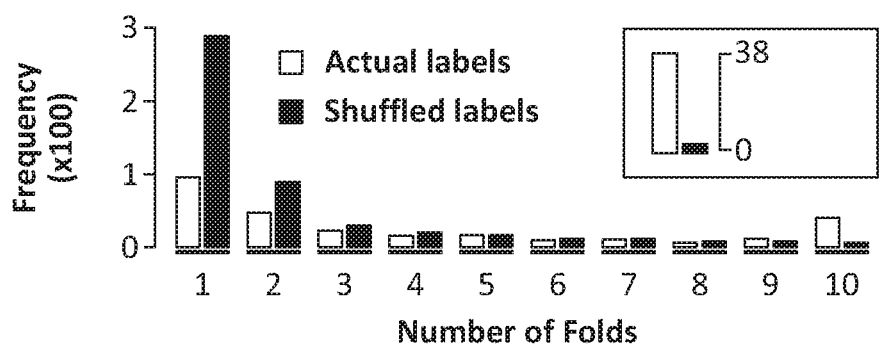
FIG. 3D depicts a histogram showing the number of CpGs that were contained in the top 100 most differentially methylated CpGs identified in only 1 fold, exactly 2 folds, exactly 3 folds, and so on. The inset depicts the number of CpGs contained in all 10 folds for both real labels and permuted labels in higher detail. Samples are split into 10 stratified equally-sized groups. A fold is formed by taking 9 of these groups and leaving one group out (allowing 10 separate analyses). For each fold, the samples in the 9 retained groups are used to identify differentially methylated CpGs using both real donor/IVF-patient labels and randomly permuted labels as a control.

To assess whether differences in methylation between groups were concentrated at particular individual CpGs or regions, differentially methylated positions (DMPs) were called using a Wilcoxon rank-sum test. As a control, this was repeated with randomly shuffled sample labels. The number of differentially methylated CpGs identified between IVF-patient samples and donor samples (here neat samples were concentrated on, as these generally showed the greater signal), both before and after correction for multiple hypothesis testing is shown in FIG. 3A. The histogram of p-values from all CpGs is displayed in FIG. 3B, and shows a sharp spike in significant p-values for actual labels, with a relatively flat distribution for the shuffled control. The significant CpGs identified when using real labels showed no discernible bias towards particular genomic regions when compared to those from the randomly shuffled control (see FIG. 3C).

Figure 3E:
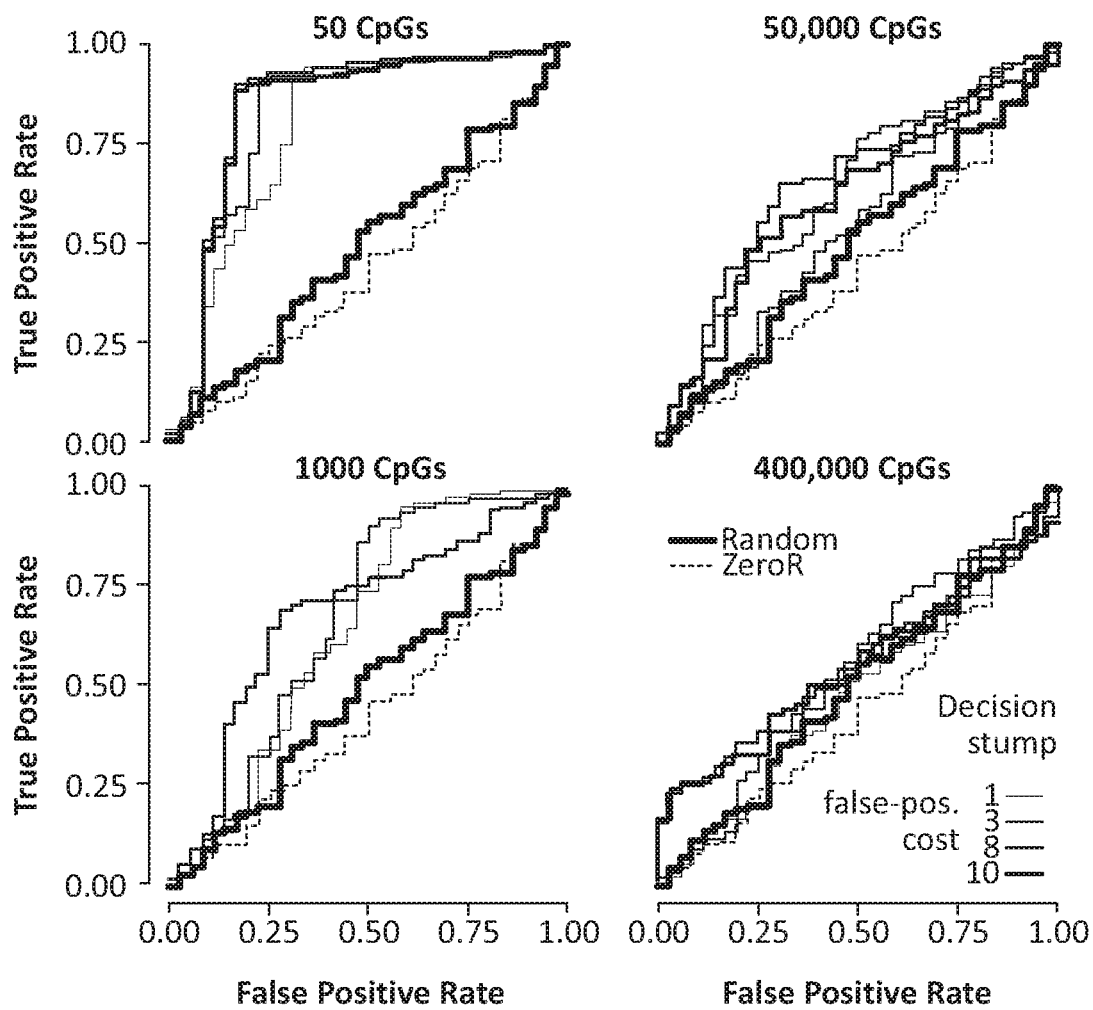
FIG. 3E depicts ROC curves for classifiers, analogous to those of FIGS. 2A-2C, that were trained using a subset of the top 50, 1,000, 50,000, and 400,000 most significantly differentially-methylated CpGs.
Figure 3F:
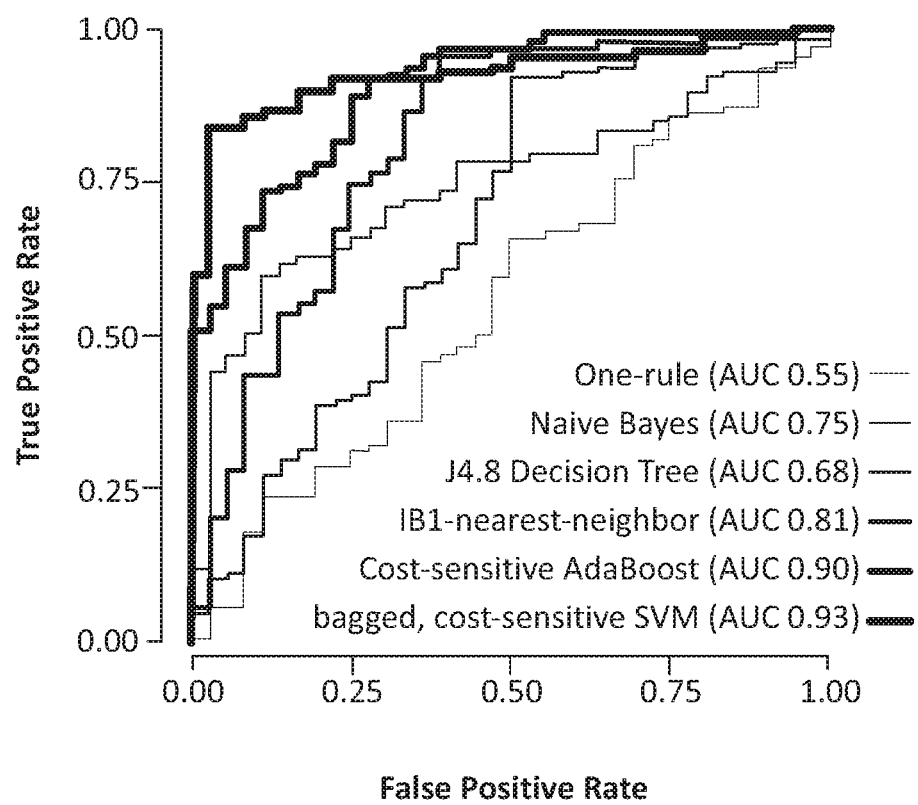
FIG. 3F depicts ROC curves for classifiers from a range of classifiers that were trained on the top 500 most differentially methylated CpGs.
Figure 6A:
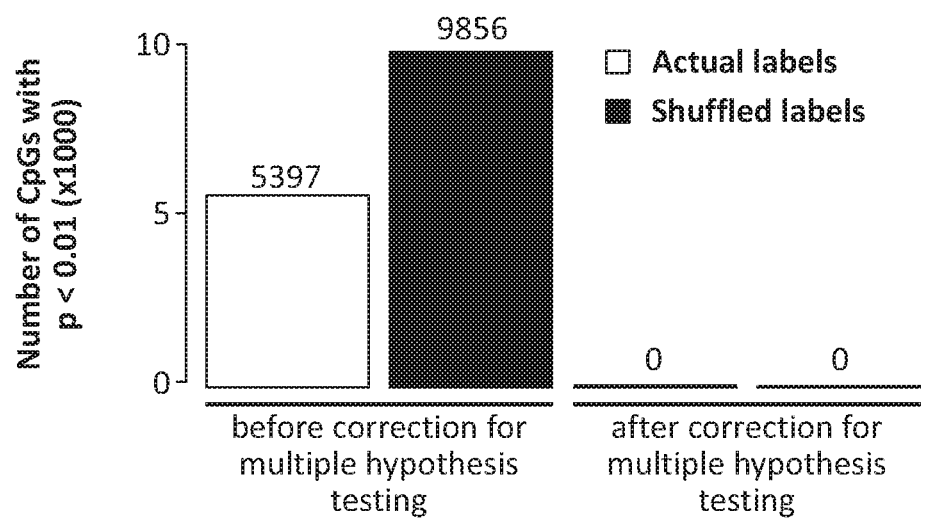
FIG. 6A depicts the number of differentially methylated CpGs between purified good and poor embryogenesis samples before and after correction for multiple hypothesis testing using both the actual good/poor labels and randomly shuffled good/poor labels as a control.
Figure 6B:
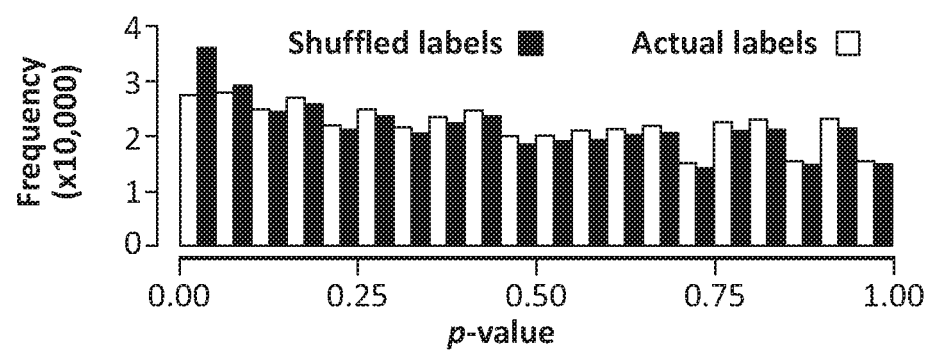
FIG. 6B depicts the distribution of p-values for all profiled CpGs from a test of differential methylation between good and poor embryogenesis using both actual labels and randomly shuffled good/poor labels as a control.

To estimate the reproducibility of the selection, the samples were broken into 10 groups of approximately equal size. For each group, the selection of DMPs was repeated with those samples held out. It was observed that the number of groups for which a CpG was selected in the top 100 most differentially methylated CpGs was generally low when using randomly shuffled labels. In contrast, when using real labels, this followed a U-shaped distribution, with a substantially larger proportion of CpGs always, or generally always, appearing in the top 100 (Table 6 gives the genes which are intersected by these consistently differentially methylated CpGs). The classifier training and evaluation, as described above, were repeated but herein only the top 50, 1,000, 50,000, or 400,000 differentially methylated CpGs were used in the training data to compute Euclidean distances. ROC curves for each are displayed in FIG. 3E, and show an advantage to classification when using fewer features. This was taken a step further by training a range of models using the raw methylation values for the selected CpGs as features (rather than Euclidean distance between samples). Using a bagged cost-sensitive support vector machine (as described above), IVF patient samples with a positive predictive value of 99% and a sensitivity of 82% were identified; ROC curves are shown in FIG. 3F. When the same approach was applied to the purified samples to identify differentially methylated CpGs, no significant CpGs were found after correction for multiple hypothesis testing (see FIG. 6A). Further, the distribution of p-values derived from the real and shuffled labels were largely identical (see FIG. 6B).

TABLE 6

Genes that overlap CpGs consistently in the top 100 most differentially methylated CpGs when comparing unpurified donor and IVF patient samples.

| Gene |
| --- |
| AHDC1 |
| ALOX5AP |
| BTBD17 |
| CXXC11 |
| EEF1A2 |
| FBLN2 |
| FGF18 |
| GRM6 |
| HIST1H4J |
| HIST1H4K |
| INPP5A |
| JAG2 |
| KCNQ1 |
| KIAA0319L |
| LRRC45 |
| MIR4734 |
| MLLT6 |
| MTMR6 |
| MXRA7 |
| NCDN |
| NDUFS6 |

TABLE 6-continued

Genes that overlap CpGs consistently in the
top 100 most differentially methylated CpGs when
comparing unpurified donor and IVF patient samples.

Gene

NDUFS8
OGFOD2
PSTPIP1
RAP1GAP2
SERPINF2
STRA13
SYT8
TCIRG1
TNNI2
USP24

Figure 6C:
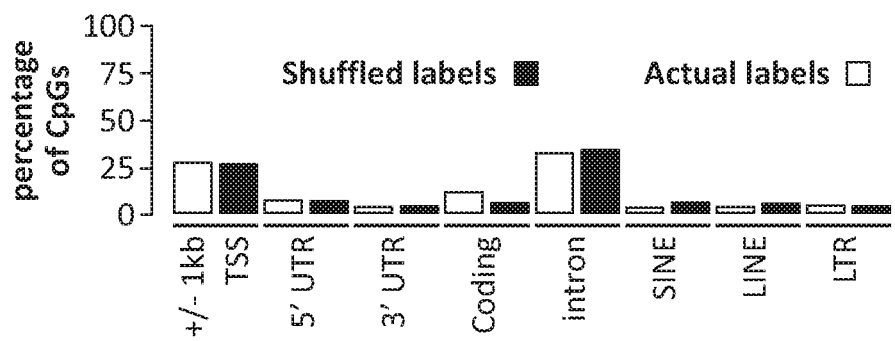
FIG. 6C depicts the proportion of differentially methylated CpGs (before correction for multiple hypothesis testing) that fall within regions annotated as shown, for both actual good/poor embryo quality labels and randomly permuted labels.
Figure 6D:
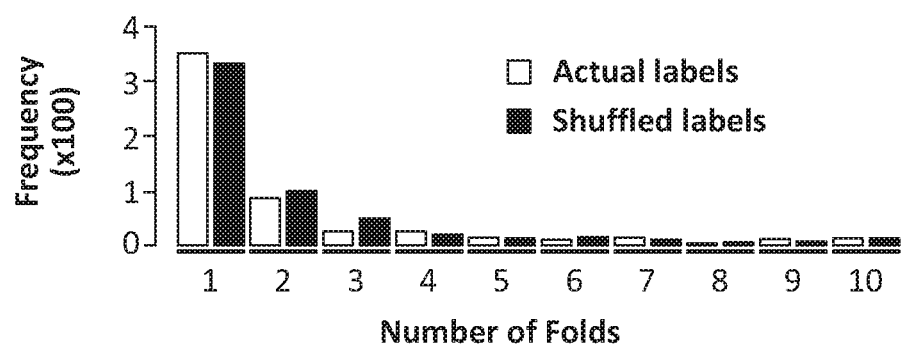
FIG. 6D depicts a histogram showing the number of CpGs that were contained in the top 100 most differentially methylated CpGs identified in only 1 fold, exactly 2 folds, exactly 3 folds, and so on. Samples are split into 10 stratified equally sized groups. A fold is formed by taking 9 of these groups and leaving one group out (allowing 10 ways of doing this). For each fold, the samples in the 9 retained groups are used to identify differentially methylated CpGs using both real good/poor embryogenesis labels and randomly permuted labels as a control.
Figure 6E:
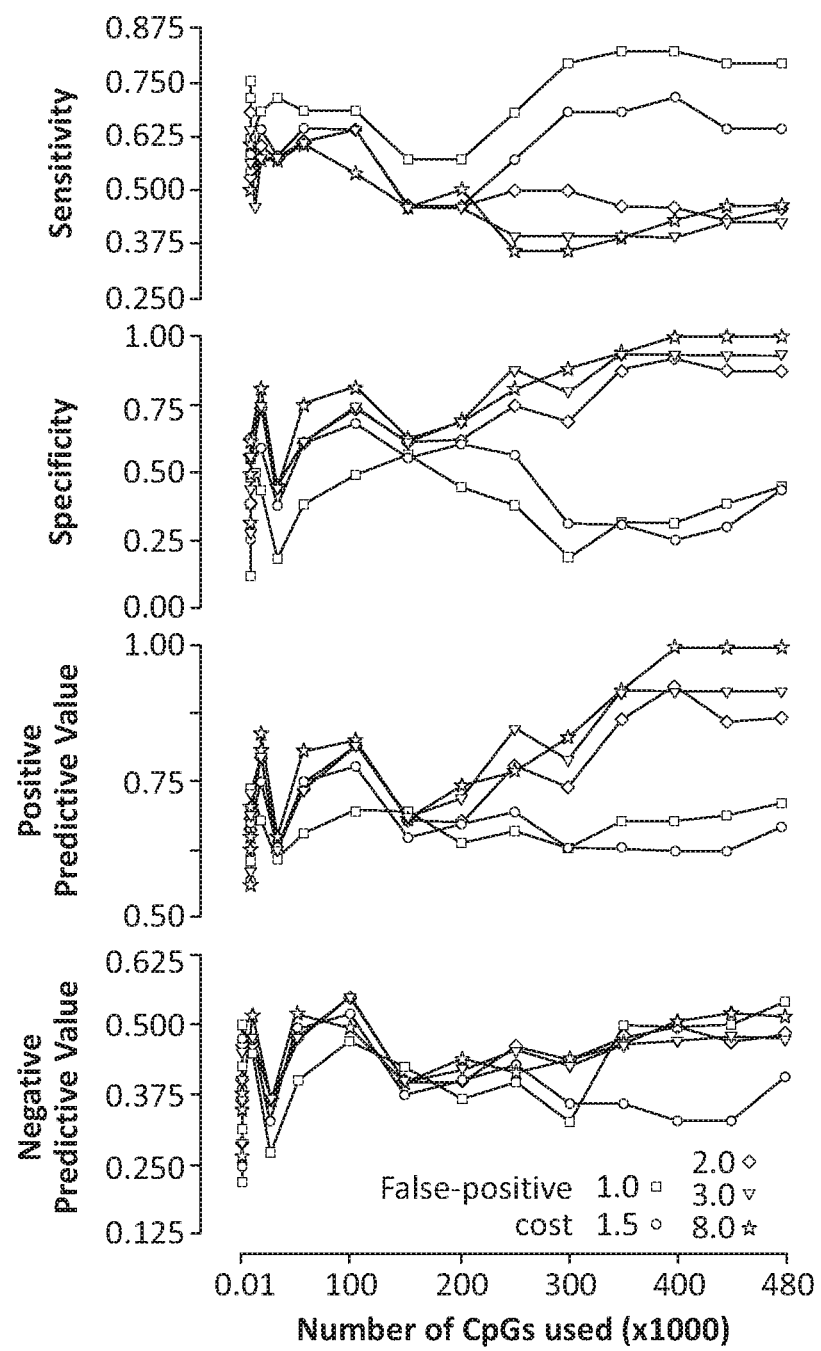
FIG. 6E depicts the evaluation of classifiers, analogous to those of FIGS. 2A-2C, that were trained using a subset of the top x most differentially-methylated CpGs (where x is varied along the x-axis of the plots). The sensitivity, specificity, positive predictive value, and negative predictive value of each were evaluated as a function of how many CpGs were selected.

As with the DMPs in the neat samples for fertility status, there was no bias towards particular regions; however, in contrast, there was also no tendency for any DMPs to consistently appear in the top 100 when using different selections of the data (see FIGS. 6C and 6D). When training distance-based classifiers as described above, it was observed that using more CpGs resulted in higher and more stable specificity and positive predictive value, while no discernible pattern in performance was apparent when attempting to use a reduced set of features (see FIG. 6E). Without being bound by theory, these results may suggest either large-scale whole-genome shifts in DNA methylation in poor embryo-quality samples, or more complex patterns that cannot be isolated by examining single CpGs.

Example 9

Figure 4A:
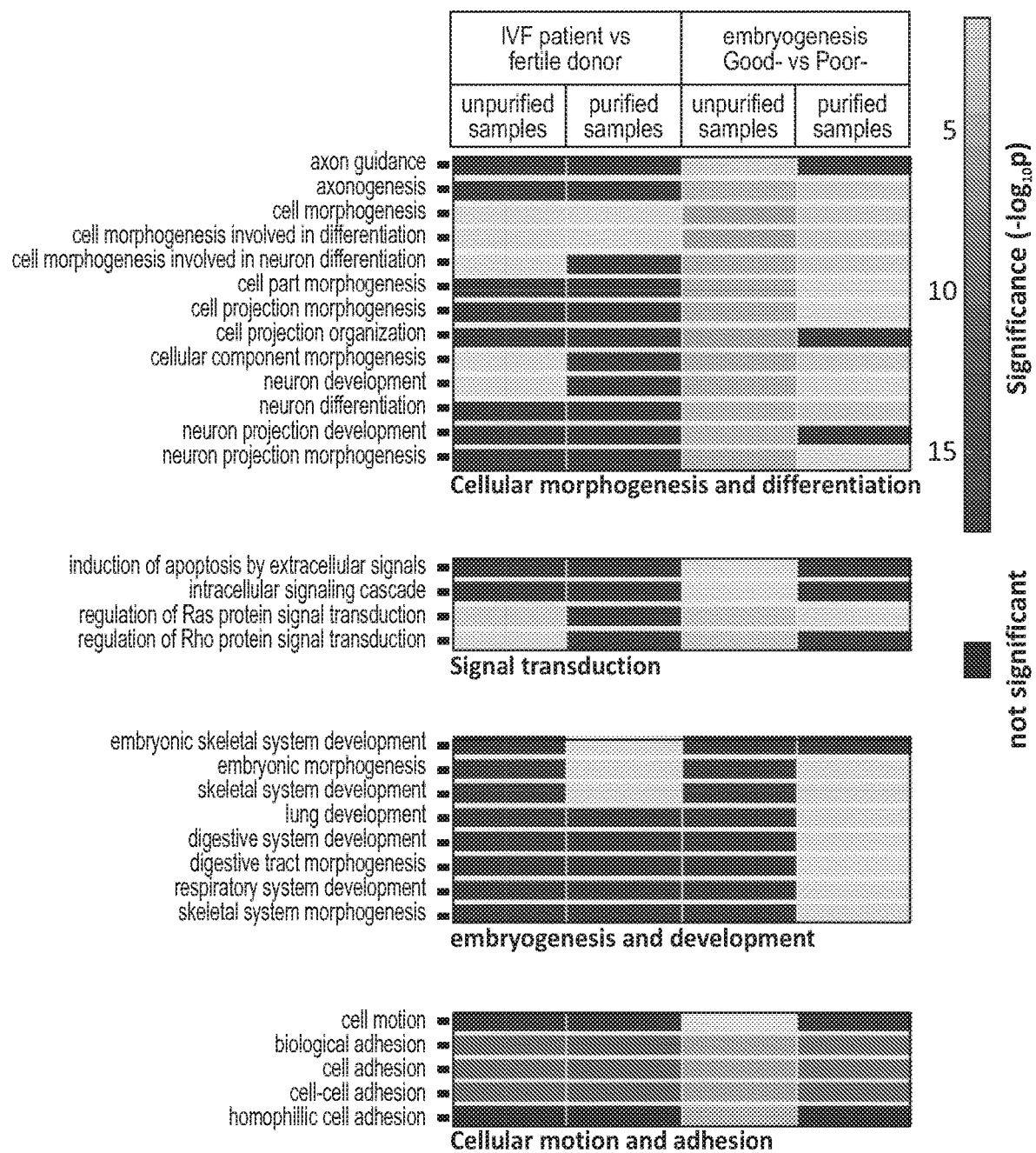
FIG. 4A depicts gene ontology (GO) analysis of the top 1,000 genes after sorting genes by number of differentially methylated CpGs. All terms that were significant (correct p-value<0.05) when either comparing IVF patient samples to fertile donors, or when comparing good- and poor-embryogenesis IVF patient samples are included, with the exception of 24 terms associated with gene expression and cellular metabolism, which are omitted for clarity of visualization.

To assess biological processes and pathways impacted by the observed changes in DNA methylation, genes were ranked by the number of CpGs that were identified as differentially methylated within their promoter regions (+/−5 kb around TSS) and GO analysis was performed on the top 1,000 genes. In all cases (both purified and neat samples for IVF patient versus fertile donor samples, and good versus poor embryo quality samples) a significant enrichment for genes involved in cell adhesion, as well as other functions, was observed (see FIG. 4A and Table 7). Additionally, several gene families associated with embryogenesis and development are differentially methylated when comparing the good and poor embryogenesis groups.

TABLE 7

|  | Embryo quality (good vs. poor) Purified | Embryo quality (good vs. poor) Neat | Source (IVF patient vs. donor) Purified | Source (IVF patient vs. donor) Neat |
|---|---|---|---|---|
| axon guidance | NA | 0.003784515 | NA | NA |
| axonogenesis | 0.008367064 | 1.10E−05 | NA | NA |
| biological adhesion | 1.36E−10 | 8.28E−07 | 6.41E−12 | 2.02E−11 |
| cell adhesion | 1.74E−10 | 1.20E−06 | 9.03E−12 | 3.86E−11 |
| cell morphogenesis | 0.008091845 | 1.14E−06 | 0.015385704 | 0.013289352 |
| cell morphogenesis involved in differentiation | 0.002429427 | 1.37E−06 | 0.015840977 | 0.013687946 |
| cell morphogenesis involved in neuron differentiation | 0.008267382 | 1.05E−05 | NA | 0.034601396 |
| cell motion | NA | 0.024863785 | NA | NA |
| cell part morphogenesis | 0.037927527 | 6.36E−06 | NA | NA |
| cell projection morphogenesis | 0.02677415 | 3.52E−06 | NA | NA |
| cell projection organization | NA | 1.02E−06 | NA | NA |
| cell-cell adhesion | 2.67E−11 | 9.53E−07 | 7.62E−12 | 2.61E−11 |
| cellular component morphogenesis | 0.008715713 | 3.86E−06 | NA | 0.039603502 |
| digestive system development | 0.02794709 | NA | NA | NA |
| digestive tract morphogenesis | 0.02794709 | NA | NA | NA |
| embryonic morphogenesis | 0.026568701 | NA | 0.014366035 | NA |
| embryonic skeletal system development | NA | NA | 0.021136452 | NA |
| homophilic cell adhesion | 8.48E−17 | 3.66E−06 | 4.22E−18 | 1.91E−18 |
| induction of apoptosis by extracellular signals | NA | 0.023856862 | NA | NA |
| intracellular signaling cascade | NA | 0.045548369 | NA | NA |
| lung development | 0.044371938 | NA | NA | NA |
| negative regulation of biosynthetic process | NA | NA | 0.002233179 | NA |
| negative regulation of cellular biosynthetic process | NA | NA | 0.001656261 | NA |
| negative regulation of gene expression | 0.029000863 | NA | 0.002005071 | NA |

TABLE 7-continued

| | Embryo quality (good vs. poor) Purified | Embryo quality (good vs. poor) Neat | Source (IVF patient vs. donor) Purified | Source (IVF patient vs. donor) Neat |
|---|---|---|---|---|
| negative regulation of macromolecule biosynthetic process | NA | NA | 0.0062529 | NA |
| negative regulation of macromolecule metabolic process | NA | NA | 0.01068737 | NA |
| negative regulation of nitrogen compound metabolic process | NA | NA | 0.008631708 | NA |
| negative regulation of nucleobase, nucleoside, nucleotide and nucleic acid metabolic process | NA | NA | 0.007122006 | NA |
| negative regulation of RNA metabolic process | 0.029592325 | NA | 0.006087709 | 0.033210106 |
| negative regulation of transcription | NA | NA | 0.004287172 | NA |
| negative regulation of transcription, DNA-dependent | 0.029393991 | NA | 0.005434563 | 0.028487512 |
| neuron development | 0.019683889 | 3.89E−06 | NA | 0.030918008 |
| neuron differentiation | 0.001351102 | 1.90E−05 | NA | NA |
| neuron projection development | NA | 1.95E−05 | NA | NA |
| neuron projection morphogenesis | 0.018289937 | 3.82E−06 | NA | NA |
| positive regulation of biosynthetic process | NA | NA | 0.013869556 | NA |
| positive regulation of cellular biosynthetic process | NA | NA | 0.011099844 | NA |
| positive regulation of gene expression | NA | NA | 0.018166293 | NA |
| positive regulation of macromolecule biosynthetic process | NA | NA | 0.006219076 | NA |
| positive regulation of macromolecule metabolic process | NA | NA | 0.006136247 | NA |
| positive regulation of nitrogen compound metabolic process | NA | NA | 0.008496523 | NA |
| positive regulation of nucleobase, nucleoside, nucleotide and nucleic acid metabolic process | NA | NA | 0.006010823 | NA |
| positive regulation of RNA metabolic process | NA | NA | 0.010851993 | NA |
| positive regulation of transcription | NA | NA | 0.012919027 | NA |
| positive regulation of transcription from RNA polymerase II promoter | NA | NA | 0.024169014 | NA |
| positive regulation of transcription, DNA-dependent | NA | NA | 0.009668106 | NA |
| regulation of generation of precursor metabolites and energy | NA | 0.014145172 | NA | NA |
| regulation of Ras protein signal transduction | 0.020126317 | 0.000569769 | NA | 0.001939159 |
| regulation of Rho protein signal transduction | NA | 0.000342889 | NA | 0.01927069 |

TABLE 7-continued

Figure 4B:
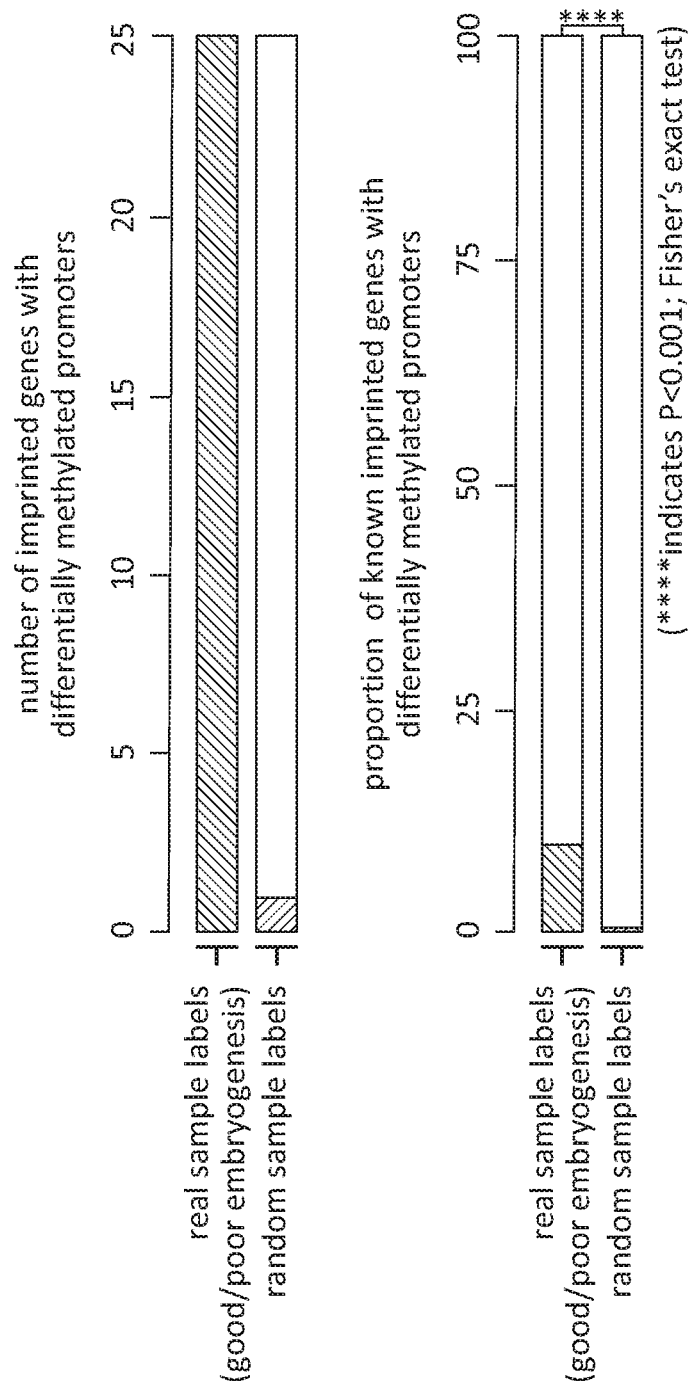
FIG. 4B depicts the absolute number and proportion of genes with differentially methylated promoter regions (p<0.01, Wilcoxon sign-rank test, purified samples) that are known to be imprinted.

| | Embryo quality (good vs. poor) Purified | Embryo quality (good vs. poor) Neat | Source (IVF patient vs. donor) Purified | Source (IVF patient vs. donor) Neat |
|---|---|---|---|---|
| regulation of small GTPase mediated signal transduction | 0.000122766 | 0.000206064 | 0.002639504 | 3.01E−06 |
| regulation of transcription from RNA polymerase II promoter | 0.01852138 | NA | 0.004058305 | NA |
| respiratory system development | 0.026362859 | NA | NA | NA |
| skeletal system development | 0.019027616 | NA | 0.020915396 | NA |
| skeletal system morphogenesis | 0.015897973 | NA | NA | NA | p-values within promoter regions for differential methylation between purified good and poor embryo-quality samples were combined to arrive at a single p-value for differential methylation of each gene. It was found that the set of differentially methylated genes identified in this way contained 25 imprinted genes, accounting for close to 10% of known imprinted genes. As a control, the labels on these samples were randomly permuted and the analysis was repeated; only one imprinted gene was identified as differentially methylated following permutation testing (see FIG. 4B).

Example 10

In predicting embryo quality, the analyses demonstrated that no individual CpG displayed significant differential methylation between the "good" and "poor" embryo groups after correcting for multiple comparisons. Predictive power was generally poor when models were trained based on a small number of CpGs. Generally, as the number of CpGs for the predictive models was increased, predictive power increased (see FIGS. 6A-6E). Without being bound by theory, this may suggest that while poor embryogenesis cannot be attributed to a few consistently altered CpGs, the genome-wide methylation profile seems to be inherently different in men in the poor embryo group. Furthermore, when density gradient purified samples were assessed, the predictive power of good versus poor embryo quality was significantly improved. Without being bound by theory, a reason for this observation may be that the purification step reduced background methylation heterogeneity, thus improving the overall methylation signatures of the two groups.

In contrast to the above-described results, comparison of sperm methylomes between fertile men and IVF patients revealed more than 8,500 significantly differentially methylated CpGs after multiple comparison correction. The same strategy for predictive modeling as was employed to classify good versus poor embryo patients was employed. Herein, it was found that models were most effective at classifying samples when samples were classified using only the most significantly differentially methylated CpGs (see FIG. 3). Comparing controls with IVF patients, whole ejaculate was more effective at classifying samples than the evaluation of methylation in purified samples.

Example 11

The genomic context of methylation alterations and the gene classes affected by differential methylation between groups were evaluated. There did not appear to be any enrichment for differential methylation within a specific genomic context (see FIGS. 3C and 6A-6E). Without being bound by theory, this may suggest that methylation perturbations associated with infertility may not be driven by CpG density or chromatin architecture. GO analysis indicated highly significant enrichment for several functional classes of genes (see FIG. 4). For example, as discussed above, genes involved in cellular adhesion were significantly over-represented among differentially methylated CpGs for all comparisons made. Genes involved in cellular morphogenesis and differentiation were also over-represented in the good versus poor embryogenesis comparison and to a lesser extent in the IVF versus fertile donor comparison. Furthermore, imprinted genes were significantly over-represented among the list of differentially methylated genes when comparing good versus poor embryogenesis samples. This enrichment was not detected when comparing IVF patients and fertile donors.

Example 12

Figure 5A:
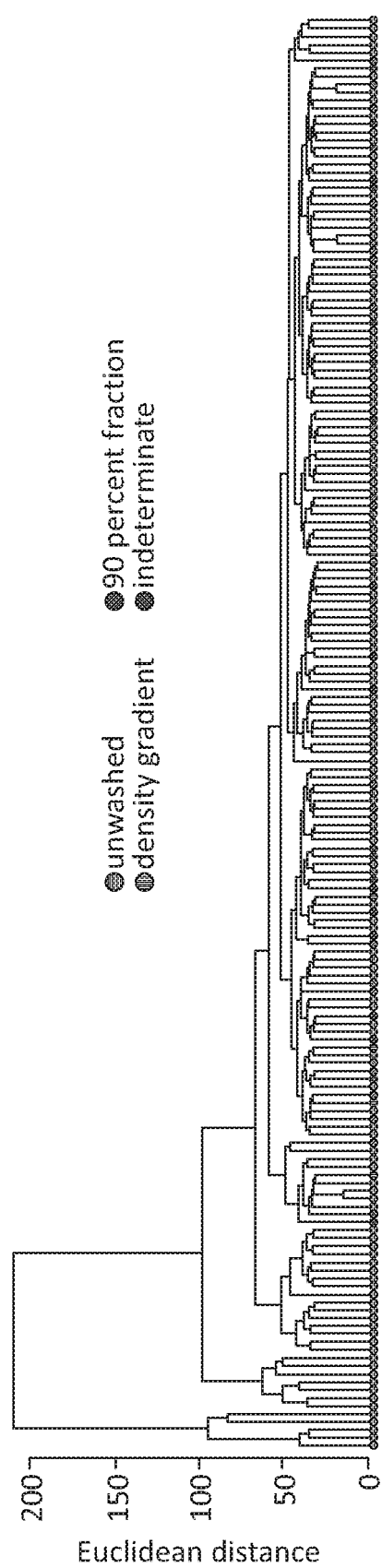
FIG. 5A depicts hierarchical clustering of global methylation profiles for 181 samples with duplicates omitted (i.e., where both purified and non-purified samples were processed from the same patient/donor, which accounts for 44 out of 225 samples, only the purified sample is included in this plot). The dendrogram is annotated with the purification method used for each sample.
Figure 5B:
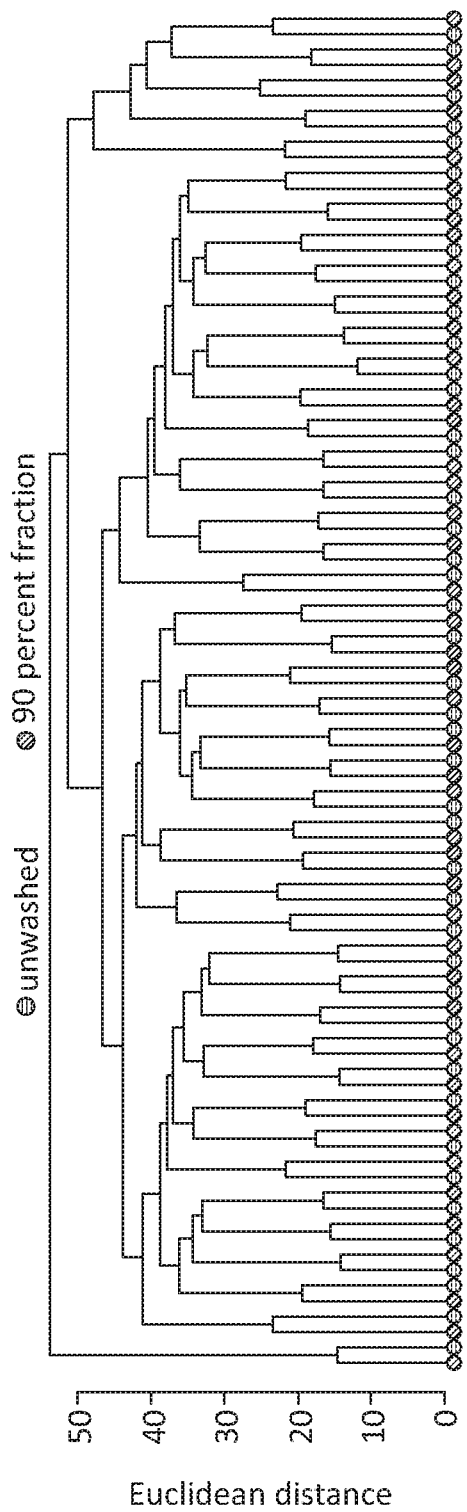
FIG. 5B depicts hierarchical clustering of methylation profiles for the 44 IVF patients for which both purified and non-purified samples were processed (i.e., 88 samples in total are plotted here). Note that for each unpurified sample, its nearest neighbor is the purified sample from the same patient.

Hierarchical clustering of samples showed that, while there were differences between purified and unpurified samples, purified and unpurified methylomes derived from the same sample always, or generally always, clustered with each other; between sample differences were greater than between purification method differences (see FIGS. 5A and 5B).

Example 13

A fertile reference methylome may be used to identify infertile samples. First, using the fertile reference methylome, aberrantly methylated CpGs can be identified as discussed above (i.e., more than 0.2 different from the maximum/minimum value observed in the reference). This can be done for infertile patient samples, as well as fertile controls (using hold-one-out cross-validation). Second, the number of times each CpG is found to be aberrantly methylated in infertile patients can be counted. Third, all CpGs can be ranked by the number of times they are differentially methylated in patients, and the top ten (10) CpGs can be selected as predictive of patient status. It need not be ten, but ten is the number used in the plot shown in FIG. 7 (described below).

Fourth, each sample can be given a score between 0 and 10, representing the number of CpGs from the above list which it has aberrantly methylated. Fifth, all of the samples can then be ranked by their score, and an ROC curve can be plotted (see FIG. 7; a "positive" here is considered to be a diagnosis of infertility).

Figure 7:
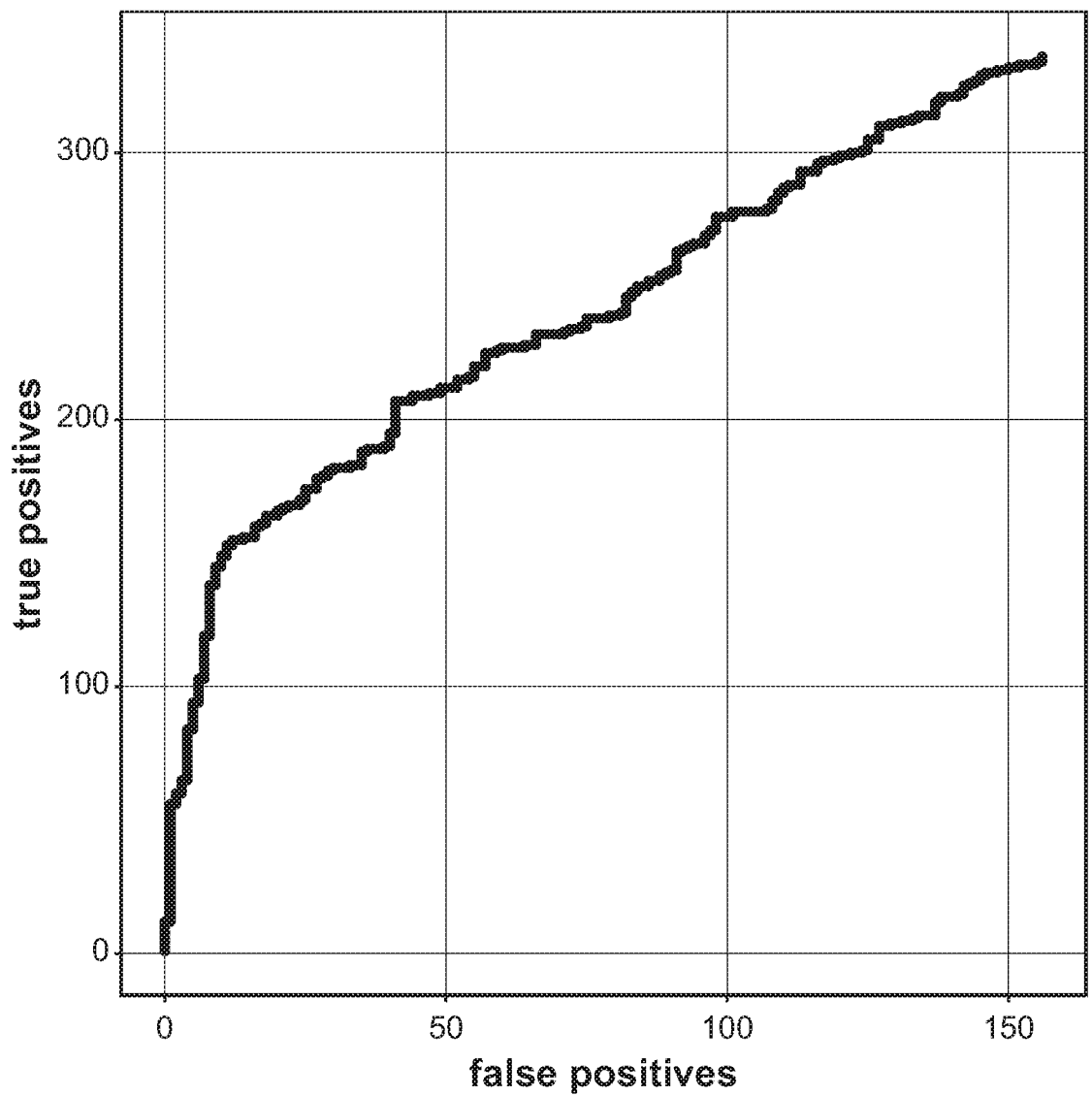
FIG. 7 depicts an exemplary ROC curve that can be plotted when using a fertile reference methylome to identify infertile samples.

As depicted in the ROC curve of FIG. 7, samples with high counts of loci showing aberrant methylation (relative to the reference) which are commonly seen in other known-infertile patient samples also tend to be patients themselves (and would be "diagnosed" as infertile using this approach).

It will be apparent to those having skill in the art that many changes may be made to the details of the above-described embodiments without departing from the underlying principles of the invention.

The invention claimed is:

1. A method comprising:
   (a) extracting a DNA from a semen sample from a male subject;
   (b) generating a methylation pattern of at least a portion of the extracted DNA, wherein the generating comprises:
      converting unmethylated cytosines to uracils in at least a portion of the extracted DNA to form converted DNA,
      (ii) hybridizing the converted DNA to a microarray,
      (iii) scanning the microarray, and
      (iv) with a first computer program, executed on a computer, generating Beta-values for a plurality of CpG sites, thereby generating the methylation pattern;
   (c) with a second computer program, executed on a computer, detecting a difference between the methylation pattern of the extracted DNA and a control pattern of DNA methylation, wherein the difference comprises aberrant methylation associated with at least five genes of the following genes: AHDC1, ALOX5AP, BTBD17, CXXC11, EEF1A2, FBLN2, FGF18, GRM6, HIST1H4J, HIST1H4K, KIAA0319L, LRRC45, MIR4734, MLLT6, MTMR6, MXRA7, NCDN, NDUFS6, NDUFS8, OGFOD2, SERPINF2, STRA13, SYT8, TCIRG1, and TNNI2; and
   (d) performing a fertility treatment with the semen of the male subject, wherein the fertility treatment comprises in vitro fertilization or artificial insemination.

2. The method of claim 1, wherein the control pattern of DNA methylation is obtained from a plurality of semen samples from fertile male subjects.

3. The method of claim 1, wherein the control pattern of DNA methylation is obtained from a plurality of semen samples from male subjects with at least partially diminished infertility.

4. The method of claim 1, wherein the methylation pattern of the extracted DNA is a genome-wide methylation pattern, wherein the genome-wide methylation pattern comprises the methylation at a plurality of loci across the genome.

5. The method of claim 1, wherein the methylation pattern of the extracted DNA comprises a methylation status of at least 50,000 cytosine-guanine dinucleotides (CpGs) from the extracted DNA.

6. The method of claim 1, wherein the methylation pattern of the extracted DNA comprises a methylation status of at least 50,000 cytosines from the extracted DNA.

7. The method of claim 1, wherein the aberrant methylation independently comprises, for each of the genes associated with the aberrant methylation, increased methylation or decreased methylation, compared to the control pattern of DNA methylation at the same gene.

8. The method of claim 1, wherein the first computer program and the second computer program are the same.

9. The method of claim 1, wherein the first computer program and the second computer program are different computer programs.

10. The method of claim 1, further comprising performing an assisted reproductive technology using the sperm of the male subject.

11. The method of claim 1, wherein the converting unmethylated cytosines to uracils comprises a bisulfite treatment.

12. A method comprising:
   (a) extracting a DNA from a semen sample from a male subject;
   (b) generating a methylation pattern of at least a portion of the extracted DNA, wherein the generating comprises:
      (i) converting unmethylated cytosines to uracils in at least a portion of the extracted DNA to form converted DNA,
      (ii) sequencing the converted DNA, and
      (iii) with a first computer program, generating a methylation pattern;
   (c) with a second computer program, executed on a computer, detecting a difference between the methylation pattern of the extracted DNA and a control pattern of DNA methylation, wherein the difference comprises aberrant methylation associated with at least five genes of the following genes: AHDC1, ALOX5AP, BTBD17, CXXC11, EEF1A2, FBLN2, FGF18, GRM6, HIST1H4J, HIST1H4K, KIAA0319L, LRRC45, MIR4734, MLLT6, MTMR6, MXRA7, NCDN, NDUFS6, NDUFS8, OGFOD2, SERPINF2, STRA13, SYT8, TCIRG1, and TNNI2; and
   (d) performing a fertility treatment with the semen of the male subject, wherein the fertility treatment comprises in vitro fertilization or artificial insemination.

13. The method of claim 12, wherein the control pattern of DNA methylation is obtained from a plurality of semen samples from fertile male subjects.

14. The method of claim 12, wherein the control pattern of DNA methylation is obtained from a plurality of semen samples from male subjects with at least partially diminished infertility.

15. The method of claim 12, wherein the methylation pattern of the extracted DNA is a genome-wide methylation pattern, wherein the genome-wide methylation pattern comprises the methylation at a plurality of loci across the genome.

16. The method of claim 12, wherein the methylation pattern of the extracted DNA comprises a methylation status of at least 50,000 cytosines from the extracted DNA.

17. The method of claim 12, wherein the aberrant methylation independently comprises, for each of the genes associated with the aberrant methylation, increased methylation or decreased methylation, compared to the control pattern of DNA methylation at the same gene.

18. The method of claim 12, wherein the first computer program and the second computer program are the same.

19. The method of claim 12, wherein the first computer program and the second computer program are different computer programs.

* * * * *